(12) United States Patent
Hubbell et al.

(10) Patent No.: US 10,953,101 B2
(45) Date of Patent: *Mar. 23, 2021

(54) GLYCOTARGETING THERAPEUTICS

(71) Applicant: École Polytechnique Fédérale de Lausanne (EPFL), Lausanne (CH)

(72) Inventors: Jeffrey A. Hubbell, Chicago, IL (US); David Scott Wilson, Lausanne (CH)

(73) Assignee: École Polytechnique Fédérale de Lausanne (EPFL), Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/925,628

(22) Filed: Mar. 19, 2018

(65) Prior Publication Data

US 2018/0271986 A1 Sep. 27, 2018

Related U.S. Application Data

(63) Continuation of application No. PCT/IB2016/001411, filed on Sep. 16, 2016, which is a continuation-in-part of application No. 15/185,564, filed on Jun. 17, 2016, now Pat. No. 10,046,056, which is a continuation-in-part of application No. 14/859,292, filed on Sep. 19, 2015, said application No. PCT/IB2016/001411 is a continuation-in-part of application No. 14/859,292, filed on Sep. 19, 2015, application No. 15/925,628, filed on Mar. 19, 2018, which is a continuation-in-part of application No. 15/185,564, filed on Jun. 17, 2016, now Pat. No. 10,046,056, which is a continuation-in-part of application No. 14/859,292, filed on Sep. 19, 2015, which is a continuation-in-part of application No. 14/627,297, filed on Feb. 20, 2015, now Pat. No. 10,821,157.

(60) Provisional application No. 61/942,942, filed on Feb. 21, 2014.

(51) Int. Cl.

| A61K 39/00 | (2006.01) |
|---|---|
| A61K 39/385 | (2006.01) |
| A61K 47/54 | (2017.01) |
| A61K 39/35 | (2006.01) |
| A61K 38/28 | (2006.01) |
| A61K 47/58 | (2017.01) |
| A61K 47/60 | (2017.01) |
| A61K 38/38 | (2006.01) |

(52) U.S. Cl.
CPC ........... *A61K 47/549* (2017.08); *A61K 38/28* (2013.01); *A61K 38/38* (2013.01); *A61K 39/001* (2013.01); *A61K 39/35* (2013.01); *A61K 39/385* (2013.01); *A61K 47/555* (2017.08); *A61K 47/58* (2017.08); *A61K 47/60* (2017.08)

(58) Field of Classification Search
None
See application file for complete search history.

(56) References Cited

U.S. PATENT DOCUMENTS

| 4,671,958 A | 6/1987 | Rodwell et al. |
|---|---|---|
| 4,741,900 A | 5/1988 | Alvarez et al. |
| 4,859,449 A | 8/1989 | Mattes |
| 4,867,973 A | 9/1989 | Goers et al. |
| 4,950,738 A | 8/1990 | King et al. |
| 5,086,002 A | 2/1992 | Hillyard et al. |
| 5,140,104 A | 8/1992 | Coughlin et al. |
| 5,156,840 A | 10/1992 | Goers et al. |
| 5,162,512 A | 11/1992 | King et al. |
| 5,227,165 A | 7/1993 | Domb et al. |
| 5,227,293 A | 7/1993 | Stengelin et al. |
| 5,346,696 A | 9/1994 | Kim et al. |
| 5,358,857 A | 10/1994 | Stengelin et al. |
| 5,470,570 A | 11/1995 | Taylor et al. |
| 5,487,890 A | 1/1996 | Taylor et al. |
| 5,681,571 A | 10/1997 | Holmgren et al. |
| 5,698,679 A | 12/1997 | Nemazee et al. |
| 5,718,915 A | 2/1998 | Virtanen et al. |
| 5,879,679 A | 3/1999 | Taylor et al. |
| 5,885,808 A | 3/1999 | Spooner et al. |
| 5,886,143 A | 3/1999 | Theodore et al. |
| 5,948,639 A | 9/1999 | Gimeno et al. |

(Continued)

FOREIGN PATENT DOCUMENTS

| CN | 102791293 A | 11/2012 |
|---|---|---|
| CN | 103282380 A | 9/2013 |

(Continued)

OTHER PUBLICATIONS

Granoff et al., J. Immunol. 167:6487-6496 (2001) (Year: 2001).‡

(Continued)

*Primary Examiner* — Thea D' Ambrosio
(74) *Attorney, Agent, or Firm* — Knobbe, Martens, Olson & Bear, LLP

(57) ABSTRACT

Several embodiments of the present disclosure relate to therapeutic compositions configured to target the liver of a subject and that are useful in the treatment or prevention of one or more of transplant rejection, autoimmune disease, food allergy, and immune response against a therapeutic agent. In several embodiments, the compositions are configured to target the liver and deliver antigens to which tolerance is desired. In several embodiments, the compositions are configured for clearance of a circulating protein or peptide or antibody associated with one or more of the above-mentioned maladies. Methods and uses of the compositions for induction of immune tolerance are also disclosed herein.

18 Claims, 32 Drawing Sheets

Specification includes a Sequence Listing.

(56) References Cited

U.S. PATENT DOCUMENTS

| | | |
|---|---|---|
| 5,985,826 A | 11/1999 | Theodore et al. |
| 5,994,104 A | 11/1999 | Anderson et al. |
| 5,997,861 A | 12/1999 | Virtanen et al. |
| 6,022,564 A | 2/2000 | Takechi et al. |
| 6,090,925 A | 7/2000 | Woiszwillo et al. |
| 6,120,770 A | 9/2000 | Adams et al. |
| 6,153,203 A | 11/2000 | Holmgren et al. |
| 6,217,869 B1 | 4/2001 | Meyer et al. |
| 6,224,794 B1 | 5/2001 | Amsden et al. |
| 6,264,950 B1 | 7/2001 | Staerz |
| 6,322,796 B1 | 11/2001 | Holmgren et al. |
| 6,365,163 B1 | 4/2002 | Holmgren et al. |
| 6,379,699 B1 | 4/2002 | Virtanen et al. |
| 6,488,927 B2 | 12/2002 | Muzykantov et al. |
| 6,512,103 B1 | 1/2003 | Dairaghi et al. |
| 6,562,347 B1 | 5/2003 | Kwak et al. |
| 6,703,488 B1 | 3/2004 | Burton et al. |
| 6,737,057 B1 | 5/2004 | Zaghouani et al. |
| 6,814,964 B2 | 11/2004 | Virtanen et al. |
| 6,905,688 B2 | 6/2005 | Rosen et al. |
| 6,953,675 B2 | 10/2005 | Leung et al. |
| 7,041,287 B2 | 5/2006 | Muzykantov et al. |
| 7,132,475 B2 | 11/2006 | Hubbel et al. |
| 7,144,569 B1 | 12/2006 | Anderson et al. |
| 7,148,329 B1 | 12/2006 | Figdor et al. |
| 7,172,760 B2 | 2/2007 | Muzykantov et al. |
| 7,175,988 B2 | 2/2007 | Roschke et al. |
| 7,192,582 B2 | 3/2007 | Hudson et al. |
| 7,285,642 B2 | 10/2007 | Figdor et al. |
| 7,420,040 B2 | 9/2008 | Young et al. |
| 7,420,041 B2 | 9/2008 | Young et al. |
| 7,541,180 B2 | 6/2009 | Valiante et al. |
| 7,585,508 B1 | 9/2009 | Prendergast |
| 7,612,180 B2 | 11/2009 | Goldenberg et al. |
| 7,704,943 B2 | 4/2010 | Griffin et al. |
| 7,704,964 B2 | 4/2010 | Delcayre et al. |
| 7,786,267 B2 | 8/2010 | Zurawski et al. |
| 7,811,809 B2 | 10/2010 | Heyduk et al. |
| 7,837,997 B2 | 11/2010 | Muzykantov et al. |
| 7,884,190 B2 | 2/2011 | Cohen et al. |
| 7,888,460 B2 | 2/2011 | Anderson et al. |
| 7,892,743 B2 | 2/2011 | Owen et al. |
| 7,932,294 B2 | 4/2011 | Satyam |
| 7,994,283 B2 | 8/2011 | Valiante et al. |
| 8,007,805 B2 | 8/2011 | George et al. |
| 8,021,689 B2 | 9/2011 | Reddy et al. |
| 8,057,798 B2 | 11/2011 | Zurawski et al. |
| 8,058,400 B2 | 11/2011 | Figdor et al. |
| 8,058,406 B2 | 11/2011 | Mi et al. |
| 8,105,599 B2 | 1/2012 | Figdor et al. |
| 8,236,934 B2 | 8/2012 | Banchereau et al. |
| 8,252,902 B2 | 8/2012 | Barbas et al. |
| 8,273,357 B2 | 9/2012 | Hacohen et al. |
| 8,277,812 B2 | 10/2012 | Iannacone et al. |
| 8,318,912 B2 | 11/2012 | Simon |
| 8,323,696 B2 | 12/2012 | Hubbel et al. |
| 8,329,144 B2 | 12/2012 | Anderson et al. |
| 8,333,973 B2 | 12/2012 | Muzykantov et al. |
| 8,343,497 B2 | 1/2013 | Shi et al. |
| 8,343,498 B2 | 1/2013 | Alexis et al. |
| 8,425,910 B2 | 4/2013 | Mi et al. |
| 8,449,888 B2 | 5/2013 | Zurawski et al. |
| 8,507,237 B2 | 8/2013 | Hermet et al. |
| 8,518,410 B2 | 8/2013 | Zurawski et al. |
| 8,551,476 B2 | 10/2013 | Mi et al. |
| 8,562,998 B2 | 10/2013 | Shi et al. |
| 8,580,253 B2 | 11/2013 | Rubin-Bejerano et al. |
| 8,586,052 B2 | 11/2013 | Zurawski et al. |
| 8,591,905 B2 | 11/2013 | von Andrian et al. |
| 8,592,364 B2 | 11/2013 | Swartz et al. |
| 8,613,903 B2 | 12/2013 | Goldenberg et al. |
| 8,617,823 B2 | 12/2013 | Rubin-Bejerano et al. |
| 8,637,028 B2 | 1/2014 | Alexis et al. |
| 8,685,408 B2 | 4/2014 | Tartour et al. |
| 8,722,047 B2 | 5/2014 | Goldenberg et al. |
| 8,728,481 B2 | 5/2014 | Banchereau et al. |
| 8,889,140 B2 | 11/2014 | Lee et al. |
| 8,906,381 B2 | 12/2014 | Iannacone et al. |
| 8,932,595 B2 | 1/2015 | Iannacone et al. |
| 8,961,991 B2 | 2/2015 | Zurawski et al. |
| 8,992,917 B2 | 3/2015 | Goldenberg et al. |
| 9,005,903 B2 | 4/2015 | Rubin-Bejerano et al. |
| 9,066,984 B2 | 6/2015 | Mi et al. |
| 9,102,730 B2 | 8/2015 | Zurawski et al. |
| 9,102,734 B2 | 8/2015 | Zurawski et al. |
| 9,187,561 B2 | 11/2015 | Goldenberg et al. |
| 9,216,156 B2 | 12/2015 | Fleury et al. |
| 9,233,072 B2 | 1/2016 | Alexis et al. |
| 9,234,040 B2 | 1/2016 | Zurawski et al. |
| 9,260,692 B2 | 2/2016 | Martin et al. |
| 9,308,280 B2 | 4/2016 | Shi et al. |
| 9,326,939 B2 | 5/2016 | Paulson et al. |
| 9,416,186 B2 | 8/2016 | Zurawski et al. |
| 9,439,859 B2 | 9/2016 | Alexis et al. |
| 9,453,074 B2 | 9/2016 | Oh et al. |
| 9,457,047 B2 | 10/2016 | Rubin-Bejerano et al. |
| 9,474,717 B2 | 10/2016 | von Andrian et al. |
| 9,517,257 B2 | 12/2016 | Hubbell et al. |
| 9,518,087 B2 | 12/2016 | Hubbell et al. |
| 9,522,183 B2 | 12/2016 | Paulson et al. |
| 9,539,210 B2 | 1/2017 | von Andrian et al. |
| 9,561,272 B2 | 2/2017 | Thomas et al. |
| 9,688,991 B2 | 6/2017 | Levy et al. |
| 9,751,945 B2 | 9/2017 | Ploegh et al. |
| 9,814,780 B2 | 11/2017 | Hubbell et al. |
| 9,850,296 B2 | 12/2017 | Hubbell et al. |
| 9,878,048 B2 | 1/2018 | Hubbell et al. |
| 9,901,645 B2 | 2/2018 | Hubbell et al. |
| 9,901,646 B2 | 2/2018 | Hubbell et al. |
| 10,046,056 B2 ‡ | 8/2018 | Hubbell ............ C07K 16/2848 |
| 2002/0004037 A1 | 1/2002 | Koteliansky et al. |
| 2002/0038002 A1 | 3/2002 | Zaghouani |
| 2002/0081298 A1 | 6/2002 | Zaghouani |
| 2002/0103343 A1 | 8/2002 | Taylor et al. |
| 2002/0187131 A1 | 12/2002 | Hawiger et al. |
| 2002/0193572 A1 | 12/2002 | Leung et al. |
| 2003/0022826 A1 | 1/2003 | Haynes |
| 2003/0082643 A1 | 5/2003 | Hudson et al. |
| 2003/0103967 A1 | 5/2003 | Zaghouani |
| 2003/0104045 A1 | 6/2003 | Virtanen et al. |
| 2003/0175921 A1 | 9/2003 | Barbas et al. |
| 2003/0190676 A1 | 10/2003 | Barbas et al. |
| 2003/0211078 A1 | 11/2003 | Heavner |
| 2004/0052815 A1 | 3/2004 | Lycke |
| 2004/0077843 A1 | 4/2004 | Burton et al. |
| 2004/0146948 A1 | 7/2004 | Britton et al. |
| 2004/0147721 A1 | 7/2004 | Valiante |
| 2004/0185057 A1 | 9/2004 | Kirkby et al. |
| 2004/0197314 A1 | 10/2004 | Delcayre et al. |
| 2004/0258688 A1 | 12/2004 | Hawiger et al. |
| 2005/0031628 A1 | 2/2005 | George et al. |
| 2005/0053579 A1 | 3/2005 | Galipeau et al. |
| 2005/0113297 A1 | 5/2005 | Francois et al. |
| 2005/0118168 A1 | 6/2005 | Figdor et al. |
| 2005/0201973 A1 | 9/2005 | Virtanen et al. |
| 2005/0203022 A1 | 9/2005 | Gotwals et al. |
| 2005/0220804 A1 | 10/2005 | Figdor et al. |
| 2005/0250936 A1 | 11/2005 | Oppermann et al. |
| 2006/0034864 A1 | 2/2006 | Zaghouani |
| 2006/0127929 A1 | 6/2006 | Swager et al. |
| 2006/0153881 A1 | 7/2006 | Narum et al. |
| 2006/0173168 A1 | 8/2006 | Carlock et al. |
| 2006/0178299 A1 | 8/2006 | Anderson et al. |
| 2006/0257412 A1 | 11/2006 | Bowdish et al. |
| 2006/0280679 A1 | 12/2006 | Bowdish et al. |
| 2007/0059794 A1 | 3/2007 | Ideno et al. |
| 2007/0111222 A1 | 5/2007 | Chasin et al. |
| 2007/0122409 A1 | 5/2007 | Zaghouani |
| 2007/0190615 A1 | 8/2007 | Cohen et al. |
| 2007/0218053 A1 | 9/2007 | Zaghouani |
| 2008/0031899 A1 | 2/2008 | Reddy et al. |
| 2008/0131428 A1 | 6/2008 | Young et al. |
| 2008/0160041 A1 | 7/2008 | Figdor et al. |
| 2008/0175971 A1 | 7/2008 | Anderson et al. |

(56) References Cited

U.S. PATENT DOCUMENTS

| | | |
|---|---|---|
| 2008/0206262 A1 | 8/2008 | Banchereau et al. |
| 2008/0213267 A1 | 9/2008 | Young et al. |
| 2008/0227707 A1 | 9/2008 | Carlock et al. |
| 2008/0233143 A1 | 9/2008 | Jackson et al. |
| 2008/0241170 A1 | 10/2008 | Zurawski et al. |
| 2008/0254044 A1 | 10/2008 | Zurawski |
| 2008/0261262 A1 | 10/2008 | Godfrin |
| 2008/0274092 A1 | 11/2008 | Godfrin et al. |
| 2008/0305104 A1 | 12/2008 | Young et al. |
| 2008/0318852 A1 | 12/2008 | Anderson et al. |
| 2009/0004218 A1 | 1/2009 | Hacohen et al. |
| 2009/0017039 A1 | 1/2009 | Mi et al. |
| 2009/0123467 A1 | 5/2009 | Bedi et al. |
| 2009/0130104 A1 | 5/2009 | Muzykantov et al. |
| 2009/0142263 A1 | 6/2009 | Young et al. |
| 2009/0149656 A1 | 6/2009 | Singaram et al. |
| 2009/0181011 A1 | 7/2009 | Zaghouani |
| 2009/0191118 A1 | 7/2009 | Young et al. |
| 2009/0202622 A1 | 8/2009 | Fleury et al. |
| 2009/0269285 A1 | 10/2009 | Anderson et al. |
| 2009/0280132 A1 | 11/2009 | Zaghouani |
| 2009/0317381 A1 | 12/2009 | Plant et al. |
| 2009/0324538 A1 | 12/2009 | Wong et al. |
| 2010/0003266 A1 | 1/2010 | Simon |
| 2010/0003338 A1 | 1/2010 | Hubbell et al. |
| 2010/0015131 A1 | 1/2010 | Mi et al. |
| 2010/0055189 A1 | 3/2010 | Hubbell et al. |
| 2010/0092425 A1 | 4/2010 | Von Andrian et al. |
| 2010/0098718 A1 | 4/2010 | Valiante |
| 2010/0129392 A1 | 5/2010 | Shi et al. |
| 2010/0129439 A1 | 5/2010 | Alexis et al. |
| 2010/0129820 A1 | 5/2010 | Kool et al. |
| 2010/0222407 A1 | 9/2010 | Segura et al. |
| 2010/0233251 A1 | 9/2010 | Von Adrian et al. |
| 2010/0239575 A1 | 9/2010 | Banchereau et al. |
| 2010/0285015 A1 | 11/2010 | Muzykantov et al. |
| 2010/0291080 A1 | 11/2010 | Lee et al. |
| 2010/0291082 A1 | 11/2010 | Zurawski |
| 2010/0297114 A1 | 11/2010 | Zurawski |
| 2010/0310612 A1 | 12/2010 | DuFour et al. |
| 2010/0316620 A1 | 12/2010 | Bourgeaux et al. |
| 2010/0322929 A1 | 12/2010 | Zurawski et al. |
| 2010/0330115 A1 | 12/2010 | Zurawski et al. |
| 2011/0014171 A1 | 1/2011 | Bourgeaux et al. |
| 2011/0033426 A1 | 2/2011 | Martin et al. |
| 2011/0044912 A2 | 2/2011 | Anderson et al. |
| 2011/0045049 A1 | 2/2011 | Rubin-Bejerano et al. |
| 2011/0064709 A1 | 3/2011 | Miller et al. |
| 2011/0064754 A1 | 3/2011 | Taylor et al. |
| 2011/0082075 A1 | 4/2011 | Prendergast |
| 2011/0091493 A1 | 4/2011 | Mohamadzadeh et al. |
| 2011/0105379 A1 | 5/2011 | Shulman et al. |
| 2011/0123536 A1 | 5/2011 | Chermann et al. |
| 2011/0143994 A1 | 6/2011 | Lycke |
| 2011/0177532 A1 | 7/2011 | Rubin-Bejerano et al. |
| 2011/0200632 A1 | 8/2011 | Jackson et al. |
| 2011/0206759 A1 | 8/2011 | Swartz et al. |
| 2011/0268804 A1 | 11/2011 | Shi et al. |
| 2011/0268805 A1 | 11/2011 | Alexis et al. |
| 2011/0293644 A1 | 12/2011 | Anderson et al. |
| 2011/0311542 A1 | 12/2011 | Mi et al. |
| 2012/0004643 A1 | 1/2012 | Zurawski et al. |
| 2012/0009140 A1 | 1/2012 | Godfrin et al. |
| 2012/0014960 A1 | 1/2012 | Mi et al. |
| 2012/0027808 A1 | 2/2012 | Iannacone |
| 2012/0039989 A1 | 2/2012 | Hubbel et al. |
| 2012/0058180 A1 | 3/2012 | Kren et al. |
| 2012/0076831 A1 | 3/2012 | Miller et al. |
| 2012/0087890 A1 | 4/2012 | Iannacone et al. |
| 2012/0107301 A1 | 5/2012 | Bowdish et al. |
| 2012/0121570 A1 | 5/2012 | Godfrin |
| 2012/0121592 A1 | 5/2012 | Oh et al. |
| 2012/0128635 A1 | 5/2012 | Gregory et al. |
| 2012/0129210 A1 | 5/2012 | Bourgeaux et al. |
| 2012/0178139 A1 | 7/2012 | Hubbel et al. |
| 2012/0207745 A1 | 8/2012 | Godfrin et al. |
| 2012/0237513 A1 | 9/2012 | Zurawski et al. |
| 2012/0276095 A1 | 11/2012 | Langermann et al. |
| 2012/0282281 A1 | 11/2012 | Banchereau et al. |
| 2013/0004427 A1 | 1/2013 | El-Sayed et al. |
| 2013/0022634 A1 | 1/2013 | Lycke |
| 2013/0053543 A1 | 2/2013 | Davis et al. |
| 2013/0059299 A1 | 3/2013 | Parr et al. |
| 2013/0071413 A1 | 3/2013 | Simon |
| 2013/0078216 A1 | 3/2013 | Dunlevy et al. |
| 2013/0078267 A1 | 3/2013 | Anderson et al. |
| 2013/0101463 A1 | 4/2013 | Mambrini et al. |
| 2013/0115230 A1 | 5/2013 | Simon |
| 2013/0129790 A1 | 5/2013 | Alexis et al. |
| 2013/0164364 A1 | 6/2013 | Paulson et al. |
| 2013/0171074 A1 | 7/2013 | Barbas et al. |
| 2013/0171233 A1 | 7/2013 | Paulson et al. |
| 2013/0236533 A1 | 9/2013 | Von Adrian et al. |
| 2013/0287810 A1 | 10/2013 | Mohamadzadeh et al. |
| 2013/0287857 A1 | 10/2013 | Von Adrian et al. |
| 2013/0295120 A1 | 11/2013 | Zurawski et al. |
| 2013/0318648 A1 | 11/2013 | Anderson et al. |
| 2013/0323786 A1 | 12/2013 | Mi et al. |
| 2013/0336991 A1 | 12/2013 | Mi et al. |
| 2014/0037736 A1 | 2/2014 | Shi et al. |
| 2014/0079728 A1 | 3/2014 | Jackson et al. |
| 2014/0127198 A1 | 5/2014 | Zurawski et al. |
| 2014/0127301 A1 | 5/2014 | Alexis et al. |
| 2014/0134168 A1 | 5/2014 | Zurawski et al. |
| 2014/0199315 A1 | 7/2014 | Mi et al. |
| 2014/0205630 A1 | 7/2014 | Tartour |
| 2014/0212445 A1 | 7/2014 | Martin et al. |
| 2014/0227268 A1 | 8/2014 | Banchereau et al. |
| 2014/0234344 A1 | 8/2014 | Banchereau et al. |
| 2014/0308238 A1 | 10/2014 | Rubin-Bejerano et al. |
| 2014/0314865 A1 | 10/2014 | Von Adrian et al. |
| 2014/0377291 A1 | 12/2014 | Fischbach et al. |
| 2015/0104478 A1 | 4/2015 | Lee et al. |
| 2015/0166659 A1 | 6/2015 | Goldenberg et al. |
| 2015/0191730 A1 | 7/2015 | Levy et al. |
| 2015/0250862 A1 | 9/2015 | Cantor et al. |
| 2015/0299329 A1 | 10/2015 | Zurawski et al. |
| 2015/0307545 A1 | 10/2015 | Jackson et al. |
| 2016/0015821 A1 | 1/2016 | Hubbell et al. |
| 2016/0022792 A1 | 1/2016 | Zurawski et al. |
| 2016/0024212 A1 | 1/2016 | Goldenberg et al. |
| 2016/0031988 A1 | 2/2016 | Zurawski et al. |
| 2016/0058792 A1 | 3/2016 | Quintana et al. |
| 2016/0060324 A1 | 3/2016 | Paulson et al. |
| 2016/0060358 A1 | 3/2016 | Hay |
| 2016/0083468 A1 | 3/2016 | Mi et al. |
| 2016/0108096 A1 | 4/2016 | Thompson et al. |
| 2016/0243248 A1 | 8/2016 | Hubbell et al. |
| 2016/0346384 A1 | 12/2016 | Porcelli et al. |
| 2016/0354453 A1 | 12/2016 | Hubbell et al. |
| 2016/0375126 A1 | 12/2016 | Oh et al. |
| 2017/0007708 A1 | 1/2017 | Hubbell et al. |
| 2017/0020926 A1 | 1/2017 | Mata-Fink et al. |
| 2017/0066825 A1 | 3/2017 | Hubbell et al. |
| 2017/0066828 A1 | 3/2017 | Goldenberg et al. |
| 2017/0121379 A1 | 5/2017 | Zhang et al. |
| 2017/0137513 A1 | 5/2017 | Vallera et al. |
| 2017/0252417 A1 | 9/2017 | Irvine et al. |
| 2017/0296636 A9 | 10/2017 | Hubbell et al. |
| 2017/0320933 A1 | 11/2017 | Mannie |
| 2017/0326213 A1 | 11/2017 | Jajosky et al. |
| 2018/0000916 A1 | 1/2018 | Zurawski et al. |
| 2018/0094071 A1 | 4/2018 | Zurawski et al. |
| 2018/0100011 A1 | 4/2018 | Hubbell et al. |
| 2018/0104284 A1 | 4/2018 | Wallecha et al. |
| 2018/0117171 A1 | 5/2018 | Mooney et al. |
| 2018/0303951 A1 ‡ | 10/2018 | Hubbell ............ C07K 16/2848 |
| 2019/0382479 A1 | 12/2019 | Hubbell et al. |
| 2020/0101146 A1 | 4/2020 | Hubbell et al. |
| 2020/0101169 A1 | 4/2020 | Hubbell et al. |
| 2020/0121762 A1 | 4/2020 | Hubbell et al. |
| 2020/0129601 A1 | 4/2020 | Hubbell et al. |

(56) References Cited

U.S. PATENT DOCUMENTS

| | | | |
|---|---|---|---|
| 2020/0129625 A1 | 4/2020 | Hubbell et al. | |
| 2020/0129629 A1 | 4/2020 | Hubbell et al. | |

FOREIGN PATENT DOCUMENTS

| | | |
|---|---|---|
| CN | 103547272 A | 1/2014 |
| EP | 0119650 | 9/1984 |
| EP | 0175617 | 10/1991 |
| EP | 0088695 | 6/1992 |
| EP | 0173629 | 6/1992 |
| EP | 0480041 | 6/1993 |
| EP | 0308208 | 12/1993 |
| EP | 0251455 | 5/1994 |
| EP | 0294294 | 5/1995 |
| EP | 0789715 | 8/1997 |
| EP | 0808366 | 11/1997 |
| EP | 0722340 | 4/1998 |
| EP | 0505357 | 3/1999 |
| EP | 0602290 | 8/1999 |
| EP | 0978564 | 2/2000 |
| EP | 1012308 | 6/2000 |
| EP | 630407 | 8/2000 |
| EP | 1046651 | 10/2000 |
| EP | 1093464 | 4/2001 |
| EP | 1301541 | 4/2003 |
| EP | 0743856 | 7/2003 |
| EP | 1370588 | 12/2003 |
| EP | 1409009 | 4/2004 |
| EP | 1292621 | 9/2006 |
| EP | 1838734 | 10/2007 |
| EP | 1853313 | 11/2007 |
| EP | 1028978 | 1/2008 |
| EP | 1086137 | 6/2008 |
| EP | 1938836 | 7/2008 |
| EP | 1440156 | 8/2008 |
| EP | 1619208 | 10/2008 |
| EP | 1996700 | 12/2008 |
| EP | 1996701 | 12/2008 |
| EP | 1045861 | 3/2009 |
| EP | 2125012 | 12/2009 |
| EP | 2178896 | 4/2010 |
| EP | 1516881 | 6/2010 |
| EP | 2238986 | 10/2010 |
| EP | 2315779 | 5/2011 |
| EP | 1417229 | 6/2011 |
| EP | 2344185 | 7/2011 |
| EP | 2344187 | 7/2011 |
| EP | 2394657 | 12/2011 |
| EP | 2394661 | 12/2011 |
| EP | 2406290 | 1/2012 |
| EP | 2428226 | 3/2012 |
| EP | 2478917 | 7/2012 |
| EP | 2066294 | 10/2012 |
| EP | 2527363 | 11/2012 |
| EP | 2598120 | 6/2013 |
| EP | 2618817 | 7/2013 |
| EP | 2620157 | 7/2013 |
| EP | 2630967 | 8/2013 |
| EP | 1904104 | 9/2013 |
| EP | 1991564 | 9/2013 |
| EP | 2115129 | 11/2013 |
| EP | 2684889 | 1/2014 |
| EP | 1443963 | 5/2014 |
| EP | 1664270 | 5/2014 |
| EP | 2115002 | 8/2014 |
| EP | 1605974 | 11/2014 |
| EP | 1850832 | 12/2014 |
| EP | 2114985 | 12/2014 |
| EP | 2283358 | 4/2015 |
| EP | 2213742 | 1/2016 |
| EP | 2982695 | 2/2016 |
| EP | 2983791 | 2/2016 |
| EP | 2989123 | 3/2016 |
| EP | 2346528 | 4/2016 |
| EP | 2406286 | 5/2016 |
| EP | 2205273 | 9/2016 |
| EP | 3091034 | 11/2016 |
| EP | 2406288 | 12/2016 |
| EP | 2406289 | 2/2017 |
| EP | 2217269 | 4/2017 |
| EP | 2344186 | 4/2017 |
| EP | 2630966 | 4/2017 |
| JP | 2003-519619 | 6/2003 |
| JP | 2004-526452 | 9/2004 |
| JP | 2007-510915 | 4/2007 |
| JP | 2007-312776 | 12/2007 |
| JP | 2009-505049 | 2/2009 |
| JP | 2009-060894 | 3/2009 |
| JP | 2009-149664 | 7/2009 |
| JP | 2013-516967 | 5/2013 |
| JP | 2018-072431 | 8/2018 |
| WO | WO 1991/008770 | 6/1991 |
| WO | WO 92/05801 | 4/1992 |
| WO | WO 1992/05801 | 4/1992 |
| WO | WO 92/22310 | 12/1992 |
| WO | WO 1992/22310 | 12/1992 |
| WO | WO 95/06737 | 3/1995 |
| WO | WO 1995/06737 | 3/1995 |
| WO | WO 95/22977 | 8/1995 |
| WO | WO 1995/22977 | 8/1995 |
| WO | WO 1996/023882 | 8/1996 |
| WO | WO 1996/040245 | 12/1996 |
| WO | WO 98/06737 | 2/1998 |
| WO | WO 1998/06737 | 2/1998 |
| WO | WO 1999/036437 | 7/1999 |
| WO | WO 2000/074717 | 12/2000 |
| WO | WO 2001/022995 | 4/2001 |
| WO | WO 2001/025793 | 4/2001 |
| WO | WO 2002/004522 | 1/2002 |
| WO | WO 2002/072799 A | 9/2002 |
| WO | WO 2002/083262 A | 10/2002 |
| WO | WO 2003/066820 | 8/2003 |
| WO | WO 2003/104273 | 12/2003 |
| WO | WO 2004/034966 A2 | 4/2004 |
| WO | WO 2004/035619 | 4/2004 |
| WO | WO 2004/098645 | 11/2004 |
| WO | WO 2005/045436 A | 5/2005 |
| WO | WO 2005/105129 | 11/2005 |
| WO | WO 2006/002382 | 1/2006 |
| WO | WO 2006/016247 | 2/2006 |
| WO | WO 2006/093524 | 9/2006 |
| WO | WO 2007/008300 | 1/2007 |
| WO | WO 2007/017556 A | 2/2007 |
| WO | WO 2007/097934 | 8/2007 |
| WO | WO 2007/098254 | 8/2007 |
| WO | WO 2007/099387 | 9/2007 |
| WO | WO 2007/099446 | 9/2007 |
| WO | WO 2007/150020 | 12/2007 |
| WO | WO 2008/063849 | 5/2008 |
| WO | WO 2009/019317 | 2/2009 |
| WO | WO 2009/056332 | 5/2009 |
| WO | WO 2009/078796 | 6/2009 |
| WO | WO 2009/086552 | 7/2009 |
| WO | WO 2010/045518 | 4/2010 |
| WO | WO 2010/060155 | 6/2010 |
| WO | WO 2010/076517 | 7/2010 |
| WO | WO 2010/085509 | 7/2010 |
| WO | WO 2011/012715 | 2/2011 |
| WO | WO 2011/051346 | 5/2011 |
| WO | WO 2011/086143 | 7/2011 |
| WO | WO2011/092715 | 8/2011 |
| WO | WO 2012/021512 | 2/2012 |
| WO | WO 2012/057671 | 5/2012 |
| WO | WO 2012/083185 | 6/2012 |
| WO | WO 2012/112690 | 8/2012 |
| WO | WO 2012/167088 | 12/2012 |
| WO | WO 2013/121296 | 8/2013 |
| WO | WO 2013/160865 | 10/2013 |
| WO | WO 2014/011465 | 1/2014 |
| WO | WO 2014/023709 | 2/2014 |
| WO | WO 2014/052545 | 4/2014 |
| WO | WO 2014/135528 | 9/2014 |
| WO | WO 2014/169255 | 10/2014 |
| WO | WO 2015/140648 | 9/2015 |

(56) References Cited

FOREIGN PATENT DOCUMENTS

| WO | WO 2015/157595 | 10/2015 |
|---|---|---|
| WO | WO 2015/171863 | 11/2015 |
| WO | WO 2015/175957 | 11/2015 |
| WO | WO 2016/022971 | 2/2016 |
| WO | WO 2016/044655 | 3/2016 |
| WO | WO 2016/044661 | 3/2016 |
| WO | WO 2016/070050 | 5/2016 |
| WO | WO 2016/210447 | 12/2016 |
| WO | WO 2017/015141 | 1/2017 |
| WO | WO 2017/023779 | 2/2017 |
| WO | WO 2017/025889 | 2/2017 |
| WO | WO 2017/041053 | 3/2017 |
| WO | WO2017/044308 | 3/2017 |
| WO | WO 2017/046652 | 3/2017 |
| WO | WO 2017/058996 | 4/2017 |
| WO | WO 2017/066484 | 4/2017 |
| WO | WO 2017/109134 | 6/2017 |
| WO | WO 2017/112899 | 6/2017 |
| WO | WO 2017/139498 | 8/2017 |
| WO | WO 2017/139787 | 8/2017 |
| WO | WO 2017/192785 | 11/2017 |
| WO | WO 2017/192786 | 11/2017 |
| WO | WO 2018/232176 | 12/2018 |
| WO | WO2019/098682 | 5/2019 |
| WO | WO 2019/191079 | 10/2019 |
| WO | WO 2019/0215590 | 11/2019 |

OTHER PUBLICATIONS

Gurwitz, Drug Development Res. 78:231-235 (2017) (Year: 2017).‡
Wilson, Nature 438:E5 (2005) (Year: 2005).‡
Nakayama et al., Frontiers Immunol. 10:1-7 (2019) (Year: 2019).‡
Baker et al., Diabetes 68:1830-1840 (2019) (Year: 2019).‡
"CMET-HGF Binding Peptide #65,", XP002717161, Retrieved From EBI Accession No. GSP:ADS33412 (Dec. 2, 2004).
"EPFL School of Life Sciences—Annual Report SV 2011," 156 Pages (Dec. 31, 2011).
"SubName: Full=Phosphate ABC Transporter, Inner Membrane Subunit PstC;", XP002717162, Retrieved From EBI Accession No. UNIPROT:C7QKI6, Database Accession No. C7QKI6 (Oct. 13, 2009).
"SubName: Full=Putative Integron Gene Cassette Protein; Flags: Fragment;", XP002717159, Retrieved From EBI Accession No. UNIPROT:B0BIT0, Database Accession No. B0BIT0 (Feb. 26, 2008).
"SubName: Full=Putative Transcriptional Regulator, ArsR Family;", XP002717163, Retrieved From EBI Accession No. UNIPROT:D2RZT2, Database Accession No. D2RZT2 (Mar. 2, 2010).
"SubName: Full=Putative Uncharacterized Protein;", XP002717158, Retrieved From EBI Accession No. UNIPROT: C0NJE0, Database Accession No. CONJE0 (May 5, 2009).
"SubName: Full=Putative Uncharacterized Protein;", XP002717160, Retrieved From EBI Accession No. UNIPROT:B9PUP0, Database Accession No. B9PUP0 (Mar. 24, 2009).
"SubName: Full=Uncharacterized Protein;", XP002717157, Retrieved From EBI Accession No. UNIPROT:B5E9K2 Database Accession No. B5E9K2 (Oct. 14, 2008).
Ahmed et al., "Carbohydrate-based materials for targeted delivery of drugs and genes to the liver." Nanomedicine (Lond.) (205) 10(14), 2263-2288.
Albert et al., "Immature dendritic cells phagocytose apoptotic cells Via vl35 and CD36, and cross-present antigens to cytotoxic T lymphocytes," Journal of Experimental Medicine, vol. 188(7): 1359-1368 (Oct. 5, 1998).
Andre et al., "Determination of modulation of ligand properties of synthetic complex-type biantennary N-glycans by introduction of bisecting GlcNAc in silico, in vitro and in vivo" Eur. J. Biochem. 2004;271(1):118-134.

Arnaboldi et al., "Suppression of Th 1 and Th17, but not Th2, responses in a CD8+ T cell-mediated model of oral tolerance," Mucosal Immunology, vol. 2(5):427-438 (Sep. 2009).
Bailon et al., "Rational design of a potent, long-lasting form of interferon: A 40 kDa branched polyethylene glycol-conjugated interferon-2a for the treatment of hepatitis C," Bioconjugate Chemistry, vol. 12(2):195-202 (2001).
Bigbee et al., "Binding specificities of eight monoclonal antibodies to human glycophorin A—studies with McM, and MkEn(UK) variant human erythrocytes and M- and MNv-type chimpanzee erythrocytes," Dec. 1, 1984, J. Immunol., 133(6): 3149-3155 (1984).
Blancher et al., "Reactivity of anti-glycophorin monoclonal antibodies (Mabs) in tests with red cells of non-human primates," Jan. 1, 1997, Transfus Clin Biol 4, 81-85 (1997).
Brack et al., "Tumor-targeting properties of novel antibodies specific to the large isoform of tenascin-C," Clinic Cancer Research, vol. 12(10):3200-3208 (May 15, 2006).
Bursch et al., "Langerhans cells are not required for the COB T cell response to epidermal self-antigens," Journal of Immunology, vol. 182(8):4657-4664 (Apr. 15, 2009).
Cao et al., "Molecular Beacon Aptamers for Protein Monitoring in Real-Time and in Homogeneous Solutions," Current Proteomics, 2:31-401, (2005).
Chasis et al., "Signal Transduction by Glycophorin A: Role of Extracellula Rand Cytoplasmic Domains in a Modulatable Process", The Journal of Cell Biology, 107:1351-1357, (Oct. 1988).
Chiarantini et al., "Red Blood Cells as Delivery System for Recombinant HSV-1 Glycoprotein B: Immunogenicity and Protection in Mice," Vaccine, 15(3):276-280, (1997).
Coulstock et al., "Liver-targeting of interferon-alpha with tissue-specific domain antibodies" PLOS ONE, Public Library of Science, US, vol. 8, No. 2, Jan. 1, 2013.
Craig et al., "Processing of C3b-Opsonized Immune Complexes Bound to Non-Complement Receptor 1 Sites on Red Cells: Phagocytosis, Transfer and Associations with CR1," J. Immunol.
Crispe et al., "Cellular and molecular mechanisms of liver tolerance," Immunol Rev., 213: 101-118 (2006).
Dane et al., "Isolation of cell specific peptide ligands using fluorescent bacterial display libraries-" Journal of Immunological Methods, vol. 309(1-2):120-129, (Jan. 2006).
Darrah et al., "IL-10 production differentially influences the magnitude, quality, and protective capacity of Th1 responses depending on the vaccine platform," Journal of Experimental Medicine, vol. 207(7):1421-1433 (2010).
Dennis et al., "Albumin Binding as a General Strategy for Improving the Pharmacokinetics of Proteins-" Journal of Biological Chemistry, vol. 277(38):35035-35043 (Sep. 20, 2002).
Devalapally et al., "Poly(ethylene oxide)-modified Poly(beta-amino ester) Nanoparticles as a pH-sensitive System for Tumor-targeted Delivery of Hydrophobic Drugs: Part 3. Therapeutic Efficacy and Safety Studies in Ovarian CanceRXenog Raft Model," Cancer Chemotherapy Pharmacology, 59:477-484, (2007).
Dhalluin et al., "Structural and biophysical characterization of the 40 kDa PEG-interferon-2a and its individual positional isomers," Bioconjugate Chemistry, vol. 16(3):504-517 (2005).
Di Lorenzo et al., "Translational Mini-Review Series on Type 1 Diabetes: Systemic analysis of T cell epitopes in autoimmune diabetes," 2007, Clin. Exp Immunol, vol. 148: 1-146.
Dienst et al., "Specific occlusion of mu rine and human tumor vasculature by VCAM-1-targeted recombinant fusion proteins," Journal of the National Cancer Institute, vol. 97(10):733-747, (2005).
Dieterich et al., "Identification of Tissue Transglutaminase as the Autoantigen of Celiac Disease," Nature Medicine vol. 3 p. 797-801 (1997).
Ducan, R. Development of HPMA copolymer-anticancer conjugates: Clinical experience and lessons learnt. Advanced Drug Delivery Reviews 61 (2009) pp. 1131-1148.
Ferguson et al., "Armed response: How dying cells influence T-cell functions," Immunology Review, vol. 241 (1 ):77-88 (May 2011 ).
Fife et al.,"Insulin-induced remission in new-onset NOD mice is maintained by the PD-1-PD-L 1 pathway," The Journal of Experimental Medicine, vol. 203(12):2737-2747, (Nov. 27, 2006).

(56) References Cited

OTHER PUBLICATIONS

Fishburn, "The pharmacology of PEGylation: balancing PD with PK to generate novel therapeutics," Journal of Pharmaceutical Sciences vol. 97(10):4167-4183 (Oct. 10, 2008).
Fonsatti et al.,"Targeting cancer vasculature via endoglin/CD105: A novel antibody-based diagnostic and therapeutic strategy in solid tumours," Cardiovascular Research, vol. 86(1):12-19, (2010).
Gadaleta et al., "Trans-arterial chemoembolization as a therapy for liver tumours: New clinical developments and suggestions for combination with angiogenesis inhibitors," Critical Reviews in Oncology/Hematology, vol. 80:40-53 (2011).
Gao et al., "In situ growth of a stoichiometric PEG-like conjugate at a protein's N-terminus with significantly improved pharmacokinetics-" Proceedings of the National Academy Sciences vol. 106(36): 15231-15236 (Sep. 8, 2009).
Geng et al., "Site-directed conjugation of "clicked" glycopolymers for form glycoprotein mimics: binding to mammalian lectin and induction of immunological function." J Am Chem Soc. Dec. 12, 2007;129(49):15156-63.
Getts et al., "Have We Overestimated the Benefit of Human(ized) Antibodies?" Landes Bioscience, 2(6):682-694, (Nov./Dec. 2010).
Getz et al., "Protease-Resistant Peptide Ligands From a Knottin Scaffold Library," ACS Chemical Biology, 8 Pages, (May 26, 2011).
Godsel et al., "Prevention of autoimmune myocarditis through the induction of antigen-specific peripheral immune tolerance-" Circulation vol. 103(12):1709-1714 (2001).
Gorovits et al., "Proposed mechanism of off-target toxicity for antibody-drug conjugates driven by mannose receptor uptake," Cancer Immunol Immunother (2013) 62:217-233.
Gorzelany et al., "Protein replacement therapies for rare diseases: a breeze for regulatory approval?" Science Translational Medicine 5, 178fs10 (2013).
Green et al.,"Immunogenic and tolerogenic cell death," National Review of Immunology vol. 9(5):353-363, (May 2009).
Grimm et al., "Memory of tolerance and induction of regulatory T cells by erythrocyte-targeted antigens." Scientific Reports, 5:159907.
Gupta et al., "Expression, purification, and characterization of an anti-RBCFab-p24 fusion protein for hemagglutination-based rapid detection of antibodies to HIV in whole blood." Protein Expression and Purification 26 (2002) 162-170.
Hackel et al., "Picomolar affinity fibronectin domains engineered utilizing loop length diversity, recursive mutagenesis, and loop shuffling," Journal of Molecular Biolology, vol. 381(5):1238-1252, (Sep. 19, 2008).
Hall et al., "Identification of peptide ligands facilitating nanoparticle attachment toerythrocytes," Biotechnology Progress, vol. 23(3):749-754 (2007).
Hasselberg et al, "ADP-ribosylation controls the outcome of tolerance or enhanced priming following mucosal immunization" The Journal of Immunology, Aug. 24, 2016.
Holz et al., "CD8+ T cell tolerance following antigen recognition on hepatocytes," Journal of Autoimmunity, vol. 34 (1):15-22 (2010).
Huang et al., "Characterization of poly(ethylene glycol) and PEGylated products by LC/MS with postcolumn addition of amines," Analytical Chemistry, vol. 81(2):567-577 (Jan. 15, 2009).
Huang et al., "Tumor infarction in mice by antibody-directed targeting of tissue factor to tumor vasculature," Science, vol. 275(5299):547-550 (Jan. 24, 1997).
Ichikawa et al., "Hepatic stellate cells function as regulatory bystanders," Journal of Immunology, vol. 186 (10):5549-5555 (May 15, 2011).
International Search Report and Written Opinion from corresponding PCT Application No. PCT/IB2013/000684, 12 pages, dated Jul. 9, 2013.
International Search Report and Written Opinion from corresponding PCT Application No. PCT/US2011/047078, 13 pages, dated May 1, 2012.
International Search Report for Application No. PCT/EP2014/054161 dated May 26, 2014.
Janeway et al., "The complement system and innate immunity," Immunology: the Immune System in Health and Disease, 5th Edition. New York: Garland Science (2001).
Janeway et al., Immuno Biology, 8th Edition, Garland Science (2012).
Jewett et al., "Cu-free click cycloaddition reactions in chemical biology," Chem Soc Rev. Apr. 2010; 39(4): 1272-1279.
Jones et al., "Localization of Pectic Galactan in Tomato Cell Walls Using a Monoclonal Antibody Specific to (1->4)-β-D-Galactan" Plant Physiol. 1997; 113:1405-1412.
Julyan et al "Preliminary clinical study of the distribution of HPMA copolymers bearing doxorubicin and galactosamine" Journal of Controlled Release 57 (1999) pp. 281-290.
Keefe et al.,"Aptamers as therapeutics," Nature Reviews Drug Discovery, vol. 9(7):537-550 (2010).
Kenrick et al., "Bacterial Display Enables Efficient and Quantitative Peptide Affinity Maturation," Protein Engineering Design & Selection, vol. 23(1 ):9-17 (2010).
Khandelwal et al., "Assessment of survival of aging erythrocyte in circulation and attendant changes in size and CD147 expression by a novel two step biotinylation method," Experimental Gerontology, vol. 41(9):855-861 (Aug. 4, 2006).
Kim et al "Imaging and therapy of liver fibrosis using bioreducible polyethylenimine/siRNA compleses conjugated with N-acetylglucosamine as a targeting moiety" Biomaterials 34:6504-6514 (2013).
Kim et el., "Specific Binding of Glucose-derivatized Polymers to the Asialoglycoprotein Receptor of Mouse Primary Hepatocytes." The Journal of Biological Chemistry, vol. 276, No. 38, pp. 35312-35319, Sep. 21, 2001.
Kina et al.,"The Monoclonal Antibody TER-119 Recognizes a Molecule Associated with Glycophorin A and Specifically Marks the Late Stages of Murine Erythroid Lineage," British Journal of Haematolgy, vol. 109:280-287 (2000).
King et al. "Antibody responses to bee melittin (Api m 4) and hornet antigen 5 (Dol m 5) in mice treated with the dominant T-cell Epitope peptides" Journal of Allergy and Clinical Immunology, vol. 101, Issue 3, Mar. 1998, pp. 397-403.
Kontos et al., "Engineering antigens for in situ erythrocyte binding induces T-cell deletion," PNAS, 2013, vol. 110, No. 1, p. E60-E68.
Kontos et al., "Improving Protein Pharmacokinetics by Engineering Erythrocyte Affinity," Molecular Pharmaceutics, 2010, vol. 7, No. 6, p. 2141-2147.
Kontos, "Engineering Erythrocyte Affinity for Improved Pharmacokinetics and Immune Tolerogenesis", Theses, 106 Pages (Jun. 23, 2011).
Kontos, "Improving Protein Pharmacokinetics by Engineering Erythrocyte Affinity", 1 Page, (2010) (Abstract Only).
Kopecek et al. "HPMA copolymers: Origins, early developments, present, and future." Advanced Drug Delivery Reviews 62, (2010) pp. 122-149.
Kravtzoff et al., "Tolerance Evaluation of L-asparaginase loaded in red blood cells," 1996, Eur J Clin Pharmacol, vol. 51: 221-225.
Krebber et al., "Reliable Cloning of Functional Antibody Variable domains from Hybridomas and Spleen Cell Repertoires Employing a Reengineered Phage Display System," Journal of Immunological Methods, vol. 201 :35-55 (1997).
La Rosa, et al., "The Innate Immune System in Allograft Rejection and Tolerance," J. Immunol., 2007, 178:7503-7509.
Langer et al., "Optimization of the Rreparation Process for Human Serum Albumin (HSA) Nanoparticles," International Journal of Pharmaceutics, 257:169-180, (2003).
Lee et al., "Aptamers as Molecular Recognition Elements for Electrical Nanobiosensors," Analytical and Bioanalytical Chemistry, 390:1023-1032, (2008).
Lee et al., "Signaling pathways downstream of pattern-recognition receptors and their cross talk," Annual Review of Biochemistry, vol. 76:447-480 (Feb. 28, 2007).
Lehrman et al., "The Binding of Fucose-containing Glycoproteins by Hepatic Lectins" The Journal of Biological Chemistry Jun. 5, 1986; 261, 7426-7432.
Lepenies et al., "Targeting C-type lectin receptors with multivalent carbohydrate ligands." Adv. Drug Deliv. Rev. (2013).

(56) References Cited

OTHER PUBLICATIONS

Li et al., "Targeting self- and foreign antigens to dendritic cells via DC-ASGPR generates IL-10pproducing suppressive CD4+ T cells," Jan. 2, 2012, Journal of Experimental Medicine 209, 109-121 (2012).

Liu et al. "Hapten may play an important role in food allergen-related intestinal immune inflammation," North American Journal of Medical Sciences, vol. 3. No. 3. (Mar. 2011).

Liu et al., "Immune tolerance after delivery of dying cells to dendritic cells in situ," Journal of Experimental Medicine, vol. 196(8): 1091-1097 (Oct. 21, 2002).

Liu et al.,"Functional Nucleic Acid Sensors", Chemical Reviews, 109(5):1948-1998, (May 2009).

Lorentz et al., "Engineered binding to erythrocytes induces immunological tolerance to E. coli asparaginase." Sci. Adv. 2015.

Luo et al., "ECDI-fixed allogeneic splenocytes induce donor-specific tolerance for long-term survival of islet transplants via two distinct mechanisms," Proceedings of National Academy of Science, vol. 105(38):14527-14532 (Sep. 23, 2008).

Lutolf et al.,"Synthesis and Physicochemical Characterization of End-Linked Poly(ethylene glycol)-co-peptide Hydrogels Formed by Michael-Type Addition," Biomacromolecules, 4:713-722, (Feb. 1, 2003).

Lutolf et al.,"Systematic modulation of Michael-type reactivity of thiols through the use of charged amino acids," Bioconjugate Chemistry vol. 12(6):1051-1056 (2001).

Lutterotti, A. et al., "Antigen-Specific Tolerance by Autologous Myelin Peptide-Coupled Cells: A Phase 1 Trial in Multiple Sclerosis," Science Translational Medicine 5, 188ra75-188ra75 (2013).

Magnani et al., "Red blood cells as an antigen-delivery system," Biotechnol Appl Biochem. Oct. 1992;16(2):188-94.

Maluccio et al., "Transcatheter arterial embolization with only particles for the treatment of unresectable hepatocellular carcinoma-" Journal of Vascular and Interventional Radiology, vol. 19(6):862-869 (2008).

Mamidyala, S. et al, "Glycomimetic ligands for the human asialoglycoprotein receptor" J. Am Chem. Soc. Feb. 1, 2012, 134(4), pp. 1978-1981.

Maynard et al., "Antibody engineering," Annual Review of Biomedical Engineering, vol. 2:339-376 (2000).

Meager et al., "Anti-cytokine autoantibodies in autoimmunity: preponderance of neutralizing autoantibodies against interferon-alpha, interferon-omega and interleukin-12 in patients with thymoma and or myasthenia gravis" Clinical and Experimental Immunology, Wiley-Blackwell Publishing Ltd, GB, vol. 132, No. 1, Apr. 1, 2003.

Medina et al., "Targeting hepatic cancer cells with pegylated dendrimers displaying N-acetylgalactosamine and SP94 peptide ligands" Advanced Healthcare Materials, vol. 2, Issue 10, pp. 1337-1350, Oct. 2013.

Miller et al., "Antigen-specific tolerance strategies for the prevention and treatment of autoimmune disease," Nature Reviews Immunology 7(9):665-677, (Sep. 2007).

Moghimi et al., "Stealth liposomes and long circulating nanoparticles: critical issues in pharmacokinetics, opsonization and protein-binding properties," Progress in Lipid Research, vol. 42(6):463-478 (2003).

Mohandas et al., "Red cell membrane: past, present, and future," Blood, vol. 112(10):3939-3948(Nov. 15, 2008).

Mueller, "Mechanisms maintaining peripheral tolerance," Nature Immunology, vol. 11(1 ):21-27 (Jan. 2010).

Murphy, "Antigen Recognition by B-Cell and T-cell Receptors," 2012, Janeway's Immuno Biology, 8th Edition, Chapter 4, Garland Science Taylor & Francis Goup, London and New York.

Murray et al., "The Mouse Immune Response to Carrier Erythrocyte Entrapped Antigens," Vaccine, 24:6129-6139, (2006).

Muzykantov, "Drug Delivery by Red Blood Cells: Vascular Carriers Designed by Mother Nature", Expert Opinion Drug Delivery, 7(4 ):403-427, (Apr. 2010).

Nardin et al., "How are immune complexes bound to the primate erythrocyte complement receptor transferred to acceptor phagocytic cells," Mol. Immunol.

Nishikawa et al. "Galactosylated proteins are recognized by the liver according to the surface density of galactose moieties" The American journal of physiology Jun. 1995; 268(5 Pt 1):G849-56, Abstract.

O'Neil et al., "Extracellular matrix binding mixed micelles for drug delivery applications," Journal of Control Release, vol. 137(2):146-151, (Mar. 27, 2009).

Parmeggiani et al., "Designed armadillo repeat proteins as general peptide-binding scaffolds: consensus design and computational optimization of the hydrophobic core," Journal of Molecular Biology, vol. 376(5):1282-1304 (2008).

Pasut et al.,"PEG conjugates in clinical development oruse as anticancer agents: An overview," Advanced Drug Delivery Reviews, vol. 61(13):1177-1188 (2009).

Qin, et al., Preparation and bioactivity of anti-hum red blood cell ScFv and CSFV E@ bifunctional fusion protein, Chin J. Biotech 2010, Jan. 25: 26(1): 28-34, Chinese Journal of Biotechnology (2010).

Reddy et al., "Exploiting lymphatic transport and complement activation in nanoparticle vaccines," Nature Biotechnology, vol. 25(10):1159-1164 (Oct. 2007).

Reddy et al., "In vivo targeting of dendritic cells in lymph nodes with poly(propylene sulfide) nanoparticles," Journal of Controlled Release, vol. 112(1):26-34, (Mar. 10, 2006).

Reinagel et al., "The Primate Erythrocyte Complement Receptor (CR1) as a Privileged Site: Binding of Immunoglobulin G to Erythrocyte CR1 Does Not Target Erythrocytes for Phagocytosis," 1997, Blood, vol. 89: p. 1068-1077.

Rice et al., "Directed evolution of a biterminal bacterial display scaffold enhances the display of diverse peptides," Protein Engineering, Design & Selection, vol. 21(7):435-442 (2008).

Rigopoulou et al., "Asialoglycoprotein receptor (ASGPR) as target autoantigen in liver autoimmunity: Lost and found," Autoimmunity Reviews, 12 (2012) 260-269.

Rockey et al., "Synthesis and radiolabeling of chelator-RNA aptamerbioconjugates with copper-64 for targeted molecular imaging-" Bioorganic & Medicinal Chemistry, vol. 19(13):4080-4090 (2011).

Ruoslahti et al., "Targeting of drugs and nanoparticles to tumors," Journal of Cell Biology, vol. 188(6):759-768 (2010).

Rybak et al., "The extra-domain A of fibronectin is a vascular marker of solid tumors and metastases," Cancer Research, vol. 67(22):10948-10957 (2007).

Saibeni et al., "Antibodies to tissue-type plasminogen activator (t-PA) in patients with inflammatory bowel disease: high prevalence, interactions with functional domains of t-PA and possible implications in thrombosis," J. Thrombosis and Haemostasis, 4:1510-1516 (2006).

Saint-Lu, N. et al., "Targeting the allergen to oral dendritic cells with mucoadhesive chitosan particles enhances tolerance induction," Allergy, vol. 64(7):1003-1013 (2009).

Sakaguchi et al., "Regulatory T Cells and Immune Tolerance," Cell 133, May 30, 2008, 775-787.

Sampson, "Aptamers and SELEX: the technology," World Patent Information, vol. (25):123-129 (2003).

Savla et al., "Tumor targeted quantum dot-mucin 1 aptamer-doxorubicin conjugate for imaging and treatment of cancer," Journal of Controlled Release, vol. 153(1):16-22, Feb. 20, 2011.

Schliemann et al., "In vivo biotinylation of the vasculature in B-cell lymphoma identifies BST-2 as a target for antibody-based therapy," Vascular Blood, vol. 115(3):736-744 (Jan. 21, 2010).

Sehon et al., "Conversion of Antigens to Tolerogenic Derivatives by Conjugation with Monomethoxypolyethylene Glycol", The Pharmacology and Toxicology of Proteins, pp. 205-219 (1987).

Sehon et al., The Pharmacology and Toxicology of Proteins, Proceedings of Cetus-UCLA Symposium Held at Lake Tahoe, Ca, Feb. 21-28, 1987, Alan r. Liss, Inc.—New York.

Seymour et al., "Hepatic Drug Targeting: Phase I evaluation of polymer-bound doxorubicin" Journal of Clinical Oncology, vol. 20, No. 6, Mar. 15, 2002, pp. 1668-1676.

(56) References Cited

OTHER PUBLICATIONS

Seymour et al., "N-(2-Hydroxypropyl)methacrylamide copolymers targeted to the hepatocyte galactose-receptor: pharmacokinetics in DBA2 mice." Br. J. Cancer (1991) 63, pp. 859-866.
Shan et al., "Structural Basis for Gluten Intolerance in Celiac Sprue," Science, 297, 2275 (2002).
Sheridan "Fresh from the biologic pipeline—2009," Nature Biotechnology, vol. 28(4):307-310 (Apr. 2010).
Silverman et al., "Engineered cystine-knot peptides that bind vβ3 integrin with antibody-like affinities," Journal of Molecular Biology, vol. 382(4):1064-1075 (Jan. 30, 2009).
Sørensen et al., "Role of sialic acid for platelet life span: exposure of β-galactose results in the rapid clearance of platelets from the circulation by asialoglycoprotein receptor-expressing liver macrophages and hepatocytes." Blood, Aug. 20, 2009. vol. 114, No. 8.
Spitzer et al., "ScFv-Mediated in Vivo Targeting of DAF to Erythrocytes Inhibits Lysis by Complement," Molecular Immunology, vol. 40:911-919 (Oct. 30, 2003).
St. Clair et al., "New Reagents on the Horizon for Immune Tolerance," Sep. 20, 2006, Annu. Rev. Med. 2007. 58:329-46.
Staud et al., "Liver uptake and hepato-biliary transfer of galactosylated proteins in rats are determined by the extent of galactosylation" Biochimica et Biophysica Acta May 1999; 1427(2):183-192, Abstract.
Steiner et al., "Efficient selection of DARPins with sub-nanomolar affinities using SRP phage display," Journal of Molecular Biology, vol. 382(5):1211-1227 (2008).
Sun, et al, "Comparison between Ovalbumin and Ovalbumin Peptide 323-339 Responses in Allergic Mice: Humoral and Celluler Aspects," Scandinavian Journal of Immunology, vol. 71: 329-335 (Jan. 2010).
Supplementary European Search Report from corresponding PCT Application No. PCT/US2011047078, 21 Pages, dated Jan. 22, 2014.
Taneja et al., "Lessons from animal models for human autoimmune diseases," Sep. 1, 2001, Nature Immunology, vol. 2, No. 9, 781-784 (Sep. 2001).
Taylor et al., "Anti-glycophorin single-chain Fv fusion to low-affinity mutant erythropoietin improves red blood cell-lineage specificity", Protein Engineering, Design & Selection, vol. 23, No. 4 pp. 251-260, 2010.
Thijssen et al., "Galectin-1 is essential in tumor angiogenesis and is a target for antiangiogenesis therapy-", Proceeding of the Natinoal Academy Sciences, vol. 103(43):15975-15980 (2006).
Thomson et al., "Antigen-presenting cell function in the tolerogenic liver environment," National Reviews Immunology, vol. 10(11):753-766 (Nov. 2010).
Tobio et al., "Stealth PLA-PEG Nanoparticles as Protein Carriers for Nasal Administration," Pharmaceutical Research, 15(2):270-275, (1998).
Trahtenherts, A. et al, "An internalizing antibody specific for the human asialoglycoprotein receptor" Hybridoma, vol. 28, No. 4, Aug. 1, 2009.
Turley et al., "Prospects for Antigen-Specific Tolerance Based Therapies for the Treatment of Multiple Selerosis," Results and Problems in Cell Differentiation, 51 :217-235, (2010).
Updike et al., "Infusion of red blood cell-loaded asparaginase in monkey: Immunologic, metabolic, and toxicologic consequences," 1983, J Lab Clin Med, vol. 101(5): p. 679-691.
Van Der Vlies et al., "Synthesis of pyridyl disulfide-functionalized nanopa rticles for conjugating thiol-containing small molecules, peptides, and proteins," Bioconjugate Chemistry, vol. 21(4):653-662 (2010).
Velluto et al., "PEG-b-PPS Diblock Copolymer Aggregates for Hydrophobic Drug Solubilization and Release: Cyclosporin A as an Example," Molecular Pharmaceutics, 11 Pages, (May 2, 2008).
Vogl et al., "Review on transarterial chemoembolization in hepatocellular carcinoma: Palliative, combined, neoadjuvant, bridging, and symptomatic indications," European Journal Radiology, vol. 72(3):505-516 (2009).
Walker et al., "Anti-serum albumin domain antibodies in the development of highly potent, efficacious and long-acting interferon," Protein Engineering Design & Selection, vol. 23(4):271-278 (2010).
Wan, "Regulatory T cells: immune suppression and beyond," May 1, 2010, Cell Mol Immunol. May 2010; 7(3):204-210.
Weisser et al., "Applications of single-chain variable fragment antibodies in therapeutics and diagnostics," Biotechnology Advances, vol. 27(4):502-520 (2009).
Wilson et al., "Rapid Whole Blood Assay for HIV-1 Seropositivity Using an Fab-Peptide Conjugate," Journal of Immunological Methods, vol. 138:111-119 (1991).
Yamazaki et al., "CD8+ CD205+ splenic dendritic cells are specialized to induce Foxp3+ regulatory T cells," Journal of Immunology, vol. 181(10):6923-6933 (2008).
Yoo et al., "N-Acetylgalactosamino dendrons as clearing agents to enhance liver targeting of model antibody-fusion protein." Bioconjugate Chemistry, vol. 24, No. 12, Dec. 18, 2013, pp. 2088-2103.
Zaitsev et al., "Targeting of a Mutant Plasminogen Activator to Circulating Red Blood Cells for Prophylactic Fibrinolysis", The Journal of Pharmacology and Experimental Therapeutics, 332(3):1022-1031 and 976 (Nov. 30, 2009).
Zhao, X. et al "Construction and characterization of an anti-asialoglycoprotein receptor single-chain variable-fragment-targeted melittin" Biotechnol Appl. Biochem, Nov.-Dec. 2011; 58(6): pp. 405-411.
Bielekova et al., "Expansion and Functional Relevance of High-Avidity Myelin-Specific CD4 T Cells in Multiple Sclerosis," J Immunol 2004; 172:3893-3904.
Dornmair Klaus et al: "T-cell-mediated autoimmunity: Novel techniques to characterize autoreactive T-cell receptors", American Journal of Pathology, vol. 163, No. 4, Oct. 2003 (Oct. 2003), pp. 1215-1226, ISSN: 0002-9440.
Folgori A et al: "A general strategy to identify mimotopes of pathological antigens using only random peptide libraries and huamn sera", EMBO (European Molecular Biology Organization) Journal, vol. 13, No. 9, May 1, 1994 (May 1, 1994), pp. 2236-2243, ISSN: 0261-4189.
Qin et al., "Galactosylated N-2-Hydroxypropyl Methacrylamide-b-N-3-Guanidinopropyl Methacrylamide Block Copolymers as Hepatocyte-Targeting Gene Carriers," Bioconjugate Chem. 22:1503-1512 (2011).
Seamons et al. Immune Tolerance to Myelin Proteins (Immunologic Research 2003; 28/3:201-221).
Teitelbaum et al., Immunomodulation of experimental autoimmune encephalomyelitis by oral administration of copolymer 1. Pro. Natl. Acad. Sci. USA vol. 96, pp. 3842-3847, Mar. 1999.
Wang et al., "Synthesis and Micellization of Thermoresponsive Galactose-Based Diblock Copolymers," J Polymer Sci. 49:3280-3290 (2011).
Yeste Ada et al: "Antigen Microarrays for the Study of Autoimmune Diseases", Clinical Chemistry, vol. 59, No. 7, Jul. 2013 (Jul. 2013), pp. 1036-1044, ISSN: 0009-9147(print).
Zhong et al., "Ligand-directed Reduction-Sensitive Shell-Sheddable Biodegradable Micelles Actively Deliver Doxorubicin into the Nuclei of Target Cancer Cells," Biomacromalecules 14:3723-3730 (2013).
Granoff et al., "A Novel Mimetic Antigen Eliciting Protective Antibody to Neisseria meningitidis" J Immunol 2001; 167:6487-6496.
Kontos, S: "Engineering Erythrocyte Affinity for Improved Pharmacokinetics and Immune Tolerogenesis", Ecole polytechnique federale de Lausanne EPFL , Apr. 27, 2011, Retrieved from the Internet: URL:http://infoscience.epfl.ch/record/165397.
Loma et al., "Multiple Sclerosis: Pathogenesis and Treatment" Department of Neurology, Curr. Neuropharmacology, 9:409-416, Year 2011.
Meyer et al. Metformin and Insulin in Type 1 Diabetes; Diabetes Care 26:1655-1656, Year: 2003.
Tye-Din, et al. "Comprehensive, Quantitative Mapping of T Cell Epitopes in Gluten in Celiac Disease", www.ScienceTranslationalMedicine.org, Jul. 21, 2010, vol. 2 Issue 41, in 14 pages.

(56) References Cited

OTHER PUBLICATIONS

Ciccocioppo, R. et al, "The immune recognition of gluten in coeliac disease", British Society for Immunology, Clinical and Experimental Immunology, Feb. 1, 2005, pp. 408-416.

Dominguez-Soto, et al., "The DC-SIGN-related lectin LSECtin mediates antigen capture and pathogen binding by human myeloid cells" www.bloodjournal.org. Immunobiology, Jun. 15, 2007, vol. 109, No. 12, pp. 5337-5345.

Immunogenic, Definition of Immunogenic by Merriam-Webster, https://www.merriam-webster.com/dictionary/immunogenic[May 10, 2019 11:59:27 AM], retrieved on May 10, 2019, in 9 pages.

Kontos, et al., "Engineering antigen-specific immunological tolerance", www.sciencedirect.com, Current Opinion in Immunology, Jul. 8, 2015, 35:80-88.

"Integer", Meriam-Webster, available online at https://www.merriam-webster.com/dictionary/integer, 12 pages (2019) (Year: 2019).

Mamidyala, et al., "Glycomimetic Ligands for the Human Asialoglycoprotein Receptor", Journal of the American Chemical Society, Jan. 24, 2012, vol. 134, p. 1978-1981.

Moreau et al, "PEPOP: Computational design of immunogenic peptides" BioMed Central, Jan. 30, 2008, 15 pages.

Rajpal, Arvind, et al. "A general method for greatly improving the affinity of antibodies by using combinatorial libraries", PNAS, www.pnas.org/cgi/doi/10.1073/pnas.0503543102, vol. 102 No. 24, pp. 8466-8471, Jun. 14, 2005.

Wu, Herren, "Simultaneous Humanization and Affinity Optimization of Monoclonal Antibodies", Methods in Molecular Biology, vo. 207: Recombinant Antibodies for Cancer Therapy: Methods and Protocols, Tolowa, NJ, pp. 197-212, Jan. 1, 2003.

Caja et al., "Antibodies in celiac disease: implications beyond diagnostics," Cellular & Molecular Immunology (2011) 8, 103-109.

https://en.wikipedia.org/wiki/Reteplase accessed Apr. 13, 2020, printed Apr. 23, 2020 in 2 pages.

https://en.wikipedia.org/wiki/Tenecteplase, accessed Apr. 13, 2020, printed Apr. 23, 2020 in 4 pages.

Lobst et al., "Selective Sugar Binding to the Carbohydrate Recognition Domains of the Rat Hepatic and Macrophage Asialoglycoprotein Receptors." The Journal of Biological Chemistry, vol. 271, No. 12, Issue Mar. 22, 1996, 6686-6693.

Mitea, C. Et Al., "A Universal Approach to Eliminate Antigenic Properties of Alpha-Gliadin Peptides in Celiac Disease." PLoS One, vol. 5, Issue 12, e15637, pp. 1-9, Dec. 2010.

Shen "A galactosamine-mediated drug delivery carrier for targeted liver cancer therapy" Pharmacological Research 64 (2011) 410-419.

‡ imported from a related application

A

B

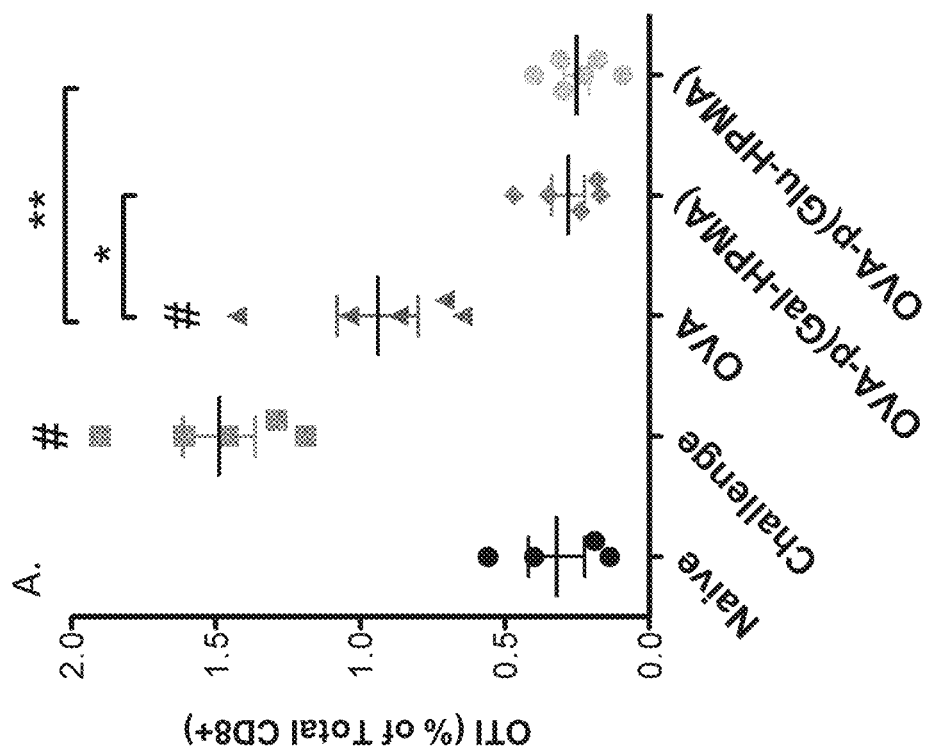
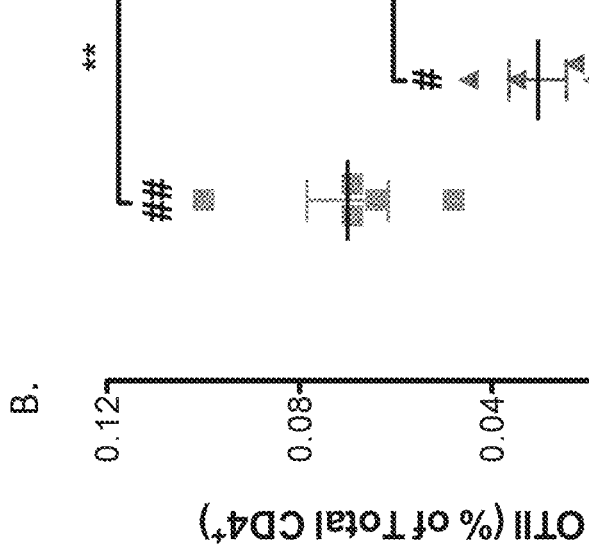

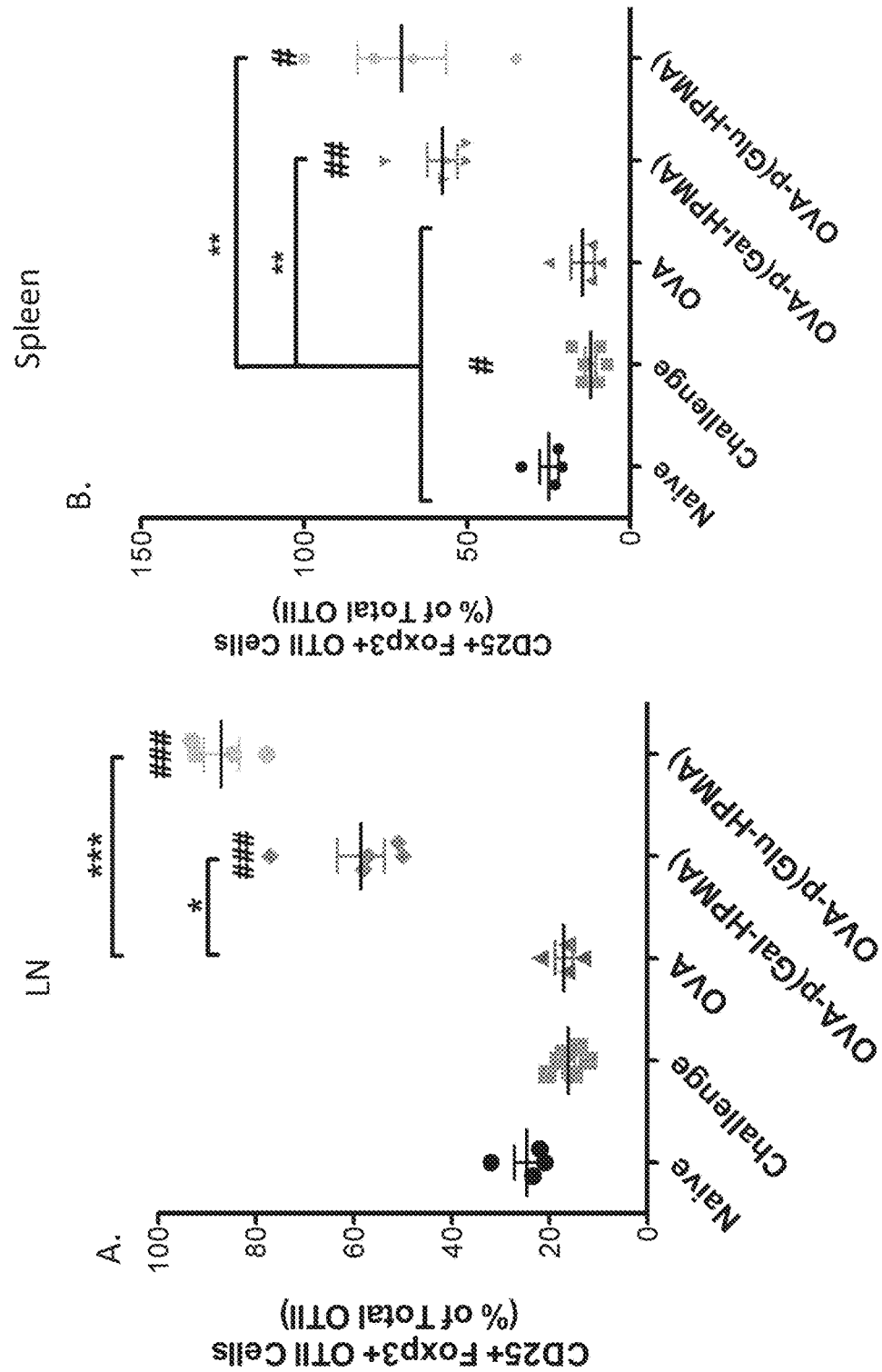
FIGS. 9A-B

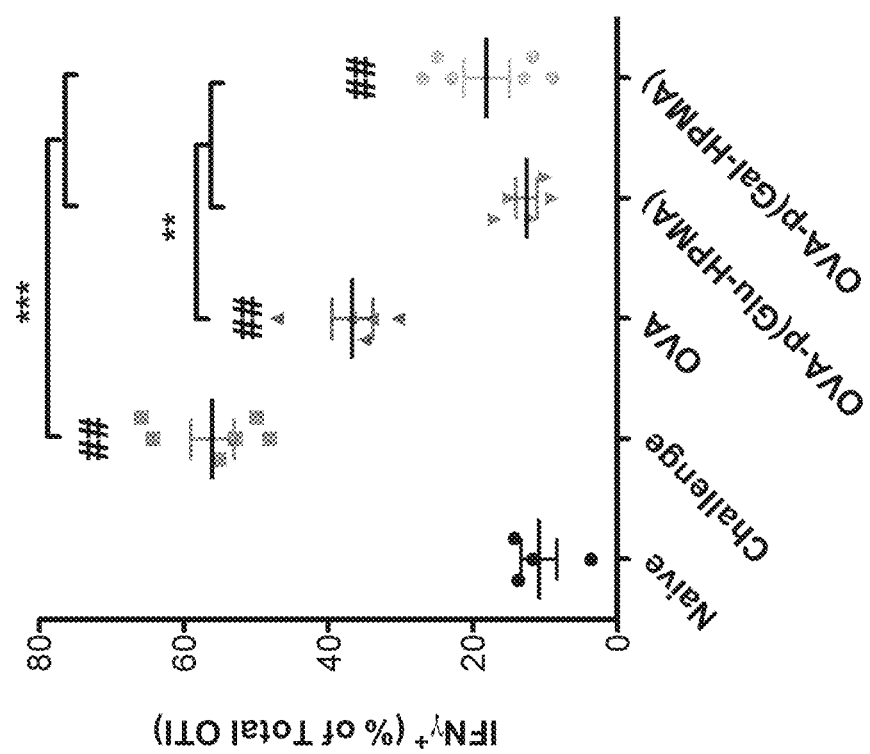

BDC2.5 Study

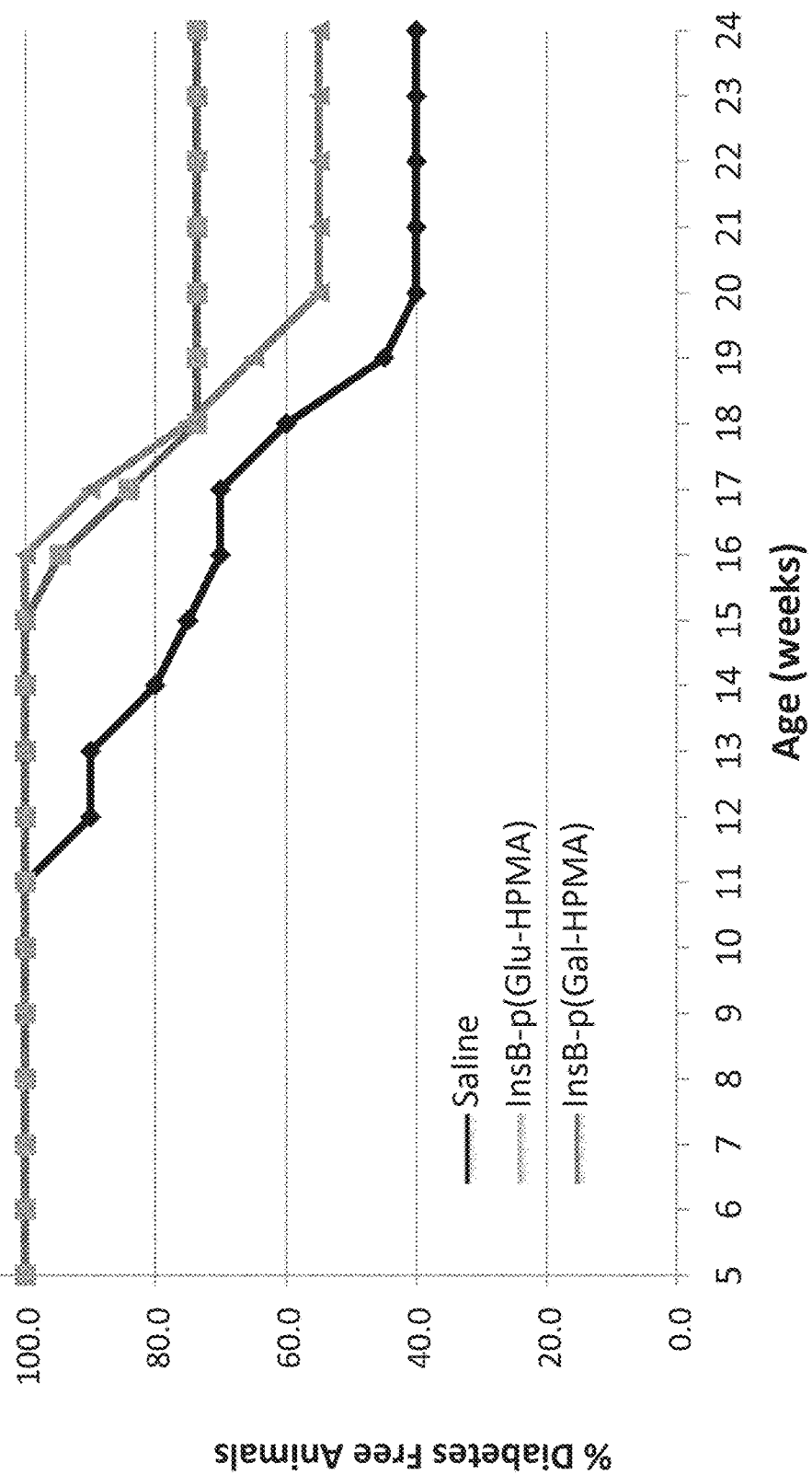

30-60: KNATGMEVGWYRSPFSRVVHLYRNGKDQDAE

SEQUENCE LISTING

```
<160> NUMBER OF SEQ ID NOS: 26

<210> SEQ ID NO 1
<211> LENGTH: 110
<212> TYPE: PRT
<213> ORGANISM: Homo sapiens

<400> SEQUENCE: 1

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 2
<211> LENGTH: 585
<212> TYPE: PRT
<213> ORGANISM: Homo sapiens
```

<400> SEQUENCE: 2

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Ser Gln Pro Pro
50                  55                  60

Arg Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
```

-continued

```
                405                 410                 415
Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 3
<211> LENGTH: 355
<212> TYPE: PRT
<213> ORGANISM: Homo sapiens

<400> SEQUENCE: 3

Met Asp Phe Leu His Arg Asn Gly Val Leu Ile Ile Gln His Leu Gln
1               5                   10                  15

Lys Asp Tyr Arg Ala Tyr Tyr Thr Phe Leu Asn Phe Met Ser Asn Val
            20                  25                  30

Gly Asp Pro Arg Asn Ile Phe Phe Ile Tyr Phe Pro Leu Cys Phe Gln
        35                  40                  45

Phe Asn Gln Thr Val Gly Thr Lys Met Ile Trp Val Ala Val Ile Gly
    50                  55                  60

Asp Trp Leu Asn Leu Ile Phe Lys Trp Ile Leu Phe Gly His Arg Pro
65                  70                  75                  80

Tyr Trp Trp Val Gln Glu Thr Gln Ile Tyr Pro Asn His Ser Ser Pro
                85                  90                  95

Cys Leu Glu Gln Phe Pro Thr Thr Cys Glu Thr Gly Pro Gly Ser Pro
            100                 105                 110

Ser Gly His Ala Met Gly Ala Ser Cys Val Trp Tyr Val Met Val Thr
        115                 120                 125

Ala Ala Leu Ser His Thr Val Cys Gly Met Asp Lys Phe Ser Ile Thr
    130                 135                 140

Leu His Arg Leu Thr Trp Ser Phe Leu Trp Ser Val Phe Trp Leu Ile
145                 150                 155                 160

Gln Ile Ser Val Cys Ile Ser Arg Val Phe Ile Ala Thr His Phe Pro
                165                 170                 175

His Gln Val Ile Leu Gly Val Ile Gly Gly Met Leu Val Ala Glu Ala
            180                 185                 190
```

```
Phe Glu His Thr Pro Gly Ile Gln Thr Ala Ser Leu Gly Thr Tyr Leu
            195                 200                 205

Lys Thr Asn Leu Phe Leu Phe Leu Phe Ala Val Gly Phe Tyr Leu Leu
        210                 215                 220

Leu Arg Val Leu Asn Ile Asp Leu Leu Trp Ser Val Pro Ile Ala Lys
225                 230                 235                 240

Lys Trp Cys Ala Asn Pro Asp Trp Ile His Ile Asp Thr Thr Pro Phe
                245                 250                 255

Ala Gly Leu Val Arg Asn Leu Gly Val Leu Phe Gly Leu Gly Phe Ala
                260                 265                 270

Ile Asn Ser Glu Met Phe Leu Leu Ser Cys Arg Gly Gly Asn Asn Tyr
            275                 280                 285

Thr Leu Ser Phe Arg Leu Leu Cys Ala Leu Thr Ser Leu Thr Ile Leu
        290                 295                 300

Gln Leu Tyr His Phe Leu Gln Ile Pro Thr His Glu Glu His Leu Phe
305                 310                 315                 320

Tyr Val Leu Ser Phe Cys Lys Ser Ala Ser Ile Pro Leu Thr Val Val
                325                 330                 335

Ala Phe Ile Pro Tyr Ser Val His Met Leu Met Lys Gln Ser Gly Lys
                340                 345                 350

Lys Ser Gln
        355

<210> SEQ ID NO 4
<211> LENGTH: 304
<212> TYPE: PRT
<213> ORGANISM: Homo sapiens

<400> SEQUENCE: 4

Met Gly Asn His Ala Gly Lys Arg Glu Leu Asn Ala Glu Lys Ala Ser
1               5                   10                  15

Thr Asn Ser Glu Thr Asn Arg Gly Glu Ser Glu Lys Lys Arg Asn Leu
            20                  25                  30

Gly Glu Leu Ser Arg Thr Thr Ser Glu Asp Asn Glu Val Phe Gly Glu
        35                  40                  45

Ala Asp Ala Asn Gln Asn Asn Gly Thr Ser Ser Gln Asp Thr Ala Val
    50                  55                  60

Thr Asp Ser Lys Arg Thr Ala Asp Pro Lys Asn Ala Trp Gln Asp Ala
65                  70                  75                  80

His Pro Ala Asp Pro Gly Ser Arg Pro His Leu Ile Arg Leu Phe Ser
                85                  90                  95

Arg Asp Ala Pro Gly Arg Glu Asp Asn Thr Phe Lys Asp Arg Pro Ser
                100                 105                 110

Glu Ser Asp Glu Leu Gln Thr Ile Gln Glu Asp Ser Ala Ala Thr Ser
            115                 120                 125

Glu Ser Leu Asp Val Met Ala Ser Gln Lys Arg Pro Ser Gln Arg His
        130                 135                 140

Gly Ser Lys Tyr Leu Ala Thr Ala Ser Thr Met Asp His Ala Arg His
145                 150                 155                 160

Gly Phe Leu Pro Arg His Arg Asp Thr Gly Ile Leu Asp Ser Ile Gly
                165                 170                 175

Arg Phe Phe Gly Gly Asp Arg Gly Ala Pro Lys Arg Gly Ser Gly Lys
                180                 185                 190

Asp Ser His His Pro Ala Arg Thr Ala His Tyr Gly Ser Leu Pro Gln
            195                 200                 205
```

```
Lys Ser His Gly Arg Thr Gln Asp Glu Asn Pro Val Val His Phe Phe
    210                 215                 220
Lys Asn Ile Val Thr Pro Arg Thr Pro Pro Ser Gln Gly Lys Gly
225                 230                 235                 240
Arg Gly Leu Ser Leu Ser Arg Phe Ser Trp Gly Ala Glu Gly Gln Arg
                245                 250                 255
Pro Gly Phe Gly Tyr Gly Gly Arg Ala Ser Asp Tyr Lys Ser Ala His
                260                 265                 270
Lys Gly Phe Lys Gly Val Asp Ala Gln Gly Thr Leu Ser Lys Ile Phe
                275                 280                 285
Lys Leu Gly Gly Arg Asp Ser Arg Ser Gly Ser Pro Met Ala Arg Arg
                290                 295                 300

<210> SEQ ID NO 5
<211> LENGTH: 247
<212> TYPE: PRT
<213> ORGANISM: Homo sapiens

<400> SEQUENCE: 5

Met Ala Ser Leu Ser Arg Pro Ser Leu Pro Ser Cys Leu Cys Ser Phe
1               5                   10                  15
Leu Leu Leu Leu Leu Leu Gln Val Ser Ser Ser Tyr Ala Gly Gln Phe
                20                  25                  30
Arg Val Ile Gly Pro Arg His Pro Ile Arg Ala Leu Val Gly Asp Glu
                35                  40                  45
Val Glu Leu Pro Cys Arg Ile Ser Pro Gly Lys Asn Ala Thr Gly Met
50                  55                  60
Glu Val Gly Trp Tyr Arg Pro Pro Phe Ser Arg Val Val His Leu Tyr
65                  70                  75                  80
Arg Asn Gly Lys Asp Gln Asp Gly Asp Gln Ala Pro Glu Tyr Arg Gly
                85                  90                  95
Arg Thr Glu Leu Leu Lys Asp Ala Ile Gly Glu Gly Lys Val Thr Leu
                100                 105                 110
Arg Ile Arg Asn Val Arg Phe Ser Asp Glu Gly Gly Phe Thr Cys Phe
                115                 120                 125
Phe Arg Asp His Ser Tyr Gln Glu Glu Ala Ala Met Glu Leu Lys Val
                130                 135                 140
Glu Asp Pro Phe Tyr Trp Val Ser Pro Gly Val Leu Val Leu Leu Ala
145                 150                 155                 160
Val Leu Pro Val Leu Leu Leu Gln Ile Thr Val Gly Leu Ile Phe Leu
                165                 170                 175
Cys Leu Gln Tyr Arg Leu Arg Gly Lys Leu Arg Ala Glu Ile Glu Asn
                180                 185                 190
Leu His Arg Thr Phe Asp Pro His Phe Leu Arg Val Pro Cys Trp Lys
                195                 200                 205
Ile Thr Leu Phe Val Ile Val Pro Val Leu Gly Pro Leu Val Ala Leu
                210                 215                 220
Ile Ile Cys Tyr Asn Trp Leu His Arg Arg Leu Ala Gly Gln Phe Leu
225                 230                 235                 240
Glu Glu Leu Arg Asn Pro Phe
                245

<210> SEQ ID NO 6
<211> LENGTH: 277
<212> TYPE: PRT
```

<213> ORGANISM: Homo sapiens

<400> SEQUENCE: 6

```
Met Gly Leu Leu Glu Cys Cys Ala Arg Cys Leu Val Gly Ala Pro Phe
1               5                   10                  15
Ala Ser Leu Val Ala Thr Gly Leu Cys Phe Phe Gly Val Ala Leu Phe
            20                  25                  30
Cys Gly Cys Gly His Glu Ala Leu Thr Gly Thr Glu Lys Leu Ile Glu
        35                  40                  45
Thr Tyr Phe Ser Lys Asn Tyr Gln Asp Tyr Glu Tyr Leu Ile Asn Val
    50                  55                  60
Ile His Ala Phe Gln Tyr Val Ile Tyr Gly Thr Ala Ser Phe Phe Phe
65                  70                  75                  80
Leu Tyr Gly Ala Leu Leu Leu Ala Glu Gly Phe Tyr Thr Thr Gly Ala
                85                  90                  95
Val Arg Gln Ile Phe Gly Asp Tyr Lys Thr Thr Ile Cys Gly Lys Gly
            100                 105                 110
Leu Ser Ala Thr Val Thr Gly Gly Gln Lys Gly Arg Gly Ser Arg Gly
        115                 120                 125
Gln His Gln Ala His Ser Leu Glu Arg Val Cys His Cys Leu Gly Lys
    130                 135                 140
Trp Leu Gly His Pro Asp Lys Phe Val Gly Ile Thr Tyr Ala Leu Thr
145                 150                 155                 160
Val Val Trp Leu Leu Val Phe Ala Cys Ser Ala Val Pro Val Tyr Ile
                165                 170                 175
Tyr Phe Asn Thr Trp Thr Thr Cys Gln Ser Ile Ala Phe Pro Ser Lys
            180                 185                 190
Thr Ser Ala Ser Ile Gly Ser Leu Cys Ala Asp Ala Arg Met Tyr Gly
        195                 200                 205
Val Leu Pro Trp Asn Ala Phe Pro Gly Lys Val Cys Gly Ser Asn Leu
    210                 215                 220
Leu Ser Ile Cys Lys Thr Ala Glu Phe Gln Met Thr Phe His Leu Phe
225                 230                 235                 240
Ile Ala Ala Phe Val Gly Ala Ala Ala Thr Leu Val Ser Leu Leu Thr
                245                 250                 255
Phe Met Ile Ala Ala Thr Tyr Asn Phe Ala Val Leu Lys Leu Met Gly
            260                 265                 270
Arg Gly Thr Lys Phe
        275
```

<210> SEQ ID NO 7
<211> LENGTH: 20
<212> TYPE: PRT
<213> ORGANISM: Homo sapiens

<400> SEQUENCE: 7

```
Lys Tyr Leu Ala Thr Ala Ser Thr Met Asp His Ala Arg His Gly Phe
1               5                   10                  15
Leu Pro Arg His
            20
```

<210> SEQ ID NO 8
<211> LENGTH: 16
<212> TYPE: PRT
<213> ORGANISM: Homo sapiens

<400> SEQUENCE: 8

Glu Asn Pro Trp His Phe Phe Lys Asn Ile Val Thr Pro Arg Thr Pro
1               5                   10                  15

<210> SEQ ID NO 9
<211> LENGTH: 19
<212> TYPE: PRT
<213> ORGANISM: Homo sapiens

<400> SEQUENCE: 9

Leu Ser Arg Phe Ser Trp Gly Ala Glu Gly Gln Arg Pro Gly Phe Gly
1               5                   10                  15

Tyr Gly Gly

<210> SEQ ID NO 10
<211> LENGTH: 25
<212> TYPE: PRT
<213> ORGANISM: Homo sapiens

<400> SEQUENCE: 10

Ala Gln Gly Thr Leu Ser Lys Ile Phe Lys Leu Gly Gly Arg Asp Ser
1               5                   10                  15

Arg Ser Gly Ser Pro Met Ala Arg Arg
            20                  25

<210> SEQ ID NO 11
<211> LENGTH: 20
<212> TYPE: PRT
<213> ORGANISM: Homo sapiens

<400> SEQUENCE: 11

Gly Gln Phe Arg Val Ile Gly Pro Arg His Pro Ile Arg Ala Leu Val
1               5                   10                  15

Gly Asp Glu Val
            20

<210> SEQ ID NO 12
<211> LENGTH: 20
<212> TYPE: PRT
<213> ORGANISM: Homo sapiens

<400> SEQUENCE: 12

Met Glu Val Gly Trp Tyr Arg Pro Pro Phe Ser Arg Trp His Leu Tyr
1               5                   10                  15

Arg Asn Gly Lys
            20

<210> SEQ ID NO 13
<211> LENGTH: 16
<212> TYPE: PRT
<213> ORGANISM: Homo sapiens

<400> SEQUENCE: 13

His Cys Leu Gly Lys Trp Leu Gly His Pro Asp Lys Phe Val Gly Ile
1               5                   10                  15

<210> SEQ ID NO 14
<211> LENGTH: 118
<212> TYPE: PRT
<213> ORGANISM: Homo sapiens

<400> SEQUENCE: 14

Met Pro Arg Glu Asp Ala His Phe Ile Tyr Gly Tyr Pro Lys Lys Gly

-continued

```
                1               5                      10                      15
His Gly His Ser Tyr Thr Thr Ala Glu Glu Ala Gly Ile Gly Ile
                        20                      25                      30

Leu Thr Val Ile Leu Gly Val Leu Leu Ile Gly Cys Trp Tyr Cys
                        35                      40                      45

Arg Arg Arg Asn Gly Tyr Arg Ala Leu Met Asp Lys Ser Leu His Val
        50                      55                      60

Gly Thr Gln Cys Ala Leu Thr Arg Arg Cys Pro Gln Glu Gly Phe Asp
65                      70                      75                      80

His Arg Asp Ser Lys Val Ser Leu Gln Glu Lys Asn Cys Glu Pro Val
                        85                      90                      95

Val Pro Asn Ala Pro Pro Ala Tyr Glu Lys Leu Ser Ala Glu Gln Ser
                        100                     105                     110

Pro Pro Pro Tyr Ser Pro
                        115

<210> SEQ ID NO 15
<211> LENGTH: 529
<212> TYPE: PRT
<213> ORGANISM: Homo sapiens

<400> SEQUENCE: 15

Met Leu Leu Ala Val Leu Tyr Cys Leu Leu Trp Ser Phe Gln Thr Ser
1               5                      10                      15

Ala Gly His Phe Pro Arg Ala Cys Val Ser Ser Lys Asn Leu Met Glu
                        20                      25                      30

Lys Glu Cys Cys Pro Pro Trp Ser Gly Asp Arg Ser Pro Cys Gly Gln
                        35                      40                      45

Leu Ser Gly Arg Gly Ser Cys Gln Asn Ile Leu Leu Ser Asn Ala Pro
        50                      55                      60

Leu Gly Pro Gln Phe Pro Phe Thr Gly Val Asp Asp Arg Glu Ser Trp
65                      70                      75                      80

Pro Ser Val Phe Tyr Asn Arg Thr Cys Gln Cys Ser Gly Asn Phe Met
                        85                      90                      95

Gly Phe Asn Cys Gly Asn Cys Lys Phe Gly Phe Trp Gly Pro Asn Cys
                        100                     105                     110

Thr Glu Arg Arg Leu Leu Val Arg Arg Asn Ile Phe Asp Leu Ser Ala
                        115                     120                     125

Pro Glu Lys Asp Lys Phe Phe Ala Tyr Leu Thr Leu Ala Lys His Thr
        130                     135                     140

Ile Ser Ser Asp Tyr Val Ile Pro Ile Gly Thr Tyr Gly Gln Met Lys
145                     150                     155                     160

Asn Gly Ser Thr Pro Met Phe Asn Asp Ile Asn Ile Tyr Asp Leu Phe
                        165                     170                     175

Val Trp Met His Tyr Tyr Val Ser Met Asp Ala Leu Leu Gly Gly Ser
                        180                     185                     190

Glu Ile Trp Arg Asp Ile Asp Phe Ala His Glu Ala Pro Ala Phe Leu
                        195                     200                     205

Pro Trp His Arg Leu Phe Leu Leu Arg Trp Glu Gln Glu Ile Gln Lys
        210                     215                     220

Leu Thr Gly Asp Glu Asn Phe Thr Ile Pro Tyr Trp Asp Trp Arg Asp
225                     230                     235                     240

Ala Glu Lys Cys Asp Ile Cys Thr Asp Glu Tyr Met Gly Gly Gln His
                        245                     250                     255
```

```
Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
    290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
        355                 360                 365

Tyr Met Asn Gly Thr Met Ser Gln Val Gln Gly Ser Ala Asn Asp Pro
    370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415

Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu

<210> SEQ ID NO 16
<211> LENGTH: 661
<212> TYPE: PRT
<213> ORGANISM: Homo sapiens

<400> SEQUENCE: 16

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95
```

```
Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
```

```
                515                 520                 525
Ser Ser Pro Gly Cys Gln Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 17
<211> LENGTH: 323
<212> TYPE: PRT
<213> ORGANISM: Homo sapiens

<400> SEQUENCE: 17

Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125

Gly Ala Gly Ile Leu Tyr Leu Val Thr Pro Pro Ser Val Val Gly Gly
    130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
            180                 185                 190

Ile Gly Phe Ser Val Ala Ile Gly His Leu Phe Ala Ile Asn Tyr Thr
        195                 200                 205

Gly Ala Ser Met Asn Pro Ala Arg Ser Phe Gly Pro Ala Val Ile Met
    210                 215                 220
```

```
Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
            245                 250                 255

Glu Phe Lys Arg Arg Phe Lys Glu Ala Phe Ser Lys Ala Ala Gln Gln
            260                 265                 270

Thr Lys Gly Ser Tyr Met Glu Val Glu Asp Asn Arg Ser Gln Val Glu
            275                 280                 285

Thr Asp Asp Leu Ile Leu Lys Pro Gly Val Val His Val Ile Asp Val
        290                 295                 300

Asp Arg Gly Glu Glu Lys Lys Gly Lys Asp Gln Ser Gly Glu Val Leu
305                 310                 315                 320

Ser Ser Val

<210> SEQ ID NO 18
<211> LENGTH: 405
<212> TYPE: PRT
<213> ORGANISM: Homo sapiens

<400> SEQUENCE: 18

Met Ala Ala Ser Gly Lys Thr Ser Lys Ser Glu Pro Asn His Val Ile
1               5                   10                  15

Phe Lys Lys Ile Ser Arg Asp Lys Ser Val Thr Ile Tyr Leu Gly Asn
                20                  25                  30

Arg Asp Tyr Ile Asp His Val Ser Gln Val Gln Pro Val Asp Gly Val
            35                  40                  45

Val Leu Val Asp Pro Asp Leu Val Lys Gly Lys Lys Val Tyr Val Thr
        50                  55                  60

Leu Thr Cys Ala Phe Arg Tyr Gly Gln Glu Asp Ile Asp Val Ile Gly
65                  70                  75                  80

Leu Thr Phe Arg Arg Asp Leu Tyr Phe Ser Arg Val Gln Val Tyr Pro
                85                  90                  95

Pro Val Gly Ala Ala Ser Thr Pro Thr Lys Leu Gln Glu Ser Leu Leu
            100                 105                 110

Lys Lys Leu Gly Ser Asn Thr Tyr Pro Phe Leu Leu Thr Phe Pro Asp
        115                 120                 125

Tyr Leu Pro Cys Ser Val Met Leu Gln Pro Ala Pro Gln Asp Ser Gly
130                 135                 140

Lys Ser Cys Gly Val Asp Phe Glu Val Lys Ala Phe Ala Thr Asp Ser
145                 150                 155                 160

Thr Asp Ala Glu Glu Asp Lys Ile Pro Lys Lys Ser Ser Val Arg Leu
                165                 170                 175

Leu Ile Arg Lys Val Gln His Ala Pro Leu Glu Met Gly Pro Gln Pro
            180                 185                 190

Arg Ala Glu Ala Ala Trp Gln Phe Phe Met Ser Asp Lys Pro Leu His
        195                 200                 205

Leu Ala Val Ser Leu Asn Lys Glu Ile Tyr Phe His Gly Glu Pro Ile
        210                 215                 220

Pro Val Thr Val Thr Val Thr Asn Asn Thr Glu Lys Thr Val Lys Lys
225                 230                 235                 240

Ile Lys Ala Phe Val Glu Gln Val Ala Asn Val Val Leu Tyr Ser Ser
                245                 250                 255

Asp Tyr Tyr Val Lys Pro Val Ala Met Glu Glu Ala Gln Glu Lys Val
            260                 265                 270
```

-continued

```
Pro Pro Asn Ser Thr Leu Thr Lys Thr Leu Thr Leu Leu Pro Leu Leu
        275                 280                 285

Ala Asn Asn Arg Glu Arg Arg Gly Ile Ala Leu Asp Gly Lys Ile Lys
290                 295                 300

His Glu Asp Thr Asn Leu Ala Ser Ser Thr Ile Ile Lys Glu Gly Ile
305                 310                 315                 320

Asp Arg Thr Val Leu Gly Ile Leu Val Ser Tyr Gln Ile Lys Val Lys
                325                 330                 335

Leu Thr Val Ser Gly Phe Leu Gly Leu Thr Ser Ser Glu Val Ala
                340                 345                 350

Thr Glu Val Pro Phe Arg Leu Met His Pro Gln Pro Glu Asp Pro Ala
        355                 360                 365

Lys Glu Ser Tyr Gln Asp Ala Asn Leu Val Phe Glu Glu Phe Ala Arg
    370                 375                 380

His Asn Leu Lys Asp Ala Gly Glu Ala Glu Glu Gly Lys Arg Asp Lys
385                 390                 395                 400

Asn Asp Val Asp Glu
                405

<210> SEQ ID NO 19
<211> LENGTH: 1247
<212> TYPE: PRT
<213> ORGANISM: Homo sapiens

<400> SEQUENCE: 19

Met Met Arg Glu Trp Val Leu Leu Met Ser Val Leu Leu Cys Gly Leu
1               5                   10                  15

Ala Gly Pro Thr His Leu Phe Gln Pro Ser Leu Val Leu Asp Met Ala
                20                  25                  30

Lys Val Leu Leu Asp Asn Tyr Cys Phe Pro Glu Asn Leu Leu Gly Met
            35                  40                  45

Gln Glu Ala Ile Gln Ala Ile Lys Ser His Glu Ile Leu Ser Ile
    50                  55                  60

Ser Asp Pro Gln Thr Leu Ala Ser Val Leu Thr Ala Gly Val Gln Ser
65                  70                  75                  80

Ser Leu Asn Asp Pro Arg Leu Val Ile Ser Tyr Glu Pro Ser Thr Pro
                85                  90                  95

Glu Pro Pro Pro Gln Val Pro Ala Leu Thr Ser Leu Ser Glu Glu Glu
                100                 105                 110

Leu Leu Ala Trp Leu Gln Arg Gly Leu Arg His Glu Val Leu Glu Gly
            115                 120                 125

Asn Val Gly Tyr Leu Arg Val Asp Ser Val Pro Gly Gln Glu Val Leu
        130                 135                 140

Ser Met Met Gly Glu Phe Leu Val Ala His Val Trp Gly Asn Leu Met
145                 150                 155                 160

Gly Thr Ser Ala Leu Val Leu Asp Leu Arg His Cys Thr Gly Gly Gln
                165                 170                 175

Val Ser Gly Ile Pro Tyr Ile Ile Ser Tyr Leu His Pro Gly Asn Thr
            180                 185                 190

Ile Leu His Val Asp Thr Ile Tyr Asn Arg Pro Ser Asn Thr Thr Thr
        195                 200                 205

Glu Ile Trp Thr Leu Pro Gln Val Leu Gly Glu Arg Tyr Gly Ala Asp
    210                 215                 220

Lys Asp Val Val Val Leu Thr Ser Ser Gln Thr Arg Gly Val Ala Glu
225                 230                 235                 240
```

-continued

Asp Ile Ala His Ile Leu Lys Gln Met Arg Arg Ala Ile Val Val Gly
            245                 250                 255

Glu Arg Thr Gly Gly Ala Leu Asp Leu Arg Lys Leu Arg Ile Gly
            260                 265                 270

Glu Ser Asp Phe Phe Phe Thr Val Pro Val Ser Arg Ser Leu Gly Pro
            275                 280                 285

Leu Gly Gly Gly Ser Gln Thr Trp Glu Gly Ser Gly Val Leu Pro Cys
            290                 295                 300

Val Gly Thr Pro Ala Glu Gln Ala Leu Glu Lys Ala Leu Ala Ile Leu
305                 310                 315                 320

Thr Leu Arg Ser Ala Leu Pro Gly Val Val His Cys Leu Gln Glu Val
                325                 330                 335

Leu Lys Asp Tyr Tyr Thr Leu Val Asp Arg Val Pro Thr Leu Leu Gln
                340                 345                 350

His Leu Ala Ser Met Asp Phe Ser Thr Val Val Ser Glu Glu Asp Leu
                355                 360                 365

Val Thr Lys Leu Asn Ala Gly Leu Gln Ala Ala Ser Glu Asp Pro Arg
    370                 375                 380

Leu Leu Val Arg Ala Ile Gly Pro Thr Glu Thr Pro Ser Trp Pro Ala
385                 390                 395                 400

Pro Asp Ala Ala Ala Glu Asp Ser Pro Gly Val Ala Pro Glu Leu Pro
                405                 410                 415

Glu Asp Glu Ala Ile Arg Gln Ala Leu Val Asp Ser Val Phe Gln Val
                420                 425                 430

Ser Val Leu Pro Gly Asn Val Gly Tyr Leu Arg Phe Asp Ser Phe Ala
                435                 440                 445

Asp Ala Ser Val Leu Gly Val Leu Ala Pro Tyr Val Leu Arg Gln Val
    450                 455                 460

Trp Glu Pro Leu Gln Asp Thr Glu His Leu Ile Met Asp Leu Arg His
465                 470                 475                 480

Asn Pro Gly Gly Pro Ser Ser Ala Val Pro Leu Leu Leu Ser Tyr Phe
                485                 490                 495

Gln Gly Pro Glu Ala Gly Pro Val His Leu Phe Thr Thr Tyr Asp Arg
                500                 505                 510

Arg Thr Asn Ile Thr Gln Glu His Phe Ser His Met Glu Leu Pro Gly
                515                 520                 525

Pro Arg Tyr Ser Thr Gln Arg Gly Val Tyr Leu Leu Thr Ser His Arg
    530                 535                 540

Thr Ala Thr Ala Ala Glu Glu Phe Ala Phe Leu Met Gln Ser Leu Gly
545                 550                 555                 560

Trp Ala Thr Leu Val Gly Glu Ile Thr Ala Gly Asn Leu Leu His Thr
                565                 570                 575

Arg Thr Val Pro Leu Leu Asp Thr Pro Glu Gly Ser Leu Ala Leu Thr
                580                 585                 590

Val Pro Val Leu Thr Phe Ile Asp Asn His Gly Glu Ala Trp Leu Gly
                595                 600                 605

Gly Gly Val Val Pro Asp Ala Ile Val Leu Ala Glu Glu Ala Leu Asp
    610                 615                 620

Lys Ala Gln Glu Val Leu Glu Phe His Gln Ser Leu Gly Ala Leu Val
625                 630                 635                 640

Glu Gly Thr Gly His Leu Leu Glu Ala His Tyr Ala Arg Pro Glu Val
                645                 650                 655

```
Val Gly Gln Thr Ser Ala Leu Leu Arg Ala Lys Leu Ala Gln Gly Ala
            660                 665                 670

Tyr Arg Thr Ala Val Asp Leu Glu Ser Leu Ala Ser Gln Leu Thr Ala
            675                 680                 685

Asp Leu Gln Glu Val Ser Gly Asp His Arg Leu Leu Val Phe His Ser
            690                 695                 700

Pro Gly Glu Leu Val Val Glu Ala Pro Pro Pro Pro Ala Val
705                 710                 715                 720

Pro Ser Pro Glu Glu Leu Thr Tyr Leu Ile Glu Ala Leu Phe Lys Thr
            725                 730                 735

Glu Val Leu Pro Gly Gln Leu Gly Tyr Leu Arg Phe Asp Ala Met Ala
            740                 745                 750

Glu Leu Glu Thr Val Lys Ala Val Gly Pro Gln Leu Val Arg Leu Val
            755                 760                 765

Trp Gln Gln Leu Val Asp Thr Ala Ala Leu Val Ile Asp Leu Arg Tyr
            770                 775                 780

Asn Pro Gly Ser Tyr Ser Thr Ala Ile Pro Leu Leu Cys Ser Tyr Phe
785                 790                 795                 800

Phe Glu Ala Glu Pro Arg Gln His Leu Tyr Ser Val Phe Asp Arg Ala
            805                 810                 815

Thr Ser Lys Val Thr Glu Val Trp Thr Leu Pro Gln Val Ala Gly Gln
            820                 825                 830

Arg Tyr Gly Ser His Lys Asp Leu Tyr Ile Leu Met Ser His Thr Ser
            835                 840                 845

Gly Ser Ala Ala Glu Ala Phe Ala His Thr Met Gln Asp Leu Gln Arg
850                 855                 860

Ala Thr Val Ile Gly Glu Pro Thr Ala Gly Ala Leu Ser Val Gly
865                 870                 875                 880

Ile Tyr Gln Val Gly Ser Ser Pro Leu Tyr Ala Ser Met Pro Thr Gln
            885                 890                 895

Met Ala Met Ser Ala Thr Thr Gly Lys Ala Trp Asp Leu Ala Gly Val
            900                 905                 910

Glu Pro Asp Ile Thr Val Pro Met Ser Glu Ala Leu Ser Ile Ala Gln
            915                 920                 925

Asp Ile Val Ala Leu Arg Ala Lys Val Pro Thr Val Leu Gln Thr Ala
            930                 935                 940

Gly Lys Leu Val Ala Asp Asn Tyr Ala Ser Ala Glu Leu Gly Ala Lys
945                 950                 955                 960

Met Ala Thr Lys Leu Ser Gly Leu Gln Ser Arg Tyr Ser Arg Val Thr
            965                 970                 975

Ser Glu Val Ala Leu Ala Glu Ile Leu Gly Ala Asp Leu Gln Met Leu
            980                 985                 990

Ser Gly Asp Pro His Leu Lys Ala Ala His Ile Pro Glu Asn Ala Lys
            995                 1000                1005

Asp Arg Ile Pro Gly Ile Val Pro Met Gln Ile Pro Ser Pro Glu
            1010                1015                1020

Val Phe Glu Glu Leu Ile Lys Phe Ser Phe His Thr Asn Val Leu
            1025                1030                1035

Glu Asp Asn Ile Gly Tyr Leu Arg Phe Asp Met Phe Gly Asp Gly
            1040                1045                1050

Glu Leu Leu Thr Gln Val Ser Arg Leu Leu Val Glu His Ile Trp
            1055                1060                1065

Lys Lys Ile Met His Thr Asp Ala Met Ile Ile Asp Met Arg Phe
```

```
                          1070                1075                1080

Asn Ile Gly Gly Pro Thr Ser Ser Ile Pro Ile Leu Cys Ser Tyr
            1085                1090                1095

Phe Phe Asp Glu Gly Pro Pro Val Leu Leu Asp Lys Ile Tyr Ser
    1100                1105                1110

Arg Pro Asp Asp Ser Val Ser Glu Leu Trp Thr His Ala Gln Val
    1115                1120                1125

Val Gly Glu Arg Tyr Gly Ser Lys Lys Ser Met Val Ile Leu Thr
    1130                1135                1140

Ser Ser Val Thr Ala Gly Thr Ala Glu Glu Phe Thr Tyr Ile Met
    1145                1150                1155

Lys Arg Leu Gly Arg Ala Leu Val Ile Gly Glu Val Thr Ser Gly
    1160                1165                1170

Gly Cys Gln Pro Pro Gln Thr Tyr His Val Asp Asp Thr Asn Leu
    1175                1180                1185

Tyr Leu Thr Ile Pro Thr Ala Arg Ser Val Gly Ala Ser Asp Gly
    1190                1195                1200

Ser Ser Trp Glu Gly Val Gly Val Thr Pro His Val Val Val Pro
    1205                1210                1215

Ala Glu Glu Ala Leu Ala Arg Ala Lys Glu Met Leu Gln His Asn
    1220                1225                1230

Gln Leu Arg Val Lys Arg Ser Pro Gly Leu Gln Asp His Leu
    1235                1240                1245

<210> SEQ ID NO 20
<211> LENGTH: 33
<212> TYPE: PRT
<213> ORGANISM: Homo sapiens

<400> SEQUENCE: 20

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 21
<211> LENGTH: 33
<212> TYPE: PRT
<213> ORGANISM: Homo sapiens

<400> SEQUENCE: 21

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
                20                  25                  30

Phe

<210> SEQ ID NO 22
<211> LENGTH: 18
<212> TYPE: PRT
<213> ORGANISM: Homo sapiens

<400> SEQUENCE: 22

Gln Gln Tyr Pro Ser Gly Gln Gly Ser Phe Gln Pro Ser Gln Gln Asn
1               5                   10                  15

Pro Gln
```

```
<210> SEQ ID NO 23
<211> LENGTH: 12
<212> TYPE: PRT
<213> ORGANISM: Homo sapiens

<400> SEQUENCE: 23

Gln Pro Phe Pro Gln Pro Glu Gln Pro Phe Pro Trp
1               5                   10

<210> SEQ ID NO 24
<211> LENGTH: 21
<212> TYPE: PRT
<213> ORGANISM: Homo sapiens

<400> SEQUENCE: 24

Met Glu Val Gly Trp Tyr Arg Ser Pro Phe Ser Arg Val Val His Leu
1               5                   10                  15

Tyr Arg Asn Gly Lys
            20

<210> SEQ ID NO 25
<211> LENGTH: 31
<212> TYPE: PRT
<213> ORGANISM: Homo sapiens

<400> SEQUENCE: 25

Lys Asn Ala Thr Gly Met Glu Val Gly Trp Tyr Arg Ser Pro Phe Ser
1               5                   10                  15

Arg Val Val His Leu Tyr Arg Asn Gly Lys Asp Gln Asp Ala Glu
            20                  25                  30

<210> SEQ ID NO 26
<211> LENGTH: 23
<212> TYPE: PRT
<213> ORGANISM: Homo sapiens

<400> SEQUENCE: 26

Gln Gln Tyr Pro Ser Gly Gln Gly Ser Phe Gln Pro Ser Gln Gln Asn
1               5                   10                  15

Pro Gln Gly Gly Gly Ser Cys
            20
```

GLYCOTARGETING THERAPEUTICS

CROSS-REFERENCE TO RELATED APPLICATION

This application is a continuation of International Application No. PCT/IB2016/001411, filed Sep. 16, 2016, which is a continuation-in-part of U.S. patent application Ser. No. 15/185,564, filed Jun. 17, 2016, which is a continuation-in-part of U.S. patent application Ser. No. 14/859,292, filed Sep. 19, 2015, each entitled "GLYCOTARGETING THERAPEUTICS." This application is a continuation of International Application No. PCT/IB2016/001411, filed Sep. 16, 2016, which is a continuation-in-part of U.S. patent application Ser. No. 14/859,292, filed Sep. 19, 2015, each entitled "GLYCOTARGETING THERAPEUTICS." This application is a continuation-in-part of U.S. patent application Ser. No. 15/185,564, filed Jun. 17, 2016, which is a continuation-in-part of U.S. patent application Ser. No. 14/859,292 filed Sep. 19, 2015, which is a continuation-in-part of U.S. patent application Ser. No. 14/627,297 filed Feb. 20, 2015, which claims the benefit of U.S. Provisional Application No. 61/942,942 filed Feb. 21, 2014, each entitled "GLYCOTARGETING THERAPEUTICS." The entirety of each of the foregoing applications is hereby incorporated by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is ANOK002P4 ST25.TXT, the date of creation of the ASCII text file is May 20, 2020, and the size of the ASCII text file is 47.8 KB.

BACKGROUND

Field

Several embodiments of the invention disclosed herein relate to pharmaceutically acceptable compositions that are useful in the treatment of transplant rejection, autoimmune disease, allergy (e.g., food allergy), and immune response against a therapeutic agent.

Description of Related Art

Various approaches have been used to induce tolerance to antigens that elicit an unwanted immune response. Some approaches employ targeting of the antigens to specific cells. Applications US 2012/0039989, US 2012/0178139 and WO 2013/121296 describe the targeting of antigens to erythrocytes to take advantage of the erythrocytes' role in antigen presentation for tolerization.

SUMMARY

Notwithstanding the positive results generated to date using cell-targeting approaches, the possibility of alternative approaches has remained of interest. In particular, several embodiments disclosed herein relate to compositions configured to target one or more cell types in the liver and, as a result, deliver an antigen to which tolerance is desired to the one or more cell types targeted, and thereby induce a processing of the antigen and induce immune tolerance to the antigen. The antigen, as disclosed in more detail below, can comprise a therapeutic agent, a protein, a protein fragment, an antigenic mimic of a protein or protein fragment (e.g., a mimotope). Additional types of antigens are discussed in more detail below. Methods and uses of such compositions are also provided for, in several embodiments.

In several embodiments, there is provided a compound comprising Formula 1:

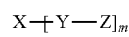

Formula 1 wherein m is an integer from about 1 to 10, X comprises molecule comprising an antigenic region, Y is of a linker moiety having a formula selected from the group consisting of:

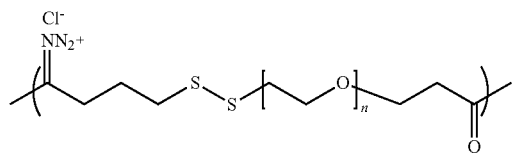

Formula Ya

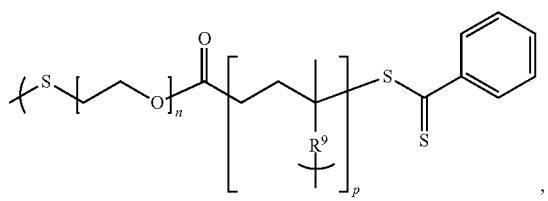

Formula Yc

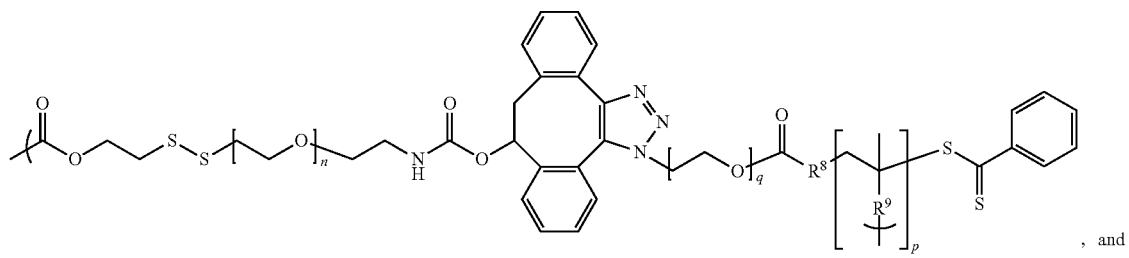

Formula Ym

, and

Formula Yn

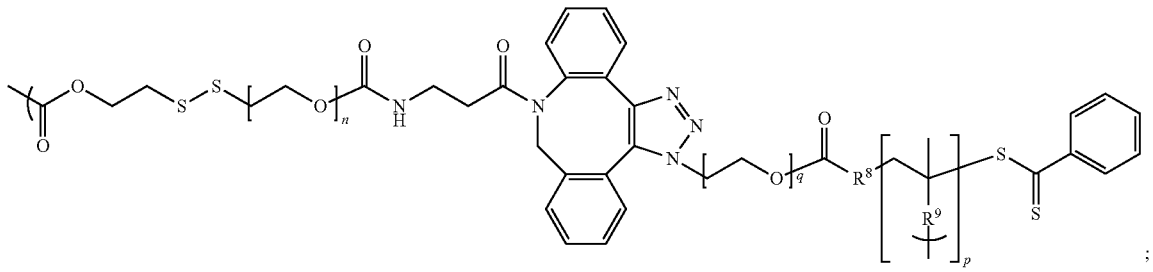

wherein the left bracket "(" indicates a bond to X, the right or bottom bracket and ")" indicates the bond between Y and Z, n is an integer from about 1 to 100, where present p is an integer from about 2 to 150, where present q is an integer from about 1 to 44, where present $R^8$ is —$CH_2$— or —$CH_2$—$CH_2$—$C(CH_3)(CN)$—; and where present $R^9$ is a direct bond or —$CH_2$—$CH_2$—NH—C(O)—, and Z comprises a liver-targeting moiety. In several embodiments, X is a protein or protein fragment comprising an antigenic region. In several embodiments, Z is galactose, while in some embodiments Z is glucose. In several embodiments, Z is galactosamine, while in some embodiments Z is glucosamine. In several embodiments, the alpha anomer of glucose or galactose is used in the composition. In several embodiments, the beta anomer of glucose or galactose is used in the composition. In several embodiments, mixtures of the alpha and beta anomers are used, including optionally mixtures of glucose and galactose. In several embodiments, Z is N-acetylgalactosamine, while in some embodiments Z is N-acetylglucosamine. In several embodiments, the alpha anomer of glucosamine or galactosamine is used in the composition. In several embodiments, the alpha anomer of glucosamine or galactosamine is used in the composition. In several embodiments, mixtures of the alpha and beta anomers are used, including optionally mixtures of glucosamine and galactosamine. Likewise, in several embodiments the alpha anomer, the beta anomer, or combinations of the alpha and beta anomers of N-acetylgalactosamine or N-acetylglucosamine. Combinations of any of the alpha or beta anomeric forms of any of the liver targeting sugars, and any combinations of the sugars can be employed in various embodiments. In several embodiments Y comprises $Y_m$ or $Y_n$, m is between 1 and 5, n is between 75 and 85, p is between 85 and 95, and q is between 2 and 6. In several embodiments m is between 1 and 3, n is 79, p is 90, and q is 4. In several embodiments, X is selected from the group consisting of insulin, proinsulin, preproinsulin, gluten, gliadin, myelin basic protein, myelin oligodendrocyte glycoprotein and proteolipid protein, Factor VIII, Factor IX, asparaginase, uricase and fragments of any of the preceding. In several embodiments, the antigen X is not a full length protein. For example, in some embodiments, the antigen is not full length gliadin, insulin, or proinsulin. In several embodiments, the antigen X is not a fragment of a protein. In several embodiments, m is not greater than 3, n is not greater than 80, p is not greater than 100 and q is not more than 5.

In several embodiments, Y is a linker moiety having a formula of:

Formula Ya

In several embodiments, Y is a linker moiety having a formula of:

Formula Yc

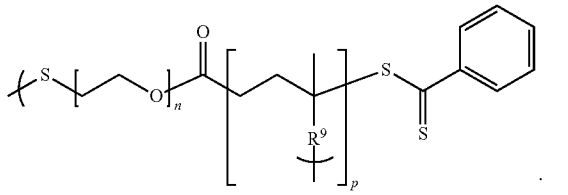

In several embodiments, Y is a linker moiety having a formula of:

Formula Ym

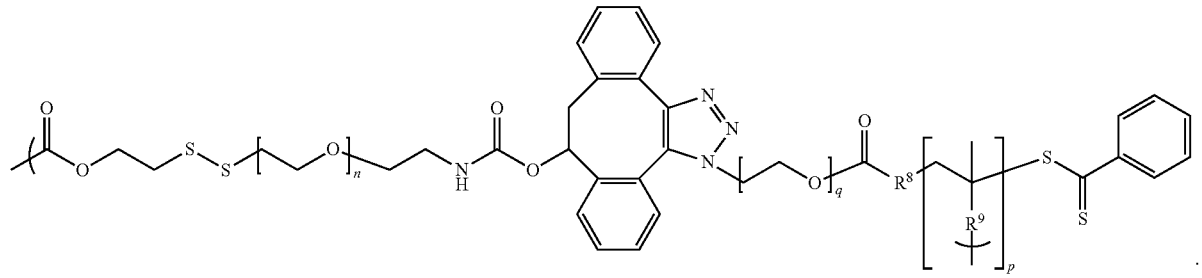

In several embodiments, Y is a linker moiety having a formula of:

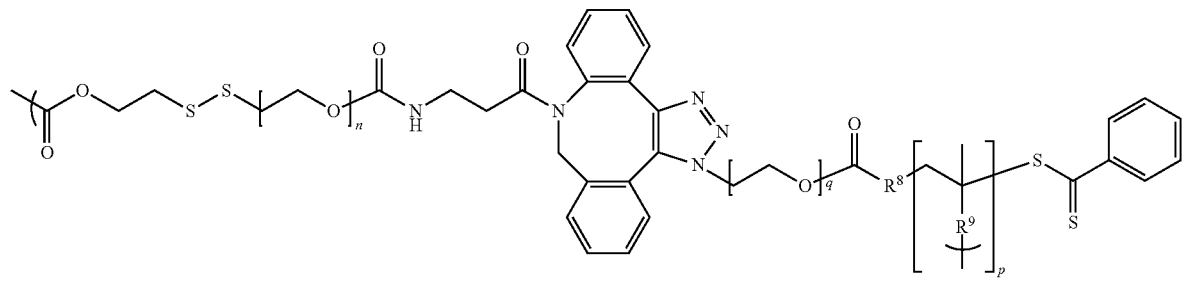

Formula Yn

In some embodiments, combinations of the linkers disclosed herein may be used, just as combinations of the liver targeting moieties can be employed.

As discussed in more detail below, there exist a variety of antigens to which tolerance may be desired. These may include, but are not limited to, exogenous antigens that result in an adverse immune response when a subject is exposed to the antigen. In several embodiments, the adverse immune response could be a result of ingestion of the antigen, e.g., orally or nasally, or via some other mucosal route. These routes could be the case, for example, with food antigens. In some embodiments, the antigen may be purposefully administered to a subject, for example, with the administration of a therapeutic composition to treat a disease or condition that the subject is affected by. In still additional embodiments, the antigen may be produced by the subject, e.g., an autoimmune antigen. For example, in several embodiments, X comprises a foreign transplant antigen against which transplant recipients develop an unwanted immune response or a tolerogenic portion thereof. In several embodiments, X comprises a foreign food, animal, plant or environmental antigen against which patients develop an unwanted immune response or a tolerogenic portion thereof. In several embodiments, X comprises a foreign therapeutic agent against which patients develop an unwanted immune response or a tolerogenic portion thereof. In several embodiments, X comprises a synthetic self-antigen against the endogenous version of which patients develop an unwanted immune response or a tolerogenic portion thereof.

In further detail to the above, there are provided in several embodiments compounds where X is a food antigen. In some such embodiments, X is one or more of conarachin (Ara h 1), allergen II (Ara h 2), arachis agglutinin, conglutin (Ara h 6), a-lactalbumin (ALA), lactotransferrin, Pen a 1 allergen (Pen a 1), allergen Pen m 2 (Pen m 2), tropomyosin fast isoform, high molecular weight glutenin, low molecular weight glutenin, alpha-gliadin, gamma-gliadin, omega-gliadin, hordein, seclain, and avenin. Fragment of any of these antigens and/or mimotopes of any of these antigens are also used, in several embodiments. In several embodiments, X is selected from the group consisting of gluten, high molecular weight glutenin, low molecular weight glutenin, alpha-gliadin, gamma-gliadin, omega-gliadin, hordein, seclain, and avenin and fragments thereof. In several embodiments, X is selected from the group consisting of gluten, high molecular weight glutenin, low molecular weight glutenin, alpha-gliadin, gamma-gliadin, and omega-gliadin and fragments thereof. In several embodiments, X is gluten or fragment thereof. In several embodiments, X is gliadin or fragment thereof.

In several embodiments, there are provided compounds where X is a therapeutic agent. In several embodiments, X is selected from the group consisting of Factor VII, Factor IX, asparaginase, and uricase and fragments thereof. In several embodiments, X is a therapeutic agent selected from the group consisting of Factor VII and Factor IX and fragments thereof. In several embodiments, X is a therapeutic agent selected from the group consisting of Factor VIII or fragment thereof. In several embodiments, when X is a therapeutic agent, the compound can be used in the treatment, prevention, reduction, or otherwise amelioration of an immune response developed against a therapeutic agent for hemophilia. As discussed herein, mimotopes of any antigenic portion of the antigens above can be used in several embodiments.

In several embodiments, X comprises asparaginase or a fragment thereof. In several embodiments, X comprises uricase or a fragment thereof. In several such embodiments, the compound can be used in the treatment, prevention, reduction, or otherwise amelioration of an immune response developed against an anti-neoplastic agent. As discussed herein, mimotopes of any antigenic portion of the antigens above can be used in several embodiments.

In several embodiments, X is associated with an autoimmune disease. For example, in several embodiments, the associated autoimmune disease is one or more of Type I diabetes, multiple sclerosis, rheumatoid arthritis, vitiligo, uveitis, pemphis vulgaris and neuromyelitis optica.

In several embodiments, the autoimmune disease is Type I diabetes and X comprises insulin or a fragment thereof. In several embodiments, the autoimmune disease is Type I diabetes and X comprises proinsulin or a fragment thereof. In several embodiments, the autoimmune disease is Type I diabetes and X comprises preproinsulin or a fragment thereof. As discussed herein, mimotopes of any antigenic portion of the antigens above can be used in several embodiments. In several embodiments, combinations of these antigens can be incorporated into the tolerogenic compound which may aid in reducing immune responses to self-antigens at multiple points along the insulin pathway.

In several embodiments, the autoimmune disease is multiple sclerosis and X comprises myelin basic protein or a fragment thereof. In several embodiments, the autoimmune disease is multiple sclerosis and X comprises myelin oligodendrocyte glycoprotein or a fragment thereof. In several embodiments, the autoimmune disease is multiple sclerosis and X comprises myelin proteolipid protein or a fragment thereof. As discussed herein, mimotopes of any antigenic portion of the antigens above can be used in several embodiments. In several embodiments, combinations of these antigens can be incorporated into the tolerogenic compound which may aid in reducing immune responses to self-antigens at multiple points along the enzymatic pathways that control myelination or myelin repair.

In several embodiments, the autoimmune disease is rheumatoid arthritis and X is selected from the group consisting of fibrinogen, vimentin, collagen type II, alpha enolase and fragments thereof.

In several embodiments, the autoimmune disease is vitiligo and X is selected from the group consisting of Pmel17, tyrosinase and fragments thereof.

In several embodiments, the autoimmune disease is uveitis and X is selected from the group consisting of retinal arrestin and interphotoreceptor retinoid-binding protein (IRBP) and fragments thereof.

In several embodiments, the autoimmune disease is pemphigus vulgaris and X is selected from the group consisting of desmoglein 3, 1 and 4, pemphaxin, desmocollins, plakoglobin, perplakin, desmoplakins, acetylcholine receptor and fragments thereof.

In several embodiments, the autoimmune disease is neuromyelitis optica and X is aquaporin-4 or a fragment thereof.

As discussed herein, mimotopes of any antigenic portion of the self-antigens above (or otherwise disclosed herein) can be used in several embodiments.

Also provided for in several embodiments is the use of the compounds disclosed above (or otherwise disclosed herein) for use in inducing tolerance to X.

There are also provided for in several embodiments herein pharmaceutically acceptable compositions comprising a compound disclosed above (or otherwise disclosed herein). There is also provided for the use of such compositions in inducing tolerance to X. In several embodiments, the pharmaceutically acceptable composition consists of, or consists essentially of a compound wherein X is a food antigen, therapeutic agent, a self antigen, or fragment thereof, a linker Y, and a liver targeting moiety Z selected from glucose, galactose, glucosamine, galactosamine, N-acetylglucosamine, and N-acetylgalactosamine.

Also provided for herein are methods of inducing tolerance to an antigen to which a subject is capable of developing an unwanted immune response, comprising administering a compounds disclosed above (or otherwise disclosed herein). In several embodiments, the compound is administered prior to the subject being exposed to the antigen. However, in several embodiments, the compound is administered after the subject has been exposed to the antigen. In several embodiments, the administration comprises at least one intravenous administration of the compound (e.g., a bolus dose followed by a series of optional maintenance doses).

In several embodiments, there is provided for the use of compounds disclosed above (or otherwise disclosed herein) in the preparation of a medicament for inducing tolerance to an antigen to which a subject develops an unwanted immune response or a tolerogenic portion thereof.

In several embodiments disclosed herein, there are provided compositions for inducing immune tolerance in a subject and methods and uses of the compositions for achieving the same. In several embodiments, immune tolerance is desired because a subject develops an unwanted immune response to an antigen. Depending on the embodiment, the antigen may be one or more of a variety of antigens, for example a foreign antigen such as a food antigen that is ingested, or an antigenic portion of a therapeutic drug given to a subject. In additional embodiments, the antigen may be a self-antigen that the subject's immune system fails to recognize (or only recognizes as self to a limited degree) and therefore mounts an immune response against, leading to autoimmune disorders.

In several embodiments, there is provided a composition comprising Formula 1:

Formula 1 wherein m is an integer from about 1 to 10, X comprises a food antigen, a therapeutic agent, a self-antigen, a fragment of any of such antigens, or a mimotope of any of such antigens, Y is of a linker moiety having the following formula:

Formula Yn

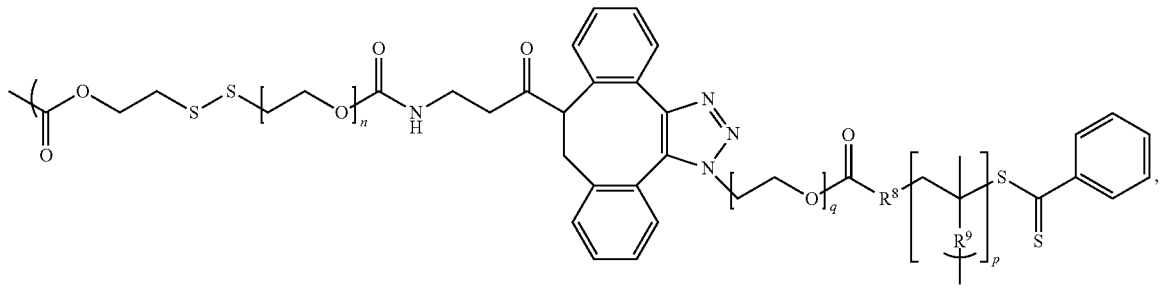

wherein: the left bracket "(" indicates a bond to X, the right or bottom bracket and ")" indicates the bond between Y and Z, n is an integer from about 70 to 85, where present p is an integer from about 85 to 95, where present q is an integer from about 1 to 10, where present $R^8$ is —$CH_2$— or —$CH_2$—$CH_2$—$C(CH_3)(CN)$—; and where present $R^9$ is a direct bond or —$CH_2$—$CH_2$—NH—C(O)—; and Z comprises a liver-targeting moiety comprising glucose or galactose. In several embodiments, m is between 1 and 3, n is 79, p is 90, and q is 4. In several embodiments, X is selected from the group consisting of insulin, proinsulin, preproinsulin, gluten, gliadin, myelin basic protein, myelin oligodendrocyte glycoprotein and proteolipid protein, Factor VIII, Factor IX, asparaginase, uricase and fragments of any of the preceding. In several embodiments, the composition comprises, consists of, or consists essentially of the antigen X, the linker Y and the liver targeting moiety Z.

In several embodiments, there is provided a compound comprising Formula 1:

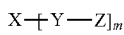

Formula 1 wherein m is an integer from about 1 to 10, X is selected from the group consisting of insulin, proinsulin, preproinsulin, gluten, gliadin, myelin basic protein, myelin oligodendrocyte glycoprotein and proteolipid protein, Factor VIII, Factor IX, asparaginase, uricase and fragments of any of the preceding, Y is of a linker moiety having the following formula:

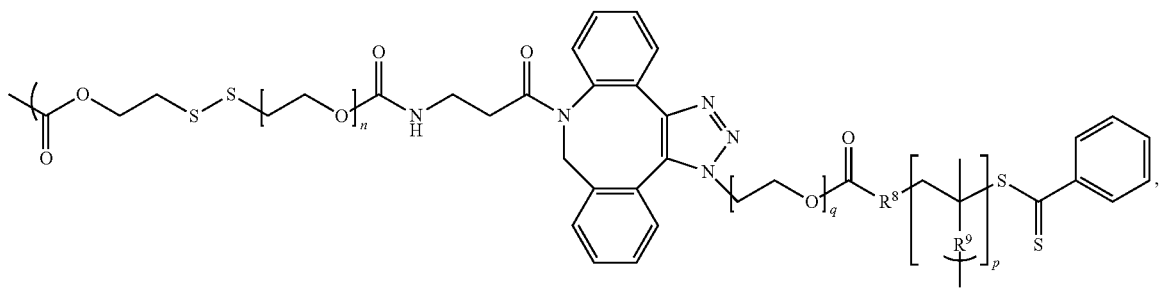

Formula Yn wherein, the left bracket "(" indicates a bond to X, the right or bottom bracket and ")" indicates the bond between Y and Z, n is an integer from about 70 to 85, where present p is an integer from about 85 to 95, where present q is an integer from about 1 to 10, where present $R^8$ is —$CH_2$— or —$CH_2$—$CH_2$—$C(CH_3)(CN)$—; and where present $R^9$ is a direct bond or —$CH_2$—$CH_2$—NH—C(O)—, and Z comprises a liver-targeting moiety comprising a sugar moiety. In several embodiments, m is between 1 and 3, n is 79, p is 90, and q is 4. In several embodiments, Z is selected from the group consisting of glucose, glucosamine, galactose, galactosamine, N-acetylgalactosamine and N-acetylglucosamine.

In several embodiments, 2,5-dioxopyrrolidin-1-yl propyl carbonate-linkers and/or 2-(ethyldisulfanyl)ethyl ethylcarbamate-linkers can be used.

In several embodiments, there is provided a composition comprising a compound of Formula 1:

Formula 1

X—(Y—Z]$_m$ wherein:

m is an integer from about 1 to 10;

X comprises an antigen to which patients develop an unwanted immune response, wherein the antigen is a food antigen, a therapeutic agent, a self-antigen, or a fragment of any of such antigens;

Y is of a linker moiety having a formula selected from the group consisting of:

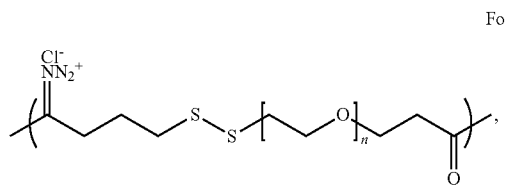

Formula Ya

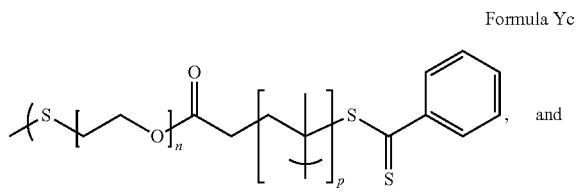

Formula Yc, and

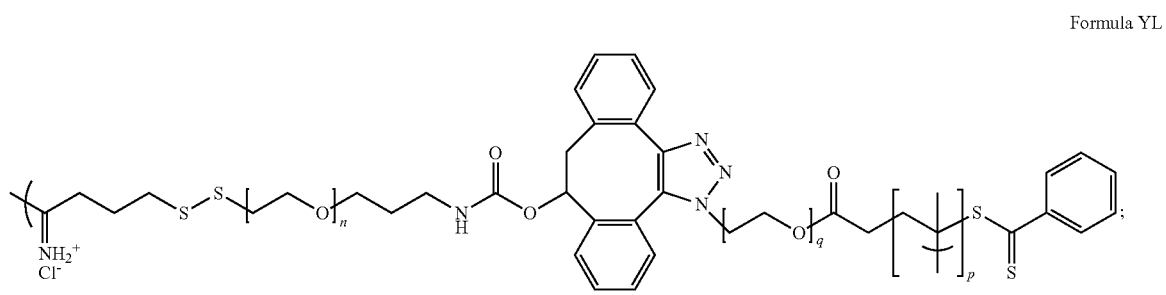

Formula YL;

wherein the left bracket "(" indicates a bond to X, where present the right ")" indicates a bond to Z, where present the bottom ")" indicates a bond to Z, where present n is an integer from about 1 to about 80, where present q is an integer from about 1 to about 4, where present p is an integer from about 1 to about 90, where present $R_8$ is —$CH_2$— or —$CH_2$—$CH_2$—$C(CH_3)(CN)$—, and Z comprises one or more liver-targeting moieties that specifically target liver cells expressing asialoglycoprotein receptors.

In several embodiments of the composition, m is 1 to 4, Y is of a linker moiety having a formula of:

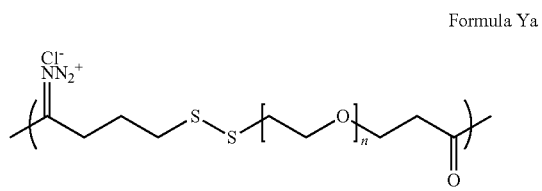

Formula Ya and Z comprises a liver-targeting moiety comprising one or more of galactose, galactosamine, or N-acetyl galactosamine.

In several embodiments, m is resolved to an integer from 1 to 4, Y is of a linker moiety having a formula of:

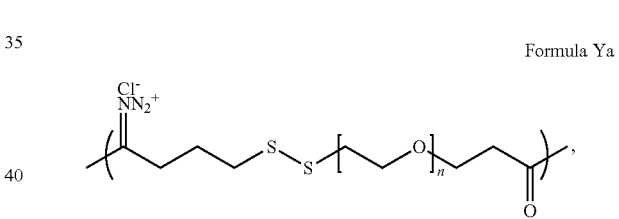

Formula Ya and Z comprises a liver-targeting moiety comprising one or more of glucose, glucosamine, or N-acetyl glucosamine.

In several embodiments, there is provided compositions of Formula 1 ($X-[Y-Z]_m$), where m is an integer from about 1 to 100, X comprises an antigen against which a patient develops an unwanted immune response, or a tolerogenic portion thereof or X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy, Y comprises a linker moiety, and Z comprises a liver-targeting moiety. In several embodiments, Z comprises galactose, galactosamine, N-acetylgalactosamine, glucose, glucosamine or N-acetylglucosamine.

In several embodiments, Y is selected from N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol) ester linkers. In some embodiments, Y comprises an antibody, antibody fragment, peptide or other ligand that specifically binds X, a disulfanyl ethyl ester, a structure represented by one of Formulae Ya to Yp:

Formula Ya
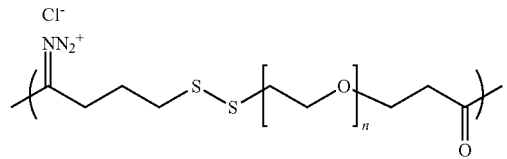
Formula Yb
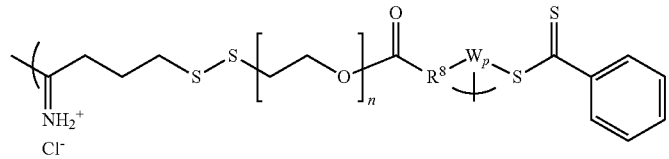
Formula Yc
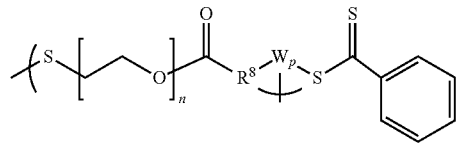
Formula Yd
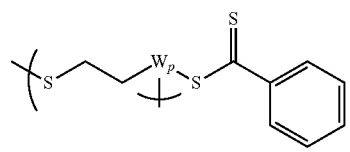
Formula Ye
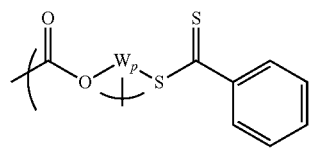
Formula Yf
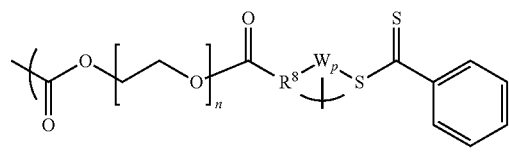
Formula Yg
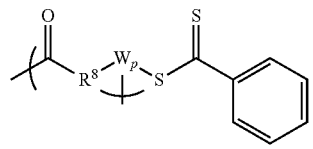
Formula Ym
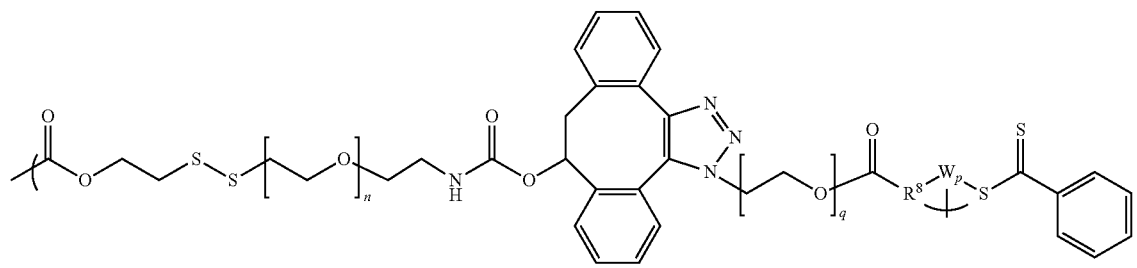
Formula Yh
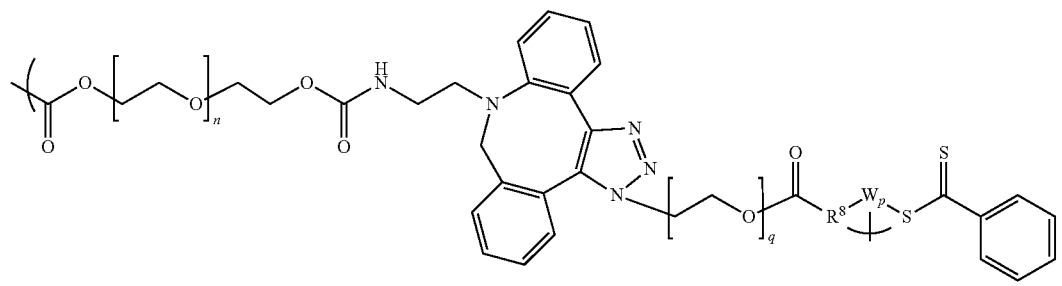

-continued
Formula Yi
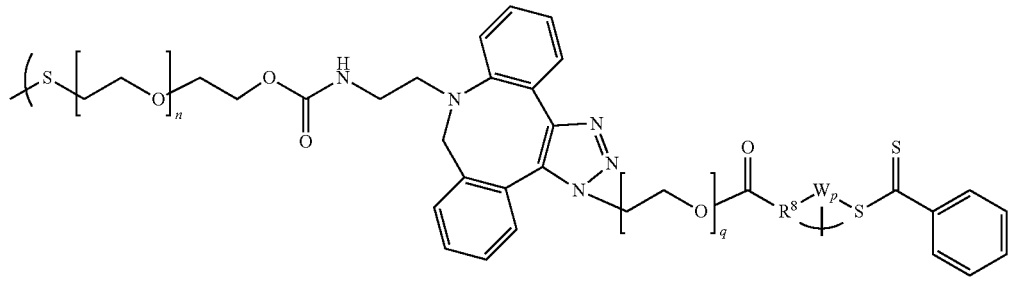
Formula Yj
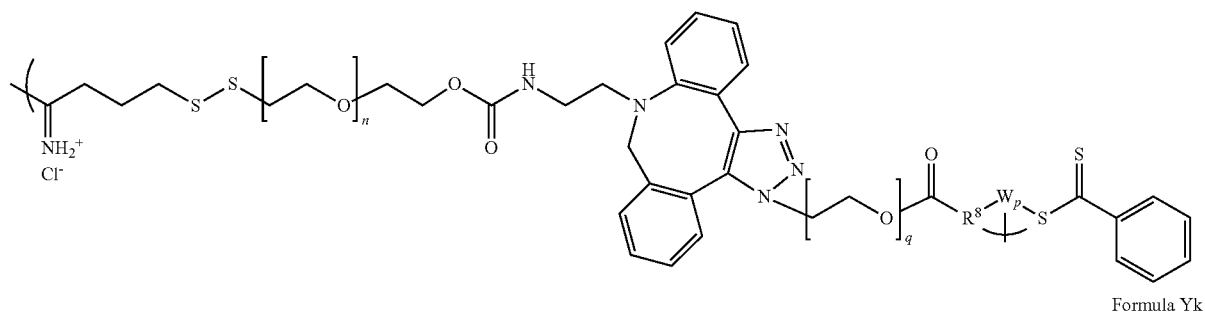
Formula Yk
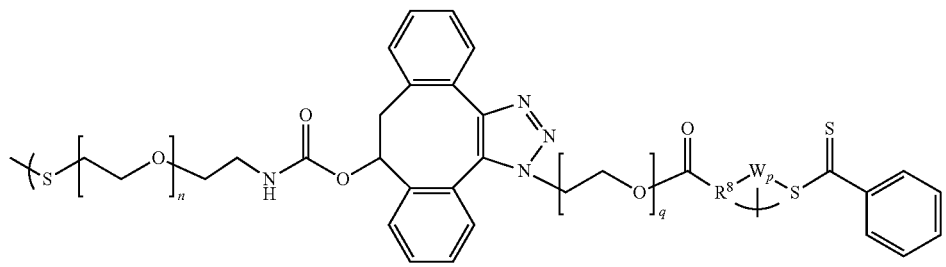
Formula YL
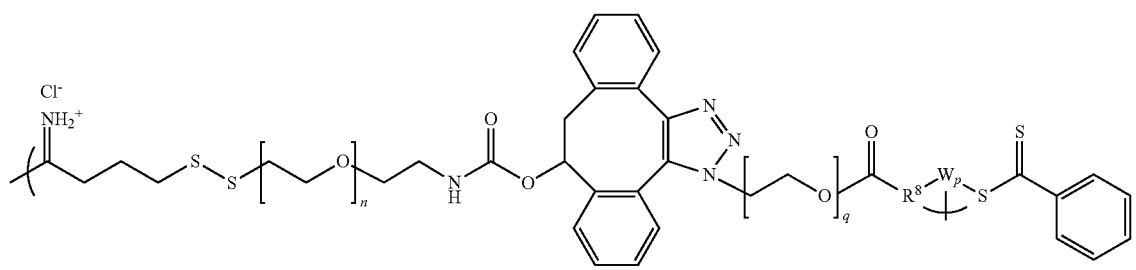
Formula Yn
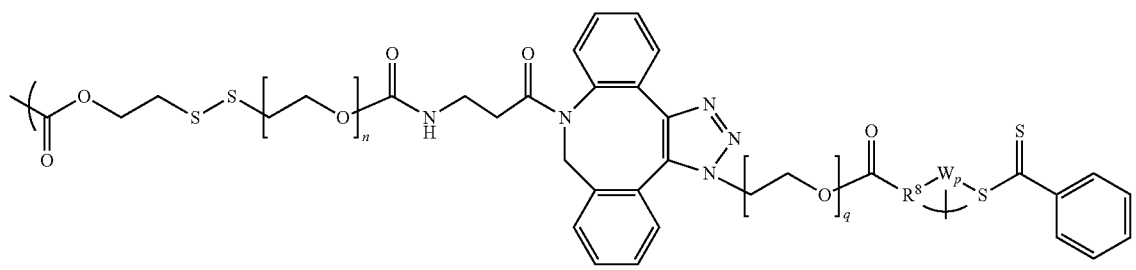
Formula Yo
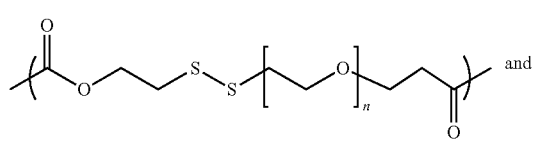
and
Formula Yp
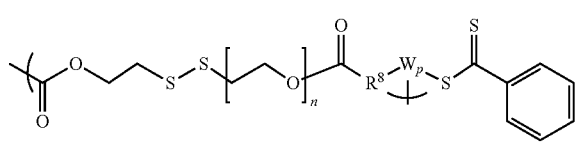

or Y has a portion represented by Formula Y'-CMP:

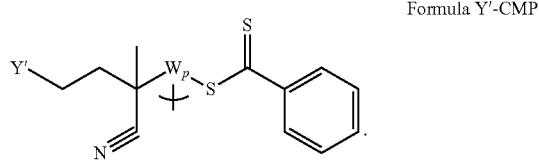

Formula Y'-CMP

In such embodiments, the left bracket "(" indicates the bond between X and Y, the right or bottom bracket and ")" indicates the bond between Y and Z, n is an integer from about 1 to 100, q is an integer from about 1 to 44, $R^8$ is —$CH_2$— or —$CH_2$—$CH_2$—$C(CH_3)(CN)$—, Y' represents the remaining portion of Y; and W represents a polymer of the same $W^1$ group, or W is a copolymer or a random copolymer of the same or different $W^1$ and $W^2$ groups, where:

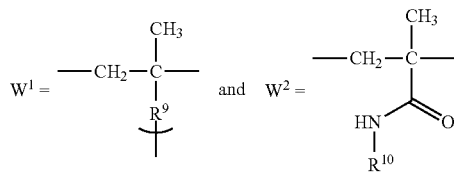

and where p is an integer from 2 to about 150, $R^9$ is a direct bond, —$CH_2$—$CH_2$—NH—C(O)— or —$CH_2$—$CH_2$—(O—$CH_2$—$CH_2$)$_t$—NH—C(O)—, t is an integer from 1 to 5; and $R^{10}$ is an aliphatic group, an alcohol or an aliphatic alcohol. In one such embodiment, m is 1 to 3, Y is represented by Formula Ym, wherein $R^8$ is —$CH_2$—$CH_2$—$C(CH_3)(CN)$—, and W is represented by a block copolymer of $W^1$ and $W^2$ where $R^9$ is —$CH_2$—$CH_2$—(O—$CH_2$—$CH_2$)$_t$—NH—C(O)—, t is 1, and $R^{10}$ is 2-hydroxypropyl; and Z comprises a liver-targeting moiety comprising one or more of galactose, galactosamine, N-acetylgalactosamine, glucose, glucosamine, N-acetylglucosamine. In several embodiments, Z is the β-anomer of the corresponding sugar.

In several additional embodiments compositions are provided for inducing tolerance to an antigen to which a subject develops an unwanted immune response, the compositions comprising a compound of Formula 1 (Formula 1 (X—[Y—Z]$_m$), where m is an integer from about 1 to 10, X comprises an antigen to which patients develop an unwanted immune response, wherein the antigen is a food antigen, a therapeutic agent, a self-antigen, or a fragment of any of such antigens, Y is of a linker moiety having a formula selected from the group consisting of:

Formula Ya

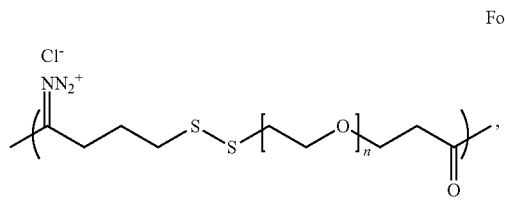

Formula Yc

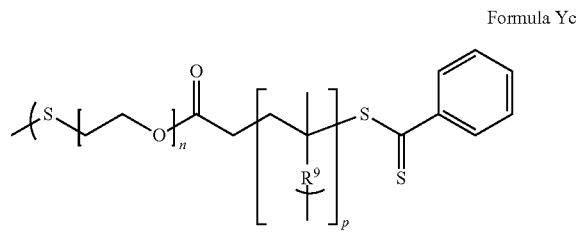

Formula Ym

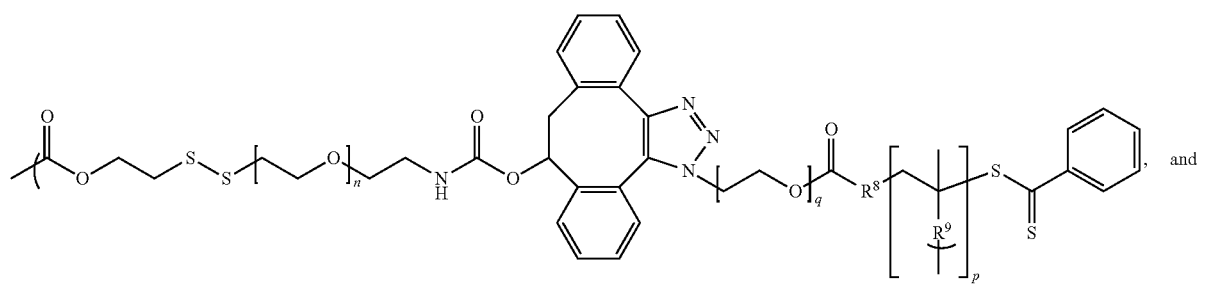

and

Formula Yn

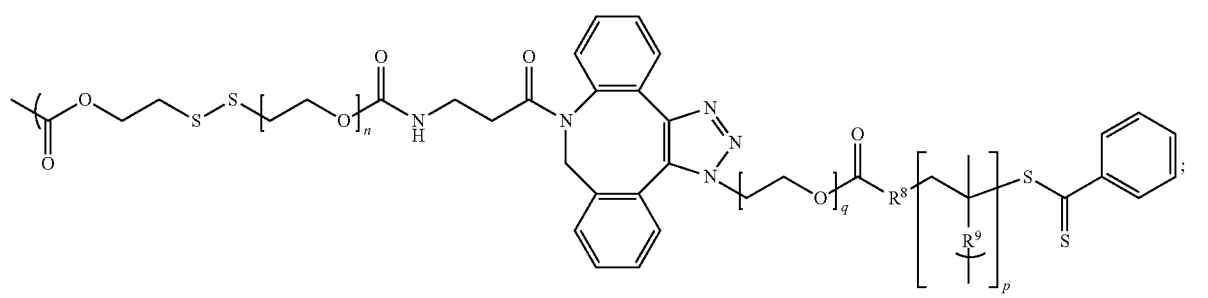

;

wherein the left bracket "(" indicates a bond to X, the right or bottom bracket and ")" indicates the bond between Y and Z, n is an integer from about 1 to 100, where present p is an integer from about 2 to 150, where present q is an integer from about 1 to 44, where present R$^8$ is —CH$_2$— or —CH$_2$—CH$_2$—C(CH$_3$)(CN)—, and where present R$^9$ is a direct bond or —CH$_2$—CH$_2$—NH—C(O)—, and Z comprises galactose, galactosamine, or N-acetylgalactosamine.

In several embodiments of such compositions, m is 1 to 3, Y is of a linker moiety having a formula of:

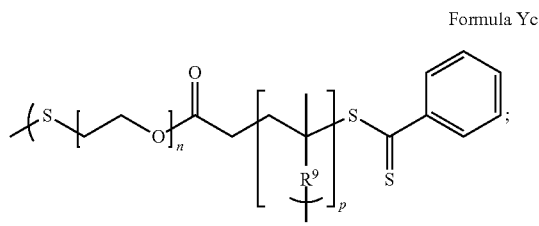

Formula Yc wherein CH$_2$—CH$_2$—NH—C(O)—; and Z comprises a liver-targeting moiety comprising one or more of galactose, galactosamine, or N-acetylgalactosamine. In several embodiments, Z is the β-anomer of the selected moiety.

As discussed above, in several embodiments, X is a self-antigen and the unwanted immune response is an autoimmune response.

A variety of self-antigens is disclosed herein, but in several particular embodiments, X is myelin oligodendrocyte glycoprotein or myelin proteolipid protein. In such embodiments, the unwanted immune response experienced by the subject is associated with multiple sclerosis. In additional embodiments, X is insulin, proinsulin, or preproinsulin and wherein the unwanted immune response is associated with diabetes mellitus. It shall be appreciated that being associated with multiple sclerosis, diabetes mellitus or other auto-immune disease need not necessarily require a formal diagnosis of such auto-immune condition, but rather can be associated with common symptoms or characteristics of a particular auto-immune disorder.

In additional embodiments, as discussed herein, an unwanted immune response can be raised against a therapeutic agent, such as a protein drug or drug derived from non-human and/or non-mammalian species. For example, in several embodiments, X is a therapeutic agent, such as Factor VIII, Factor IX, or other hemostasis-inducing agent. In such embodiments, the unwanted immune response is against the agent and the associated disease is hemophilia, which fails to improve (in the absence of the composition) because of the autoimmune response. However, upon administration of the composition, the hemophilia can improve because the composition aids in inducing tolerance to the agent, reducing the response to agent, and allowing reduced symptoms of hemophilia. In still additional embodiments, X is a therapeutic agent such as asparaginase and uricase. As discussed above, an unwanted immune response can result from administration of such agents, as they are derived from non-human sources. The ability of the compositions disclosed herein to induce tolerance to these agents allows these agents to continue to be used by a subject in need of therapy, while the side effects from an immune reaction are reduced, lessened, eliminated or otherwise ameliorated.

In several embodiments, X is a food antigen. Many food antigens are known to cause allergies upon ingestion, however, in several embodiments, X is selected from the group consisting of conarachin (Ara h 1), allergen II (Ara h 2), arachis agglutinin, conglutin (Ara h 6), a-lactalbumin (ALA), lactotransferrin, Pen a 1 allergen (Pen a 1), allergen Pen m 2 (Pen m 2), tropomyosin fast isoform, high molecular weight glutenin, low molecular weight glutenin, alpha-gliadin, gamma-gliadin, omega-gliadin, hordein, seclain, and avenin. In several embodiments, treatment with the compositions disclosed herein where X is a food antigen allows the subject to have a significantly reduced immune response to the antigen, e.g., many peanut allergies are so severe that exposure to peanut dust or oil can cause anaphylaxis. In some embodiments, treatment reduces and/or eliminates responses to such incidental exposure to the antigen. In additional embodiments, treatment allows the subject to ingest the food from which the antigen is derived with limited or no adverse immune response.

In several embodiments, administration of the composition to the subject results in a greater degree of proliferation of antigen-specific T cells as compared to proliferation of antigen-specific T cells resulting from administration of the antigen alone. In such embodiments, the proliferation of antigen-specific T cells indicates that delivery of the antigen (via the composition) to the molecular processing machinery that processes antigens as self/non-self is enhanced versus administration of the antigen alone. In other words, in such embodiments the targeted delivery is effective. In still additional embodiments, administration of the compositions disclosed herein results in a greater expression of exhaustion markers or markers of apoptosis on antigen-specific T cells as compared to expression of exhaustion markers or markers of apoptosis on antigen-specific T cells resulting from administration of the antigen alone. This result in indicative of specific reduction in activity of T cells directed against the antigen of interest and/or deletion of T cells directed against the antigen of interest. In several embodiments, these molecular hallmarks of induction of tolerance are the precursor of the reduction or amelioration of immune response symptoms that the subject would have previously experienced when exposed to the antigen.

In several embodiments, Z comprises a liver-targeting moiety that is a carbohydrate. In several embodiments, the carbohydrate is a short-chain carbohydrate. In several embodiments, Z is a sugar. In several embodiments, Z is galactose, galactosamine, N-acetylgalactosamine, glucose, glucosamine, or N-acetylglucosamine. In several embodiments, the induction of immune tolerance is greater when a glucose, glucosamine, or N-acetylglucosamine is used for Z. In still additional embodiments, enhancements in induction of immune tolerance can be achieved when the liver targeting moiety is a sugar and the sugar is in the 6-anomer configuration. In several embodiments, Z is galactose, galactosamine, N-acetylgalactosamine, glucose, glucosamine, or N-acetylglucosamine and conjugated at its C1, C2 or C6 to Y.

Also provided herein are methods of inducing tolerance to antigens which, when administered alone (e.g., without the presently disclosed compositions) would result in an adverse immune response. Such methods, depending on the embodiments, involved the administration either before, or after, exposure to the antigen. In several embodiments, administration prior to exposure serves a prophylactic effect, which in several embodiments essentially avoids or significantly reduces in the immune response. Administration of the compositions can be via a variety of methods, including, but not limited to intravenous, intramuscular, oral, transdermal, or other infusion route. Administration can be daily, weekly, multiple times per day, or on an as needed basis (e.g., prior to an anticipated exposure).

Also provided for herein are uses of the compositions disclosed herein for the treatment of unwanted immune responses after exposure to an antigen. As discussed herein, such use can be for prophylactic effects and/or for reducing symptoms from prior exposure to antigens (or prior adverse immune effects, such as those in the auto-immune setting). For example, provided herein are uses of compositions according to Formula 1 for the treatment of unwanted side effects due to exposure to a therapeutic antigen, exposure to a food antigen, or an adverse effect from an immune response against a self-antigen. The compositions disclosed herein are suitable for administration to a subject in conjunction with such use, for example by oral, IV, IM, or other suitable route. Uses of the compositions disclosed herein, in several embodiments, unexpectedly result in the reduction, elimination or amelioration of adverse immune responses to antigens of interest.

Additional compositions and methods of using them are provided herein. For example, in several embodiments, there is provided a pharmaceutically acceptable composition for inducing tolerance to a therapeutic protein in a subject having an deficiency in production of a functional analogous native protein, comprising a compound of Formula 1 (X—[—Y—Z]$_m$), where m is an integer from about 1 to 10, X comprises an antigenic protein or protein fragment, Y is of a linker moiety having a formula selected from the group consisting of Formula Ya, Formula Yc, Formula Ym, Formula Yn, wherein, the left bracket "(" indicates a bond to X, the right or bottom bracket and ")" indicates the bond between Y and Z, n is an integer from about 1 to 100, where present p is an integer from about 2 to 150, where present q is an integer from about 1 to 44, where present $R^8$ is —CH$_2$— or —CH$_2$—CH$_2$—C(CH$_3$)(CN)—, where present $R^9$ is a direct bond or —CH$_2$—CH$_2$—NH—C(O)—, and Z comprises galactose, galactosamine, or N-acetylgalactosamine.

In several embodiments of the composition, m is 1 to 3, Y is of a linker moiety having a formula of:

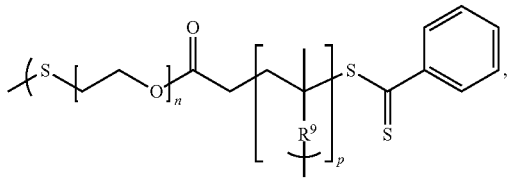

Formula Yc wherein CH$_2$—CH$_2$—NH—C(O)—, and Z comprises a liver-targeting moiety comprising one or more of glucose, glucosamine, N-acetylglucosamine, galactose, galactosamine, or N-acetylgalactosamine. In several embodiments, the galactose, galactosamine, or N-acetylgalactosamine are the β-anomers. In several embodiments, combinations of galactose, galactosamine, N-acetylgalactosamine, glucose, glucosamine, or N-acetylglucosamine are used.

Also provided for herein is a pharmaceutically acceptable composition for inducing tolerance to a therapeutic protein in a subject having an deficiency in production of a functional analogous native protein, comprising a compound of Formula 1 (X—[—Y—Z]$_m$), where m is an integer from about 1 to 10, X comprises a antigenic protein or protein fragment, Y is of a linker moiety having a formula selected from the group consisting of Formula Ya, Formula Yc, Formula Ym, or Formula Ym, wherein the left bracket "(" indicates a bond to X, where present the right ")" indicates a bond to Z, where present the bottom ")" indicates a bond to Z, where present n is an integer from about 1 to about 80, where present q is an integer from about 1 to about 4, where present p is an integer from about 1 to about 90, where present $R^8$ is —CH$_2$— or —CH$_2$—CH$_2$—C(CH$_3$)(CN)—, and where present W represents a polymer of the Formula $W^1$ or $W^2$ group or W is a copolymer of Formula $W^1$ or $W^2$ where:

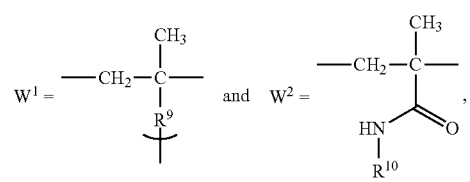

where $R^9$ is a direct bond, —CH$_2$—CH$_2$—NH—C(O)— or —CH$_2$—CH$_2$—(O—CH$_2$—CH$_2$)$_t$—NH—C(O)—, t is an integer from 1 to 5, $R^{10}$ is an aliphatic group, an alcohol or an aliphatic alcohol; and Z comprises glucose, glucosamine, N-acetylglucosamine, galactose, galactosamine, or N-acetylgalactosamine. In several embodiments, the galactose, galactosamine, or N-acetylgalactosamine are the β-anomers. In several embodiments, combinations of galactose, galactosamine, N-acetylgalactosamine, glucose, glucosamine, or N-acetylglucosamine are used. In several embodiments of the composition, m is 1 to 3, Y is represented by Formula Ym, wherein $R^8$ is —CH$_2$—CH$_2$—C(CH$_3$)(CN)—, and W is represented by a block copolymer of $W^1$ and $W^2$ where $R^9$ is —CH$_2$—CH$_2$—(O—CH$_2$—CH$_2$)$_t$—NH—C(O)—, t is 1, and $R^{10}$ is 2-hydroxypropyl; and Z comprises a liver-targeting moiety comprising one or more of glucose, glucosamine, N-acetylglucosamine, galactose, galactosamine, or N-acetylgalactosamine. In several embodiments, the galactose, galactosamine, or N-acetylgalactosamine are the β-anomers. In several embodiments, combinations of galactose, galactosamine, N-acetylgalactosamine, glucose, glucosamine, or N-acetylglucosamine are used.

In several embodiments, X comprises an antigenic region of myelin basic protein, myelin oligodendrocyte glycoprotein, or myelin proteolipid protein. In additional embodiments, X comprises an antigenic region of Factor VIII, Factor IX, insulin, uricase, PAL, or asparaginase. In additional embodiments, X comprises a foreign antigen such as conarachin (Ara h 1), allergen II (Ara h 2), arachis agglutinin, conglutin (Ara h 6), a-lactalbumin (ALA), lactotransferrin, Pen a 1 allergen (Pen a 1), allergen Pen m 2 (Pen m 2), tropomyosin fast isoform, high molecular weight glutenin, low molecular weight glutenin, alpha-gliadin, gamma-gliadin, omega-gliadin, hordein, seclain, and avenin.

Additionally provided for herein are compositions comprising a compound of Formula 1 (X—[—Y—Z]m), where m is an integer from about 1 to 100, X comprises an antigen against which a patient develops an unwanted immune response, or a tolerogenic portion thereof, or X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy, Y comprises a linker moiety, and Z comprises a liver-targeting moiety.

In several embodiments, Z galactose, galactosamine, N-acetylgalactosamine, glucose, glucosamine or N-acetylglucosamine. Combinations of galactose, galactosamine, N-acetylgalactosamine, glucose, glucosamine or N-acetylglucosamine may also be used, in several embodiments. Further, in several embodiments, the galactose, galactosamine, N-acetylgalactosamine, glucose, glucosamine or N-acetylglucosamine are optionally the β anomer. In several embodiments, Z is conjugated at its C1, C2 or C6 to Y.

In several embodiments, Y is selected from N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol) ester linkers. In several embodiments, Y comprises an antibody, antibody fragment, peptide or other ligand that specifically binds X, a disulfanyl ethyl ester, a structure represented by one of Formulae Ya to Yp, or Y has a portion represented by Formula Y'-CMP:

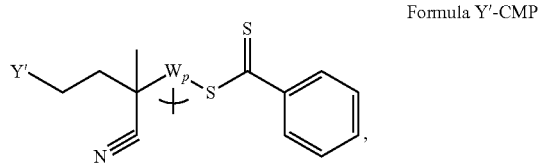

Formula Y'-CMP where the left bracket "(" indicates the bond between X and Y, the right or bottom bracket and ")" indicates the bond between Y and Z, n is an integer from about 1 to 100, q is an integer from about 1 to 44, $R^8$ is —CH$_2$— or —CH$_2$—CH$_2$—C(CH$_3$)(CN)—, Y' represents the remaining portion of Y, and W represents a polymer of the same $W^1$ group, or W is a copolymer or a random copolymer of the same or different $W^1$ and $W^2$ groups, where:

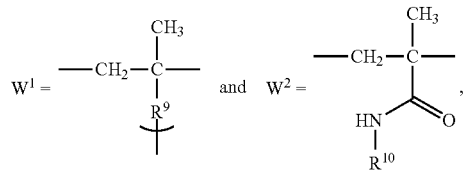

where p is an integer from 2 to about 150, $R^9$ is a direct bond, —CH$_2$—CH$_2$—NH—C(O)— or —CH$_2$—CH$_2$—(O—CH$_2$—CH$_2$)$_t$—NH—C(O)—, t is an integer from 1 to 5; and $R^{19}$ is an aliphatic group, an alcohol or an aliphatic alcohol.

In some such embodiments, n is about 40 to 80, p is about 10 to 100, q is about 3 to 20, $R^8$ is —CH$_2$—CH$_2$—C(CH$_3$)(CN)—, when R9 is —CH$_2$—CH$_2$—NH—C(O)—, Z is glucose, galactose, N-acetylgalactosamine or N-acetylglucosamine conjugated at its C1, and when W is a copolymer, R10 is 2-hydroxypropyl. In some embodiments, Y comprises Formula Ya, Formula Yb, Formula Yc, Formula Yf, Formula Yg, Formula Yh, Formula Yi, Formula Yk, Formula Ym or Formula Yn. In some embodiments, Y comprises Formula Ya, Formula Yb, Formula Yc, Formula Ym or Formula Yn. In still additional embodiments, Y comprises Formula Ya, Formula Yb, Formula Yc, Formula Ym or Formula Yn.

In several embodiments, X comprises a foreign transplant antigen against which transplant recipients develop an unwanted immune response, a foreign food, animal, plant or environmental antigen against which patients develop an unwanted immune response, a foreign therapeutic agent against which patients develop an unwanted immune response, or a synthetic self-antigen against the endogenous version of which patients develop an unwanted immune response, or a tolerogenic portion thereof. Specific examples of various antigens are disclosed herein.

Also provided for herein is are methods of treatment for an unwanted immune response against an antigen by administering to a mammal in need of such treatment an effective amount of a composition comprising a compound of Formula 1 (X—[—Y—Z]m), where m is an integer from about 1 to 100, X comprises an antigen against which a patient develops an unwanted immune response, or a tolerogenic portion thereof or X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy, Y comprises a linker moiety, and Z comprises a glucosylated liver-targeting moiety.

In several such embodiments, X comprises an antigen against which a patient develops an unwanted immune response, or a tolerogenic portion thereof, and Y comprises, an antibody, antibody fragment, peptide or other ligand that specifically binds X, a disulfanyl ethyl ester, a structure represented by one of Formulae Ya to Yp or Y has a portion represented by Formula Y'-CMP where, the left bracket "(" indicates the bond between X and Y, the right or bottom bracket and ")" indicates the bond between Y and Z, n is an integer from about 1 to 100, q is an integer from about 1 to 44, $R^8$ is —CH$_2$— or —CH$_2$—CH$_2$—C(CH$_3$)(CN)—, Y' represents the remaining portion of Y, and W represents a polymer of the same $W^1$ group, or W is a copolymer or a random copolymer of the same or different $W^1$ and $W^2$ groups, where:

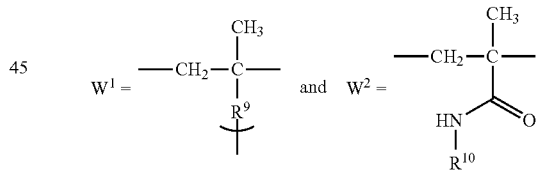

where p is an integer from 2 to about 150, $R^9$ is a direct bond, —CH$_2$—CH$_2$—NH—C(O)— or —CH$_2$—CH$_2$—(O—CH$_2$—CH$_2$)$_t$—NH—C(O)—, t is an integer from 1 to 5, and $R^{10}$ is an aliphatic group, an alcohol or an aliphatic alcohol. In several such treatment method embodiments, X comprises the antibody, antibody fragment or ligand, and the composition is administered for clearance of a circulating protein or peptide or antibody that specifically binds to X, which circulating protein or peptide or antibody is causatively involved in transplant rejection, immune response against a therapeutic agent, autoimmune disease, hypersensitivity and/or allergy.

In still additional embodiments, X comprises the antibody, antibody fragment or ligand, and the composition is administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration.

In several such treatment embodiments, compositions are administered for tolerization of the patient with respect to antigen moiety X.

In several embodiments X comprises a foreign transplant antigen against which transplant recipients develop an unwanted immune response, a foreign food, animal, plant or environmental antigen against which patients develop an unwanted immune response, a foreign therapeutic agent against which patients develop an unwanted immune response, or a synthetic self-antigen against the endogenous version of which patients develop an unwanted immune response, or a tolerogenic portion thereof.

Several embodiments disclosed herein provide a composition comprising a compound of Formula 1:

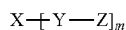

Formula 1 where:
m is an integer from about 1 to 100;
X comprises an antigen against which a patient develops an unwanted immune response, or a tolerogenic portion thereof; or
X comprises an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy;
Y comprises a linker moiety; and
Z comprises a liver-targeting moiety.

Z can also comprise galactose, galactosamine, N-acetylgalactosamine, glucose, glucosamine or N-acetylglucosamine, for example, conjugated at its C1, C2 or C6 to Y. N-acetylglucosamine and glucose bind to different lectin receptors as do N-acetylgalactosamine and galactose. In the examples below the experimental data (and the full disclosure of this application) indicate that the selection of Z as N-acetylglucosamine leads to elevated levels of regulatory T cell responses compared to those achieved with N-acetylgalactosamine. In several embodiments, this results in unexpectedly enhanced induction of immune tolerance and/or clearance of antigens from the blood of a subject.

Y can be selected from N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, and nitrophenoxy poly(ethylene glycol)ester linkers.

Y can also comprise: an antibody, antibody fragment, peptide or other ligand that specifically binds X; a disulfanyl ethyl ester; a structure represented by one of Formulae Ya to Yp:

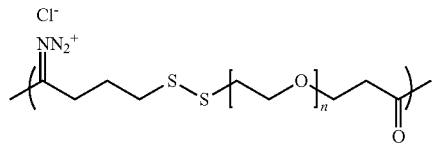

Formula Ya

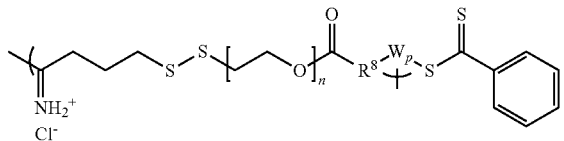

Formula Yb

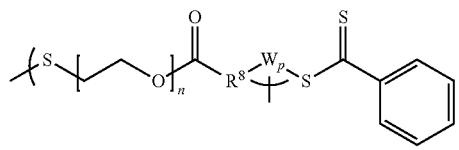

Formula Yc

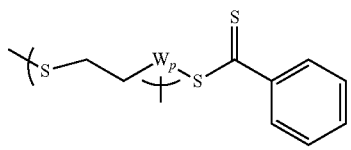

Formula Yd

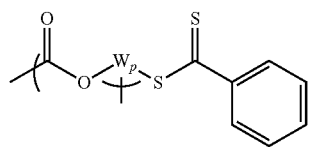

Formula Ye

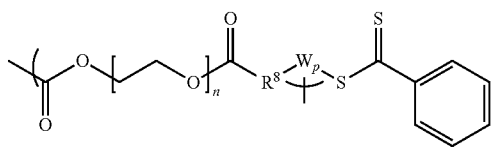

Formula Yf

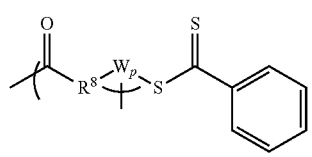

Formula Yg

-continued
Formula Yh
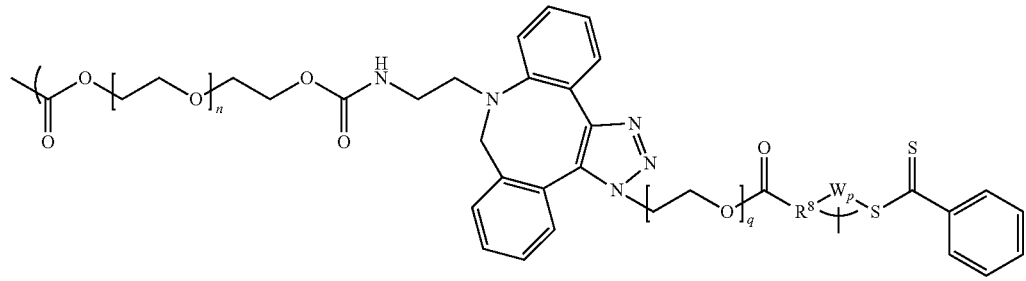
Formula Yi
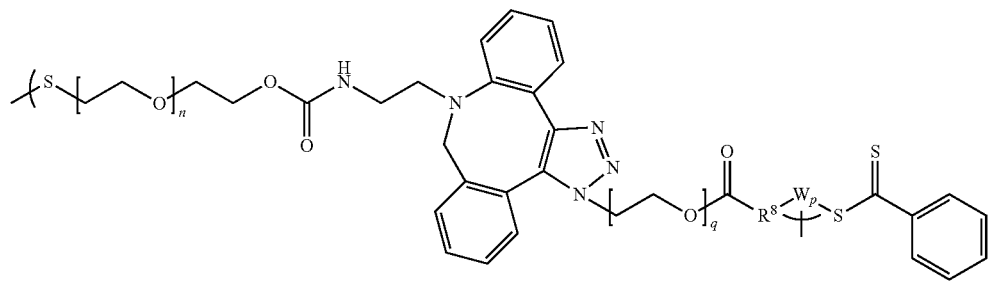
Formula Yj
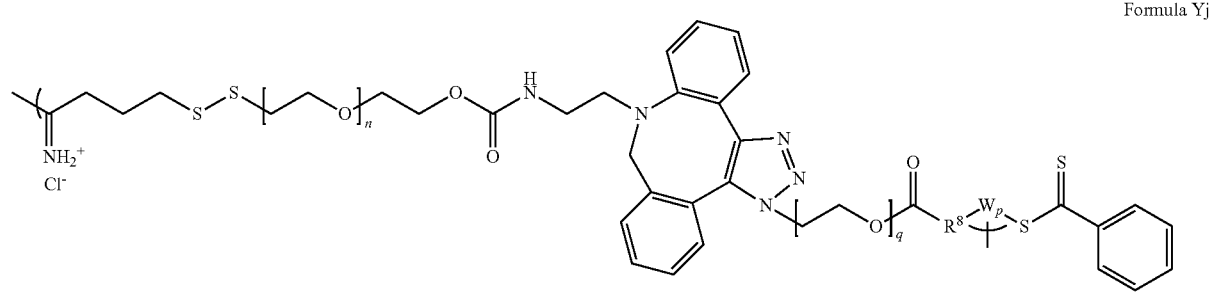
Formula Yk
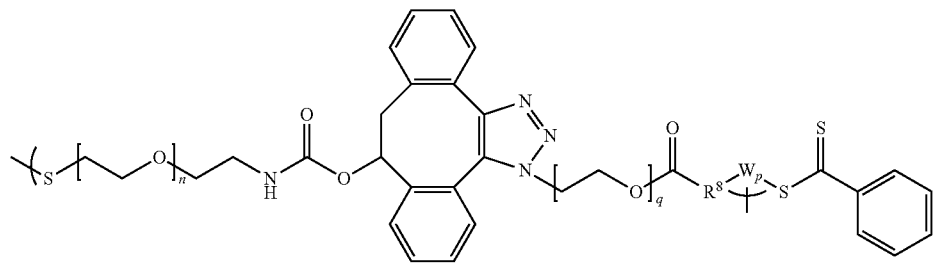
Formula YL
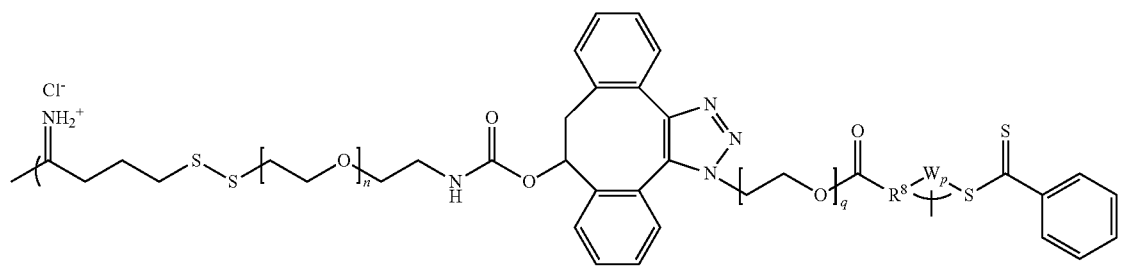

-continued

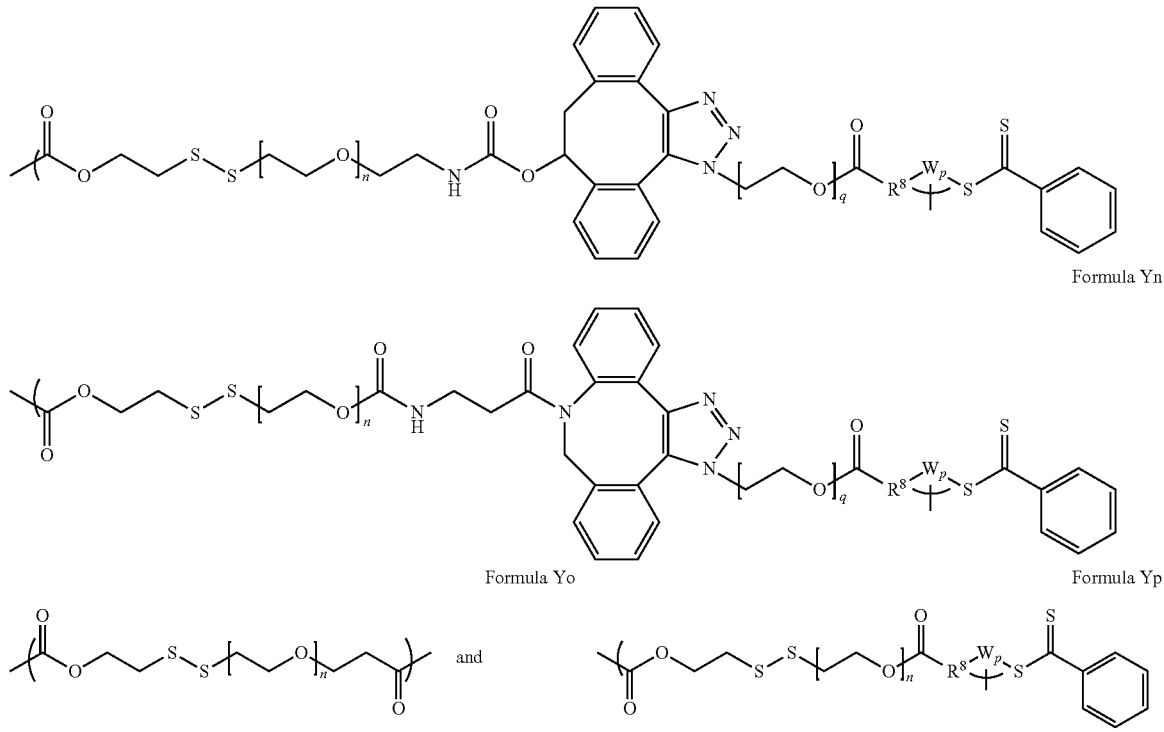

Formula Ym

Formula Yn

Formula Yo

Formula Yp or Y has a portion represented by Formula Y'-CMP:

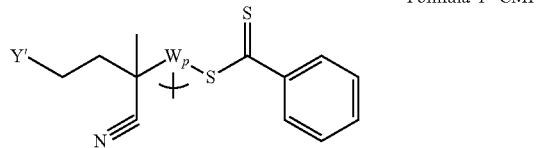

Formula Y'-CMP where:
the left bracket "(" indicates the bond between X and Y;
the right or bottom bracket and ")" indicates the bond between Y and Z;
n is an integer from about 1 to 100;
q is an integer from about 1 to 44;
$R^8$ is —$CH_2$— or —$CH_2$—$CH_2$—$C(CH_3)(CN)$—;
Y' represents the remaining portion of Y (e.g., HS-PEG); and
W represents a polymer of the same $W^1$ group, or W is a copolymer (preferably a random copolymer) of the same or different $W^1$ and $W^2$ groups, where:

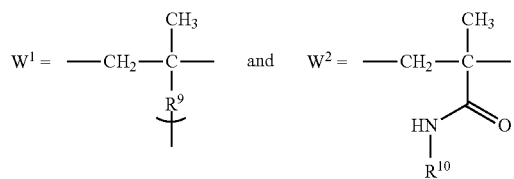

where:
p is an integer from 2 to about 150;
$R^9$ is a direct bond, —$CH_2$—$CH_2$—NH—C(O)— (i.e., an ethylacetamido group or "EtAcN") or —$CH_2$—$CH_2$—(O—$CH_2$—$CH_2$)$_t$—NH—C(O)— (i.e., a pegylated ethylacetamido group or "Et-PEG$_t$-AcN")
t is an integer from 1 to 5, (particularly 1 to 3, and more particularly 1 or 2); and
$R^{10}$ is an aliphatic group, an alcohol or an aliphatic alcohol. In some embodiments, $R^{10}$ is a $C_f$alkyl or $C_f$alkylOH$_g$ where f is independently an integer between 0 and 10 and g is independently an integer between 0 and 10. In some embodiments, $R^{10}$ is 2-hydroxypropyl.

In several embodiments, particular linkers are preferred. For example, in several embodiments, linkers according to Ym yield unexpectedly effective tolerance endpoints. In additional embodiments, linkers according to formula Yn yield unexpectedly effective tolerance endpoints. In still additional embodiments, formulations of F1m'-OVA-m$_{1-3}$-n$_{79}$-p$_{90}$-q$_4$-CMP-poly-(EtPEG$_1$AcN-1NAcGLU$_{30}$-ran-HPMA$_{60}$ achieve particularly effective tolerance-associated endpoints. In several embodiments, combinations of these linkers lead to synergistic results and still further unexpected increases in immune tolerance induction.

In another aspect of the above, n is about 40 to 80, p is about 10 to 100, q is about 3 to 20, $R^8$ is —$CH_2$—$CH_2$—$C(CH_3)(CN)$—; and when $R^9$ is —$CH_2$—$CH_2$—NH—C(O)—, Z is galactose or N-acetylgalactosamine conjugated at its C1.

In still another aspect of the above, Y comprises Formula Ya, Formula Yb, Formula Yh, Formula Yi, Formula Yk, Formula Ym or Formula Yn, particularly Formula Ya, Formula Yb, Formula Ym or Formula Yn.

X can further comprise: a foreign transplant antigen against which transplant recipients develop an unwanted immune response; a foreign food, animal, plant or environmental antigen against which patients develop an unwanted immune response; a foreign therapeutic agent against which patients develop an unwanted immune response; or a synthetic self-antigen against the endogenous version of which patients develop an unwanted immune response, or a tolerogenic portion thereof.

The disclosure also pertains to a method of treatment for an unwanted immune response against an antigen by administering to a mammal in need of such treatment an effective amount of a composition comprising a compound of Formula 1 as disclosed herein. In some such methods the composition can be administered for clearance of a circulating protein or peptide or antibody that specifically binds to antigen moiety X, which circulating protein or peptide or antibody is causatively involved in transplant rejection, immune response against a therapeutic agent, autoimmune disease, hypersensitivity and/or allergy. The composition can be administered in an amount effective to reduce a concentration of the antibodies that are causatively involved in transplant rejection, immune response against a therapeutic agent, autoimmune disease, hypersensitivity and/or allergy in blood of the patient by at least 50% w/w, as measured at a time between about 12 to about 48 hours after the administration. The composition can administered for tolerization of a patient with respect to antigen moiety X.

BRIEF DESCRIPTION OF THE DRAWINGS

FIG. 1A depicts that F1aA-PE-$m_4$-$n_{80}$ (Gal-PE) preferentially targets PE to sinusoidal endothelial cells (LSECs) of the liver. FIG. 1B depicts that F1aA-PE-$m_4$-$n_{80}$ (Gal-PE) preferentially targets PE to Kupffer cells (KC) of the liver. FIG. 1C depicts that F1aA-PE-$m_4$-$n_{80}$ (Gal-PE) preferentially targets PE to hepatocytes. FIG. 1D depicts that F1aA-PE-$m_4$-$n_{80}$ (Gal-PE) preferentially targets PE to other antigen presenting cells (APCs) of the liver. *=P<0.05.

FIG. 3A shows the percentage of OT-I CD8$^+$ T cells expressing PD-1 ("PD1+") in generations of proliferating T cells treated with saline, OVA or F1aA-OVA-$m_4$-$n_{80}$ (GAL-OVA), with greatest level of PD-1 in the gal-OVA-treated group. FIG. 3B shows the percentage of OT-I CD8$^+$ T cells expressing phosphatidylserine (stained as "Annexin V+") in generations of proliferating T cells treated with saline, OVA or F1aA-OVA-$m_4$-$n_{80}$ (GAL-OVA), with greatest level of Annexin-V+ cells in the gal-OVA-treated group.

FIG. 6A shows the immune response in mice challenged with OVA and LPS. FIG. 6B shows the immune response in mice treated with OVA, while FIG. 6C shows the immune response in naïve mice. FIGS. 6D and 6E (respectively) show that F1aA-OVA-$m_4$-$n_{80}$ (mGal-OVA; 6D) and F1b-OVA-$m_1$-$n_{44}$-$p_{34}$ (pGal-OVA; 6E) are able to mitigate the OVA-specific immune response in draining lymph nodes after intradermal challenge with OVA and the adjuvant LPS. FIG. 6F is from a parent application and does not form a part of the present disclosure.

FIG. 7A shows size-exclusion HPLC traces of F1aA-OVA-$m_4$-$n_{80}$ (open triangles), F1b-OVA-$m_1$-$n_{44}$-$p_{34}$ (filled circles) and unconjugated OVA (solid line). Shift to the left represents an increase in molecular weight. FIG. 7B shows polyacrylamide gel demonstrating increased molecular weight after OVA conjugation: (1.) Unconjugated OVA, (2.) F1aA-OVA-$m_4$-$n_{80}$ and (3.) F1b-OVA-$m_1$-$n_{44}$-$p_{34}$.

FIGS. 8A-8B depict data related to the reduction in antigen-specific immune response after administration of F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ [labeled OVA-p(Glu-HPMA) and shown as filled circles] or F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ [labeled OVA-p(Gal-HPMA) and shown as filled diamonds]. FIG. 8A depicts flow cytometric detection of OTI CD8+ T-cell populations (CD3e$^+$/CD8$\alpha^+$/CD45.2$^+$) quantified from the draining lymph nodes (inguinal and popliteal) 4 days following antigen challenge in CD45.1$^+$ mice. Significant reductions in OT-I CD8+ T-cells were detected following administration of OVA-p(Gal-HPMA) and OVA-p(Glu-HPMA). FIG. 8B depicts flow cytometric detection of OTII CD4+ T-cell populations (CD3e$^+$/CD4$^+$/CD45.2$^+$) quantified from the draining lymph nodes (inguinal and popliteal) 4 d following antigen challenge in CD45.1$^+$ mice. Significant reductions in OT-II CD4+ T-cells were detected following administration of OVA-p(Gal-HPMA) and OVA-p (Glu-HPMA) *=P<0.05, **=P<0.01; #=P<0.05, ##=P<0.01 (#'s represent significance as compared to naïve animals).

FIGS. 9A-9B depict data related to the increase in antigen-specific regulatory T-cells in the lymph nodes and spleen of mice after antigen challenge. FIG. 9A depicts flow cytometric detection of an F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ [labeled OVA-p(Glu-HPMA) and shown as filled circles] and F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ [labeled OVA-p(Gal-HPMA) and shown as filled diamonds]-induced increase in OTII T-regulator cells (CD3e+CD4+CD45.2+CD25+FoxP3+) collected from the lymph nodes 4 d following antigen challenge in CD45.1+ mice. FIG. 9B shows the corresponding analysis from the spleen of mice treated with OVA-p (Glu-HPMA) or OVA-p(Gal-HPMA) as compared to animals treated with OVA or saline (i.e. Challenge) *=P<0.05, =P<0.01; *=P<0.001; #=P<0.01, ##=P<0.01; ###=P<0.001 (#'s represent significance as compared to naïve animals).

FIG. 10 depicts flow cytometry data related to a decrease in the percentage of antigen-specific effector cells (IFNγ+ OTI CD8+ T-cells (CD3e+CD8α+CD45.2+IFNγ+) 4 d following antigen challenge in CD45.1+ mice. Mice treated with F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ [labeled OVA-p(Glu-HPMA) and shown as filled circles] or F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ [labeled OVA-p(Gal-HPMA) and shown as filled diamonds] conjugates generated significantly fewer IFNγ+ OTI CD8+ T-cells after antigen challenge as compared to mice treated with OVA or saline (i.e. Challenge) *=P<0.01, **=P<0.01; ##=P<0.01 (#'s represent significance as compared to naïve animals).

Figures 11A, 11B:
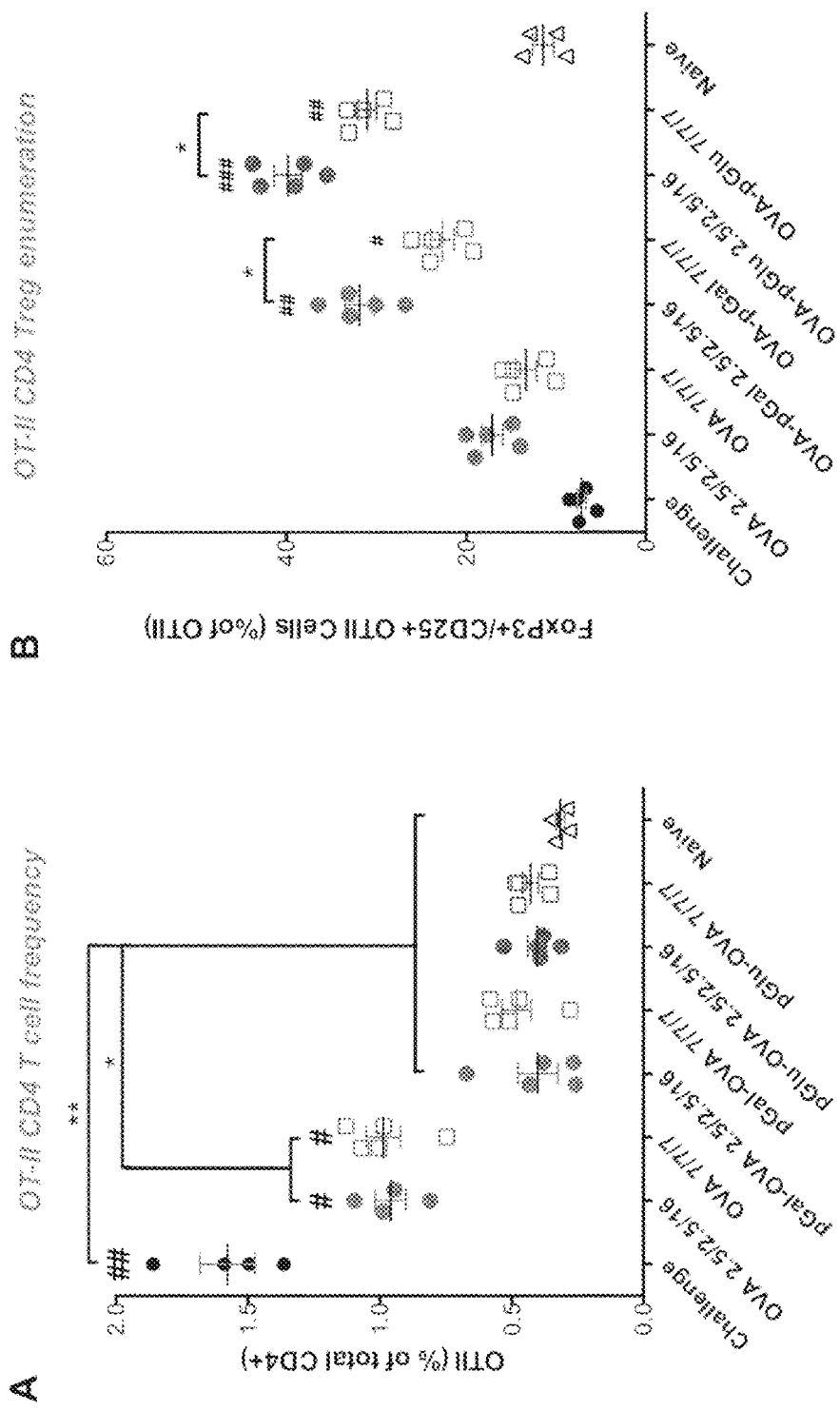

FIGS. 11A-11B depict data related to T cell deletion and regulation in an OTII adoptive transfer model, in which OTII cells (CD4$^+$ T cells from a CD45.2$^+$ mouse) are adoptively transferred into a CD45.1$^+$ recipient, which is treated with F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ ["OVA-p(Gal-HPMA)"] or F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ ["OVA-p(Glu-HPMA)"], or OVA not linked to a polymer ["OVA"] to induce T regulatory responses and prevent subsequent responses to vaccine-mediated antigen challenge. Both 3×10$^5$ CFSE-labeled OTI and 3×10$^5$ CFSE-labeled OTII cells were adoptively transferred to CD45.1$^+$ mice (n=8 mice per group) on day 0. On days 1, 4 and 7, tolerogenic doses or control doses were administered. In one regimen, OVA was provided at a dose of 2.5 µg at day 1, 2.5 µg at day 4, and 16 µg at day 7. In another, OVA was provided at a dose of 7 µg at day 1, 7 µg at day 4, and 7 µg at day 7, for the same total dose. Likewise, pGal-OVA and pGlu-OVA were each administered in other groups at the same dosings of 2.5 µg at day 1, 2.5 µg at day 4, and 16 µg at day 7 or 7 µg at day 1, 7 µg at day 4, and 7 µg at day 7, all doses being on an OVA equivalent dose basis. In a final group, saline was administered on the same days. On day 14, the recipient mice were then challenged with OVA (10 µg) adjuvanted with lipopolysaccharide (50 ng) by intradermal injection. Characterization of the draining lymph nodes was done on day 19, to allow determination as to whether or not deletion actually took place and whether regulatory T cells were induced from the adoptively transferred cells. FIG. 11A shows the number of OTII cells present after challenge, and FIG. 11B shows the frequency of FoxP3$^+$CD25$^+$ cells (markers of T regulatory cells). * and # indicate p<0.05, ** and ## indicate p<0.01, and ### indicates P<0.001.

Figure 12A:
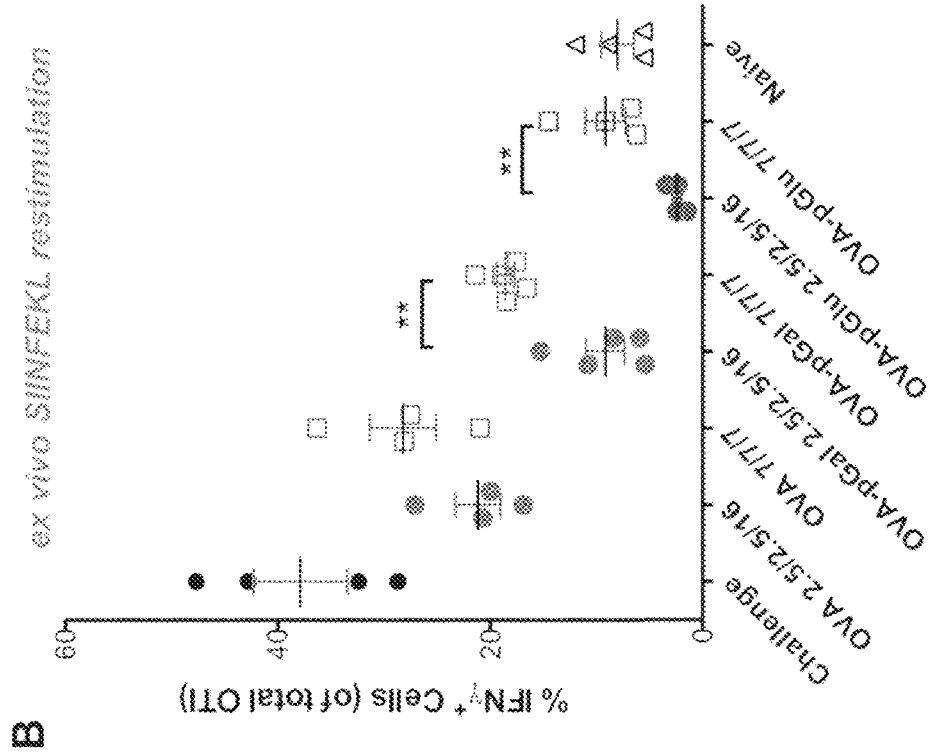
Figure 12B:
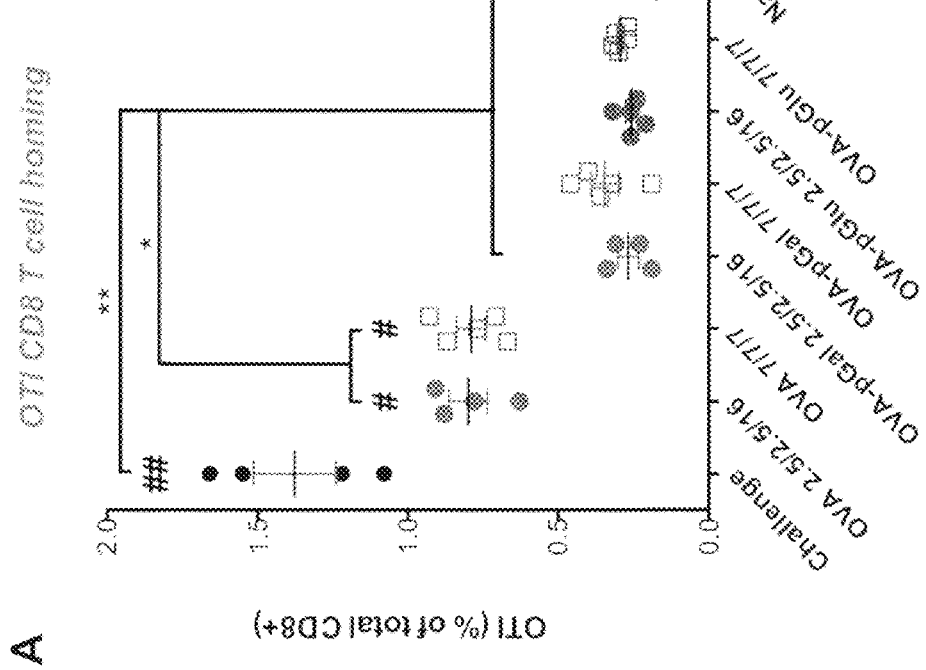

FIGS. 12A-12B depicts data related to T cell deletion and regulation in an OTI adoptive transfer model, in which OTI cells (CD8$^+$ T cells from a CD45.2$^+$ mouse) are adoptively transferred into a CD45.1$^+$ recipient, which is treated with F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ ["OVA-p(Gal-HPMA)"] or F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ ["OVA-p(Glu-HPMA)"], or OVA not linked to a polymer ["OVA"] to induce T regulatory responses and prevent subsequent responses to vaccine-mediated antigen challenge. Both 3×10$^5$ CFSE-labeled OTI and 3×10$^5$ CFSE-labeled OTII cells were adoptively transferred to CD45.1$^+$ mice (n=8 mice per group) on day 0. On days 1, 4 and 7, tolerogenic doses or control doses were administered. In one regimen, OVA was provided at a dose of 2.5 µg at day 1, 2.5 µg at day 4, and 16 µg at day 7. In another, OVA was provided at a dose of 7 µg at day 1, 7 µg at day 4, and 7 µg at day 7, for the same total dose. Likewise, pGal-OVA and pGlu-OVA were each administered in other groups at the same dosings of 2.5 µg at day 1, 2.5 µg at day 4, and 16 µg at day 7 or 7 µg at day 1, 7 µg at day 4, and 7 µg at day 7, all doses being on an OVA equivalent dose basis. In a final group, saline was administered on the same days. On day 14, the recipient mice were then challenged with OVA (10 µg) adjuvanted with lipopolysaccharide (50 ng) by intradermal injection. Characterization of the draining lymph nodes was done on day 19, to allow determination as to whether or not deletion actually took place and whether T cells were responsive to antigen re-exposure though their cytokine expression. FIG. 12A shows the number of OTI cells present after challenge, and FIG. 12B shows the frequency of IFNγ-expressing cells (lack thereof indicating anergy). * and # indicate p<0.05, ** and ## indicate p<0.01).

Figure 13:
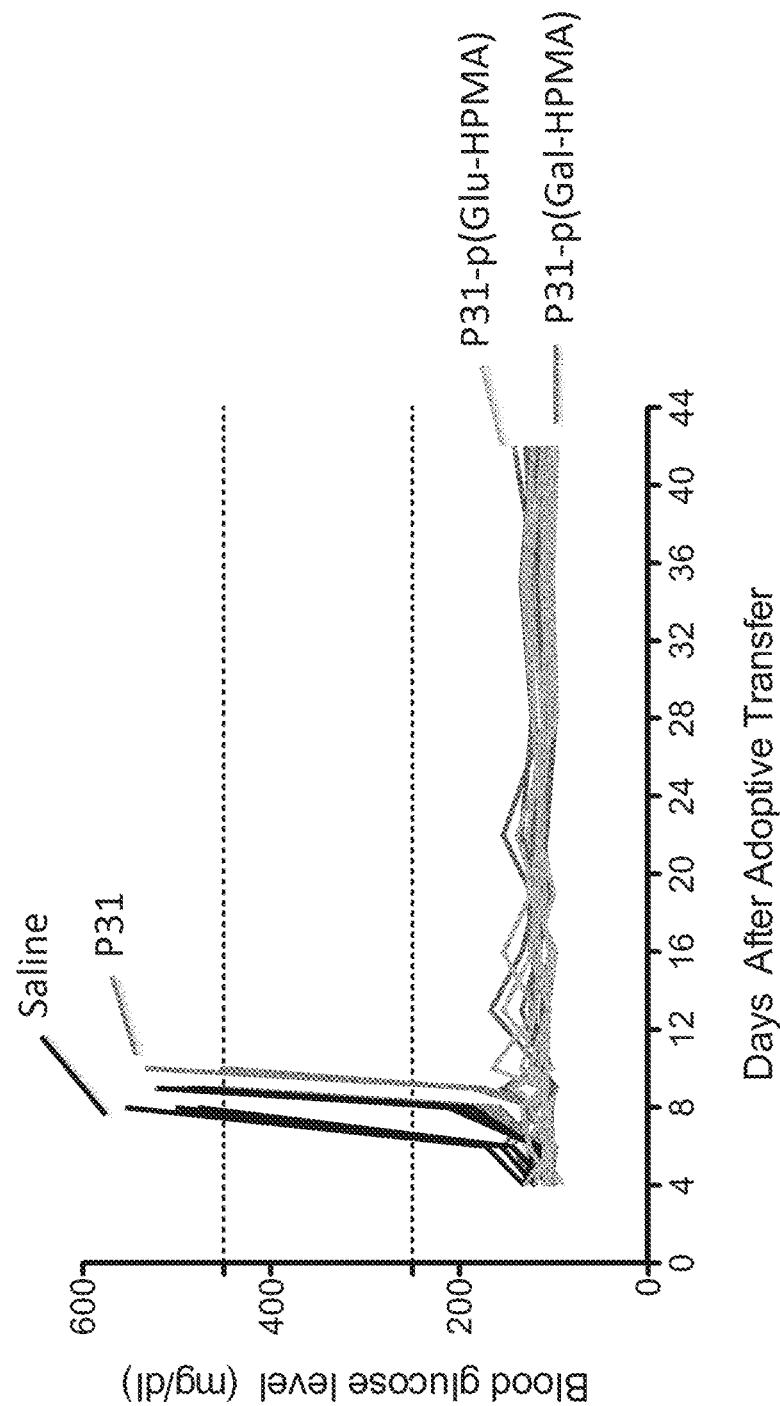

FIG. 13 depicts data related to blood glucose levels. Mice were treated with F1m'-P31-$m_{1-3}$-$n_{79}$-$p_{90}$-$q_4$-CMP-poly-(EtPEG$_1$AcN-1NAcGLU$_{30}$-ran-HPMA$_{60}$ [labeled P31-p(Glu-HPMA)], F1m'-P31-$m_{1-3}$-$n_{79}$-$p_{90}$-$q_4$-CMP-poly-(EtPEG$_1$AcN-1NAcGAL$_{30}$-ran-HPMA$_{60}$ [labeled P31-p(Gal-HPMA) conjugates (or saline). Animals receiving P31-p(Glu-HPMA) or P31-p(Gal-HPMA) maintained normal blood glucose levels for 42 days, whereas animals treated with P31 or Saline developed rapid hyperglycemia within 5-10 days, demonstrating that conjugates disclosed herein protect mice from T-cell induced autoimmune diabetes.

FIG. 14 depicts data related to the generation of spontaneous diabetes in non-obese diabetic (NOD) mice. Mice treated with F1c'-Insulin-B-$m_1$-$n_4$-$p_{90}$-CMP-poly-(EtPEG$_1$AcN-1NAcGLU$_{30}$-ran-HPMA$_{60}$ are shown as filled squares. Mice treated with F1c'-Insulin-B-$m_1$-$n_4$-$p_{90}$-CMP-poly-(EtPEG$_1$AcN-1NAcGAL$_{30}$-ran-HPMA$_{60}$ are shown as filled triangles. Mice treated with saline are shown as filled diamonds. Treating animals with the compounds of Formula 1 reduced the incidences of diabetes onset in NOD mice as compared to animals treated with saline.

Figures 15A, 15B:
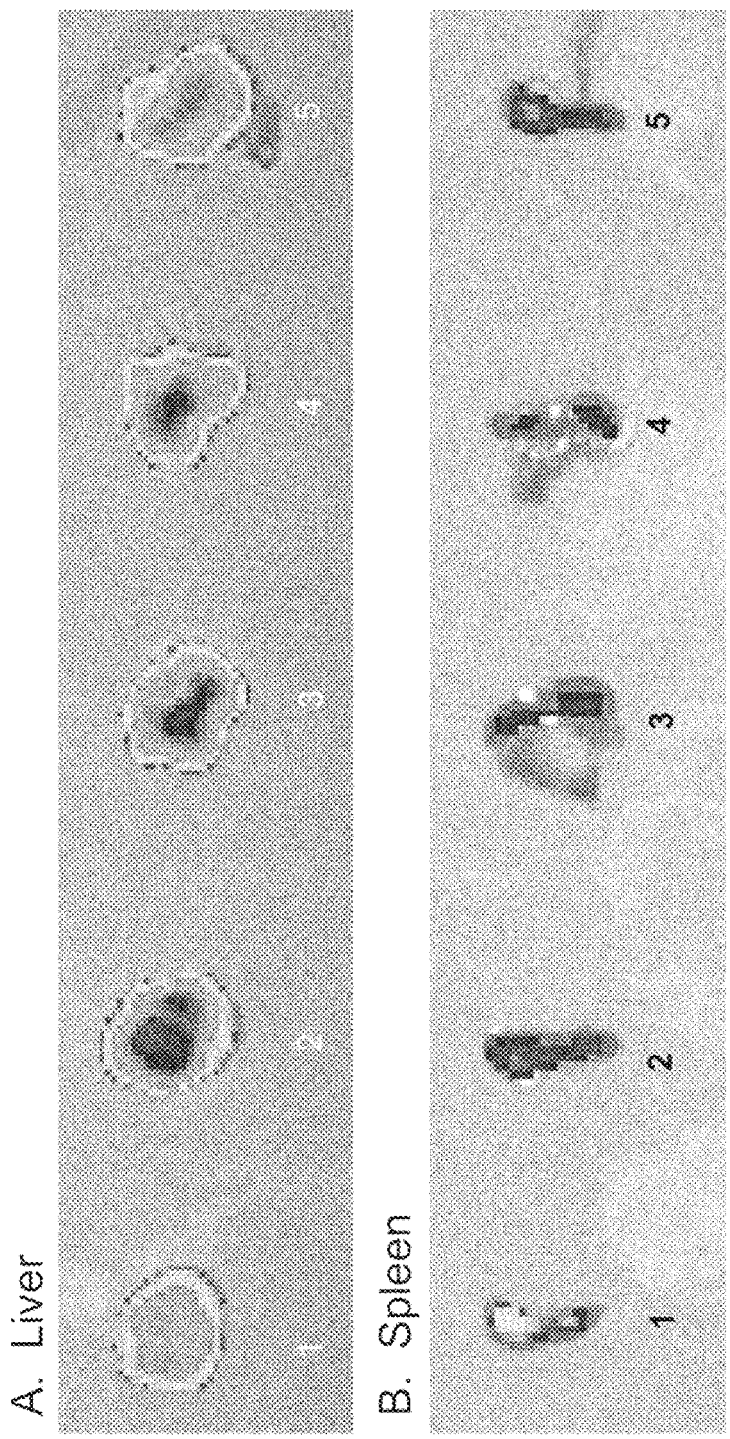

FIGS. 15A-15B depicts data related to biodistribution of the model antigen OVA tethered to the synthetic glycopolymers, showing uptake in the liver while limiting uptake in the spleen. A. Fluorescent signal of perfused livers taken from animals treated with OVA (1) or OVA conjugated to various glycopolymers (2-5). B. Fluorescent images of spleens taken from animals treated with OVA (1) or OVA conjugated to various glycopolymers (2-5). Formulations are as follows: 1. OVA, 2. OVA-p(Galβ-HPMA), 3. OVA-p(Gal-HPMA), 4. OVA-p(Gluβ-HPMA), 5. OVA-p(Glu-HPMA).

Figures 16A, 16B:
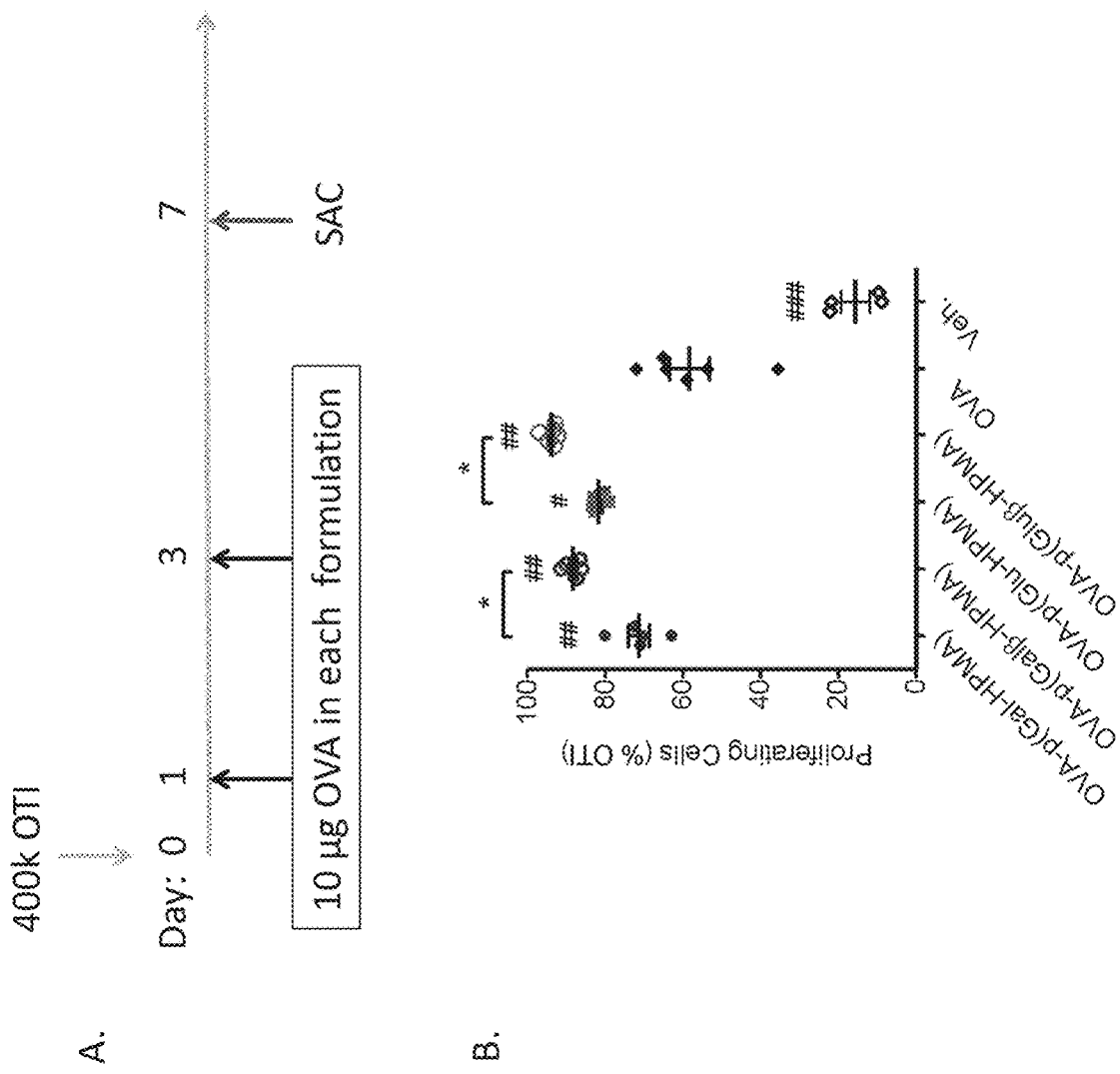
Figures 16C, 16D:
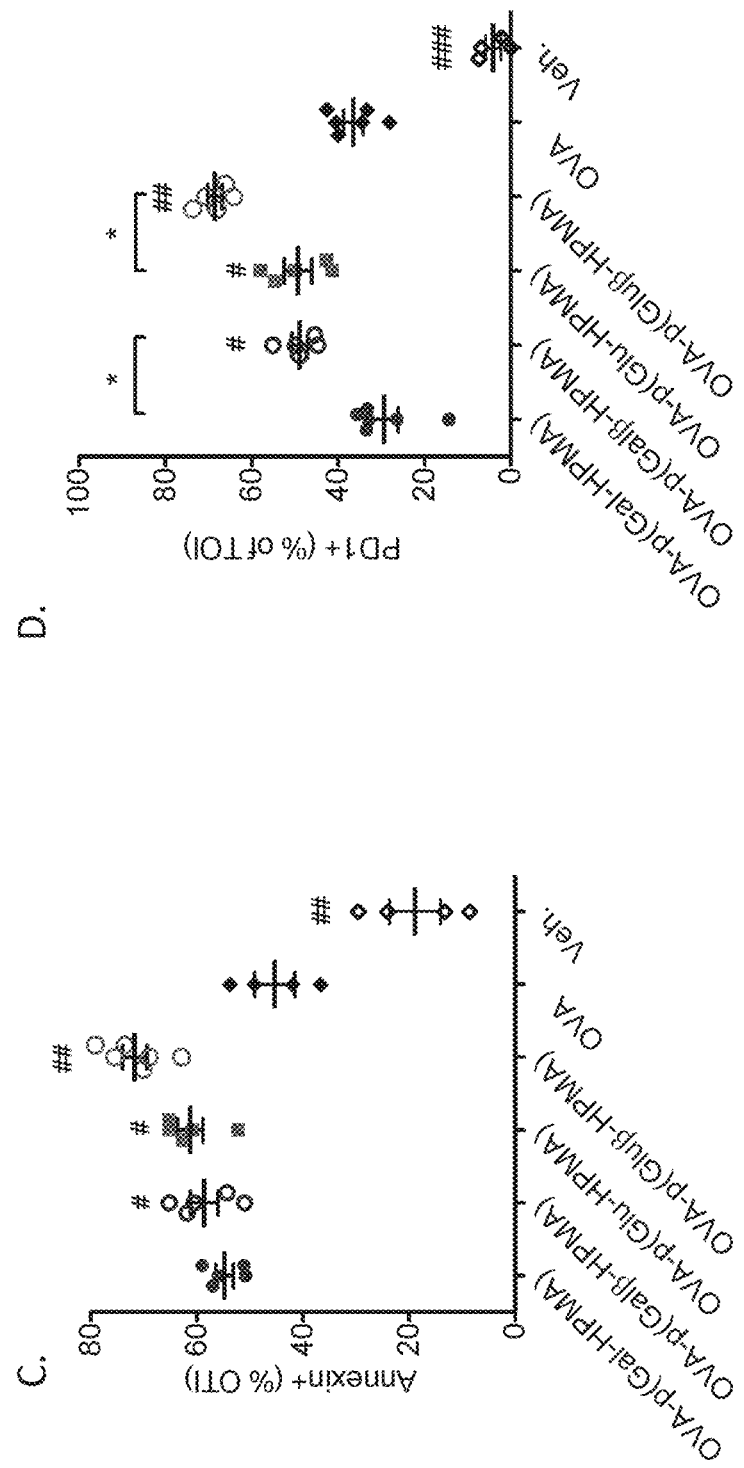
Figures 16E, 16F:
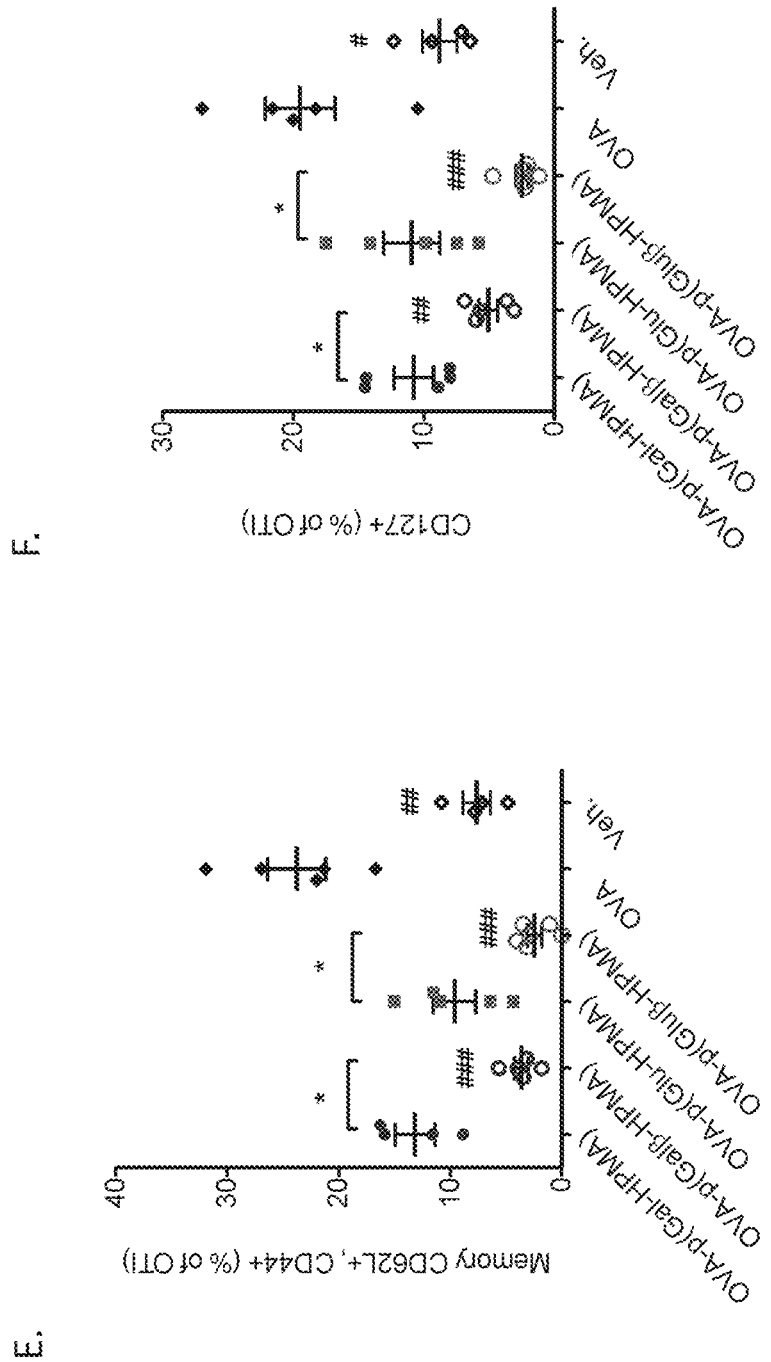

FIGS. 16A-16F depict data related to experiments comparing linker moieties. OVA-p(Gal-HPMA), OVA-p(Glu-HPMA), OVA-p(Galβ-HPMA), and OVA-p(Gluβ-HPMA) conjugates were synthesized and tested for their ability to induce antigen-specific T cell anergy and eliminate the T cell population responsible for long term memory. FIG. 16A shows a schematic of the treatment regimen for 7-day experiment. FIG. 16B depicts the percentage of proliferating OTI splenic T cells as assayed by CSFE dilution. FIG. 16C depicts the percentage of Annexin V+ OTI T cells in the spleens of animals treated with OVA-glycopolymer conjugates or free OVA. FIG. 16D depicts the percentage of PD-1+ splenic OTI cells. FIG. 16E depicts the percentage of T memory cells in the OTI population, where T memory cells was defined as CD62L+ and CD44+. FIG. 16 F depicts the percentage of OTI cells expressing CD127. Of particular note is the unexpectedly enhanced efficacy of compositions employing glucose or galactose in the β-conformation, as compared to the α-conformation. *=P<0.05**=P<0.01; #=P<0.05, ##=P<0.01 and ###=P<0.001 (#'s represent significance as compared to animals treated with OVA alone).

Figure 17:
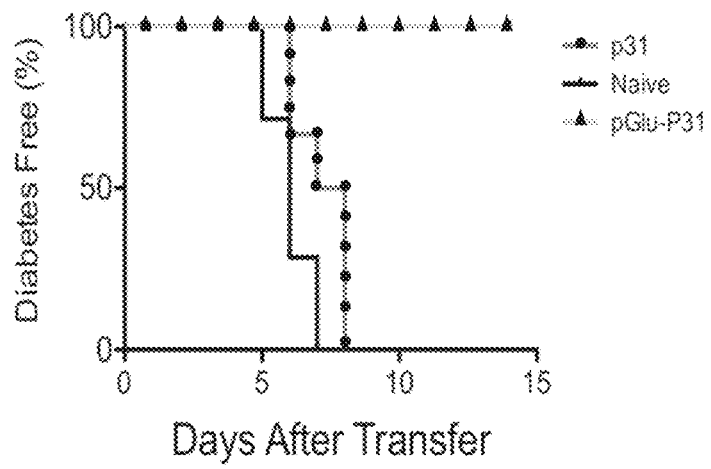

FIG. 17 depicts data related to development of symptoms of diabetes in naïve, control, and experimental groups.

Figure 18:
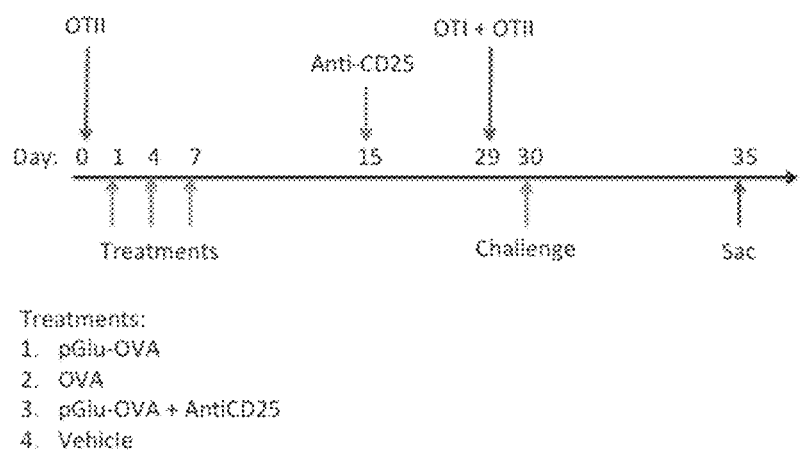

FIG. 18 depicts the various treatment groups and the experimental timeline used in an experiment related to evaluation of induction of long-lasting tolerance in transferred T cells.

Figures 19A, 19B:
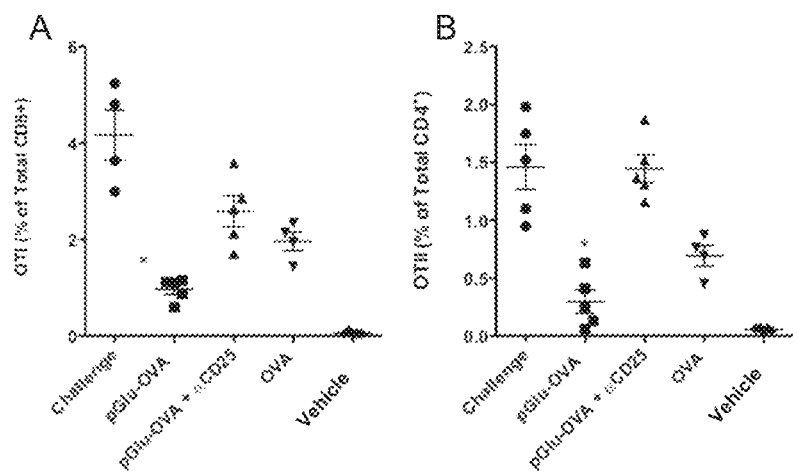

FIGS. 19A-19B depict data related to T cell composition in the lymph node. FIG. 19A depicts the remaining OTI cells after antigen challenge (as a percentage of total CD8$^+$ cells)

in the various treatment groups. FIG. 19B depicts the remaining OTII cells after antigen challenge (as a percentage of total CD4+ cells) in the various treatment groups.

Figure 20:
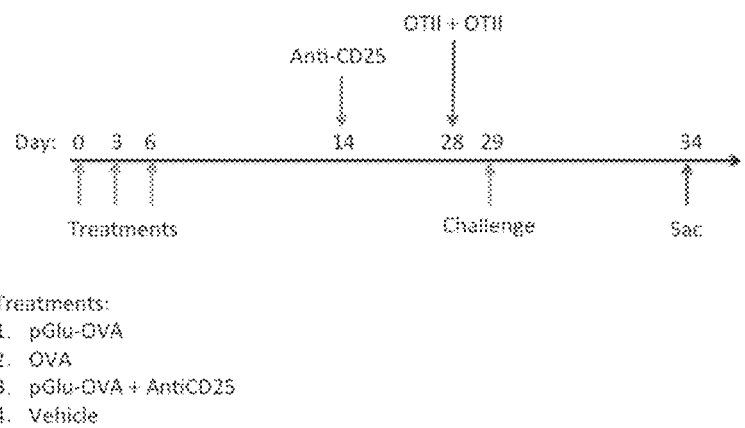

FIG. 20 depicts the various treatment groups and the experimental timeline used in an experiment related to evaluation of induction of long-lasting tolerance in endogenous T cells.

Figures 21A, 21B:
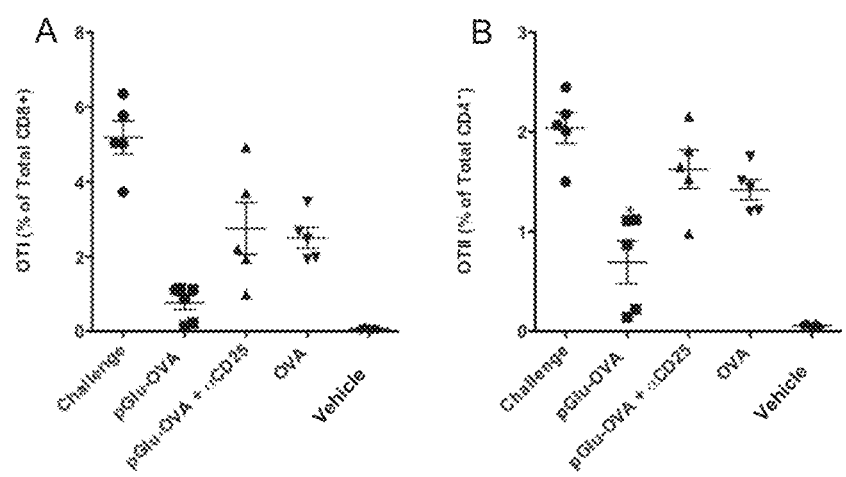

FIGS. 21A-21B depict data related to T cell composition in the lymph node. FIG. 21A depicts the remaining OTI cells after antigen challenge (as a percentage of total CD8+ cells) in the various treatment groups. FIG. 21B depicts the remaining OTII cells after antigen challenge (as a percentage of total CD4+ cells) in the various treatment groups.

Figure 22:
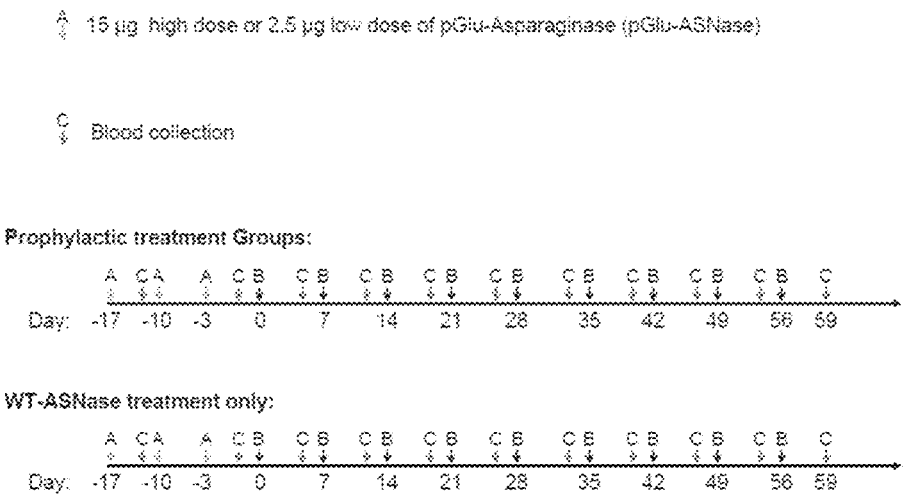

FIG. 22 depicts the experimental design used to evaluate the ability of compositions as disclosed herein to prophylactically reduce antibody response.

Figure 23:
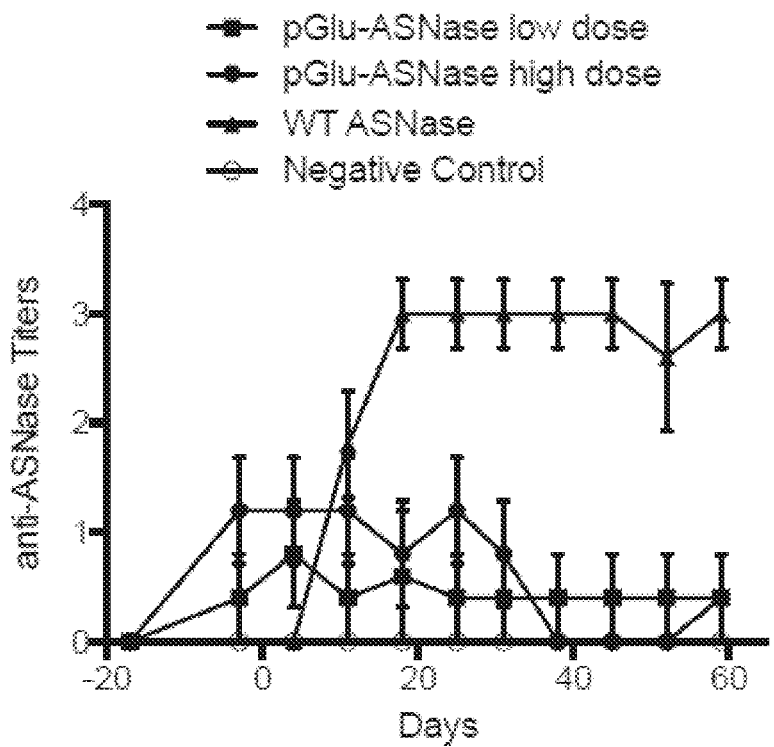

FIG. 23 depicts experimental data related to the amount of anti-asparaginase antibodies from mice in the various treatment groups.

Figure 24A:
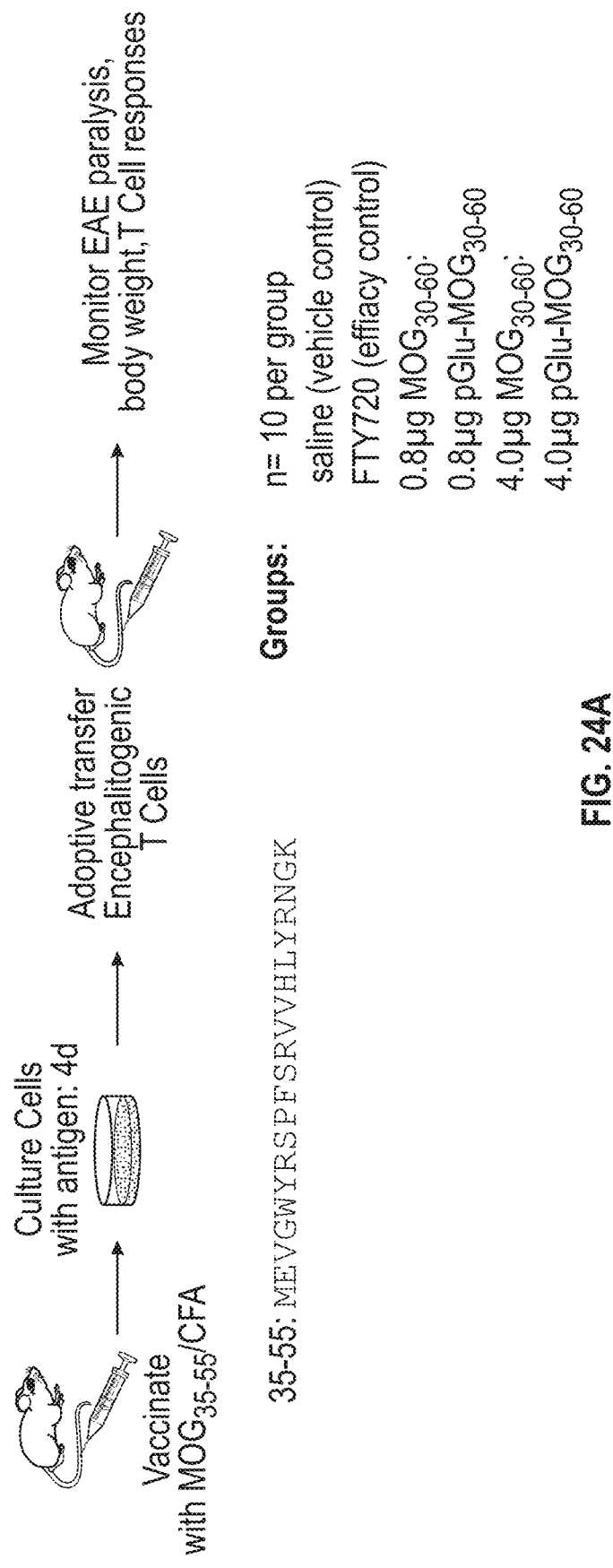
Figure 24B:
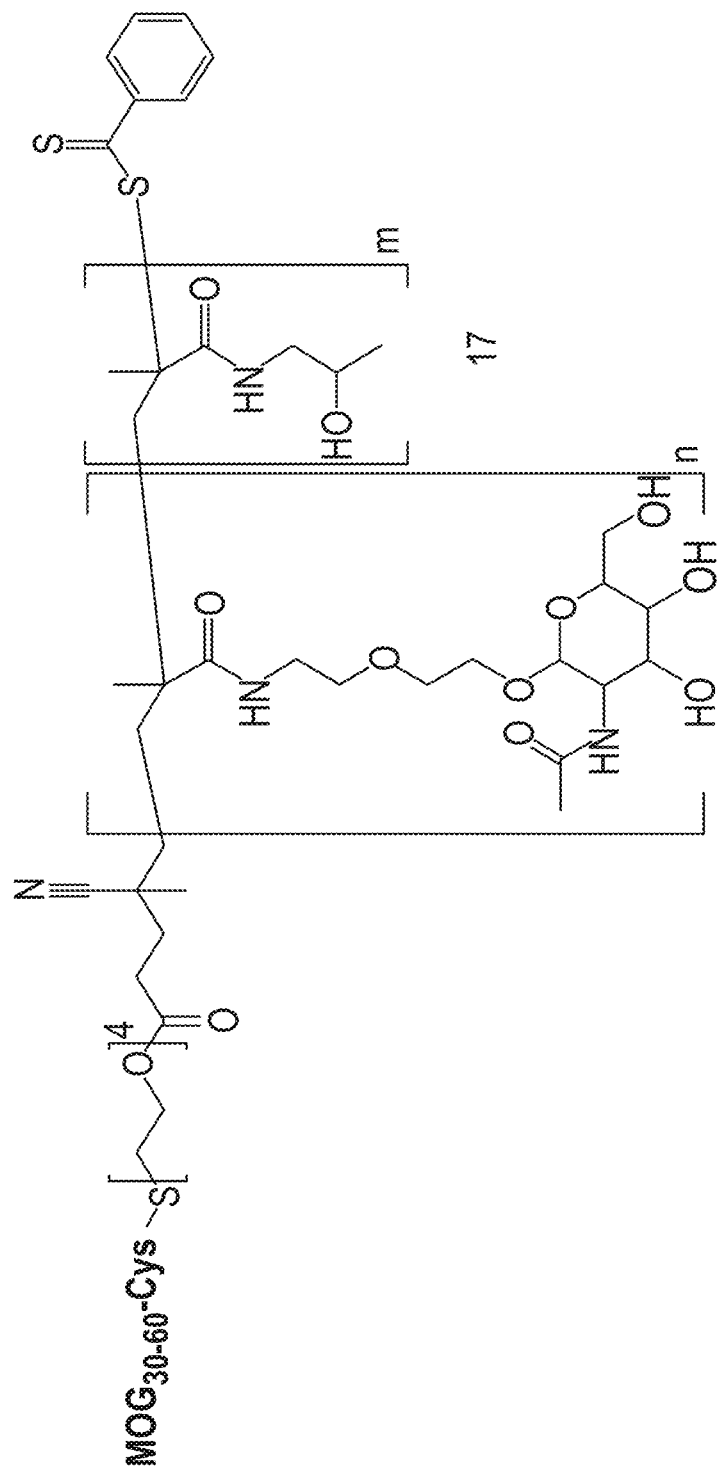

FIGS. 24A-24B depict the experimental design and composition used in evaluating tolerance to myelin oligodendrocyte glycoprotein (MOG). FIG. 24A shows the experimental protocol used in immunizing donor mice and treating recipient mice. FIG. 24B shows one example of a tolerogenic composition in accordance with several embodiments disclosed herein.

Figure 25A:
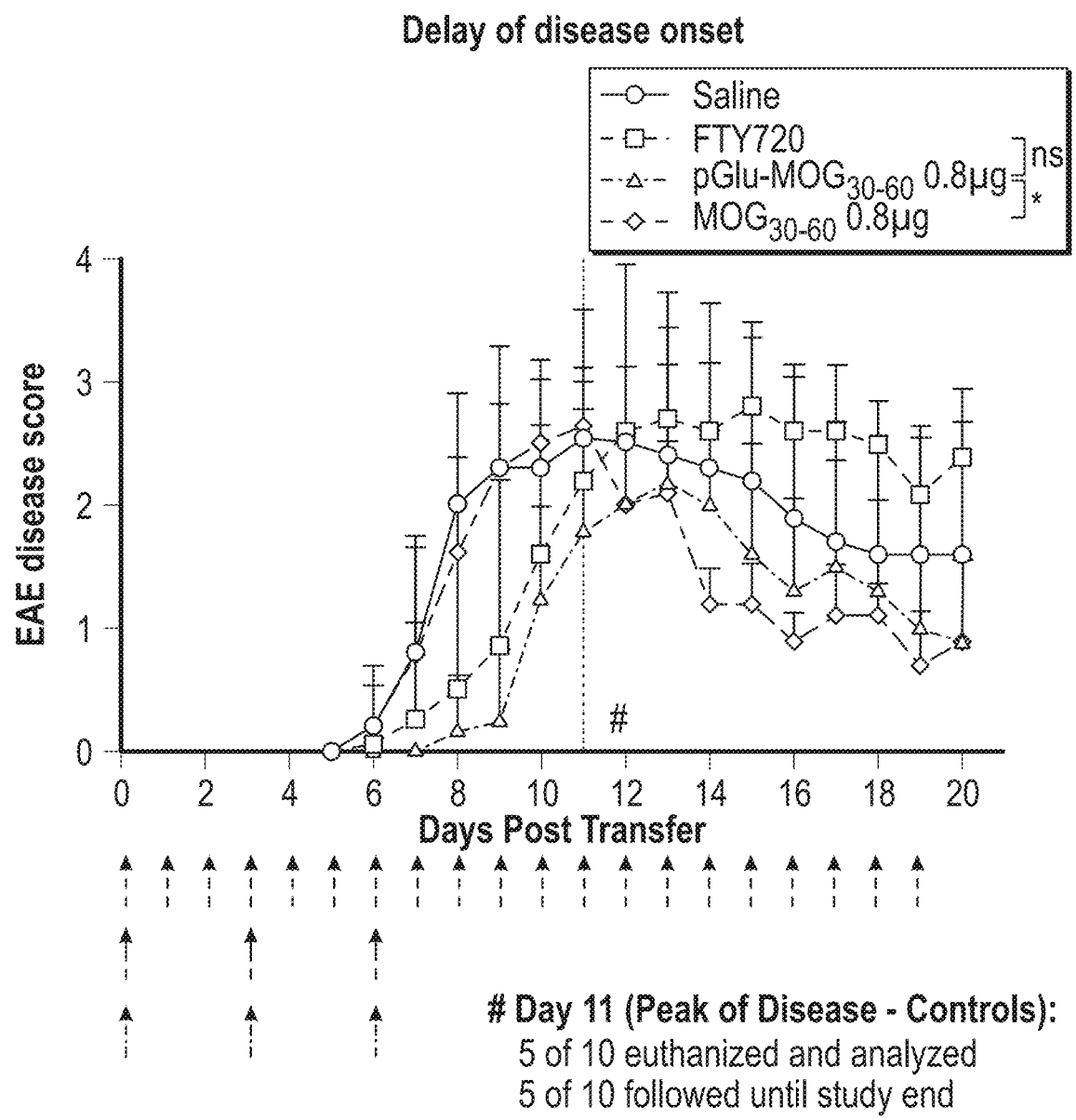
Figure 25B:
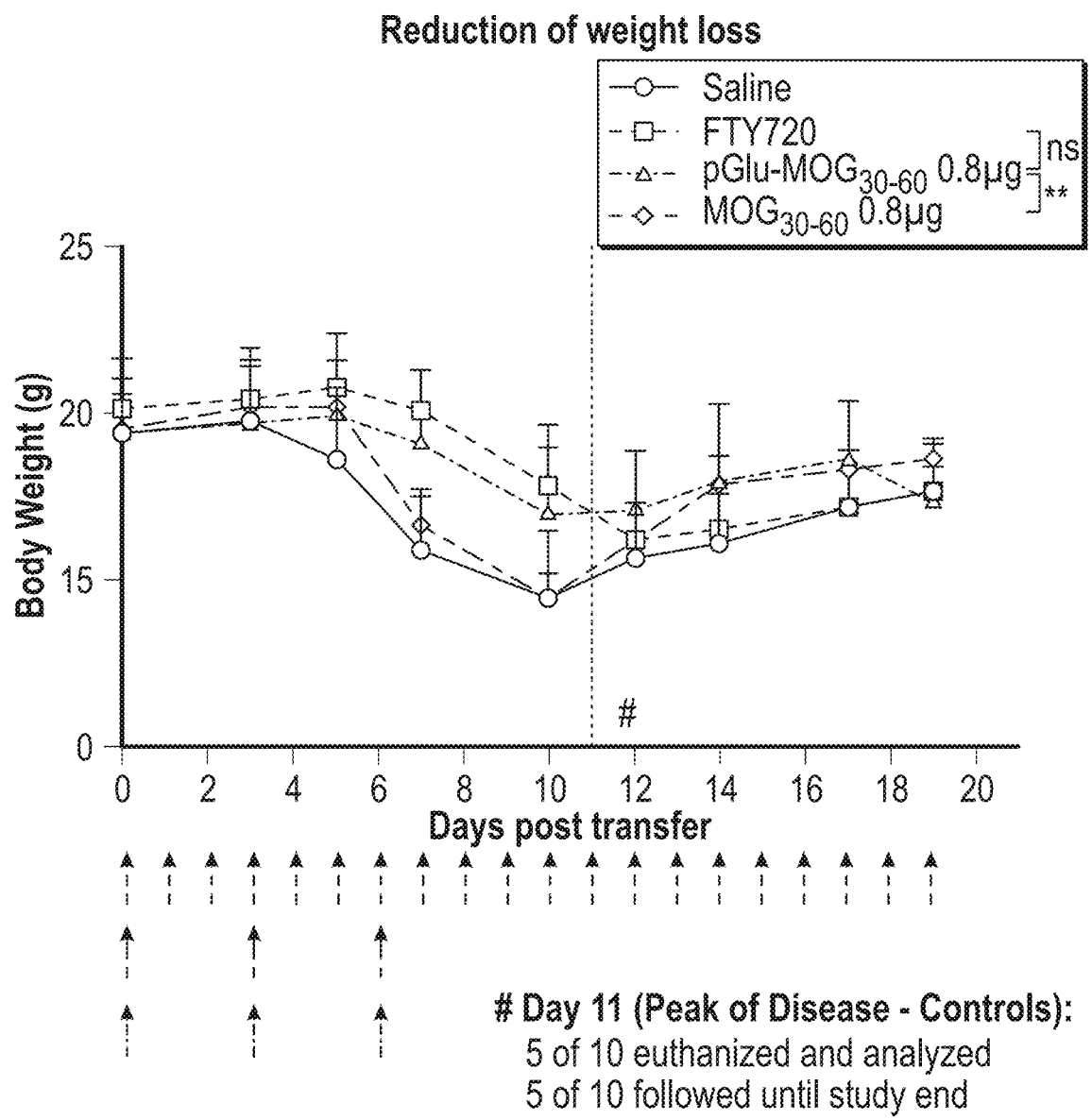

FIGS. 25A-25B depict experimental data related to induction of tolerance against MOG using a first concentration of the tolerogenic composition. FIG. 25A depicts data related to delay of disease onset in the various treatment groups. FIG. 25B depicts data related to reduction of weight loss in the various treatment groups.

Figure 26A:
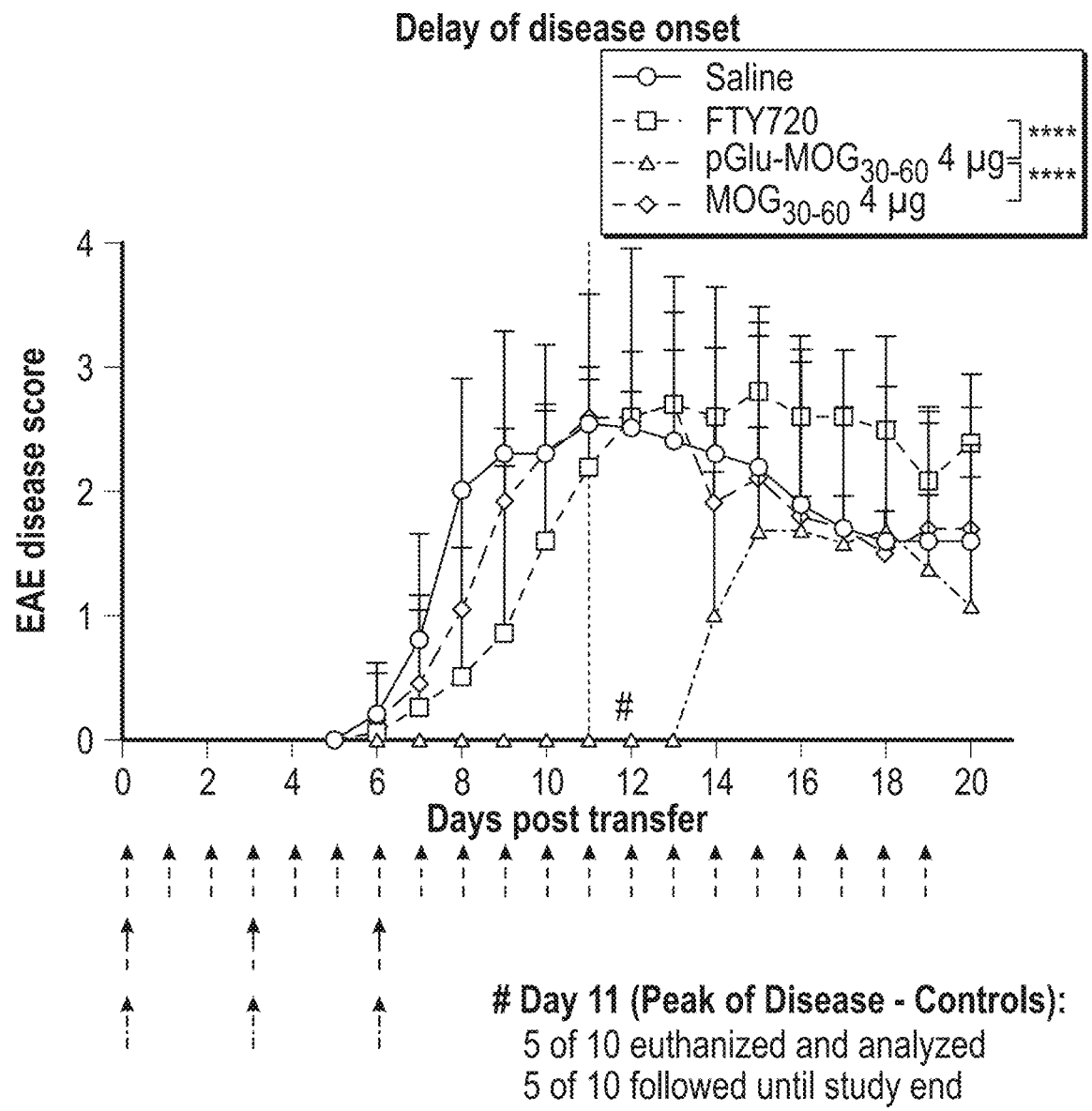
Figure 26B:
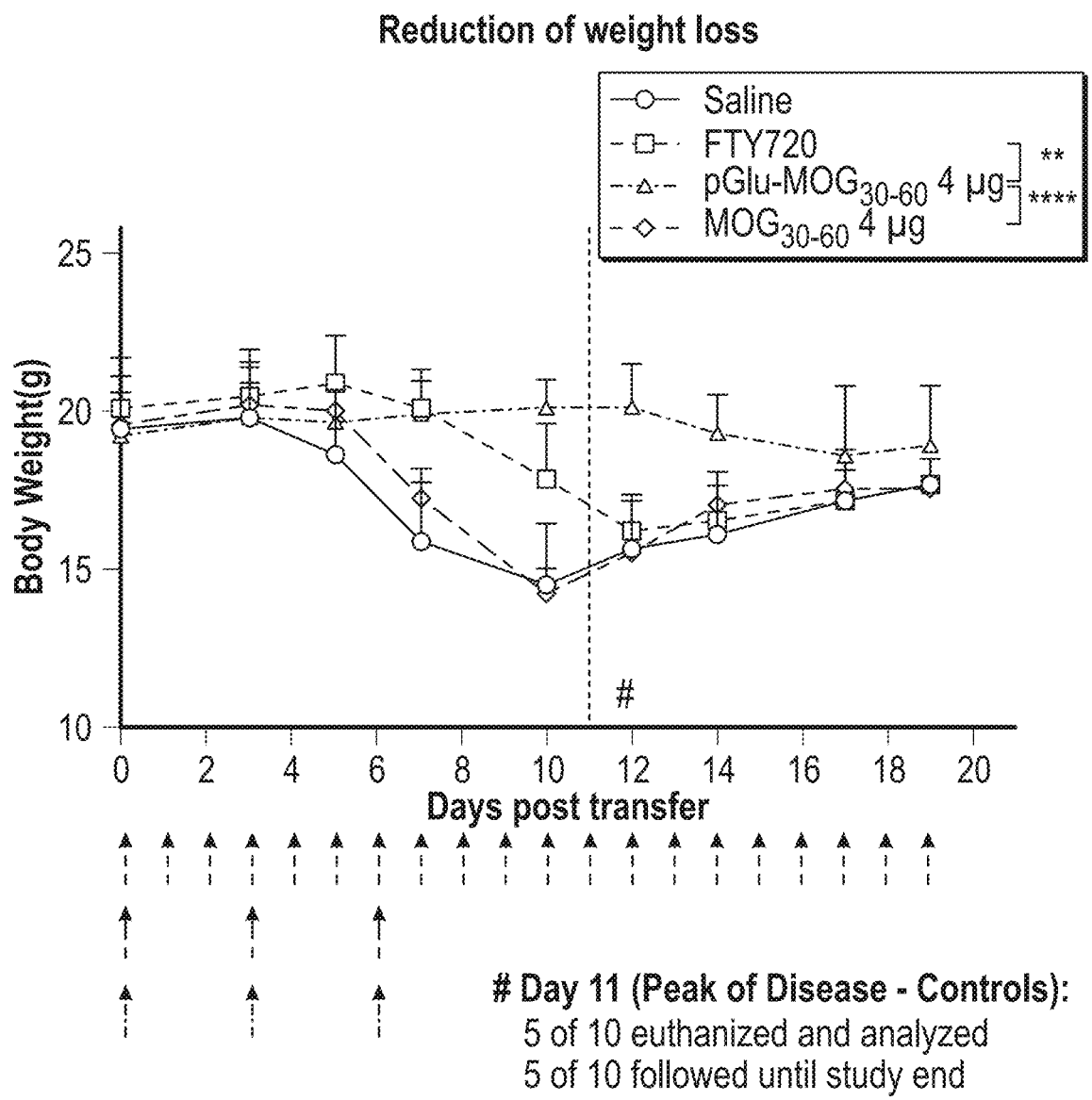

FIGS. 26A-26B depict experimental data related to induction of tolerance against MOG using an additional concentration of the tolerogenic composition. FIG. 26A depicts data related to delay of disease onset in the various treatment groups. FIG. 26B depicts data related to reduction of weight loss in the various treatment groups.

Figure 27A:
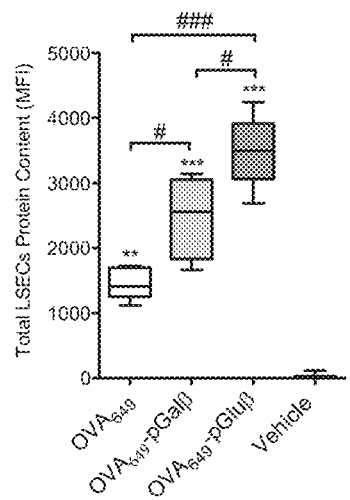
Figure 27B:
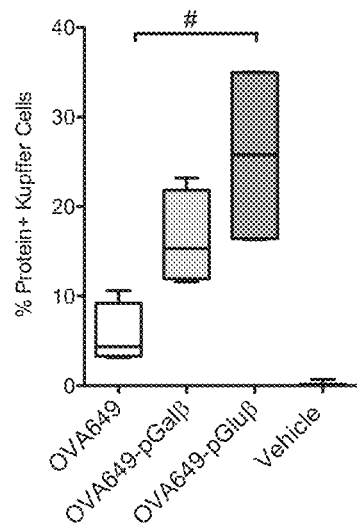
Figure 27C:
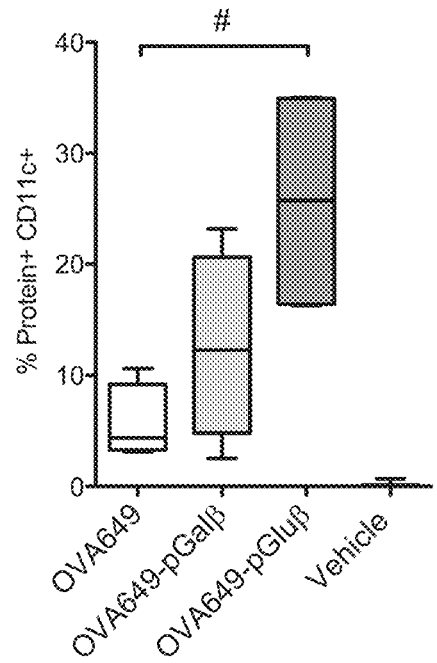
Figure 27D:
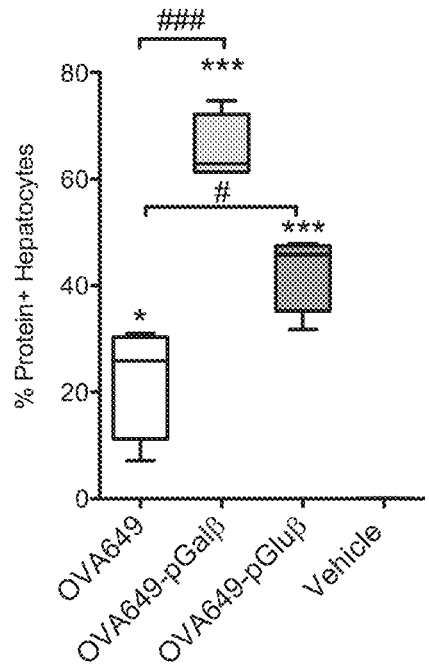
Figure 27E:
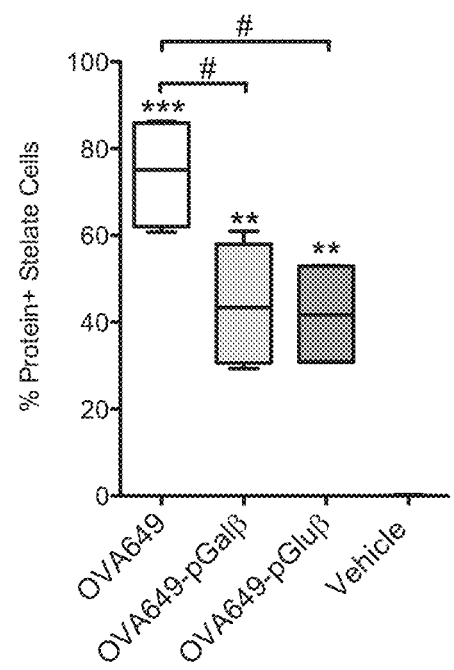

FIGS. 27A-27E depict experimental data related to the biodistribution of pGal and pGlu compositions in the beta conformation. FIG. 27A depicts targeting of OVA via various conjugates to LSECs in the liver. FIG. 27B depicts targeting of OVA via various conjugates to Kupffer cells in the liver. FIG. 27C depicts targeting of OVA via various conjugates to CD11c+ cells in the liver. FIG. 27D depicts targeting of OVA via various conjugates to hepatocytes in the liver. FIG. 27E depicts targeting of OVA via various conjugates to stellate cells in the liver.

DETAILED DESCRIPTION

Two known asialoglycoprotein receptors ("ASGPRs") are expressed on hepatocytes and liver sinusoidal endothelial cells (or "LSECs"). Other galactose/galactosamine/N-acetylgalactosamine receptors can be found in various forms on multiple cell types [e.g., dendritic cells, hepatocytes, LSECs, and Kupffer cells]. While the molecular and cellular targets of glucose, glucosamine and N-acetylglucosamine can be distinct from those of the corresponding galactose isomers, it has been found that the corresponding compounds of Formula 1 where Z is a glucosylating moiety are comparably effective in some instances, while in some embodiments disclosed herein, they are unexpectedly effective. Dendritic cells are considered "professional antigen presenting cells," because their primary function is to present antigens to the immune system for generating immune responses. Some cells within the liver are known to be able to present antigens, but the liver is more known to be involved in tolerogenesis. The liver is understood to be a tolerogenic organ. For example, lower incidences of rejection are reported in cases of multiple organ transplants when the liver is one of the organs transplanted. LSECs are much newer to the literature; consequently their role in tolerogenesis and/or moderation of inflammatory immune responses is not yet widely acknowledged or well understood. However, it is becoming clear that they also can play a significant role in the induction of antigen-specific tolerance.

One of the distinctive features of the erythrocyte surface is its glycosylation, i.e., the presence of significant numbers of glycosylated proteins. Indeed, the glycophorins (e.g., glycophorin A) have been employed as targets for erythrocyte binding. Glycophorins are proteins with many covalently attached sugar chains, the terminus of which is sialic acid. As an erythrocyte ages and becomes ripe for clearance, the terminal sialic acid of its glycophorins tends to be lost, leaving N-acetylgalactosamine at the free end. N-acetylgalactosamine is a ligand selectively received by the ASGPR associated with hepatic cells, leading to binding of N-acetylgalactosamine-containing substances by hepatic cells and their subsequent uptake and processing in the liver.

Heretofore, it has been understood by those skilled in the art that glycosylation of a therapeutic agent in a manner that results in hepatic targeting should be avoided due to first-pass clearance by the liver resulting in poor circulation half-life of the therapeutic agent. By the same token, some monoclonal antibodies need to be specifically glycosylated at ASN297 for optimal binding to their Fc receptors. It has now surprisingly been found, and is disclosed herein, that galactosylation and glucosylation can be used in a manner that induces tolerogenesis.

The present disclosure provides, in several embodiments, certain therapeutic compositions that are targeted for delivery to (and for uptake by) the liver, particularly hepatocytes, LSECs, Kupffer cells and/or stellate cells, more particularly hepatocytes and/or LSECs, and even more particularly to specifically bind ASGPR. Liver-targeting facilitates two mechanisms of treatment: tolerization and clearance. Tolerization takes advantage of the liver's role in clearing apoptotic cells and processing their proteins to be recognized by the immune system as "self," as well as the liver's role in sampling peripheral proteins for immune tolerance. Clearance takes advantage of the liver's role in blood purification by rapidly removing and breaking down toxins, polypeptides and the like. Targeting of these compositions to the liver is accomplished by a galactosylating moiety (e.g., galactose, galactosamine and N-acetylgalactosamine, particularly conjugated at C1, C2 or C6, though some embodiments involved conjugation at other or any carbon in the molecule), by a glucosylating moiety (e.g., glucose, glucosamine and N-acetylglucosamine, particularly conjugated at C1, C2 or C6, though some embodiments involved conjugation at other or any carbon in the molecule), or by de-sialylating a polypeptide for which such liver-targeting is desired. The galactosylating or glucosylating moiety can be chemically conjugated or recombinantly fused to an antigen, whereas desialylation exposes a galactose-like moiety on an antigen polypeptide. The antigen can be endogenous (a self-antigen) or exogenous (a foreign antigen), including but not limited to: a foreign transplant antigen against which transplant recipients develop an unwanted immune response (e.g., transplant rejection), a foreign food, animal, plant or environmental antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease), or a tolerogenic portion (e.g., a fragment or an epitope) thereof; these compositions are useful for inducing tolerization to the antigen. Alternatively, the galactosylating or other liver-targeting moiety can be conjugated to an antibody, antibody fragment or ligand that specifically binds a circulating protein or peptide or antibody, which circulating protein or peptide or antibody is causatively involved in transplant rejection, immune response against a therapeutic agent, autoimmune disease, and/or allergy (as discussed above); these compositions are useful for clearing the circulating protein, peptide or antibody. Accordingly, the compositions of the present disclosure can be used for treating an unwanted immune response, e.g., transplant rejection, an immune response against a therapeutic agent, an autoimmune disease, and/or an allergy, depending on the embodiment. Also provided are pharmaceutical compositions containing a therapeutically effective amount of a composition of the disclosure admixed with at least one pharmaceutically acceptable excipient. In another aspect, the disclosure provides methods for the treatment of an unwanted immune response, such as transplant rejection, response against a therapeutic agent, autoimmune disease or allergy.

Definitions

As used in the present specification, the following words and phrases are generally intended to have the meanings as set forth below, except to the extent that the context in which they are used indicates otherwise.

The singular forms "a," "an," and "the" include plural referents, unless the context clearly indicates otherwise.

The term "about" when used in connection with a numerical value is meant to encompass numerical values within a range typically having a lower limit that is, e.g., 5-10% smaller than the indicated numerical value and having an upper limit that is, e.g., 5-10% larger than the indicated numerical value. Also included are any values within the disclosed range, including the listed endpoints.

As used herein, an "antigen" is any substance that serves as a target for the receptors of an adaptive immune response, such as the T cell receptor, major histocompatibility complex class I and II, B cell receptor or an antibody. In some embodiments, an antigen may originate from within the body (e.g., "self," "auto" or "endogenous"). In additional embodiments, an antigen may originate from outside the body ("non-self," "foreign" or "exogenous"), having entered, for example, by inhalation, ingestion, injection, or transplantation, transdermally, etc. In some embodiments, an exogenous antigen may be biochemically modified in the body. Foreign antigens include, but are not limited to, food antigens, animal antigens, plant antigens, environmental antigens, therapeutic agents, as well as antigens present in an allograft transplant.

An "antigen-binding molecule" as used herein relates to molecules, in particular to proteins such as immunoglobulin molecules, which contain antibody variable regions providing a binding (specific binding in some embodiments) to an epitope. The antibody variable region can be present in, for example, a complete antibody, an antibody fragment, and a recombinant derivative of an antibody or antibody fragment. The term "antigen-binding fragment" of an antibody (or "binding portion"), as used herein, refers to one or more fragments of an antibody that retain the ability to specifically bind a target sequence. Antigen-binding fragments containing antibody variable regions include (without limitation) "Fv", "Fab", and "F(ab')$_2$" regions, "single domain antibodies (sdAb)", "nanobodies", "single chain Fv (scFv)" fragments, "tandem scFvs" ($V_H$A-$V_L$A-$V_H$B-$V_L$B), "diabodies", "triabodies" or "tribodies", "single-chain diabodies (scDb)", and "bi-specific T-cell engagers (BiTEs)".

As used herein, a "chemical modification" refers to a change in the naturally occurring chemical structure of one or more amino acids of a polypeptide. Such modifications can be made to a side chain or a terminus, e.g., changing the amino-terminus or carboxyl terminus. In some embodiments, the modifications are useful for creating chemical groups that can conveniently be used to link the polypeptides to other materials, or to attach a therapeutic agent.

The term "comprising", which is synonymous with "including," "containing," or "characterized by," is inclusive or open-ended and does not exclude additional, unrecited elements or method steps. The phrase "consisting of" excludes any element, step, or ingredient not specified. The phrase "consisting essentially of" limits the scope of described subject matter to the specified materials or steps and those that do not materially affect its basic and novel characteristics. It is understood that wherever embodiments are described herein with the language "comprising", otherwise analogous embodiments described in terms of "consisting of" and/or "consisting essentially of" are also provided. When used in the claims as transitional phrases, each should be interpreted separately and in the appropriate legal and factual context (e.g., "comprising" is considered more of an open-ended phrase while "consisting of" is more exclusive and "consisting essentially of" achieves a middle ground).

"Conservative changes" can generally be made to an amino acid sequence without altering activity. These changes are termed "conservative substitutions" or mutations; that is, an amino acid belonging to a grouping of amino acids having a particular size or characteristic can be substituted for another amino acid. Substitutes for an amino acid sequence can be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such substitutions are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence can undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free —NH$_2$. Yet another type of conservative substitution constitutes the case where amino acids with desired chemical reactivities are introduced to impart reactive sites for chemical conjugation reactions, if the need for chemical derivatization arises. Such amino acids include but are not limited to Cys (to insert a sulfhydryl group), Lys (to insert a primary amine), Asp and Glu (to insert a carboxylic acid group), or specialized noncanonical amino acids containing ketone, azide, alkyne, alkene, and tetrazine side-chains. Conservative substitutions or additions of free —NH₂ or —SH bearing amino acids can be particularly advantageous for chemical conjugation with the linkers and galactosylating moieties of Formula 1. Moreover, point mutations, deletions, and insertions of the polypeptide sequences or corresponding nucleic acid sequences can in some cases be made without a loss of function of the polypeptide or nucleic acid fragment. Substitutions can include, e.g., 1, 2, 3, 4, 5, 6, 7, 8, 9, 10, 15, 20, 25, 30, 35, 40, 45, 50 or more residues (including any number of substitutions between those listed). A variant usable in the present invention may exhibit a total number of up to 200 (e.g., up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200, including any number in between those listed) changes in the amino acid sequence (e.g., exchanges, insertions, deletions, N-terminal truncations, and/or C-terminal truncations). In several embodiments, the number of changes is greater than 200. Additionally, in several embodiments, the variants include polypeptide sequences or corresponding nucleic acid sequences that exhibit a degree of functional equivalence with a reference (e.g., unmodified or native sequence). In several embodiments, the variants exhibit about 80%, about 85%, about 90%, about 95%, about 97%, about 98%, about 99% functional equivalence to an unmodified or native reference sequence (and any degree of functional equivalence between those listed). The amino acid residues described herein employ either the single letter amino acid designator or the three-letter abbreviation in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

The terms "effective amount" or "therapeutically effective amount" refer to that amount of a composition of the disclosure that is sufficient to effect treatment, as defined below, when administered to a mammal in need of such treatment. This amount will vary depending upon the subject and disease condition being treated, the weight and age of the subject, the severity of the disease condition, the particular composition of the disclosure chosen, the dosing regimen to be followed, timing of administration, manner of administration and the like, all of which can readily be determined by one of ordinary skill in the art.

An "epitope", also known as antigenic determinant, is the segment of a macromolecule, e.g. a protein, which is recognized by the adaptive immune system, such as by antibodies, B cells, major histocompatibility complex molecules, or T cells. An epitope is that part or segment of a macromolecule capable of binding to an antibody or antigen-binding fragment thereof. In this context, the term "binding" in particular relates to a specific binding. In the context of several embodiments of the present invention, it is preferred that the term "epitope" refers to the segment of protein or polyprotein that is recognized by the immune system.

The term galactose refers to a monosaccharide sugar that exists both in open-chain form and in cyclic form, having D- and L-isomers. In the cyclic form, there are two anomers, namely alpha and beta. In the alpha form, the C1 alcohol group is in the axial position, whereas in the beta form, the C1 alcohol group is in the equatorial position. In particular, "galactose" refers to the cyclic six-membered pyranose, more in particular the D-isomer and even more particularly the alpha-D-form (α-D-galactopyranose) the formal name for which is (2R,3R,4S,5R,6R)-6-(hydroxymethyl)tetrahydro-2H-pyran-2,3,4,5-tetraol. Glucose is an epimer of galactose; the formal name is (2R,3R,4S,5S,6R)-6-(hydroxymethyl)tetrahydro-2H-pyran-2,3,4,5-tetraol. The structure and numbering of galactose and glucose are shown giving two non-limiting examples of stereochemical illustration.

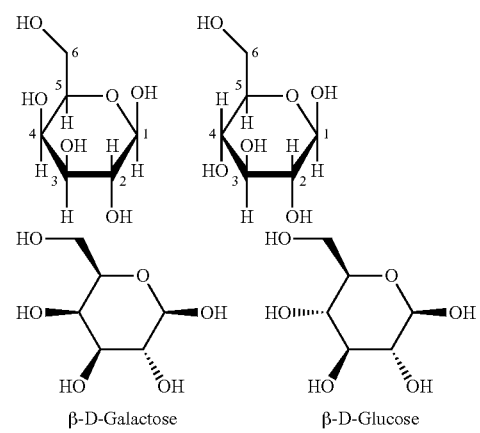

β-D-Galactose     β-D-Glucose

The term "galactosylating moiety" refers to a particular type of liver-targeting moiety. Galactosylating moieties include, but are not limited to a galactose, galactosamine and/or N-acetylgalactosamine residue. A "glucosylating moiety" refers to another particular type of liver-targeting moiety and includes, but is not limited to glucose, glucosamine and/or N-acetylglucosamine.

The term "liver-targeting moiety", refers to moieties having the ability to direct, e.g., a polypeptide, to the liver. The liver comprises different cell types, including but not limited to hepatocytes, sinusoidal epithelial cells, Kupffer cells, stellate cells, and/or dendritic cells. Typically, a liver-targeting moiety directs a polypeptide to one or more of these cells. On the surface of the respective liver cells, receptors are present which recognize and specifically bind the liver-targeting moiety. Liver-targeting can be achieved by chemical conjugation of an antigen or ligand to a galactosylating or glucosylating moiety, desialylation of an antigen or ligand to expose underlying galactosyl or glucosyl moieties, or specific binding of an endogenous antibody to an antigen or ligand, where the antigen or ligand is: desialylated to expose underlying galactosyl or glucosyl moieties, conjugated to a galactosylating or a glucosylating moiety. Naturally occurring desialylated proteins are not encompassed within the scope of certain embodiments of the present disclosure.

The "numerical values" and "ranges" provided for the various substituents are intended to encompass all integers within the recited range. For example, when defining n as an integer representing a mixture including from about 1 to 100, particularly about 8 to 90 and more particularly about 40 to 80 ethylene glycol groups, where the mixture typically encompasses the integer specified as n±about 10% (or for smaller integers from 1 to about 25, ±3), it should be understood that n can be an integer from about 1 to 100 (e.g., 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110, or any between those listed, including the endpoints of the range)

and that the disclosed mixture encompasses ranges such as 1-4, 2-4, 2-6, 3-8, 7-13, 6-14, 18-23, 26-30, 42-50, 46-57, 60-78, 85-90, 90-110 and 107-113 ethylene glycol groups. The combined terms "about" and "±10%" or "±3" should be understood to disclose and provide specific support for equivalent ranges wherever used.

The term "optional" or "optionally" means that the subsequently described event or circumstance may or may not occur, and that the description includes instances where said event or circumstance occurs and instances in which it does not.

A peptide that specifically binds a particular target is referred to as a "ligand" for that target.

A "polypeptide" is a term that refers to a chain of amino acid residues, regardless of post-translational modification (e.g., phosphorylation or glycosylation) and/or complexation with additional polypeptides, and/or synthesis into multisubunit complexes with nucleic acids and/or carbohydrates, or other molecules. Proteoglycans therefore also are referred to herein as polypeptides. A long polypeptide (having over about 50 amino acids) is referred to as a "protein." A short polypeptide (having fewer than about 50 amino acids) is referred to as a "peptide." Depending upon size, amino acid composition and three dimensional structure, certain polypeptides can be referred to as an "antigen-binding molecule," "antibody," an "antibody fragment" or a "ligand." Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "purified" as used herein with reference to a polypeptide refers to a polypeptide that has been chemically synthesized and is thus substantially uncontaminated by other polypeptides, or has been separated or isolated from most other cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, a FLAG® tag, or other affinity tag) that facilitates purification or marking (e.g., capture onto an affinity matrix, visualization under a microscope). Thus, a purified composition that comprises a polypeptide refers to a purified polypeptide unless otherwise indicated. The term "isolated" indicates that the polypeptides or nucleic acids of the disclosure are not in their natural environment. Isolated products of the disclosure can thus be contained in a culture supernatant, partially enriched, produced from heterologous sources, cloned in a vector or formulated with a vehicle, etc.

The term "random copolymer" refers to the product of simultaneous polymerization of two or more monomers in admixture, where the probability of finding a given monomeric unit at any given site in a polymer chain is independent of the nature of the neighboring units at that position (Bernoullian distribution). Thus, when the variable group identified as $W_p$ represents a random copolymer, the chain can comprise any sequence from 2 up to about 150 $W^1$ and $W^2$ groups, such as: $—W^1—W^2—W^1—W^2—$; $—W^2—W^1—W^2—W^1—$; $—W^1—W^1—W^1—W^2$; $—W^1—W^1—W^2—W^2—$; $—W^1—W^2—W^2—W^1—$; $—W^1—W^2—W^1—W^2—W^1—W^2—W^1—$; $—W^1—W^1—W^2—W^2—W^1—W^2—W^2—W^1$; $—W^1—W^1—W^2—W^2—W^1—$; and $W^2—W^2—W^1—W^2—W^1—W^1—W^1—W^2—W^2—W^1—W^2—W^2—W^1$; ad infinitum, where Z attached to the various $W^1$ groups and the $W^1$ and $W^2$ groups themselves can be the same or different.

The term "sequence identity" is used with regard to polypeptide (or nucleic acid) sequence comparisons. This expression in particular refers to a percentage of sequence identity, for example at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Particularly, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide.

"Specific binding," as that term is commonly used in the biological arts, refers to a molecule that binds to a target with a relatively high affinity as compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and certain protein-receptor interactions; while such molecules might bind tissues besides their specific targets from time to time, to the extent that such non-target binding is inconsequential, the high-affinity binding pair can still fall within the definition of specific binding.

The term "treatment" or "treating" means any treatment of a disease or disorder in a mammal, including:
preventing or protecting against the disease or disorder, that is, causing the clinical symptoms not to develop;
inhibiting the disease or disorder, that is, arresting or suppressing the development of clinical symptoms; and/or
relieving the disease or disorder, that is, causing the regression of clinical symptoms.

The term "unwanted immune response" refers to a reaction by the immune system of a subject, which in the given situation is not desirable. The reaction of the immune system is unwanted if such reaction does not lead to the prevention, reduction, or healing of a disease or disorder but instead causes, enhances or worsens, or is otherwise associated with induction or worsening of a disorder or disease. Typically, a reaction of the immune system causes, enhances or worsens a disease if it is directed against an inappropriate target. Exemplified, an unwanted immune response includes but is not limited to transplant rejection, immune response against a therapeutic agent, autoimmune disease, and allergy or hypersensitivity.

The term "variant" is to be understood as a protein (or nucleic acid) which differs in comparison to the protein from which it is derived by one or more changes in its length, sequence, or structure. The polypeptide from which a protein variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence or structure in comparison to the parent molecule. Also encompassed are modified molecules such as but not limited to post-translationally modified proteins (e.g. glycosylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Naturally occurring and artificially constructed variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, e.g., is functionally active. A variant can be characterized by a certain degree of sequence identity to the parent polypeptide from which it is derived. More precisely, a protein variant in the context of the present disclosure may exhibit at least 80% sequence identity to its parent polypeptide. Preferably, the sequence identity of protein variants is over a continuous stretch of 20, 30, 40, 45, 50, 60, 70, 80, 90, 100 or more amino acids. As discussed above, in several embodiments variants exhibit about 80%, about 85%, about 90%, about 95%, about 97%, about 98%, about 99% functional equivalence to an unmodified or native reference sequence (and any degree of functional equivalence between those listed).

Compositions

One aspect of the present disclosure relates to compositions, pharmaceutical formulations, and methods of treatment employing such compositions, as represented by Formula 1:

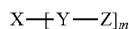

Formula 1 where:
  m is an integer from about 1 to 100, particularly from about 1 to 20, and most particularly 1 to about 10;
  X is an antigen moiety, particularly a foreign antigen or self-antigen against which a patient develops an unwanted immune response, or a tolerogenic portion (e.g., a fragment or an epitope) of such an antigen moiety;
  Y is a linker moiety or a direct bond, or an antibody, antibody fragment, peptide or other ligand that specifically binds X; and
  Z is a liver-targeting moiety, in particular galactosylating or a glucosylating moiety.

The value for m in Formula 1 will depend upon the nature of X, in that each antigen, antibody, antibody fragment or ligand will have an individual number and density of sites (predominantly the N-terminal amine, lysine residues and cysteine residues) to which a linker, a galactosylating moiety or a glucosylating moiety can be bound. Antigens having a limited number of such sites can be derivatized, for example, at the N or C terminus, by adding lysine or cysteine residues (optionally via a cleavable linker, particularly a linker having an immunoproteosome cleavage site). Generally, it is preferred to provide an adequate degree of galactosylation/glucosylation in compositions of Formula 1 so as to facilitate uptake by liver cells. Pharmaceutical formulations and methods of the disclosure can employ a cocktail of compositions of Formula 1, respectively bearing different X moieties (e.g., several epitopes associated with a particular unwanted immune response).

The compositions of Formula 1 include the sub-genuses where X is a foreign transplant antigen against which transplant recipients develop an unwanted immune response (e.g., transplant rejection), a foreign food, animal, plant or environmental antigen against which patients develop an unwanted immune (e.g., allergic or hypersensitivity) response, a foreign therapeutic agent against which patients develop an unwanted immune response (e.g., hypersensitivity and/or reduced therapeutic activity), or a self-antigen against which patients develop an unwanted immune response (e.g., autoimmune disease); where Y is a linker of Formulae Ya through Yp; and/or where Z is galactose, galactosamine, N-acetylgalactosamine, glucose, glucosamine or N-acetylglucosamine as illustrated by Formulae 1a through 1p as described below with reference to the Reaction Schemes.

In additional embodiments, in the compositions of Formula 1, X can be an antibody, antibody fragment or ligand that specifically binds a circulating protein or peptide or antibody, which circulating protein or peptide or antibody is causatively involved in transplant rejection, immune response against a therapeutic agent, autoimmune disease, hypersensitivity and/or allergy.

Antigens

The antigen employed as X in the compositions of Formula 1 can be a protein or a peptide, e.g. the antigen may be a complete or partial therapeutic agent, a full-length transplant protein or peptide thereof, a full-length autoantigen or peptide thereof, a full-length allergen or peptide thereof, and/or a nucleic acid, or a mimetic of an aforementioned antigen. A listing of any particular antigen in a category or association with any particular disease or reaction does not preclude that antigen from being considered part of another category or associated with another disease or reaction.

Antigens employed in the practice of the present disclosure can be one or more of the following:
  Therapeutic agents that are proteins, peptides, antibodies and antibody-like molecules, including antibody fragments and fusion proteins with antibodies and antibody fragments. These include human, non-human (such as mouse) and non-natural (i.e., engineered) proteins, antibodies, chimeric antibodies, humanized antibodies, and non-antibody binding scaffolds, such as fibronectins, DARPins, knottins, and the like.
  Human allograft transplantation antigens against which transplant recipients develop an unwanted immune response.
  Self-antigens that cause an unwanted, autoimmune response. Those skilled in the art will appreciate that while self-antigens are of an endogenous origin in an autoimmune disease patient, the polypeptides employed in the disclosed compositions are typically synthesized exogenously (as opposed to being purified and concentrated from a source of origin).
  Foreign antigens, such as food, animal, plant and environmental antigens, against which a patient experiences an unwanted immune response. Those skilled in the art will appreciate that while a therapeutic protein can also be considered a foreign antigen due to its exogenous origin, for purposes of clarity in the description of the present disclosure such therapeutics are described as a separate group. Similarly, a plant or an animal antigen can be eaten and considered a food antigen, and an environmental antigen may originate from a plant. They are, however, all foreign antigens. In the interest of simplicity no attempt will be made to describe distinguish and define all of such potentially overlapping groups, as those skilled in the art can appreciate the antigens that can be employed in the compositions of the disclosure, particularly in light of the detailed description and examples.

The antigen can be a complete protein, a portion of a complete protein, a peptide, or the like, and can be derivatized (as discussed above) for attachment to a linker and/or galactosylating moiety, can be a variant and/or can contain conservative substitutions, particularly maintaining sequence identity, and/or can be desialylated.

In the embodiments where the antigen is a therapeutic protein, peptide, antibody or antibody-like molecule, specific antigens can be selected from: Abatacept, Abciximab, Adalimumab, Adenosine deaminase, Ado-trastuzumab emtansine, Agalsidase alfa, Agalsidase beta, Aldeslukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin [including recombinant human insulin ("rHu insulin") and bovine insulin], Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Natalizumab, Octreotide, Ofatumumab, Oprelvekin, Pancreatic amylase, Pancreatic lipase, Papain, Peg-asparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, vW factor. The therapeutic protein can be obtained from natural sources (e.g., concentrated and purified) or synthesized, e.g., recombinantly, and includes antibody therapeutics that are typically IgG monoclonal or fragments or fusions.

Particular therapeutic protein, peptide, antibody or antibody-like molecules include Abciximab, Adalimumab, Agalsidase alfa, Agalsidase beta, Aldeslukin, Alglucosidase alfa, Factor VIII, Factor IX, Infliximab, Insulin (including rHu Insulin), L-asparaginase, Laronidase, Natalizumab, Octreotide, Phenylalanine ammonia-lyase (PAL), or Rasburicase (uricase) and generally IgG monoclonal antibodies in their varying formats.

Another particular group includes the hemostatic agents (Factor VIII and IX), Insulin (including rHu Insulin), and the non-human therapeutics uricase, PAL and asparaginase.

Unwanted immune response in hematology and transplant includes autoimmune aplastic anemia, transplant rejection (generally), and Graft vs. Host Disease (bone marrow transplant rejection). In the embodiments where the antigen is a human allograft transplantation antigen, specific sequences can be selected from: subunits of the various MHC class I and MHC class II haplotype proteins (for example, donor/recipient differences identified in tissue cross-matching), and single-amino-acid polymorphisms on minor blood group antigens including RhCE, Kell, Kidd, Duffy and Ss. Such compositions can be prepared individually for a given donor/recipient pair.

In the embodiments where the antigen is a self-antigen, specific antigens (and the autoimmune disease with which they are associated) can be selected from:

In type 1 diabetes mellitus, several main antigens have been identified: insulin, proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β); other antigens include ICA69, ICA12 (SOX-13), carboxypeptidase H, Imogen 38, GLIMA 38, chromogranin-A, HSP-60, carboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. It should be noted that insulin is an example of an antigen that can be characterized both as a self-antigen and a therapeutic protein antigen. For example, rHu Insulin and bovine insulin are therapeutic protein antigens (that are the subject of unwanted immune attack), whereas endogenous human insulin is a self-antigen (that is the subject of an unwanted immune attack). Because endogenous human insulin is not available to be employed in a pharmaceutical composition, a recombinant form is employed in certain embodiments of the compositions of the disclosure.

Human insulin, including an exogenously obtained form useful in the compositions of the disclosure, has the following sequence (UNIPROT P01308):

```
                                    (SEQ ID NO: 1)
MALWMRLLPL LALLALWGPD PAAAFVNQHL CGSHLVEALY

LVCGERGFFY TPKTRREAED LQVGQVELGG GPGAGSLQPL

ALEGSLQKRG IVEQCCTSIC SLYQLENYCN.
```

GAD-65, including an exogenously obtained form useful in the compositions of the disclosure, has the following sequence (UNIPROT Q05329):

```
                                    (SEQ ID NO: 2)
MASPGSGFWS FGSEDGSGDS ENPGTARAWC QVAQKFTGGI

GNKLCALLYG DAEKPAESGG SQPPRAAARK AACACDQKPC

SCSKVDVNYA FLHATDLLPA CDGERPTLAF LQDVMNILLQ

YVVKSFDRST KVIDFHYPNE LLQEYNWELA DQPQNLEEIL

MHCQTTLKYA IKTGHPRYFN QLSTGLDMVG LAADWLTSTA
```

```
NTNMFTYEIA PVFVLLEYVT LKKMREIIGW PGGSGDGIFS

PGGAISNMYA MMIARFKMFP EVKEKGMAAL PRLIAFTSEH

SHFSLKKGAA ALGIGTDSVI LIKCDERGKM IPSDLERRIL

EAKQKGFVPF LVSATAGTTV YGAFDPLLAV ADICKKYKIW

MHVDAAWGGG LLMSRKHKWK LSGVERANSV TWNPHKMMGV

PLQCSALLVR EEGLMQNCNQ MHASYLFQQD KHYDLSYDTG

DKALQCGRHV DVFKLWLMWR AKGTTGFEAH VDKCLELAEY

LYNIIKNREG YEMVFDGKPQ HTNVCRNYIP PSLRTLEDNE

ERMSRLSKVA PVIKARMMEY GTTMVSYQPL GDKVNFFRMV

ISNPAATHQD IDFLIEEIER LGQDL.
```

IGRP, including an exogenously obtained form useful in the compositions of the disclosure, has the following sequence (UNIPROT QN9QR9):

```
                                            (SEQ ID NO: 3)
MDFLHRNGVLIIQHLQKDYRAYYTFLNFMSNVGDPRNIFFIYFPLCFQFN

QTVGTKMIWVAVIGDWLNLIFKWILFGHRPYWWVQETQIYPNHSSPCLEQ

FPTTCETGPGSPSGHAMGASCVWYVMVTAALSHTVCGMDKFSITLHRLTW

SFLWSVFWLIQISVCISRVFIATHFPHQVILGVIGGMLVAEAFEHTPGIQ

TASLGTYLKTNLFLFLFAVGFYLLLRVLNIDLLWSVPIAKKWCANPDWIH

IDTTPFAGLVRNLGVLFGLGFAINSEMFLLSCRGGNNYTLSFRLLCALTS

LTILQLYHFLQIPTHEEHLFYVLSFCKSASIPLTVVAFIPYSVHMLMKQS

GKKSQ.
```

In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor.

In Addison's Disease, main antigens include 21-hydroxylase, 17α-hydroxylase, and P450 side chain cleavage enzyme (P450scc); other antigens include ACTH receptor, P450c21 and P450c17.

In premature ovarian failure, main antigens include FSH receptor and α-enolase.

In autoimmune hypophysitis, or pituitary autoimmune disease, main antigens include pituitary gland-specific protein factor (PGSF) 1a and 2; another antigen is type 2 iodothyronine deiodinase.

In multiple sclerosis, main antigens include myelin basic protein ("MBP"), myelin oligodendrocyte glycoprotein ("MOG") and myelin proteolipid protein ("PLP").

MBP, including an exogenously obtained form useful in the compositions of the disclosure, has the following sequence (UNIPROT P02686):

```
                                            (SEQ ID NO: 4)
MGNHAGKRELNAEKASTNSETNRGESEKKRNLGELSRTTSEDNEVFGEAD

ANQNNGTSSQDTAVTDSKRTADPKNAWQDAHPADPGSRPHLIRLFSRDAP

GREDNTFKDRPSESDELQTIQEDSAATSESLDVMASQKRPSQRHGSKYLA

TASTMDHARHGFLPRHRDTGILDSIGRFFGGDRGAPKRGSGKDSHHPART

AHYGSLPQKSHGRTQDENPVVHFFKNIVTPRTPPPSQGKGRGLSLSRFSW

GAEGQRPGFGYGGRASDYKSAHKGFKGVDAQGTLSKIFKLGGRDSRSGSP

MARR.
```

MOG, including an exogenously obtained form useful in the compositions of the disclosure, has the following sequence (UNIPROT Q16653):

```
                                            (SEQ ID NO: 5)
MASLSRPSLPSCLCSFLLLLLLQVSSSYAGQFRVIGPRHPIRALVGDEVE

LPCRISPGKNATGMEVGWYRPPFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLIFLCLQYRLRGKLRAEIENLHRTFDPH

FLRVPCWKITLFVIVPVLGPLVALIICYNWLHRRLAGQFLEELRNPF.
```

PLP, including an exogenously obtained form useful in the compositions of the disclosure, has the following sequence (UNIPROT P60201):

```
                                            (SEQ ID NO: 6)
MGLLECCARCLVGAPFASLVATGLCFFGVALFCGCGHEALTGTEKLIETY

FSKNYQDYEYLINVIHAFQYVIYGTASFFFLYGALLLAEGFYTTGAVRQI

FGDYKTTICGKGLSATVTGGQKGRGSRGQHQAHSLERVCHCLGKWLGHPD

KFVGITYALTVVWLLVFACSAVPVYIYFNTVVTTCQSIAFPSKTSASIGS

LCADARMYGVLPWNAFPGKVCGSNLLSICKTAEFQMTFHLFIAAFVGAAA

TLVSLLTFMIAATYNFAVLKLMGRGTKF.
```

Peptides/epitopes useful in the compositions of the disclosure for treating multiple sclerosis include some or all of the following sequences, individually in a composition of Formula 1 or together in a cocktail of compositions of Formula 1:

```
MBP13-32:
                                            (SEQ ID NO: 7)
    KYLATASTMDHARHGFLPRH;

MBP83-99:
                                            (SEQ ID NO: 8)
    ENPWHFFKNIVTPRTP;

MBP111-129:
                                            (SEQ ID NO: 9)
    LSRFSWGAEGQRPGFGYGG;

MBP146-170:
                                            (SEQ ID NO: 10)
    AQGTLSKIFKLGGRDSRSGSPMARR;

MOG1-20:
                                            (SEQ ID NO: 11)
    GQFRVIGPRHPIRALVGDEV;

MOG35-55:
                                            (SEQ ID NO: 12)
    MEVGWYRPPFSRWHLYRNGK;
``` and

PLP139-154:

(SEQ ID NO: 13)
HCLGKWLGHPDKFVGI.

In rheumatoid arthritis, main antigens include collagen II, immunoglobulin binding protein, the fragment crystallizable region of immunoglobulin G, double-stranded DNA, and the natural and cirtullinated forms of proteins implicated in rheumatoid arthritis pathology, including fibrin/fibrinogen, vimentin, collagen I and II, and alpha-enolase.

In autoimmune gastritis, a main antigen is H+,K+-ATPase.

In pernicious angemis, a main antigen is intrinsic factor.

In celiac disease, main antigens are tissue transglutaminase and the natural and deamidated forms of gluten or gluten-like proteins, such as alpha-, gamma-, and omega-gliadin, glutenin, hordein, secalin, and avenin. Those skilled in the art will appreciate, for example, that while the main antigen of celiac disease is alpha gliadin, alpha gliadin turns more immunogenic in the body through deamidation by tissue glutaminase converting alpha gliadin's glutamines to glutamic acid. Thus, while alpha gliadin is originally a foreign food antigen, once it has been modified in the body to become more immunogenic it can be characterized as a self-antigen.

In vitiligo, a main antigen is tyrosinase, and tyrosinase related protein 1 and 2.

MART1, Melanoma antigen recognized by T cells 1, Melan-A, including an exogenously obtained form useful in the compositions of the disclosure, has the following sequence (UNIPROT Q16655):

(SEQ ID NO: 14)
MPREDAHFIYGYPKKGHGHSYTTAEEAAGIGILTVILGVLLLIGCWYCRR

RNGYRALMDKSLHVGTQCALTRRCPQEGFDHRDSKVSLQEKNCEPVVPNA

PPAYEKLSAEQSPPPYSP.

Tyrosinase, including an exogenously obtained form useful in the compositions of the disclosure, has the following sequence (UNIPROT P14679):

(SEQ ID NO: 15)
MLLAVLYCLLWSFQTSAGHFPRACVSSKNLMEKECCPPWSGDRSPCGQLS

GRGSCQNILLSNAPLGPQFPFTGVDDRESWPSVFYNRTCQCSGNFMGFNC

GNCKFGFWGPNCTERRLLVRRNIFDLSAPEKDKFFAYLTLAKHTISSDYV

IPIGTYGQMKNGSTPMFNDINIYDLFVWMHYYVSMDALLGGSEIWRDIDF

AHEAPAFLPWHRLFLLRWEQEIQKLTGDENFTIPYWDWRDAEKCDICTDE

YMGGQHPTNPNLLSPASFFSSWQIVCSRLEEYNSHQSLCNGTPEGPLRRN

PGNHDKSRTPRLPSSADVEFCLSLTQYESGSMDKAANFSFRNTLEGFASP

LTGIADASQSSMHNALHIYMNGTMSQVQGSANDPIFLLHHAFVDSIFEQW

LRRHRPLQEVYPEANAPIGHNRESYMVPFIPLYRNGDFFISSKDLGYDYS

YLQDSDPDSFQDYIKSYLEQASRIWSWLLGAAMVGAVLTALLAGLVSLLC

RHKRKQLPEEKQPLLMEKEDYHSLYQSHL.

Melanocyte protein PMEL, gp100, including an exogenously obtained form useful in the compositions of the disclosure, has the following sequence (UNIPROT P40967):

(SEQ ID NO: 16)
MDLVLKRCLLHLAVIGALLAVGATKVPRNQDWLGVSRQLRTKAWNRQLYP

EVVTEAQRLDCWRGGQVSLKVSNDGPTLIGANASFSIALNFPGSQKVLPD

GQVIWVNNTIINGSQVWGGQPVYPQETDDACIFPDGGPCPSGSWSQKRSF

VYVWKTWGQYWQVLGGPVSGLSIGTGRAMLGTHTMEVTVYHRRGSRSYVP

LAHSSSAFTITDQVPFSVSVSQLRALDGGNKHFLRNQPLTFALQLHDPSG

YLAEADLSYTWDFGDSSGTLISRALVVTHTYLEPGPVTAQVVLQAAIPLT

SCGSSPVPGTTDGHRPTAEAPNTTAGQVPTTEVVGTTPGQAPTAEPSGTT

SVQVPTTEVISTAPVQMPTAESTGMTPEKVPVSEVMGTTLAEMSTPEATG

MTPAEVSIVVLSGTTAAQVTTTEWVETTARELPIPEPEGPDASSIMSTES

ITGSLGPLLDGTATLRLVKRQVPLDCVLYRYGSFSVTLDIVQGIESAEIL

QAVPSGEGDAFELTVSCQGGLPKEACMEISSPGCQPPAQRLCQPVLPSPA

CQLVLHQILKGGSGTYCLNVSLADTNSLAVVSTQLIMPGQEAGLGQVPLI

VGILLVLMAVVLASLIYRRRLMKQDFSVPQLPHSSSHWLRLPRIFCSCPI

GENSPLLSGQQV.

In myasthenia gravis, a main antigen is acetylcholine receptor.

In pemphigus vulgaris and variants, main antigens are desmoglein 3, 1 and 4; other antigens include pemphaxin, desmocollins, plakoglobin, perplakin, desmoplakins, and acetylcholine receptor.

In bullous pemphigoid, main antigens include BP180 and BP230; other antigens include plectin and laminin 5.

In dermatitis herpetiformis Duhring, main antigens include endomysium and tissue transglutaminase.

In epidermolysis bullosa acquisita, a main antigen is collagen VII.

In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jo1, NAG-2, centromere proteins, topoisomerase I, nucleolar proteins, RNA polymerase I, II and III, PM-Slc, fibrillarin, and B23.

In mixed connective tissue disease, a main antigen is U1snRNP.

In Sjogren's syndrome, the main antigens are nuclear antigens SS-A and SS-B; other antigens include fodrin, poly(ADP-ribose) polymerase and topoisomerase, muscarinic receptors, and the Fc-gamma receptor IIIb.

In systemic lupus erythematosus, main antigens include nuclear proteins including the "Smith antigen," SS-A, high mobility group box 1 (HMGB1), nucleosomes, histone proteins and double-stranded DNA (against which auto-antibodies are made in the disease process).

In Goodpasture's syndrome, main antigens include glomerular basement membrane proteins including collagen IV.

In rheumatic heart disease, a main antigen is cardiac myosin.

In autoimmune polyendocrine syndrome type 1 antigens include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

In neuromyelitis optica, a main antigen is AQP4.

Aquaporin-4, including an exogenously obtained form useful in the compositions of the disclosure, has the following sequence (UNIPROT P55087):

```
                                           (SEQ ID NO: 17)
MSDRPTARRWGKCGPLCTRENIMVAFKGVWTQAFWKAVTAEFLAMLIFVL

LSLGSTINWGGTEKPLPVDMVLISLCFGLSIATMVQCFGHISGGHINPAV

TVAMVCTRKISIAKSVFYIAAQCLGAIIGAGILYLVTPPSVVGGLGVTMV

HGNLTAGHGLLVELIITFQLVFTIFASCDSKRTDVTGSIALAIGFSVAIG

HLFAINYTGASMNPARSFGPAVIMGNWENHWIYWVGPIIGAVLAGGLYEY

VFCPDVEFKRRFKEAFSKAAQQTKGSYMEVEDNRSQVETDDLILKPGVVH

VIDVDRGEEKKGKDQSGEVLSSV.
```

In uveitis, main antigens include Retinal S-antigen or "S-arrestin" and interphotoreceptor retinoid binding protein (IRBP) or retinol-binding protein 3.

S-arrestin, including an exogenously obtained form useful in the compositions of the disclosure, has the following sequence (UNIPROT P10523):

```
                                           (SEQ ID NO: 18)
MAASGKTSKS EPNHVIFKKI SRDKSVTIYL GNRDYIDHVS

QVQPVDGVVL VDPDLVKGKK VYVTLTCAFR YGQEDIDVIG

LTFRRDLYFS RVQVYPPVGA ASTPTKLQES LLKKLGSNTY

PFLLTFPDYL PCSVMLQPAP QDSGKSCGVD FEVKAFATDS

TDAEEDKIPK KSSVRLLIRK VQHAPLEMGP QPRAEAAWQF

FMSDKPLHLA VSLNKEIYFH GEPIPVTVTV TNNTEKTVKK

IKAFVEQVAN VVLYSSDYYV KPVAMEEAQE KVPPNSTLTK

TLTLLPLLAN NRERRGIALD GKIKHEDTNL ASSTIIKEGI

DRTVLGILVS YQIKVKLTVS GFLGELTSSE VATEVPFRLM

HPQPEDPAKE SYQDANLVFE EFARHNLKDA GEAEEGKRDK

NDVDE.
```

IRBP, including an exogenously obtained form useful in the compositions of the disclosure, has the following sequence (UNIPROT P10745):

```
                                           (SEQ ID NO: 19)
MMREWVLLMSVLLCGLAGPTHLFQPSLVLDMAKVLLDNYCFPENLLGMQE

AIQQAIKSHEILSISDPQTLASVLTAGVQSSLNDPRLVISYEPSTPEPPP

QVPALTSLSEEELLAWLQRGLRHEVLEGNVGYLRVDSVPGQEVLSMMGEF

LVAHVWGNLMGTSALVLDLRHCTGGQVSGIPYIISYLHPGNTILHVDTIY

NRPSNTTTEIWTLPQVLGERYGADKDVVVLTSSQTRGVAEDIAHILKQMR

RAIVVGERTGGGALDLRKLRIGESDFFFTVPVSRSLGPLGGGSQTWEGSG

VLPCVGTPAEQALEKALAILTLRSALPGVVHCLQEVLKDYYTLVDRVPTL

-continued
LQHLASMDFSTVVSEEDLVTKLNAGLQAASEDPRLLVRAIGPTETPSWPA

PDAAAEDSPGVAPELPEDEAIRQALVDSVFQVSVLPGNVGYLRFDSFADA

SVLGVLAPYVLRQVWEPLQDTEHLIMDLRHNPGGPSSAVPLLLSYFQGPE

AGPVHLFTTYDRRTNITQEHFSHMELPGPRYSTQRGVYLLTSHRTATAAE

EFAFLMQSLGWATLVGEITAGNLLHTRTVPLLDTPEGSLALTVPVLTFID

NHGEAWLGGGVVPDAIVLAEEALDKAQEVLEFHQSLGALVEGTGHLLEAH

YARPEVVGQTSALLRAKLAQGAYRTAVDLESLASQLTADLQEVSGDHRLL

VFHSPGELVVEEAPPPPPAVPSPEELTYLIEALFKTEVLPGQLGYLRFDA

MAELETVKAVGPQLVRLVWQQLVDTAALVIDLRYNPGSYSTAIPLLCSYF

FEAEPRQHLYSVFDRATSKVTEVWTLPQVAGQRYGSHKDLYILMSHTSGS

AAEAFAHTMQDLQRATVIGEPTAGGALSVGIYQVGSSPLYASMPTQMAMS

ATTGKAWDLAGVEPDITVPMSEALSIAQDIVALRAKVPTVLQTAGKLVAD

NYASAELGAKMATKLSGLQSRYSRVTSEVALAEILGADLQMLSGDPHLKA

AHIPENAKDRIPGIVPMQIPSPEVFEELIKFSFHTNVLEDNIGYLRFDMF

GDGELLTQVSRLLVEHIWKKIMHTDAMIIDMRFNIGGPTSSIPILCSYFF

DEGPPVLLDKIYSRPDDSVSELVVTHAQVVGERYGSKKSMVILTSSVTAG

TAEEFTYIMKRLGRALVIGEVTSGGCQPPQTYHVDDTNLYLTIPTARSVG

ASDGSSWEGVGVTPHVVVPAEEALARAKEMLQHNQLRVKRSPGLQDHL.
```

In the embodiments where the antigen is a foreign antigen against which an unwanted immune response can be developed, such as food antigens, specific antigens can be:

from peanut: conarachin (Ara h 1), allergen II (Ara h 2), arachis agglutinin, conglutin (Ara h 6);

conarachin, for example has the sequence identified as UNIPROT Q6PSU6 from apple: 31 kda major allergen/disease resistance protein homolog (Mal d 2), lipid transfer protein precursor (Mal d 3), major allergen Mal d 1.03D (Mal d 1);

from milk: α-lactalbumin (ALA), lactotransferrin; from kiwi: actinidin (Act c 1, Act d 1), phytocystatin, thaumatin-like protein (Act d 2), kiwellin (Act d 5);

from egg whites: ovomucoid, ovalbumin, ovotransferrin, and lysozyme;

from egg yolks: livetin, apovitillin, and vosvetin;

from mustard: 2S albumin (Sin a 1), 11S globulin (Sin a 2), lipid transfer protein (Sin a 3), profilin (Sin a 4);

from celery: profilin (Api g 4), high molecular weight glycoprotein (Api g 5);

from shrimp: Pen a 1 allergen (Pen a 1), allergen Pen m 2 (Pen m 2), tropomyosin fast isoform;

from wheat and/or other cereals: high molecular weight glutenin, low molecular weight glutenin, alpha-, gamma- and omega-gliadin, hordein, secalin and/or avenin;

peptides/epitopes useful in the compositions of the disclosure for treating Celiac Disease include some or all of the following sequences, individually in a composition of Formula 1 or together in a cocktail of compositions of Formula 1:

```
DQ-2 relevant, Alpha-gliadin "33-mer" native:
                                        (SEQ ID NO: 20)
LQLQPFPQPQLPYPQPQLPYPQPQLPYPQPQPF DQ-2 relevant, Alpha-gliadin "33-mer" deamidated:
                                        (SEQ ID NO: 21)
LQLQPFPQPELPYPQPELPYPQPELPYPQPQPF DQ-8 relevant, Alpha-gliadin:
                                        (SEQ ID NO: 22)
QQYPSGQGSFQPSQQNPQ DQ-8 relevant, Omega-gliadin (wheat, U5UA46):
                                        (SEQ ID NO: 23)
QPFPQPEQPFPW
``` from strawberry: major strawberry allergy Fra a 1-E (Fra a 1); and from banana: profilin (Mus xp 1).

In the embodiments where the antigen is a foreign antigen against which an unwanted immune response is developed, such as to animal, plant and environmental antigens, specific antigens can, for example, be: cat, mouse, dog, horse, bee, dust, tree and goldenrod, including the following proteins or peptides derived from:

weeds, (including ragweed allergens amb a 1, 2, 3, 5, and 6, and Amb t 5; pigweed Che a 2 and 5; and other weed allergens Par j 1, 2, and 3, and Par o 1);

grass (including major allergens Cyn d 1, 7, and 12; Dac g 1, 2, and 5; Hol l 1.01203; Lol p 1, 2, 3, 5, and 11; Mer a 1; Pha a 1; Poa p 1 and 5);

pollen from ragweed and other weeds (including curly dock, lambs quarters, pigweed, plantain, sheep sorrel, and sagebrush), grass (including Bermuda, Johnson, Kentucky, Orchard, Sweet vernal, and Timothy grass), and trees (including catalpa, elm, hickory, olive, pecan, sycamore, and walnut);

dust (including major allergens from species *Dermatophagoides pteronyssinus*, such as Der p 1, 2, 3, 4, 5, 6, 7, 8, 9, 10, 11, 14, 15, 18, 20, 21, and 23; from species *Dermatophagoides farina*, such as Der f 1, 2, 3, 6, 7, 10, 11, 13, 14, 15, 16, 18, 22, and 24; from species *Blomia tropicalis* such as Blo t 1, 2, 3, 4, 5, 6, 10, 11, 12, 13, 19, and 21; also allergens Eur m 2 from *Euroglyphus maynei*, Tyr p 13 from *Tyrophagus putrescentiae*, and allergens Bla g 1, 2, and 4; Per a 1, 3, and 7 from cockroach);

pets (including cats, dogs, rodents, and farm animals; major cat allergens include Fel d 1 through 8, cat IgA, BLa g 2, and cat albumin; major dog allergens include Can f 1 through 6, and dog albumin);

bee stings, including major allergens Api m 1 through 12; and fungus, including allergens derived from, species of *Aspergillus* and *Penicillium*, as well as the species *Alternaria alternata, Davidiella tassiana*, and *Trichophyton rubrum*.

As will be appreciated by those skilled in the art, a patient can be tested to identify an antigen against which an unwanted immune response has developed, and a protein, peptide or the like can be developed based on that antigen and incorporated as X in a composition of the present disclosure.

Sialated Antigens, Antibodies, Antibody Fragments

Following are non-limiting examples of antigens, antibodies, antibody fragments having sialylation that can be removed to leave glycosylation specifically targeting the ASGPR: follicle stimulating hormone (FSH), human chorionic gonadotropin (HCG), luteinizing hormone (LH), osteopontin, thyroid stimulating hormone (TSH), agalsidase alfa, agalsidase beta (FABRAZYME®; Genzyme), epoetin alfa and epoetin beta, follitropin alfa (GONAL-F®; Merck/Serono) and follitropin beta (FOLLISTIM®; Schering-Plough), insulin growth factor binding protein 6 (IGFBP-6), lutropin alfa (LUVERIS®; Merck/Serono), transforming growth factor β1, antithrombin (ATryn®/TROMBATE-III®; Genzyme/Talecris Biotherapeutics), thyrotropin alfa (THYROGEN®; Genzyme), lenograstim, sargramostim (LEUKINE®; Genzyme), interleukin-3, prourokinase, lymphotoxin, C1-esterase inhibitor (Berinert®; CSL), IgG-like antibodies, interferon beta, coagulation factor VIIa (NOVO-SEVEN®; Novo Nordisk), coagulation factor VIII (moroctocog alfa), coagulation factor IX (nonacog alfa) (BENEFIX®; Wyeth), and the p55 tumor necrosis receptor fusion protein. (See: Byrne et al., Drug Discovery Today, Vol 12, No. 7/8, pages 319-326, April 2007 and Sola et al., *BioDrugs*. 2010; 24(1): 9-21). Pharmaceutically relevant proteins that have previously been hyperglycosylated and can be desialylated for hepatocyte-ASGPR targeting include: interferon alfa and gamma, luteinizing hormone, Fv antibody fragments, asparaginase, cholinesterase, darbepoetin alfa (AraNESP®; Amgen), thrombopoietin, leptin, FSH, IFN-α2, serum albumin, and corifollitropin alfa.

Proteins with glycans that do not normally terminate in sialic acids, including proteins produced in bacteria or yeast (such as arginase, some insulins, and uricase) would not be amenable to desialylation.

Those skilled in the art will appreciate that publicly available references, such as UNIPROT, disclose the presence and location of sites for desialylation on most if not all antigens, antibodies, antibody fragments and ligands of interest.

Antibodies and Peptide Ligands

In the embodiments employing an antibody, antibody fragment or ligand, such moieties are chosen to specifically bind a targeted circulating protein or peptide or antibody, and result in hepatic uptake of the circulating targeted moiety, possibly as an adduct with the targeting moiety, ultimately resulting in the clearance and inactivation of the circulating targeted moiety. For example, liver-targeted Factor VIII will bind and clear circulating anti-Factor VIII antibodies. Procedures for the identification of such moieties will be familiar to those skilled in the art.

Linkers

The linkers employed in the compositions of the present disclosure ("Y" in Formula 1) can include N-hydroxysuccinamidyl linkers, malaemide linkers, vinylsulfone linkers, pyridyl di-thiol-poly(ethylene glycol) linkers, pyridyl di-thiol linkers, n-nitrophenyl carbonate linkers, NHS-ester linkers, nitrophenoxy poly(ethylene glycol)ester linkers and the like.

One particular group of linkers comprises linkers of Formula Y'-CMP below (where Y' indicates the remaining portion of the linker and $R^9$ and Z are as defined). More particularly, in the group of linkers including Formula Y'-CMP, in several embodiments the $R^9$ substituent is an ethylacetamido group, and even more particularly the ethylacetamido is conjugated with C1 of N-acetylgalactosamine or N-acetylglucosamine.

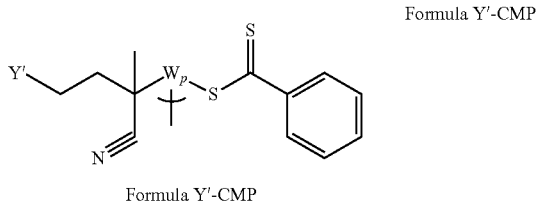

Formula Y'-CMP

Formula Y'-CMP

Di-thiol-containing linkers, particularly disulfanylethyl carbamate-containing linkers (named including a free amine of X, otherwise named a "disulfanyl ethyl ester" without including the free amine of X) are particularly advantageous in the present compositions as having the ability to cleave and release an antigen in its original form once inside a cell, for example as illustrated below (where Y' indicates the remaining portion of the linker and X' and Z are as defined).

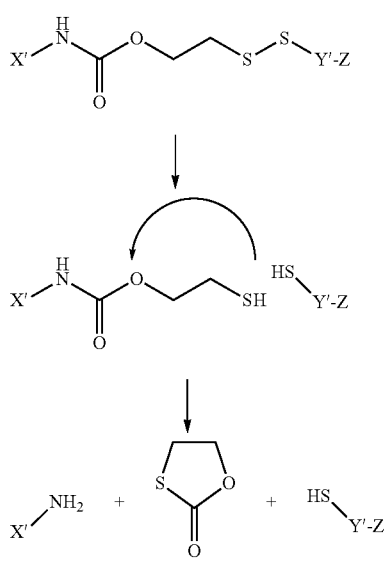

Particularly with regard to the linkers illustrated below in Formula Ya through Formula Yp:
 the left bracket "(" indicates the bond between X and Y;
 the right or bottom bracket ")" indicates the bond between Y and Z;
 n is an integer representing a mixture including from about 1 to 100, particularly about 8 to 90 (e.g., 7, 8, 9, 10, 11, 12, 13, 14, 15, 16, 17, 18, 19, 20, 25, 30, 35, 40, 45, 50, 55, 60, 65 70, 75, 80, 85, 90 or 95), more particularly about 40 to 80 (e.g., 39, 40, 43, 45, 46, 48, 50, 52, 53, 55, 57, 60, 62, 65, 66, 68, 70, 73, 75, 78, 80 or 81) ethylene glycol groups, where the mixture typically encompasses the integer specified as n±10%;
 p is an integer representing a mixture including from about 2 to 150, particularly about 20 to 100 (e.g., 18, 19, 20, 25, 30, 35, 40, 45, 50, 55, 60, 65 70, 75, 80, 85, 90, 95, 100 or 105) and more particularly about 30 to 40 (e.g., 28, 29, 30, 31, 32, 33, 34, 35, 36, 37, 38, 39, 40, 41, 42, 43 or 44), where the mixture typically encompasses the integer specified as p±10%;
 q is an integer representing a mixture including from about 1 to 44, particularly about 3 to 20 (e.g., 3, 4, 5, 6, 7, 8, 9, 10, 11, 12, 13, 14, 15, 16, 17, 18, 19, 20, 21 or 22) and more particularly about 4 to 12 (e.g., 4, 5, 6, 7, 8, 9, 10, 11, 12 or 13), where the mixture typically encompasses the integer specified as q±10%; and
 $R^8$ is —$CH_2$— ("methyl") or —$CH_2$—$CH_2$—$C(CH_3)$(CN)— ("1-cyano-1-methyl-propyl" or "CMP").
Y' represents the remaining portion of Y (e.g., HS-PEG); and
W represents a polymer of the same $W^1$ group, or W is a copolymer (preferably a random
copolymer) of the same or different $W^1$ and $W^2$ groups, where:

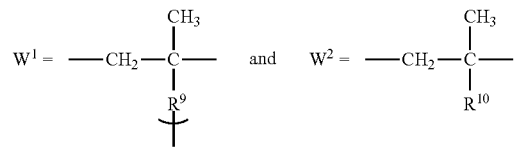

where:
 p is an integer from 2 to about 150;
 $R^9$ is a direct bond, —$CH_2$—$CH_2$—NH—C(O)— (i.e., an ethylacetamido group or "EtAcN") or —$CH_2$—$CH_2$—(O—$CH_2$—$CH_2$)$_t$—NH—C(O)— (i.e., a pegylated ethylacetamido group or "Et-PEG$_t$-AcN")
 t is an integer from 1 to 5, (particularly 1 to 3, and more particularly 1 or 2); and
 $R^{10}$ is an aliphatic group, an alcohol or an aliphatic alcohol, particularly N-(2-hydroxypropyl)methylacrylamide; and
 Z (not shown) is galactose, glucose, galactosamine, glucosamine, N-acetylgalactosamine or N-acetylglucosamine.
Formulae Ya Through Yp Formula Ya

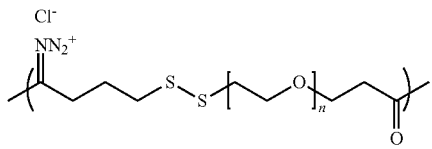

Formula Yb

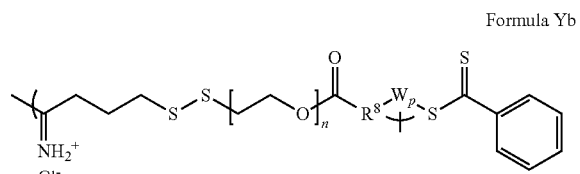

Formula Yc

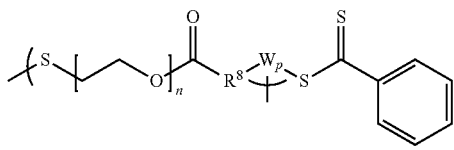

Formula Yd

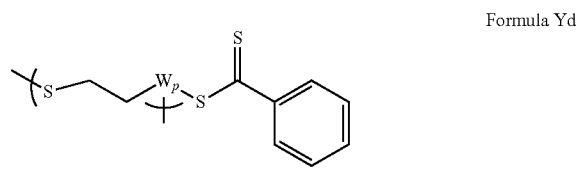

-continued
Formula Ye
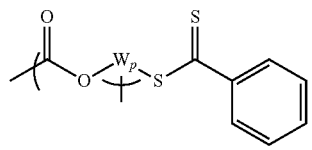
Formula Yf
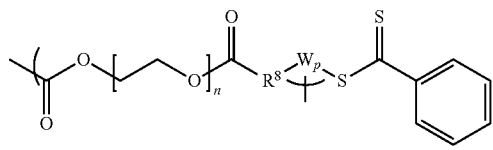
Formula Yg
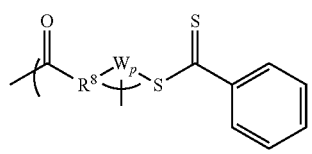
Formula Yh
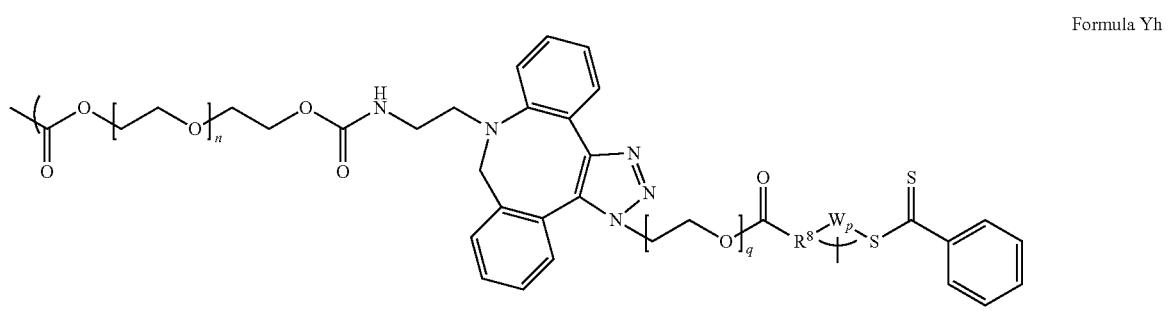
Formula Yi
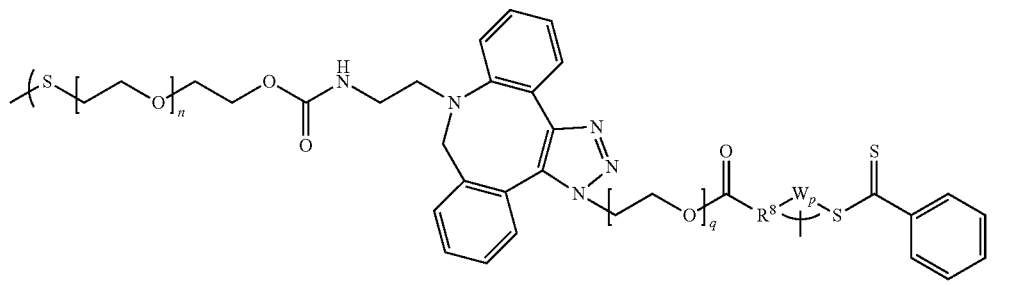
Formula Yj
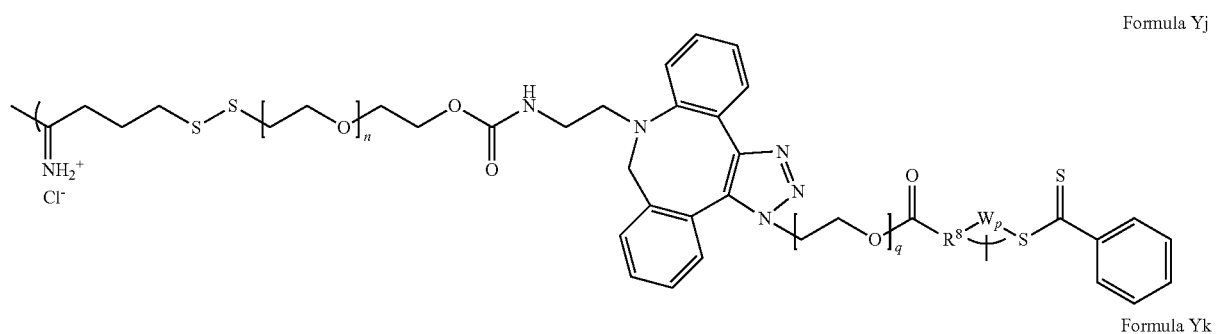
Formula Yk
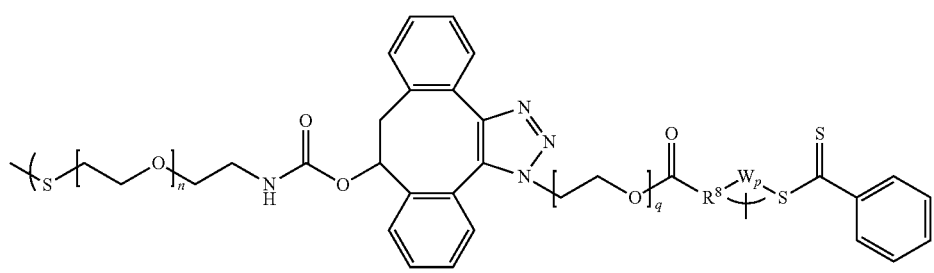

Formula YL

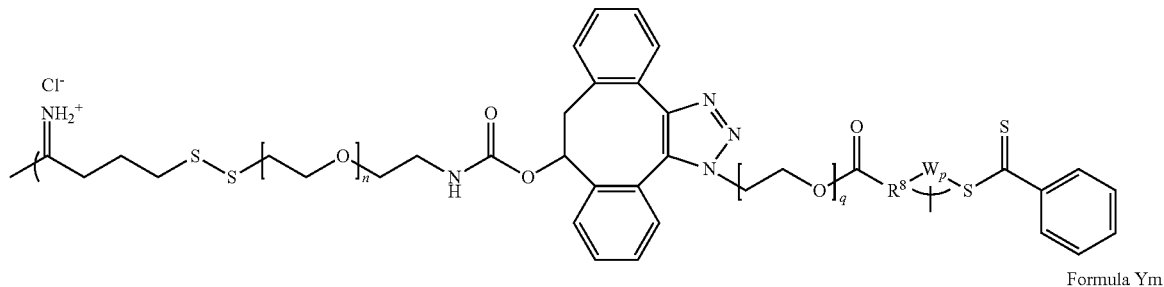

Formula Ym

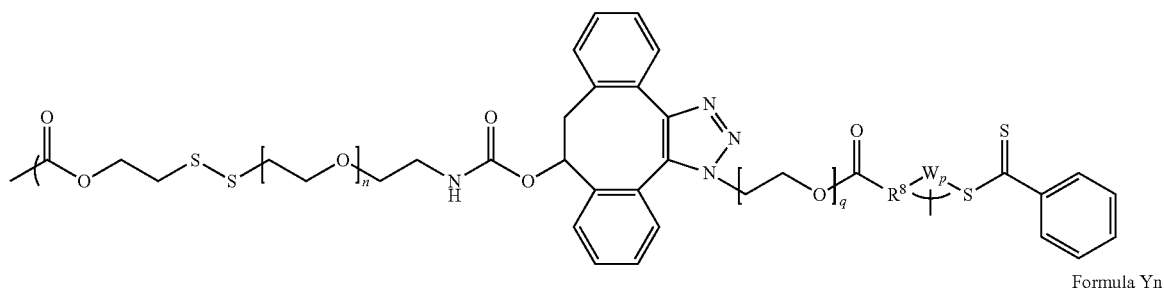

Formula Yn

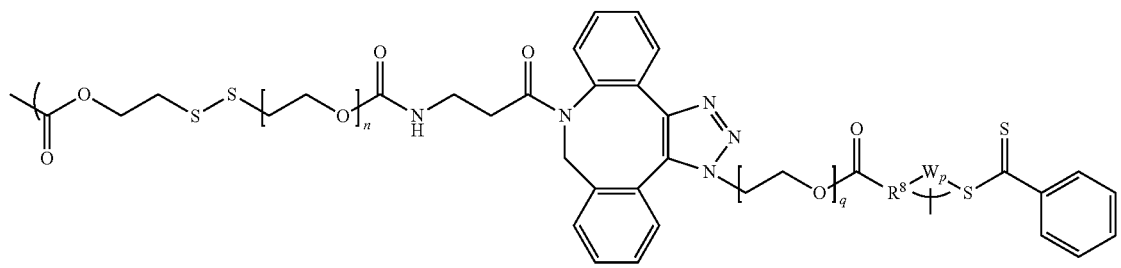

(Linkers of Formula Yn can be synthesized via certain precursors that render Yn particularly suitable for conjugation to hydrophobic antigens.)

Formula Yo

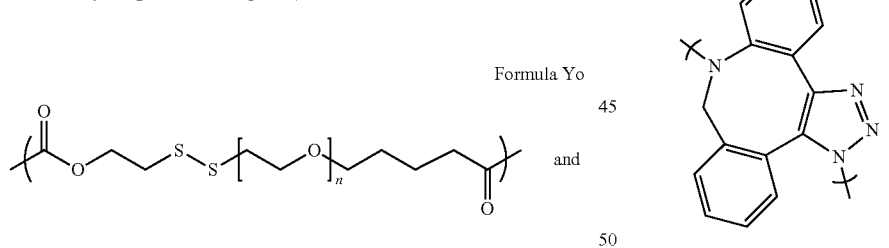

and

Formula Yp

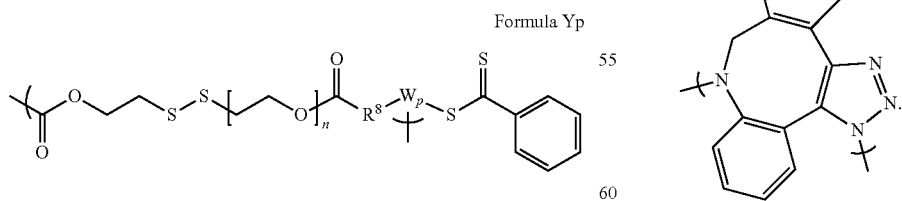

The linkers shown above as Formulae Yh through Yn are synthesized as isomers that are employed without separation. For example, the linkers of Formulae Yh, Yi, Yj and Yn will be a mixture of the 8,9-dihydro-1H-dibenzo[b,f][1,2,3]triazolo[4,5-d]azocin-8yl and 8,9-dihydro-3H-dibenzo[b,f][1,2,3]triazolo[4,5-d]azocin-8yl structures illustrated below:

The linkers of Formulae Yk, YL and Ym will be a mixture of the 8,9-dihydro-1H-dibenzo[3,4:7,8]cycloocta[1,2-d][1,2,3]triazol-8-yl and 8,9-dihydro-1H-dibenzo[3,4:7,8]cycloocta[1,2-d][1,2,3]triazol-9-yl structures illustrated below:

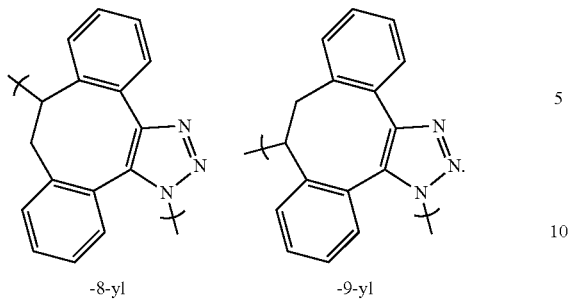

-8-yl      -9-yl

The presence of such isomeric mixtures does not impair the functionality of the compositions employing such linkers.

Liver-Targeting Moieties

The galactosylating moieties employed in the compositions of the present disclosure serve to target the compositions to liver cells (for example, specifically binding hepatocytes) and can be selected from: galactose, galactosamine or N-acetylgalactosamine. The glucosylating moieties employed in the compositions of the present disclosure serve to target the compositions to liver cells (for example, specifically binding hepatocytes or LSECs) and can be selected from: glucose, glucosamine or N-acetylglucosamine. It has been reported that ASGPR affinity can be retained while modifying either side of galactose's C3/C4-diol anchor (Mamidyala, Sreeman K., et al., *J. Am. Chem. Soc.* 2012, 134, 1978-1981), therefore the points of conjugation used in several embodiments are particularly at C1, C2 and C6.

Particular liver-targeting moieties include galactose or glucose conjugated at C1 or C6, galactosamine or glucosamine conjugated at C2, and N-acetylgalactosamine or N-acetylglucosamine conjugated at C6. Other particular liver-targeting moieties include N-acetylgalactosamine or N-acetylglucosamine conjugated at C2, more particularly conjugated to a linker bearing an $R^9$ substituent that is $CH_2$. Still other particular liver-targeting moieties include galactose, galactosamine, N-acetylgalactosamine, glucose, glucosamine or N-acetylglucosamine conjugated at C1, more particularly conjugated to a linker bearing an $R^9$ substituent that is an ethylacetamido group.

Nomenclature

The compositions of Formula 1 can be named using a combination of IUPAC and trivial names. For example, a compound corresponding to Formula 1 where X is a cyclobutyl moiety (shown instead of an antigen for illustrative purposes), Y is Formula Ya, m is 1, n is 4 and Z is N-acetylgalactosamin-2-yl or N-acetylglucosamin-2-yl:

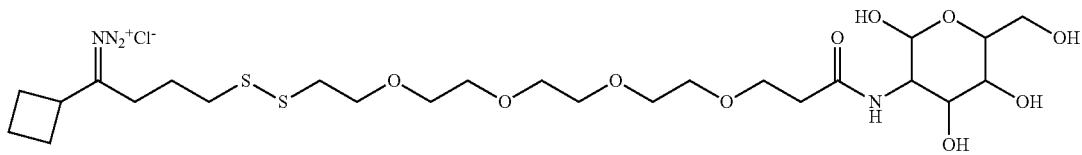

can be named (Z)-(21-cyclobutyl-1-oxo-1-((2,4,5-trihydroxy-6-(hydroxymethyl)tetrahydro-2H-pyran-3-yl)amino)-4,7,10,13-tetraoxa-16,17-dithiahenicosan-21-ylidene)triaz-1-yn-2-ium chloride, so the corresponding composition of the disclosure where X is tissue transglutaminase can be named (Z)-(21-(tissue transglutaminase)-1-oxo-1-((2,4,5-trihydroxy-6-(hydroxymethyl)tetrahydro-2H-pyran-3-yl)amino)-4,7,10,13-tetraoxa-16,17-dithiahenicosan-21-ylidene)triaz-1-yn-2-ium chloride. The corresponding composition of the disclosure where X' is tissue transglutaminase, m is 2, n is 4 and Z' is N-acetylgalactosamin-2-yl or N-acetylglucosamin-2-yl can be named (3Z)-((tissue transgultaminase)-1,3-diylbis(1-oxo-1-((2,4,5-trihydroxy-6-(hydroxymethyl)tetrahydro-2H-pyran-3-yl)amino)-4,7,10,13-tetraoxa-16,17-dithiahenicosan-21-yl-21-ylidene))bis(triaz-1-yn-2-ium) chloride.

In the interest of simplification, the compositions of Formula 1 can be named using an alternative naming system by reference to X and correspondence to one of Formulae 1a to 1p (as illustrated in the reaction schemes) followed by recitation of the integers for variables m, n, p and/or q, $R^8$, $R^9$ and identification of the galactosylating moiety and the position at which it is conjugated. In some embodiments, the compounds where W is a copolymer are designated by the letter of the "Y group" followed by a "prime" (e.g., F1c') and include the number and an identification of the comonomers. Under this system, the composition of Formula 1a where X is ovalbumin, m is 2, n is 4 and Z is N-acetylgalactosamin-2-yl can be named "F1a-OVA-$m_2$-$n_4$-2NAcGAL." The corresponding composition of Formula 1a where X is ovalbumin, m is 2, n is 4 and Z is N-acetylglucosamin-2-yl can be named "F1a-OVA-$m_2$-$n_4$-2NAcGLU."

Similarly, the following composition of Formula 1

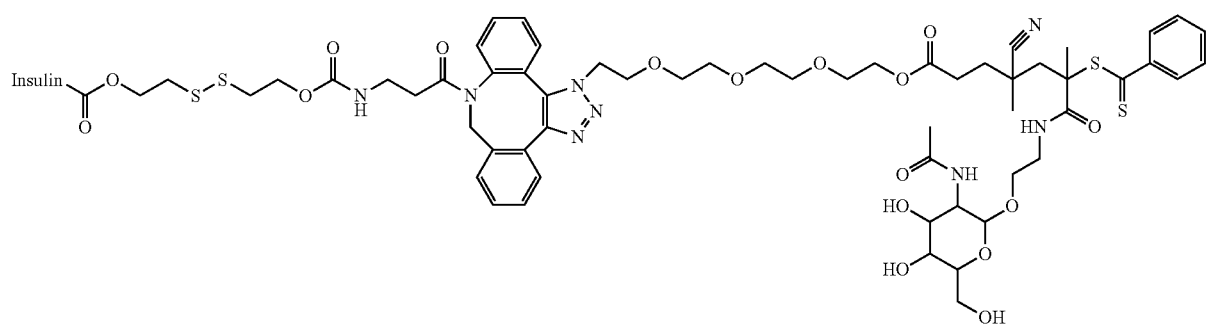

can be named "2-((2-(((3-(3-(22-((3-acetamido-4,5-dihydroxy-6-(hydroxymethyl)tetrahydro-2H-pyran-2-yl)oxy)-16-cyano-16,18-dimethyl-13,19-dioxo-18-((phenylcarbonothioyl)thio)-3,6,9,12-tetraoxa-20-azadocosyl)-3,9-dihydro-8H-dibenzo[b,f][1,2,3]triazolo[4,5-d]azocin-8-yl)-3-oxopropyl)carbamoyl)oxy)ethyl)disulfanyl)ethyl insulin carboxylate." The isomer:

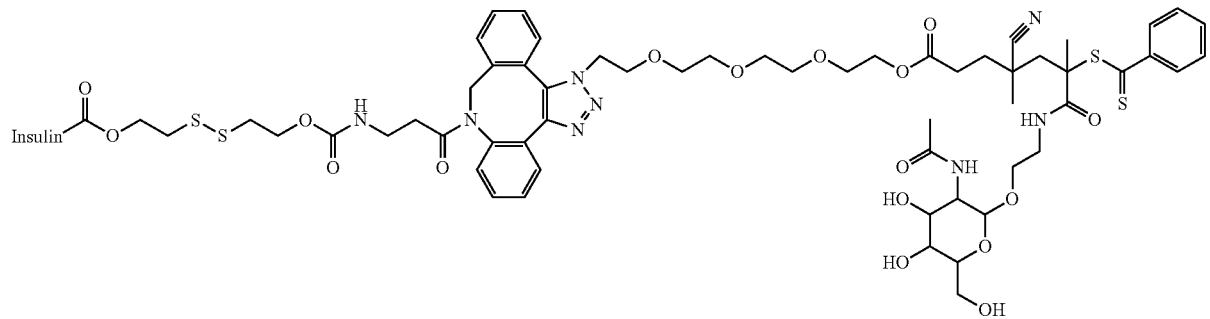

can be named "2-((2-(((3-(1-(22-((3-acetamido-4,5-dihydroxy-6-(hydroxymethyl)tetrahydro-2H-pyran-2-yl)oxy)-16-cyano-16,18-dimethyl-13,19-dioxo-18-((phenylcarbonothioyl)thio)-3,6,9,12-tetraoxa-20-azadocosyl)-1,9-dihydro-8H-dibenzo[b,f][1,2,3]triazolo[4,5-d]azocin-8-yl)-3-oxopropyl)carbamoyl)-oxy)ethyl)disulfanyl)ethyl insulin carboxylate" (bold lettering highlights added for convenience in identifying the difference between the formal names). Employing the naming system adopted for the present disclosure, both isomers can be named "F1n-insulin-$m_1$-$n_1$-$p_1$-$q_4$-CMP-EtAcN-1NAcGAL" (or ""F1n-insulin-$m_1$-$n_1$-$p_1$-$q_4$-CMP-EtAcN-1NAcGLU" because no stereochemistry is shown for the sugar ring) where CMP indicates that $R^8$ is 1-cyano-1-methyl-propyl, EtAcN indicates that $R^9$ is ethylacetamido and 1NAcGAL indicates Z" is N-acetylgalactosamine conjugated at C1. Absence of the abbreviation EtAcN before the designation for Z would indicate that $R^9$ is a direct bond.

The following composition of Formula 1 exemplifies compounds where W is a copolymer comprising QQYPSGQGSFQPSQQNPQGGGSC (SEQ ID NO:26):

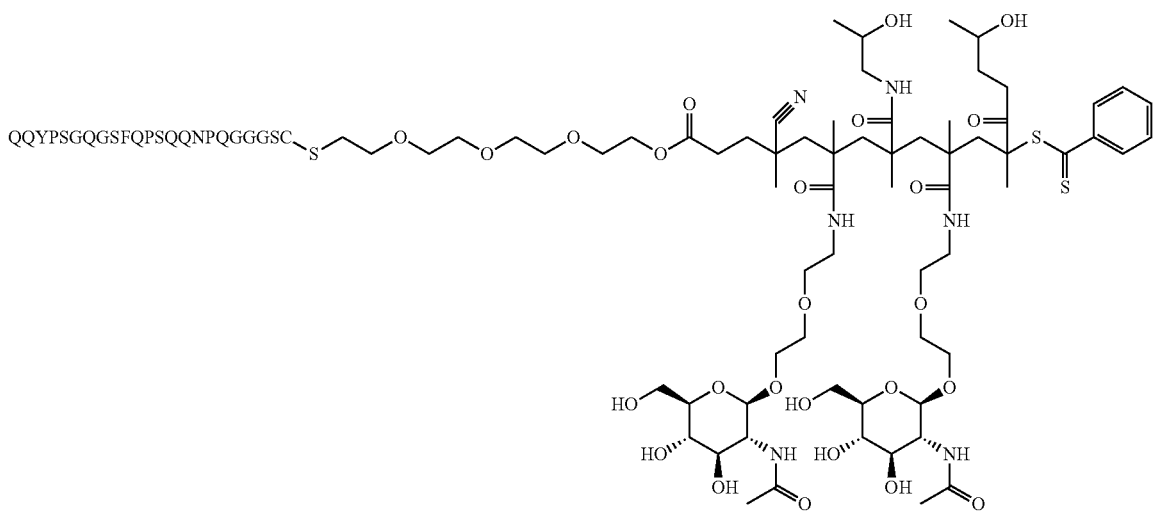

and can be named 2-(2-(2-(2-(QQYPSGQGSFQP-SQQNPQGGGSC-sulfanyl)ethoxy)ethoxy)ethoxy)ethyl 6,10-bis((2-(2-(((2R,3R,4R,5S,6R)-3-acetamido-4,5-dihydroxy-6-(hydroxymethyl)tetrahydro-2H-pyran-2-yl)oxy)ethoxy)ethyl)carbamoyl)-4-cyano-13-((2-hydroxypropyl)amino)-8-((2-hydroxypropyl)carbamoyl)-4,6,8,10,12-pentamethyl-13-oxo-12-((phenylcarbonothioyl)thio)tridecanoate. Employing the naming system adopted for the present disclosure the compound can be named "F1c'-DQ8-relevant Alpha Gliadin-$m_1$-$n_4$-$p_4$-CMP-poly-(EtPEG$_1$AcN-1NAcGLU$_2$-HPMA$_2$)".

Preparation of the Compositions of the Disclosure

The compositions of Formula 1 can be prepared, for example, by adjusting the procedures described in Zhu, L., et al., *Bioconjugate Chem.* 2010, 21, 2119-2127. Syntheses of certain compositions of Formula 1 are also described below with reference to Reaction Schemes 1 to 14. Other synthetic approaches will be apparent to those skilled in the art.

Formula 101 (below) is an alternative representation of X

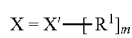

where $R^1$ is a free surface amino (—NH$_2$) or thiol (—SH) moiety positioned on X's three-dimensional structure so as to be accessible for conjugation to a linker, and X' represents the remainder of X excluding the identified free amino group(s) [(X" is used in the reaction schemes to represent the remainder of X excluding free thiol group(s)]. Depending upon the identity of X, there will be at least one (the N-terminal amine) and can be multiple $R^1$ groups (predominantly from lysine residues or cysteine residues that are not involved in disulfide bonding), as represented by m, which is an integer from about 1 to 100, more typically 1 or from about 4 to 20, and most typically 1 to about 10.

Variables employed in the reaction schemes are as defined above, and additionally include the following, which should be understood to have these meanings absent any specific indication otherwise with respect to a particular reaction scheme or step.

$R^2$ is OH or a protecting group;
$R^3$ is OH, NH$_2$, NHAc, a protecting group or NH-protecting group;
$R^4$ is OH or a protecting group;
$R^5$ is OH or a protecting group;
$R^6$ is OH or a protecting group;
Z' is galactose or glucose conjugated at C1 or C6, galactosamine or glucosamine conjugated at C2, or N-acetylgalactosamine conjugated or N-acetylglucosamine at C6;
$R^8$ is —CH$_2$— or —CH$_2$—CH$_2$—C(CH$_3$)(CN)—; and
$R^9$ is a direct bond and Z" is N-acetylgalactosamine conjugated at C2; or
$R^9$ is an ethylacetamido or a pegylated ethylacetamido group and Z" is galactose, glucose, galactosamine, glucosamine, N-acetylgalactosamine or N-acetylglucosamine conjugated at C1.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present disclosure are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, centrifugal size exclusion chromatography, high-performance liquid chromatography, recrystallization, sublimation, fast protein liquid chromatography, gel electrophoresis, dialysis, or a combination of these procedures. Specific illustrations of suitable separation and isolation procedures can be had by reference to the examples hereinbelow. However, other equivalent separation or isolation procedures can, of course, also be used.

Unless otherwise specified (including in the examples), all reactions are conducted at standard atmospheric pressure (about 1 atmosphere) and ambient (or room) temperature (about 20° C.), at about pH 7.0-8.0.

Characterization of reaction products can be made by customary means, e.g., proton and carbon NMR, mass spectrometry, size exclusion chromatography, infrared spectroscopy, gel electrophoresis.

Reaction Scheme 1 illustrates the preparation of compositions of Formula 1 where Z can be galactose, glucose, galactosamine, glucosamine, N-acetylgalactosamine or N-acetylglucosamine. In that regard and as defined above, Z' as employed in Reaction Scheme 1 encompasses galactose or glucose conjugated at C1 and C6 and corresponding to the following structures according to Formula 1:

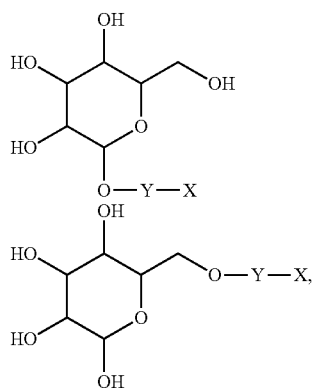

galactosamine or glucosamine conjugated at C2 and corresponding to the following structure according to Formula 1:

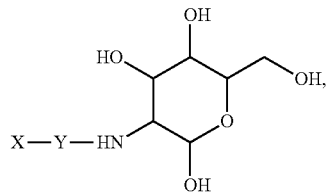

and N-acetylgalactosamine or N-acetylglucosamine conjugated at C6 and corresponding to the following structure according to Formula 1:

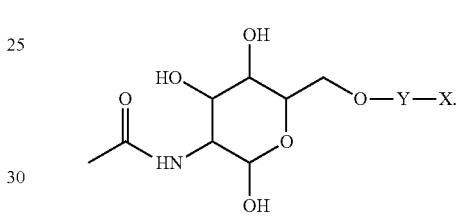

Reaction Scheme 1

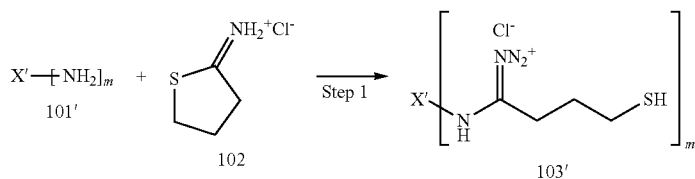

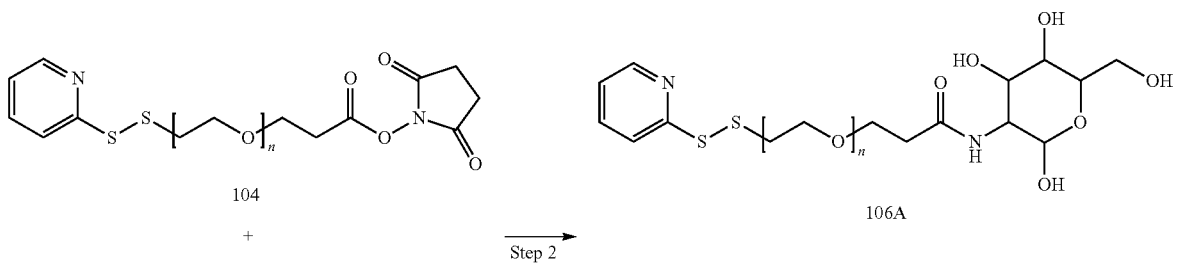

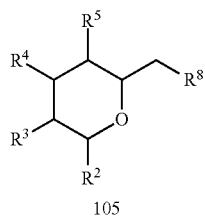

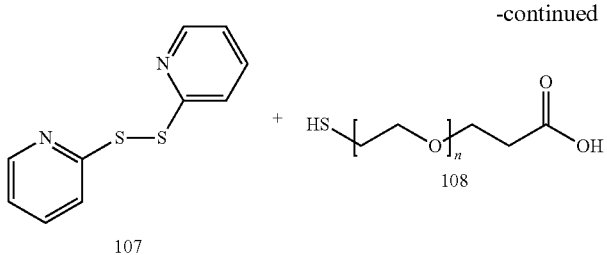

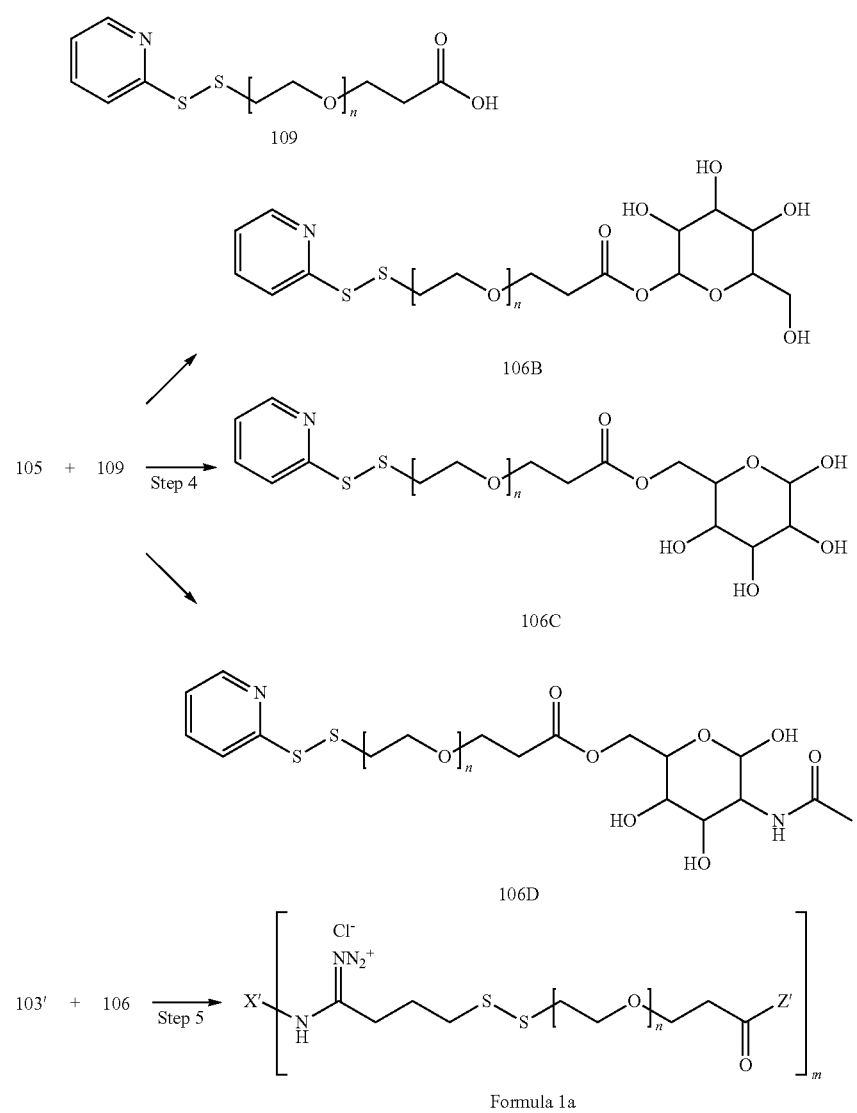

As illustrated above in Reaction Scheme 1, Step 1, surface thiol group(s) can be generated on an antigen, antibody, antibody fragment or ligand having free surface amino group(s) (Formula 101') by contact with a Traut reagent (Formula 102) at a pH of about 8.0 for about 1 hour to give the Formula 103', from which unreacted Traut's reagent is removed, e.g., via centrifugal size exclusion chromatography. The two structures shown below, illustrate the product of Reaction Scheme 1, Step 1, respectively showing the free surface amino group(s) originally found on X (i.e., Formula 103' where X' represents the remainder of X excluding the identified free surface amino groups) and omitting the free surface amino group(s) (i.e., Formula 103). This parallels the distinction illustrated as between X and Formula 101. The convention has been followed in the subsequent reaction schemes.

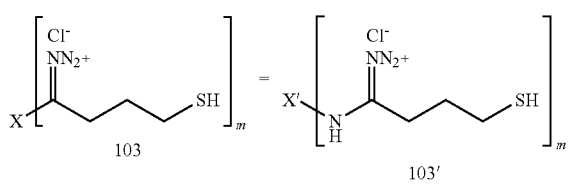

In Reaction Scheme 1, Step 2, a pyridyl di-thiol-poly (ethylene glycol)-NHS ester (Formula 104) is contacted with galactosamine or glucosamine (Formula 105 where $R^3$ is $NH_2$ and $R^2$, $R^4$, $R^5$ and $R^6$ are OH) with stirring at about pH 8 for about 1 hour to give the corresponding pyridyl di-thiol-poly(ethylene glycol)-sugar of Formula 106A, which can be used without further purification.

In Reaction Scheme 1, Step 3, 4,4'-dithiodipyridine (Formula 107) is contacted with a thiol-poly(ethylene glycol) propanoic acid (Formula 108) to give the corresponding pyridyl di-thiol-poly(ethylene glycol)propanoic acid (Formula 109).

In Reaction Scheme 1, Step 4, the acid of Formula 109 is contacted with a protected galactose or N-acetylgalactosamine of Formula 105 where $R^2$ is OH and $R^3$, $R^4$, $R^5$ and $R^6$ are protecting groups ("PG"), where $R^6$ is OH and $R^2$, $R^3$, $R^4$ and $R^5$ are PG, or where $R^6$ is N-acetyl and $R^2$, $R^3$, $R^4$ and $R^5$ are PG to give the corresponding pyridyl di-thiol-poly (ethylene glycol)-sugars of Formulae 106B, 106C and 106D, which can be used following de-protection.

In Reaction Scheme 1, Step 5, to a stirred solution of the product of Step 1 (Formula 103') is added an excess (corresponding to the value of m) of the product of Step 2 or Step 4 (Formula 106, i.e., 106A, 106B, 106C or 106D) for about 1 hour, followed by centrifugal sized exclusion chromatography to remove any free remaining reactants to yield the corresponding product according to Formula 1a, respectively, Formula 1aA, Formula 1aB, Formula 1aC and Formula 1aD.

The compositions corresponding to Formula 1a can be named, respectively, e.g., as follows:

"F1aA-X'-$m_m$-$n_n$" or "F1a-X'-$m_m$-$n_n$-2NGAL"
"F1aB-X'-$m_m$-$n_n$" or "F1a-X'-$m_m$-$n_n$-1GAL"
"F1aC-X'-$m_m$-$n_n$" or "F1a-X'-$m_m$-$n_n$-6GAL"
"F1aD-X'-$m_m$-$n_n$" or "F1a-X'-$m_m$-$n_n$-6NAcGAL"
"F1aA-X'-$m_m$-$n_n$" or "F1a-X'-$m_m$-$n_n$-2NGLU"
"F1aB-X'-$m_m$-$n_n$" or "F1a-X'-$m_m$-$n_n$-1GLU"
"F1aC-X'-$m_m$-$n_n$" or "F1a-X'-$m_m$-$n_n$-6GLU"
"F1aD-X'-$m_m$-$n_n$" or "F1a-X'-$m_m$-$n_n$-6NAcGLU"

respectively, for products made employing an intermediate according to Formulae 106A-D.

Reaction Schemes 2-14 illustrate preparation of the compounds where W is a polymer of the same $W^1$ group. For the purposes of the nomenclature employed therewith, except as expressly stated otherwise, Z" refers to N-acetylgalactosamine or N-acetylglucosamine conjugated at C2:

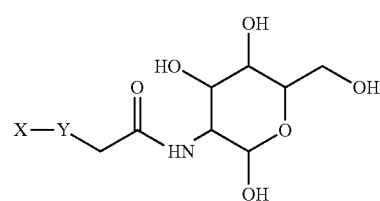

or to galactose, glucose, galactosamine, glucosamine, N-acetylgalactosamine or N-acetylglucosamine conjugated at C1. It should be noted that, according to several embodiments, in order to improve yields, the C1 conjugated compositions can be protected during synthesis, for example by cyclizing the amine with the C3 hydroxyl and de-protecting following incorporation of the protected galactosamine into the adjacent portion of the linker.

The poly(galactose methacrylate) and poly(glucose methacrylate) reactants of Formulae 201, 401, 501, 601, 701, 803 and 1401 can be prepared by methacrylating galactose or glucose, e.g., contacting galactosamine or glucosamine and methacrylate anhydride, followed by reversible addition-fragmentation chain transfer (RAFT) polymerization with a corresponding RAFT agent in the presence of azobisisobutyronitrile (AIBN) in a suitable solvent, starting with freeze-thaw cycles followed by heating at about 60-80° C., preferably 70° C. for about 5-8, preferably about 6 hours. The polymer can be precipitated in a lower alkanol, preferably methanol.

Reaction Scheme 2

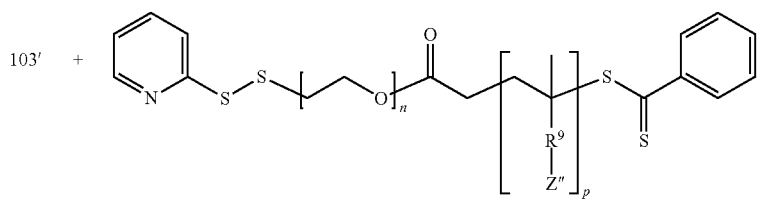

201

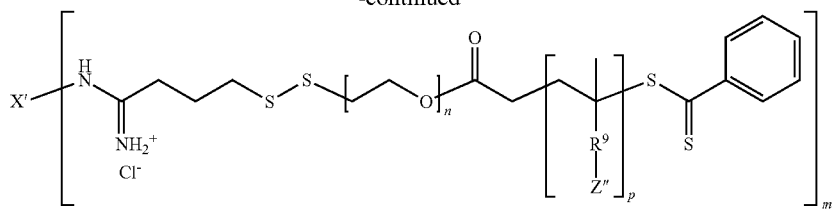

Formula 1b

As illustrated in Reaction Scheme 2, an antigen, antibody, antibody fragment or ligand having free surface thiol group(s) prepared, e.g., as described with reference to Reaction Scheme 1, Step 1 (Formula 103') is contacted with an excess (corresponding to the value of m) of a pyridyl di-thiol-poly(ethylene glycol) of Formula 201 for about 1 hour to yield the corresponding product according to Formula 1b.

The compositions of Formula 1b can be named as follows:

"F1b-X'-$m_m$-$n_n$-$p_p$-2NAcGAL"  "F1b-X'-$m_m$-$n_n$-$p_p$-2NAcGLU" or "F1b-X'-$m_m$-$n_n$-$p_p$-EtAcN-Z".

For example, the composition of Formula 1b where X' is uricase, m is 1, n is 4, p is 4 and Z" is N-acetylgalactosamine conjugated at C2 can be named "F1b-uricase-$m_1$-$n_4$-$p_4$-2NAcGAL" or "30-(uricase)-3,5,7,9-tetramethyl-12-oxo-1-phenyl-1-thioxo-3,5,7,9-tetrakis((2,4,5-trihydroxy-6-(hydroxymethyl)tetrahydro-2H-pyran-3-yl)carbamoyl)-13,16,19,22-tetraoxa-2,25,26-trithiatriacontan-30-iminium".

Reaction Scheme 3

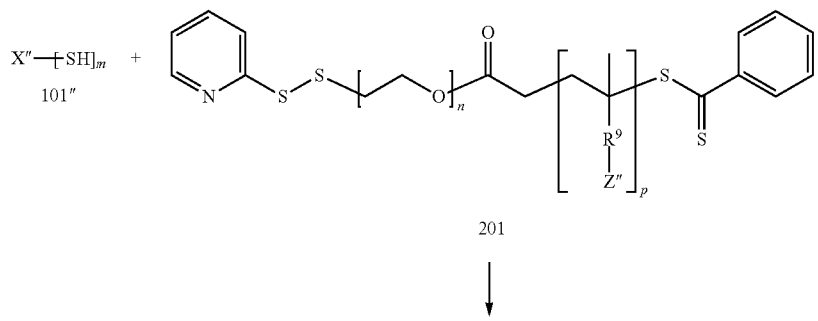

201

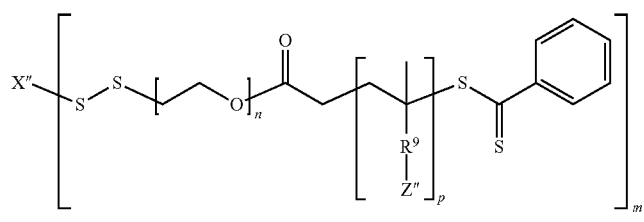

Formula 1c

As illustrated in Reaction Scheme 3, an antigen, antibody, antibody fragment or ligand having native free surface thiol group(s) (cysteines) [Formula 101" corresponding to Formula 101 and illustrating where X", as the term will be subsequently employed, represents X excluding the identified free surface thiol group(s)] is contacted with an excess (corresponding to the value of m) of a pyridyl di-thiol-poly (ethylene glycol) of Formula 201 to yield the corresponding product according to Formula 1c.

The compositions corresponding to Formula 1c can be named as follows:
"F1c-X'-$m_m$-$n_n$-$p_p$-2NAcGAL"    "F1c-X'-$m_m$-$n_n$-$p_p$-2NAcGLU" or "F1c-X'-$m_m$-$n_n$-$p_p$-EtAcN-Z".

Reaction Scheme 4

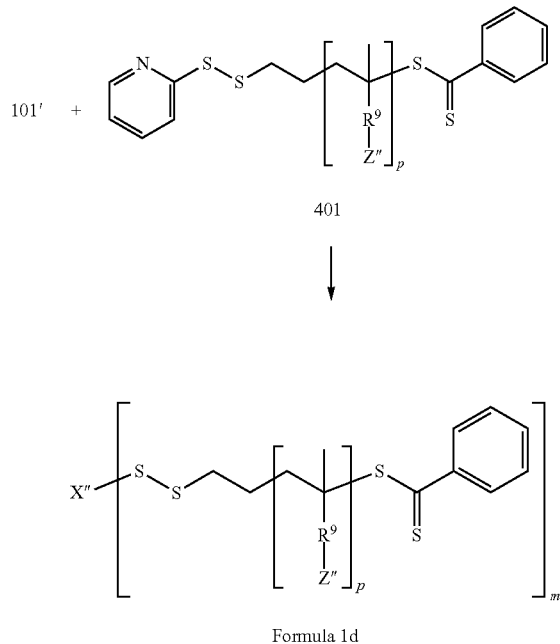

Formula 1d

As illustrated in Reaction Scheme 4, an antigen, antibody, antibody fragment or ligand having native free surface thiol group(s) of Formula 101" is contacted with an excess (corresponding to the value of m) of a pyridyl di-thiol of Formula 401 to yield the corresponding product according to Formula 1d.

The compositions corresponding to Formula 1d can be named as follows:
"F1d-X'-$m_m$-$p_p$-2NAcGAL"  "F1d-X'-$m_m$-$p_p$-2NAcGLU" or "F1d-X'-$m_m$-$p_p$-EtAcN-Z".

Reaction Scheme 5

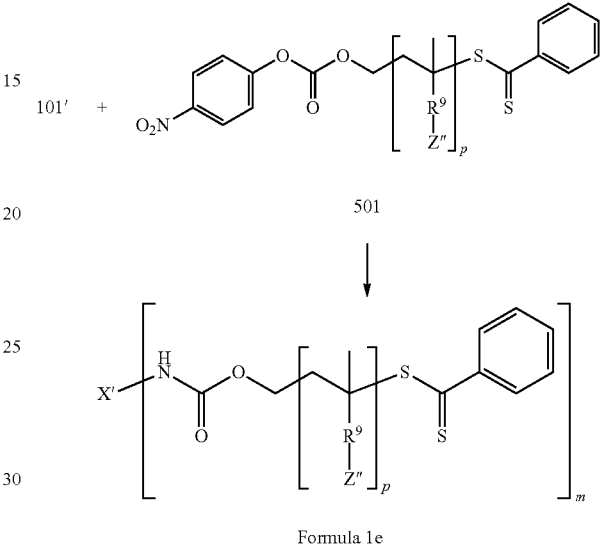

Formula 1e

As illustrated in Reaction Scheme 5, an antigen, antibody, antibody fragment or ligand having native free surface amino group(s) of Formula 101' is contacted with an excess (corresponding to the value of m) of a n-nitrophenyl carbonate of Formula 501 to yield the corresponding product according to Formula 1e.

The compositions corresponding to Formula 1e can be named as follows:
"F1e-X'-$m_m$-$p_p$-2NAcGAL"  "F1e-X'-$m_m$-$p_p$-2NAcGLU" or "F1e-X'-$m_m$-$p_p$-EtAcN-Z".

Reaction Scheme 6

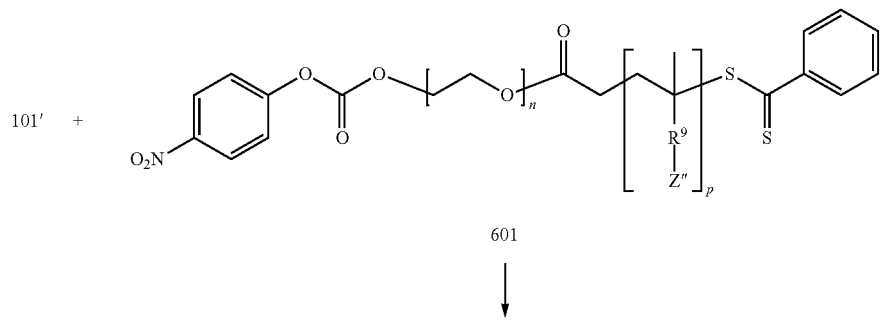

601

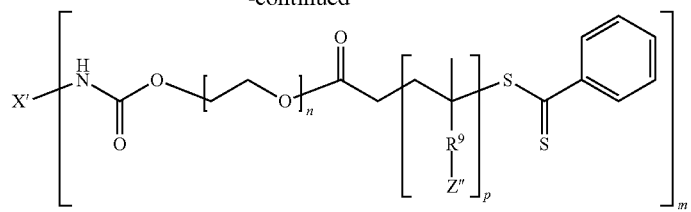

Formula 1f

As illustrated in Reaction Scheme 6, an antigen, antibody, antibody fragment or ligand having native free surface amino group(s) of Formula 101' is contacted with an excess (corresponding to the value of m) of a n-nitrophenyl carbonate poly(ethylene glycol)ester of Formula 601 to yield the corresponding product according to Formula 1f.

The compositions corresponding to Formula 1f can be named as follows:

"F1f-X'-$m_m$-$n_n$-$p_p$-2NAcGAL" "F1f-X'-$m_m$-$n_n$-$p_p$-2NAcGLU" or "F1f-X'-$m_m$-$n_n$-$p_p$-EtAcN-Z".

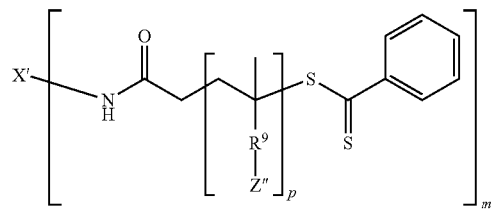

Formula 1g

As illustrated in Reaction Scheme 7, an antigen, antibody, antibody fragment or ligand having native free surface amino group(s) of Formula 101' is contacted with an excess (corresponding to the value of m) of a NHS-ester poly (ethylene glycol)ester of Formula 701 to yield the corresponding product according to Formula 1g.

The compositions corresponding to Formula 1g can be named as follows:

"F1g-X'-$m_m$-$p_p$-2NAcGAL" "F1g-X'-$m_m$-$p_p$-2NAcGLU" or "F1g-X'-$m_m$-$p_p$-EtAcN-Z"

Reaction Scheme 7

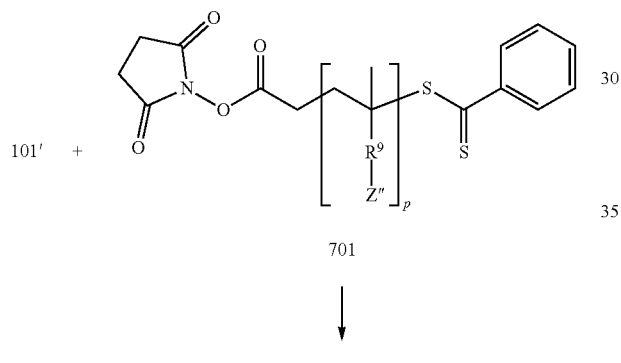

101'  +

701

↓

Reaction Scheme 8

101'  +

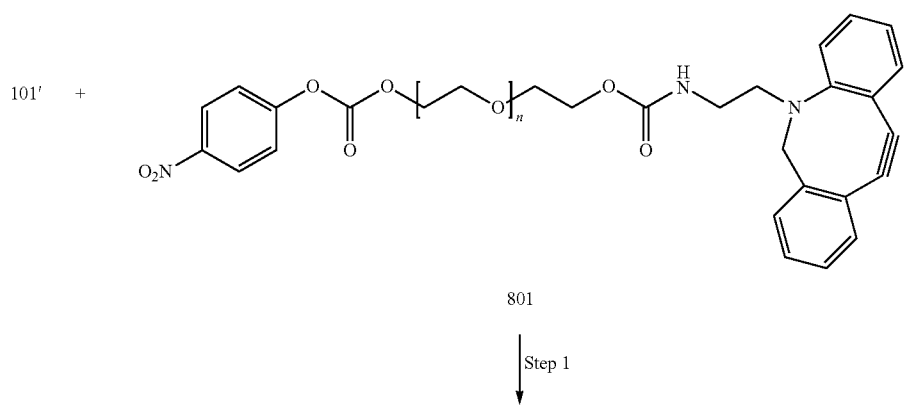

801

↓ Step 1

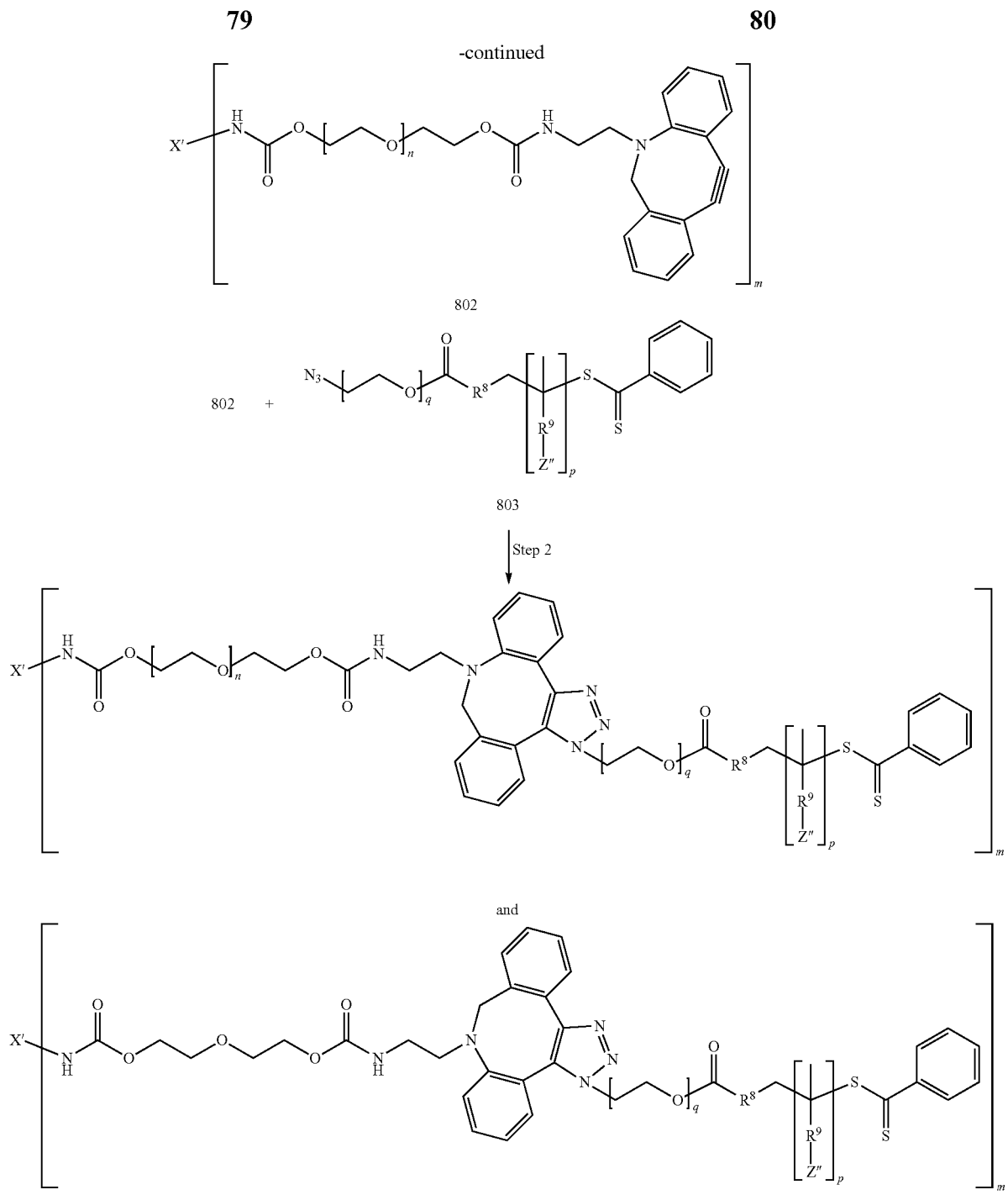

Both, Formula 1h

As illustrated in Reaction Scheme 8, Step 1, an antigen, antibody, antibody fragment or ligand having native free surface amino group(s) of Formula 101' is contacted with an excess (corresponding to the value of m) of an amine-reactive linker for Click chemistry of Formula 801 to yield the corresponding product according to Formula 802.

In Reaction Scheme 8, Step 2, the product of Formula 802 is then contacted with an equivalent amount (again corresponding to the value of m) of a galactos(amine) polymer of Formula 803 to yield the corresponding isomeric product according to Formula 1h. The two isomers, illustrated above, result from non-specific cyclization of the azide of Formula 803 with the triple bond of Formula 802. Such non-specific cyclization occurs in the synthesis of other compositions where Y is selected from Formulae Yh through Yn, but will not be illustrated in each instance.

The compositions corresponding to Formula 1h can be named as follows:

"F1h-X'-$m_m$-$n_n$-$p_p$-$q_q$-2NAcGAL" "F1h-X'-$m_m$-$n_n$-$p_p$-$q_q$-2NAcGLU" or "F1h-X'-$m_m$-$n_n$-$p_p$-$q_q$-EtAcN-Z".

Reaction Scheme 9
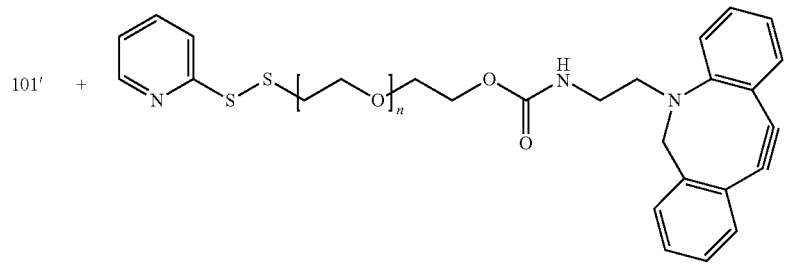
901
Step 1
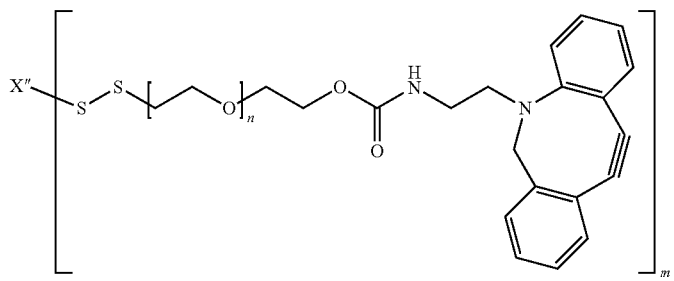
902
902 +
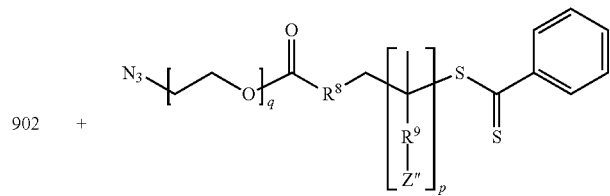
803
Step 2
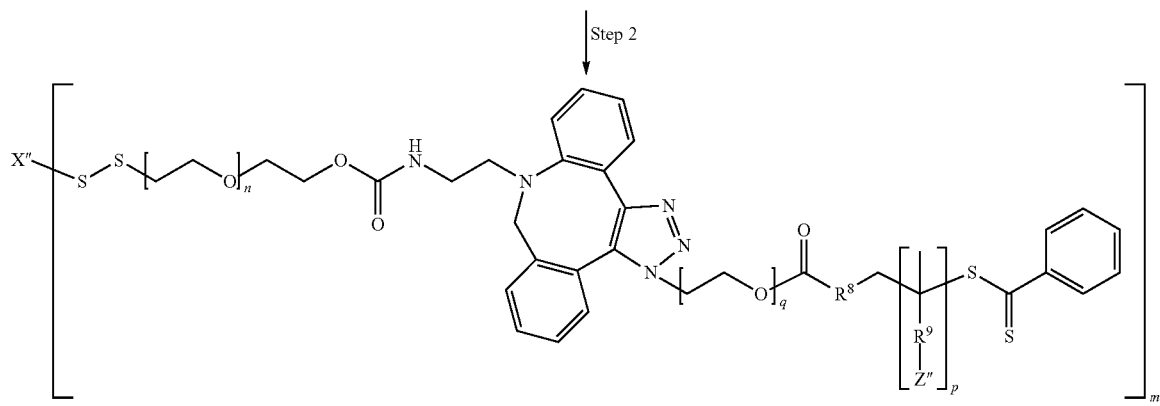
Formula 1i As illustrated in Reaction Scheme 9, Step 1, an antigen, antibody, antibody fragment or ligand having native free surface thiol group(s) of Formula 101" is contacted with an excess (corresponding to the value of m) of a thiol-reactive linker for Click chemistry of Formula 901 to yield the corresponding product according to Formula 902".

In Reaction Scheme 9, Step 2, the product of Formula 902" is then contacted with an equivalent amount (again corresponding to the value of m) of a galactos(amine) polymer of Formula 803 to yield the corresponding isomeric product according to Formula 1i.

The compositions corresponding to Formula 1i can be named as follows:

"F1i-X'-$m_m$-$n_n$-$p_p$-$q_q$-2NAcGAL" "F1i-X'-$m_m$-$n_n$-$p_p$-$q_q$-2NAcGLU" or "F1i-X'-$m_m$-$n_n$-$p_p$-$q_q$-EtAcN-Z".

By following the procedures described with regard to Reaction Scheme 9, but substituting starting material 101" with a compound of Formula 103' (derivatized with the Traut reagent) there is obtained the corresponding isomeric product of Formula 1j as shown below.

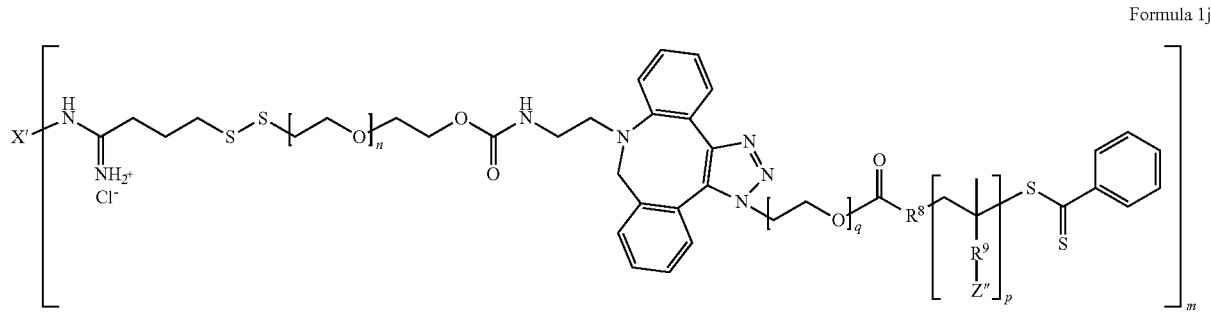

Formula 1j

The compositions corresponding to Formula 1j can be named as follows:

"F1j-X'-$m_m$-$n_n$-$p_p$-$q_q$-2NAcGAL" "F1j-X'-$m_m$-$n_n$-$p_p$-$q_q$-2NAcGLU" or "F1j-X'-$m_m$-$n_n$-$p_p$-$q_q$-EtAcN-Z".

Reaction Scheme 10

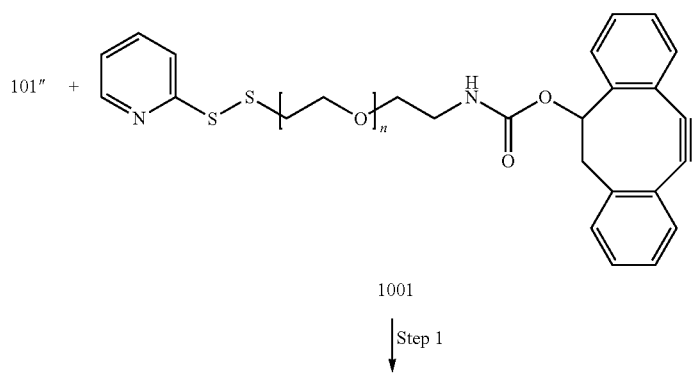

1001

Step 1

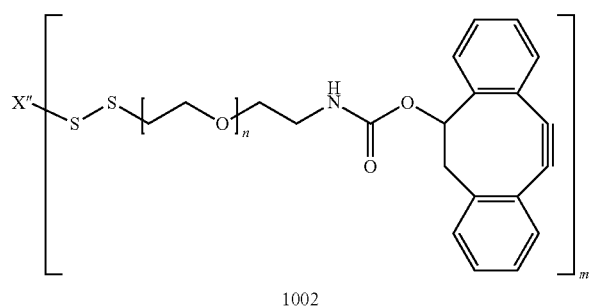

1002

-continued

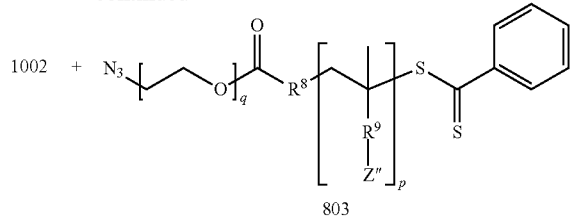

Step 2

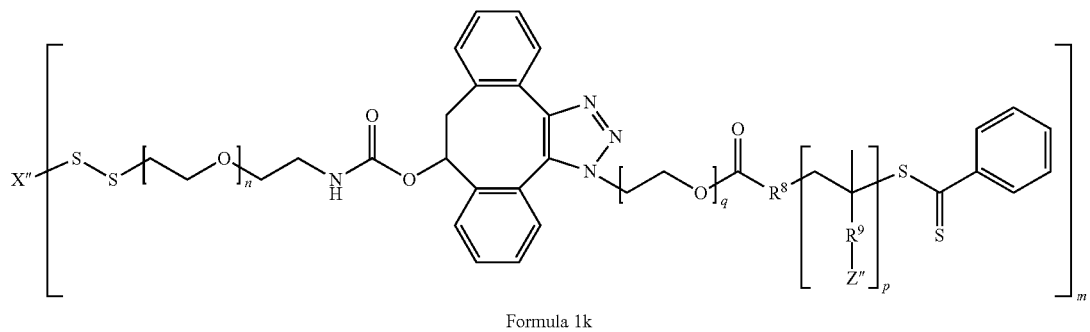

Formula 1k

As illustrated in Reaction Scheme 10, Step 1, an antigen, antibody, antibody fragment or ligand having native free surface thiol group(s) of Formula 101" is contacted with an excess (corresponding to the value of m) of a thiol-reactive linker for Click chemistry of Formula 1001 to yield the corresponding product according to Formula 1002.

In Reaction Scheme 10, Step 2, the product of Formula 1002 is then contacted with an equivalent amount (again corresponding to the value of m) of a galactos(amine) polymer of Formula 803 to yield the corresponding isomeric product according to Formula 1k.

The compositions corresponding to Formula 1k can be named as follows:

"F1k-X'-$m_m$-$n_n$-$p_p$-$q_q$-2NAcGAL" "F1k-X'-$m_m$-$n_n$-$p_p$-$q_q$-2NAcGLU" or "F1k-X'-$m_m$-$n_n$-$p_p$-$q_q$-EtAcN-Z".

By following the procedures described with regard to Reaction Scheme 10, but substituting starting material 101" with a compound of Formula 103' (derivatized with the Traut reagent) there is obtained the corresponding isomeric product of Formula 1L as shown below.

Formula 1L

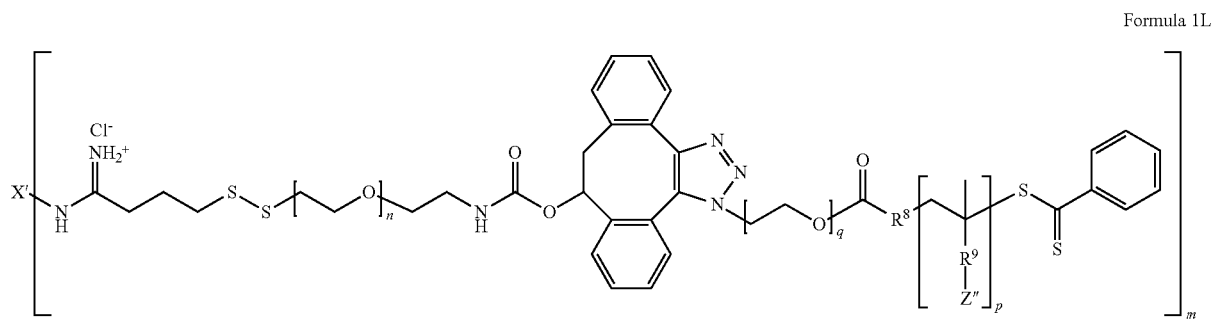

The compositions corresponding to Formula 1L can be named as follows:
"F1L-X'-$m_m$-$n_n$-$p_p$-$q_q$-2NAcGAL"  "F1L-X'-$m_m$-$n_n$-$p_p$-$q_q$-2NAcGLU" or "F1L-X'-$m_m$-$n_n$-$p_p$-$q_q$-EtAcN-Z".
Reaction Scheme 11
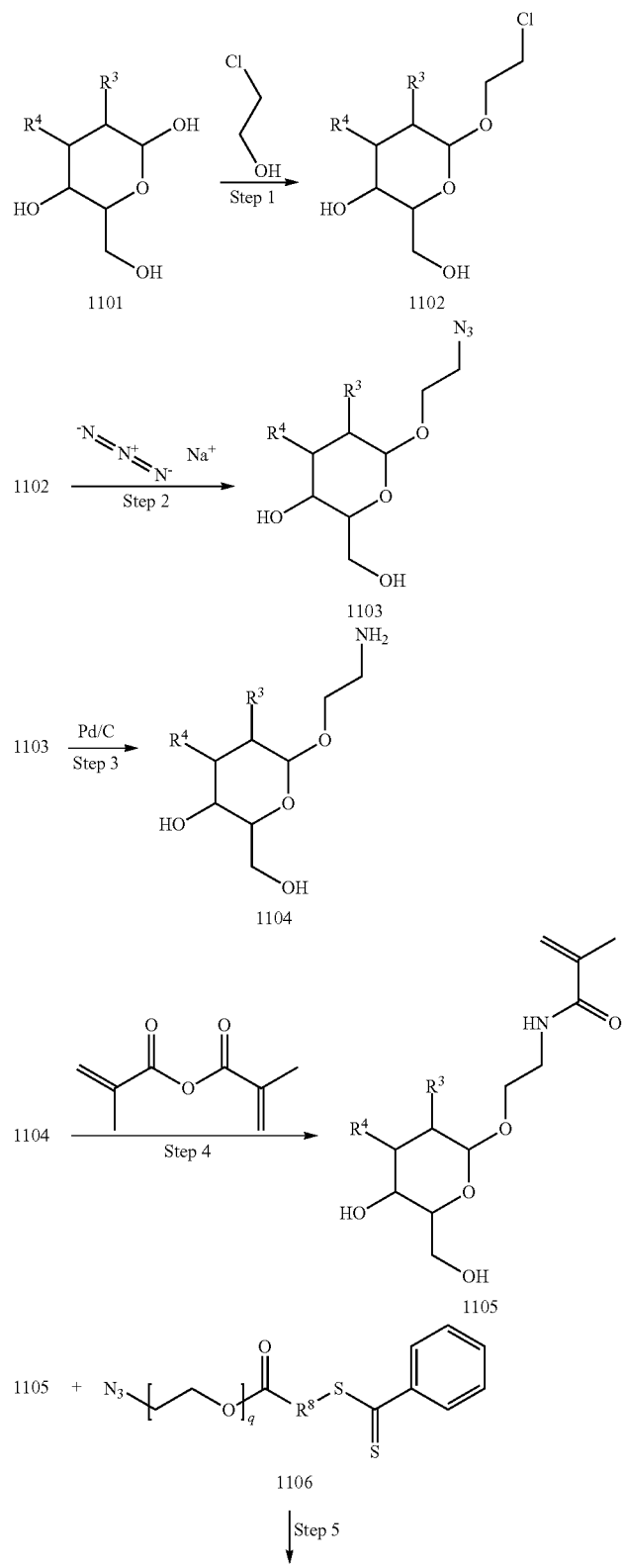

-continued
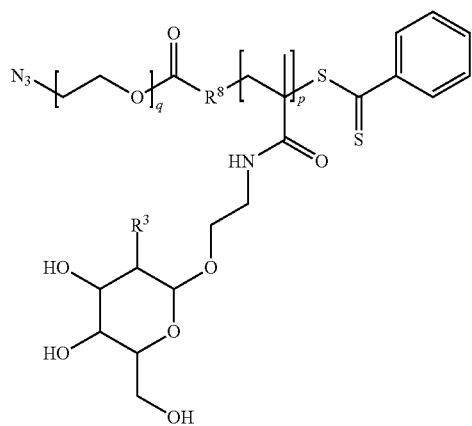
1107
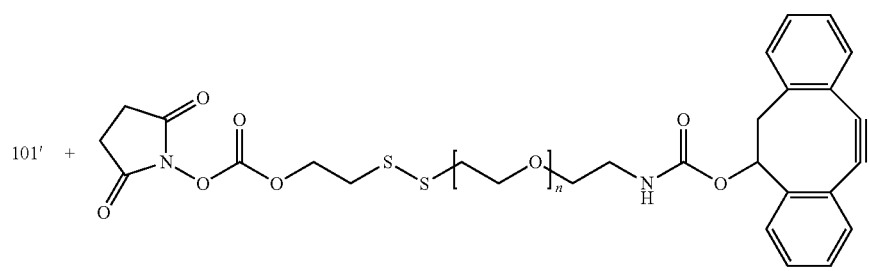
1108
Step 6
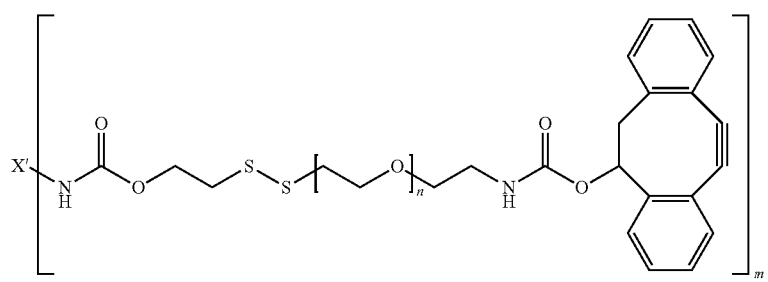
1109
1109 + 1107
Step 7

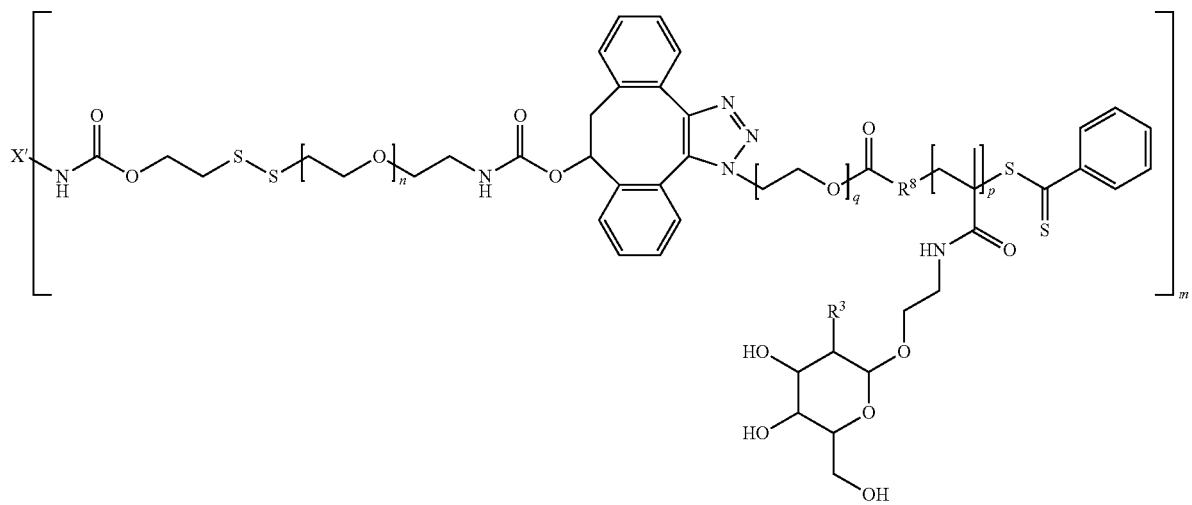

Formula 1m

As illustrated in Reaction Scheme 11, Step 1, galactose, protected galactosamine or N-Acetyl-D-galactosamine (Formula 1101 where $R^3$ and $R^4$ are OH, $R^3$ is NH-protecting group (e.g., cyclized with $R^4$) or $R^3$ is NHAc and $R^4$ is OH, respectively) is contacted with 2-chloroethan-1-ol followed by cooling and the dropwise addition of acetylchloride. The solution is warmed to room temperature and then heated to 70° C. for several hours. Ethanol is added to the crude product and the resulting solution is stirred in the presence of carbon and then filtered followed by solvent removal to yield the corresponding product of Formula 1102.

As illustrated in Reaction Scheme 11, Step 2, the product of Formula 1102 is added to an excess of sodium azide and heated to 90° C. for several hours, then filtered followed by solvent removal to yield the corresponding product of Formula 1103.

As illustrated in Reaction Scheme 11, Step 3, the product of Formula 1103 is added to a solution of palladium on carbon and ethanol, and stirred under hydrogen gas (3 atm) for several hours, then filtered followed by solvent removal to yield the corresponding product of Formula 1104.

As illustrated in Reaction Scheme 11, Step 4, the product of Formula 1104 is added to a solution of methacrylate anhydride. Triethylamine is added and the reaction stirred for 2 hours followed by solvent removal and isolation to yield the corresponding product of Formula 1105.

As illustrated in Reaction Scheme 11, Step 5, an azide-modified uRAFT agent (Formula 1106) is added to a solution of the product of Formula 1105 with azobisisobutyronitrile, subjected to 4 free-pump-thaw cycles and then stirred at 70° C. After several hours the corresponding polymer product of Formula 1107 is precipitated by addition of a lower alkanol followed by solvent removal. Where $R^3$ is NH-protecting group (e.g., cyclized with $R^4$) the protecting group(s) is(are) removed at this point.

As illustrated in Reaction Scheme 11, Step 6, an antigen, antibody, antibody fragment or ligand having native free surface amino group(s) of Formula 101' is added to a pH 8.0 buffer and contacted with an excess (corresponding to the value of m) of a dioxopyrrolidine of Formula 1108 with stirring. After 1 hour, unreacted Formula 1108 is removed and the resulting product of Formula 1109 is used without further purification.

As illustrated in Reaction Scheme 11, Step 7, the product of Formula 1107 is added to a pH 8.0 buffer, to which is added the product of Formula 1109. After stirring for 2 hours, the excess Formula 1107 is removed to yield the corresponding isomeric product of Formula 1m.

By substituting N-(2,4,5-trihydroxy-6-(hydroxymethyl) tetrahydro-2H-pyran-3-yl)methacrylamide for the product of Formula 1105 in Step 5 and continuing with Steps 6 and 7, the corresponding isomeric product of Formula 1m where Z" is N-acetylgalactosamine conjugated at C2 are obtained.

The compositions corresponding to Formula 1m can be named as follows:

"F1m-X'-$m_m$-$n_n$-$p_p$-$q_q$-EtAcN-Z" where Z" is 1GAL, 1NGAL, 1NAcGAL, "F1m-X'-$m_m$-$n_n$-$p_p$-$q_q$- 2NAcGAL" or "F1m-X'-$m_m$-$n_n$-$p_p$-$q_q$-2NAcGLU" (or the corresponding 1GAL, 1GLU, 1NGAL, 1NGLU, 1NAcGAL or 1NAcGLU compounds).

Reaction Scheme 12

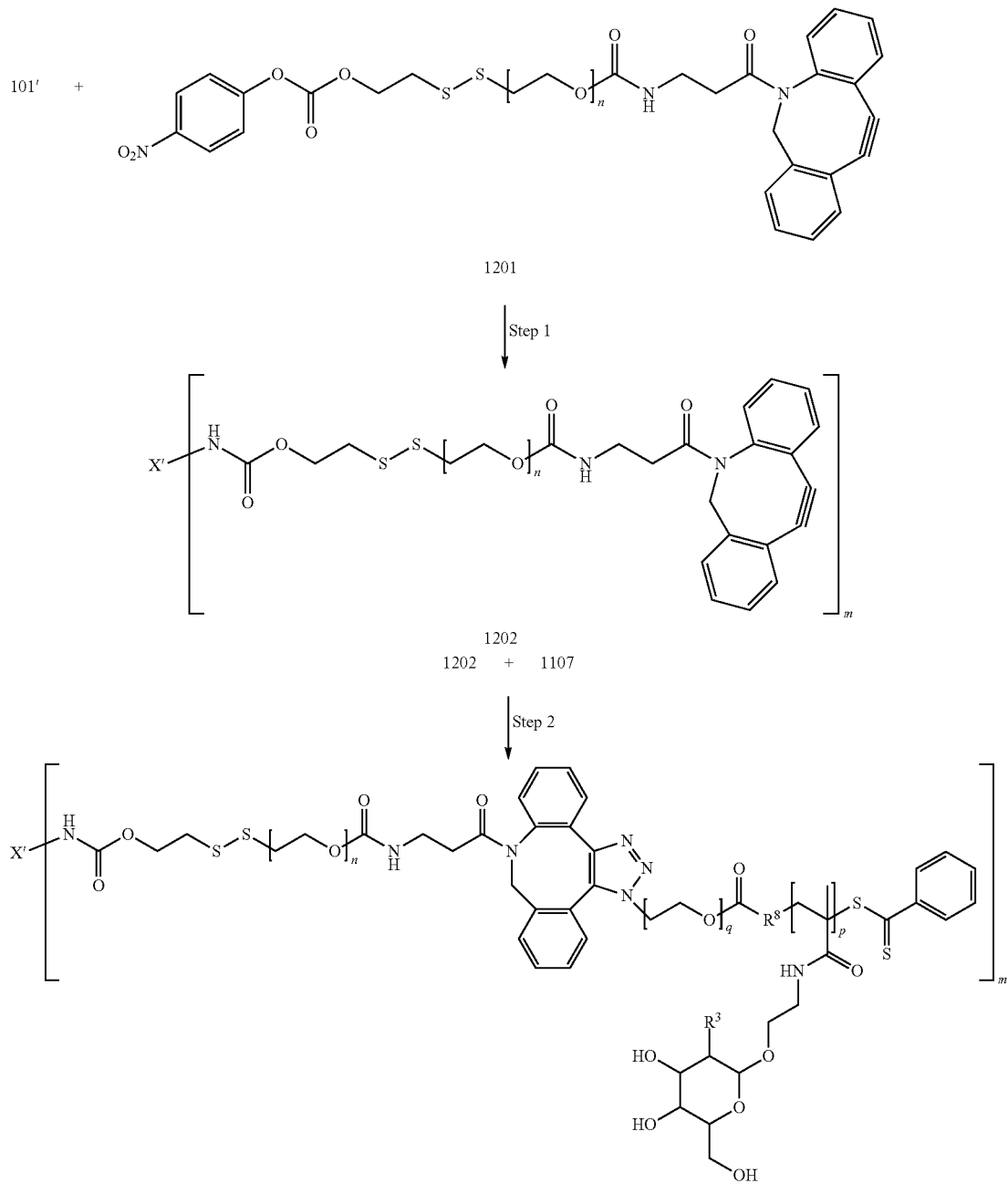

Formula 1n

The synthetic approach of Reaction Scheme 12 is particularly suitable for hydrophobic antigens, antibodies, antibody fragments and ligands (e.g., Insulin) due to the use of organic solvents.

As illustrated in Reaction Scheme 12, Step 1, an antigen, antibody, antibody fragment or ligand having native free surface amino group(s) of Formula 101' is dissolved in an organic solvent (e.g., DMF) containing triethylamine. To this is added an amount (corresponding to the value of m) of a compound of Formula 1201 followed by stirring and the addition of t-butyl methyl ether. The corresponding product of Formula 1202 is recovered as a precipitate.

The product of Formula 1202 is resuspended in the organic solvent and an amount (corresponding to the value of m) of Formula 1107 (obtained, e.g., as described with reference to Reaction Scheme 11) is added followed by stirring. The reaction product is precipitated via the addition of dichloromethane, followed by filtration and solvent removal. Purification (e.g., resuspension in PBS followed by centrifugal size exclusion chromatography yields the corresponding isomeric product of Formula 1n.

The compositions corresponding to Formula 1n can be named as follows:

"F1n-X'-$m_m$-$n_n$-$p_p$-$q_q$-EtAcN-Z" where Z" is 1GAL, 1NGAL, 1NAcGAL, 1GLU, 1NGLU, 1NAcGLU, or "F1m-X'-$n_m$-$n_n$-$p_p$-$q_q$-2NAcGAL" or "F1m-X'-$n_m$-$n_n$-$p_p$-$q_q$-2NAcGLU".

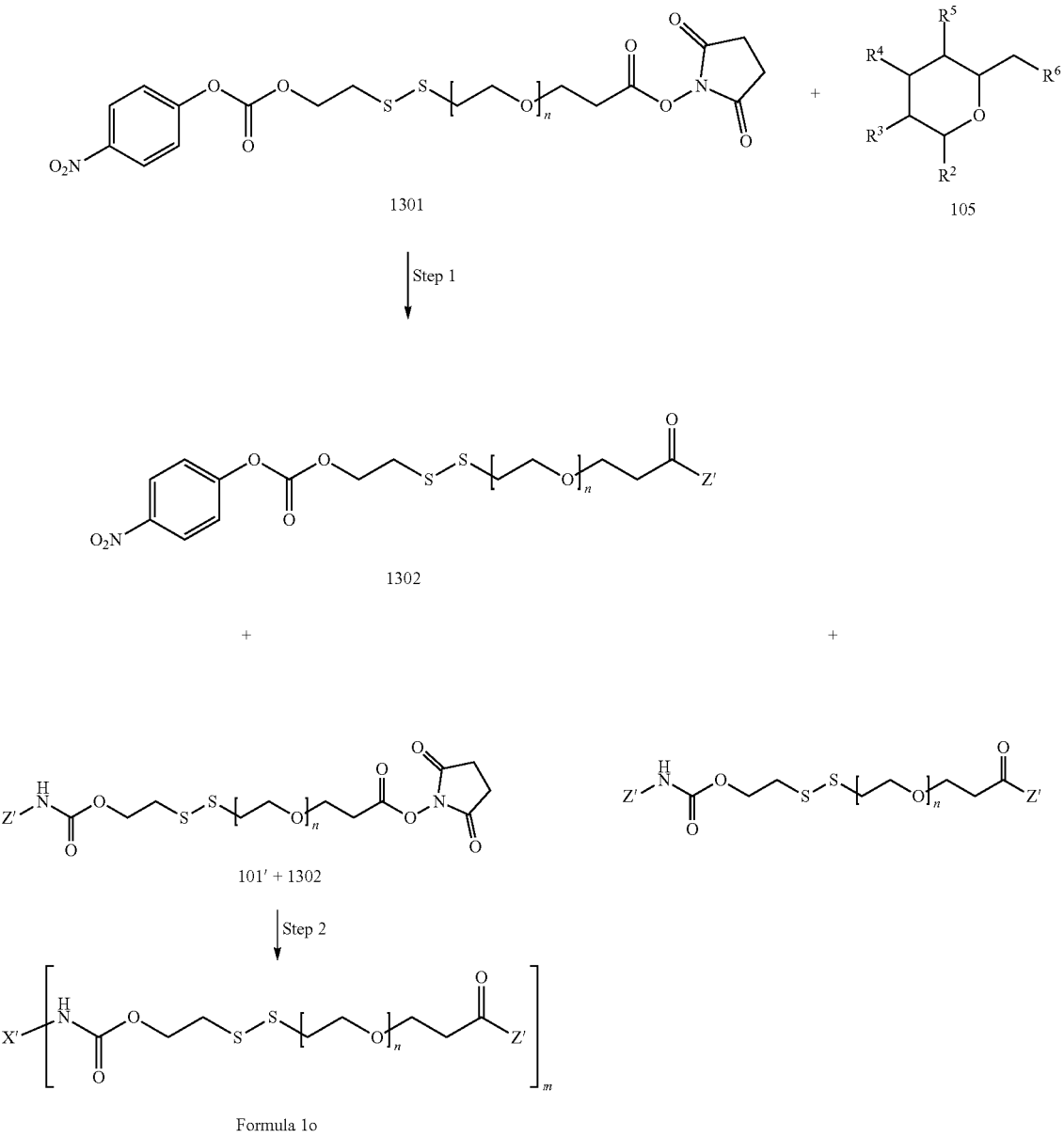

Reaction Scheme 13

Formula 1o

In Reaction Scheme 13, Step 1, a nitrophenoxycarbonyl-oxyalkyl di-thiol-poly(ethylene glycol)-NHS ester (Formula 1301) is contacted with galactose, galactosamine or N-acetylgalactosamine (Formula 105) to give the corresponding product of Formula 1302, along with the other two illustrated products, from which the desired nitrophenoxy-carbonyl di-thiol-poly(ethylene glycol)-carboxyethyl galactose, galactosamine or N-acetylgalactosamine of Formula 1302 is isolated before proceeding to the next step.

As illustrated in Reaction Scheme 13, Step 2, an antigen, antibody, antibody fragment or ligand having native free surface amino group(s) of Formula 101' is contacted with an excess (corresponding to the value of m) of the product of Formula 1302 to yield the corresponding product according to Formula 1o.

The compositions corresponding to Formula 1o can be named as follows:

"F1o-X'-$m_m$-$n_n$-Z'."

Reaction Scheme 14

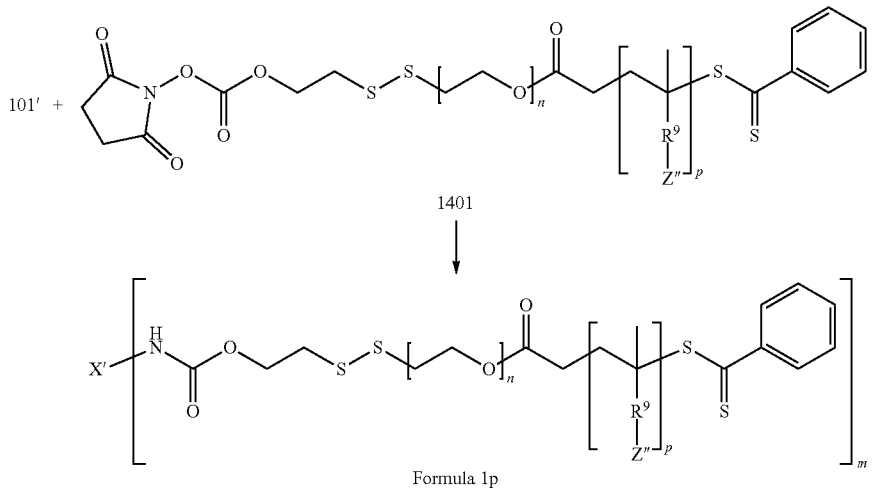

Formula 1p

As illustrated in Reaction Scheme 14, an antigen, antibody, antibody fragment or ligand having native free surface amino group(s) (Formula 101') is contacted with an excess (corresponding to the value of m) of a pyridyl di-thiol-poly (ethylene glycol)-NHS ester of Formula 1401 to yield the corresponding product according to Formula 1p.

"F1p-X'-$m_m$-$n_n$-$p_p$-2NAcGAL"   "F1p-X'-$m_m$-$n_n$-$p_p$-2NAcGLU" or "F1p-X'-$m_m$-$n_n$-$p_p$-EtAcN-Z".

Reaction Schemes 15-18 illustrate preparation of the compounds where W is a copolymer of the same or different $W^1$ and $W^2$ groups.

Reaction Scheme 15

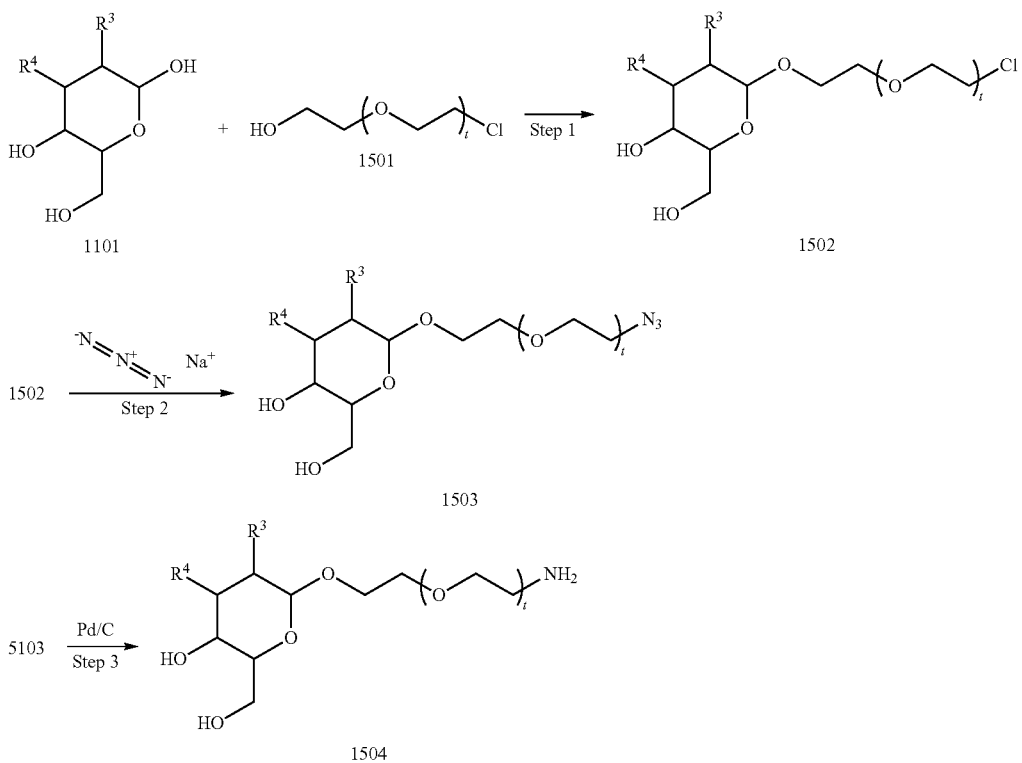

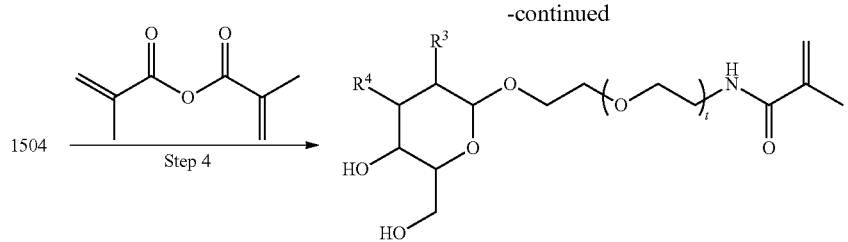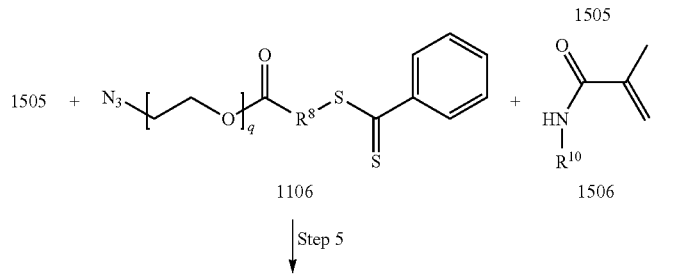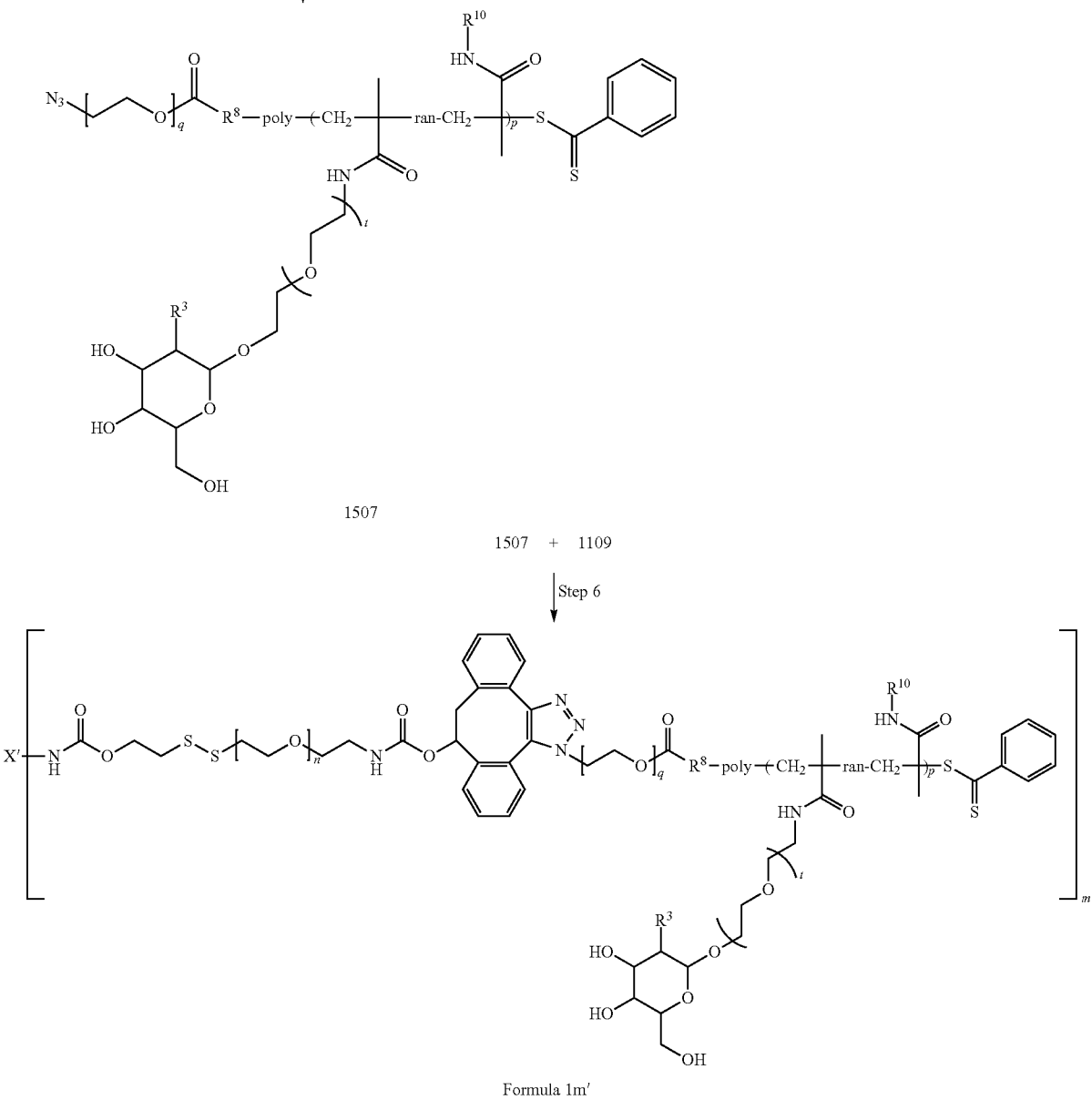
Formula 1m'

As illustrated in Reaction Scheme 15, Step 1, galactose or glucose (Formula 1101 where $R^3$ and $R^4$ are OH), protected galactosamine or protected glucosamine (Formula 1101 where $R^3$ is NH-protecting group, e.g., cyclized with $R^4$) or N-acetyl-D-galactosamine or N-acetyl-D-glucosamine (Formula 1101 where $R^3$ is NHAc and $R^4$ is OH) is contacted with a 2-(poly-(2-chloroethoxy)ethoxy)ethan-1-ol of Formula 1501 (where t is 1 to 5) followed by cooling and the dropwise addition of acetylchloride. The solution is warmed to room temperature and then heated to 70° C. for several hours. Ethanol is added to the crude product and the resulting solution is stirred in the presence of carbon and then filtered followed by solvent removal to yield the corresponding product of Formula 1502.

As illustrated in Reaction Scheme 15, Step 2, the product of Formula 1502 is added to an excess of sodium azide and heated to 90° C. for several hours, then filtered followed by solvent removal to yield the corresponding product of Formula 1503.

As illustrated in Reaction Scheme 15, Step 3, the product of Formula 1503 is added to a solution of palladium on carbon and ethanol, and stirred under hydrogen gas (3 atm) for several hours, then filtered followed by solvent removal to yield the corresponding product of Formula 1504.

As illustrated in Reaction Scheme 15, Step 4, the product of Formula 1504 is added to a solution of methacrylate anhydride. Triethylamine is added and the reaction stirred for 2 hours followed by solvent removal and isolation to yield the corresponding product of Formula 1505. Alternatively, pentafluorophenyl methacrylate (or another acrylating agent) can be used to prepare the corresponding product of Formula 1505. In some embodiments, the product of formula 1504 is added to DMF. Triethyl amine (e.g., an organic base) is added and the mixture is cooled (e.g., to 4° C. using an ice bath). Subsequently, pentafluorophenyl methacrylate (or another acrylating agent) is added (e.g., drop-wise with constant stirring). After a period of time (e.g., 30 minutes), the cooling (e.g., ice-bath) is removed and the reaction is allowed to stir at room temperature for a period of time (e.g., 4 hours). In some embodiments, the solvent is then removed. In some embodiments, the product is purified using flash chromatography.

As illustrated in Reaction Scheme 15, Step 5, an azide-modified uRAFT agent of Formula 1106 and a methacrylamide of Formula 1506 are added to a solution of the product of Formula 1505 with azobisisobutyronitrile, subjected to 4 free-pump-thaw cycles and then stirred at 70° C. After several hours the corresponding random copolymer product of Formula 1507 is precipitated by addition of a lower alkanol or acetone followed by solvent removal. Where $R^3$ is NH-protecting group (e.g., cyclized with $R^4$) the protecting group(s) is(are) removed at this point.

As illustrated in Reaction Scheme 15, Step 6, the product of Formula 1507 is added to a pH 8.0 buffer, to which is added the product of Formula 1109 (prepared, for example, as described with reference to Reaction Scheme 11). After stirring for 2 hours, the excess Formula 1109 is removed to yield the corresponding isomeric random copolymer product of Formula 1m'.

By adding more than one methacrylamide of Formula 1505 in Step 5 (for example, glucose and galactose methacrylamides, or two or more methacrylamides having different values for t) and/or two or more methacrylamides of Formula 1506, and continuing with Step 6, the corresponding product of Formula 1m' having a mixture of $R^3$ and/or PEG ("t") and/or $R^{10}$ groups, i.e., compounds of Formula 1 where W is a random copolymer of different $W^1$ and $W^2$ groups are obtained.

The compositions corresponding to Formula 1m' can be named as follows:

"F1m'-X'-$m_m$-$n_n$-$p_p$-$q_q$-$R^8$-poly-($W^1_tZ"_{W1p}$-ran-$W^2_{W2p}$)".

Reaction Scheme 16

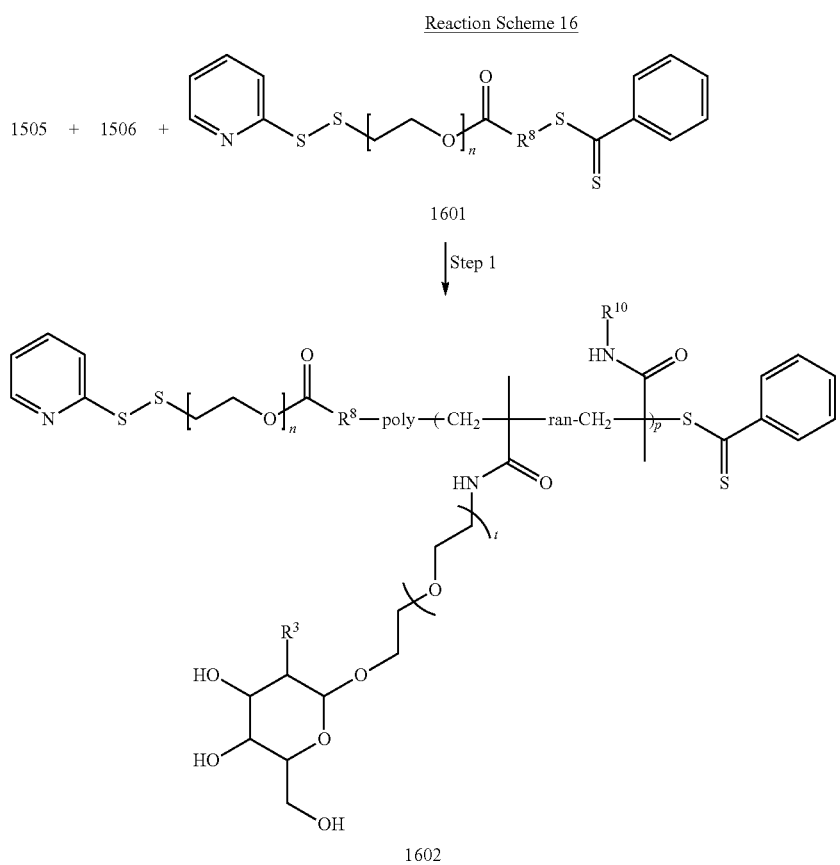

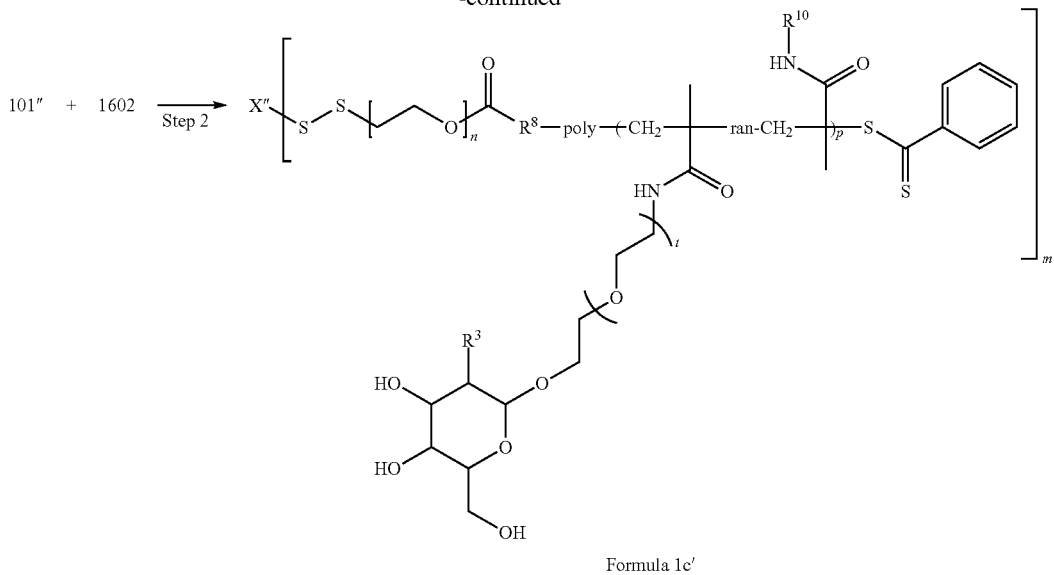

Formula 1c′

As illustrated in Reaction Scheme 16, Step 1, a compound of Formula 1601 is contacted with compounds of Formulae 1505 and 1506 under conditions analogous to those of Reaction Scheme 15, Step 5, to afford the corresponding compound of Formula 1602.

In some embodiments, the following synthesis is performed to form compound 1601a (an embodiment of 1601):

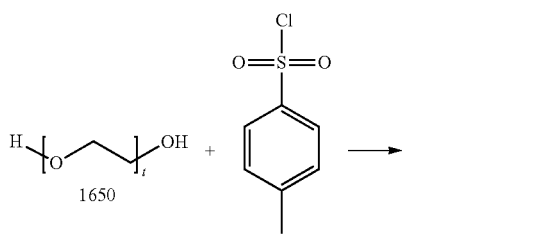

1650

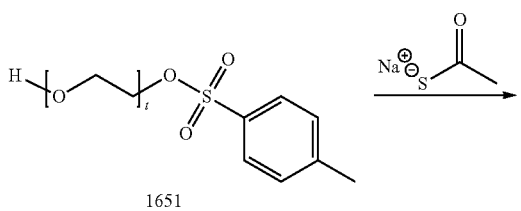

1651

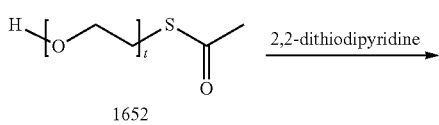

1652

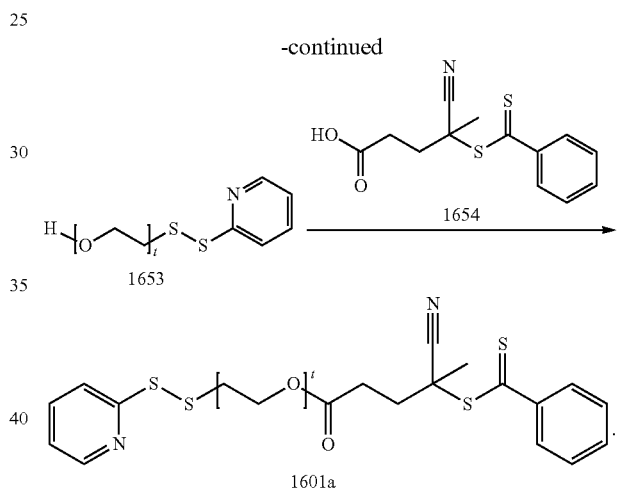

1653

1601a

In some embodiments, t is an integer from about 1 to about 10 or about 1 to about 5. In some embodiments, an oligoethylene glycol (1650) is reacted with p-toluenesulfonyl chloride (or some other agent capable of functionalizing 1650 with a leaving group) to form oligoethylene glycol mono p-toluenesulfonate (1651)(or some other oligoethylene glycol functionalized with a leaving group). In some embodiments, compound 1651 can be reacted with potassium thioacetate to form compound 1652. In some embodiments, compound 1652 is reacted with 2,2-dithiodipyridine to form compound 1653. In some embodiments, compound 1653 is coupled to compound 1654 to form compound 1601a.

As illustrated in Reaction Scheme 16, Step 2, the compound of Formula 1602 is contacted with a compound of Formula 101″ under conditions analogous to those of Reaction Scheme 15, Step 6, to afford the corresponding compound of Formula 1c′.

The compositions corresponding to Formula 1c′ can be named as follows:

"F1c′-X′-$m_m$-$n_n$-$p_p$-$R^8$-poly-($W^1_r Z''$-ran-$W^2$)".

Reaction Scheme 17
1505 + 1506 +
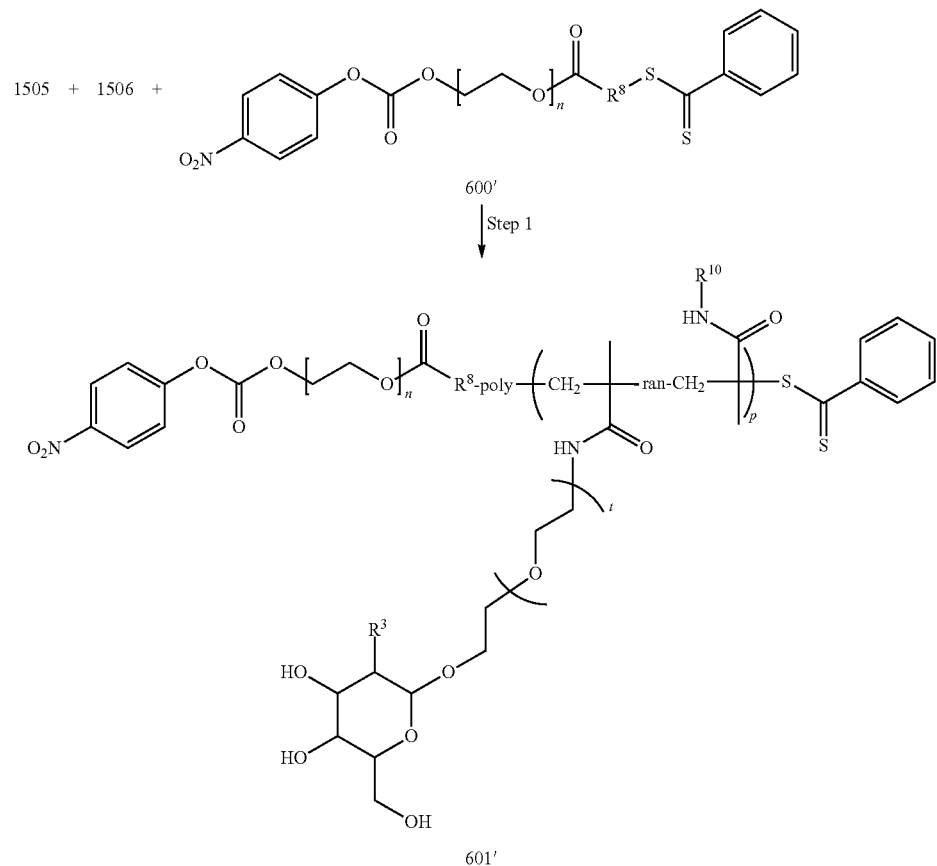
601'
101' + 601'
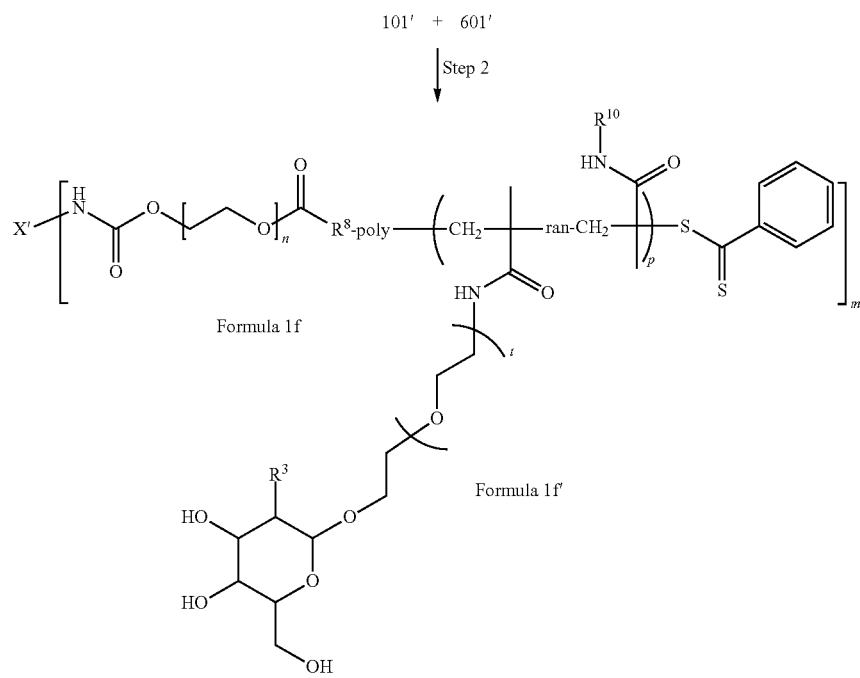
Formula 1f
Formula 1f'

As illustrated in Reaction Scheme 17, Step 1, a compound of Formula 600' is contacted with compounds of Formulae 1505 and 1506 under conditions analogous to those of Reaction Scheme 15, Step 5, to afford the corresponding compound of Formula 601'.

As illustrated in Reaction Scheme 17, Step 2, the compound of Formula 601' is contacted with a compound of Formula 101' under conditions analogous to those of Reaction Scheme 15, Step 6, to afford the corresponding compound of Formula 1f'.

The compositions corresponding to Formula 1f' can be named as follows:

"F1f'-X'-$m_m$-$n_n$-$p_p$-$R^8$-poly-($W^1_tZ''$-ran-$W^2$)".

Reaction Scheme 18

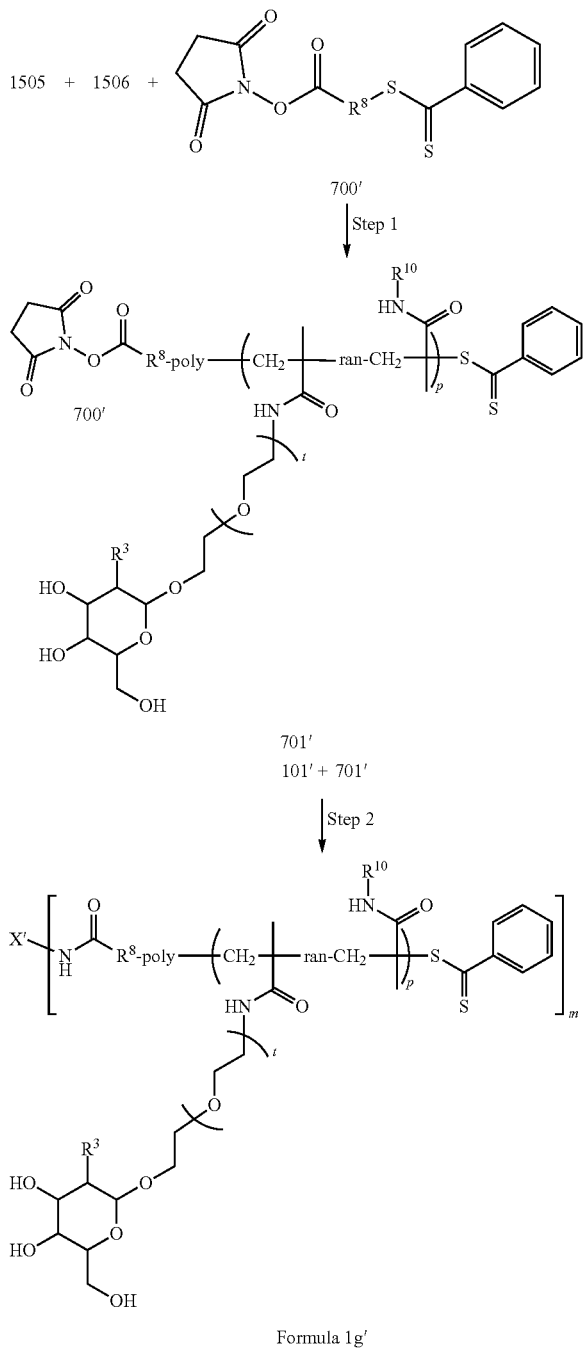

Formula 1g'

As illustrated in Reaction Scheme 18, Step 1, a compound of Formula 700' is contacted with compounds of Formulae 1505 and 1506 under conditions analogous to those of Reaction Scheme 15, Step 5, to afford the corresponding compound of Formula 701'.

As illustrated in Reaction Scheme 18, Step 2, the compound of Formula 701' is contacted with a compound of Formula 101' under conditions analogous to those of Reaction Scheme 15, Step 6, to afford the corresponding compound of Formula 1g'.

The compositions corresponding to Formula 1g' can be named as follows:

"F1g'-X'-$m_m$-$p_p$-$R^8$-poly-($W^1_tZ''$-ran-$W^2$)".

Particular Processes and Last Steps

A compound of Formula 103' is contacted with an excess (corresponding to the value of m) of a compound of Formula 106 to give the corresponding product of Formula 1a.

A compound of Formula 103' is contacted with an excess (corresponding to the value of m) of a compound of Formula 201 to give the corresponding product of Formula 1b.

A compound of Formula 802, 902 or 1002 is contacted with an excess (corresponding to the value of m) of a compound of Formula 803 to give the corresponding product of Formula 1h, Formula 1i or Formula 1k, respectively.

A compound of Formula 1109 is contacted with an excess (corresponding to the value of m) of a compound of Formula 1107 to give the corresponding product of Formula 1m, particularly where n is about 80, p is about 30, q is about 4, and m being a function of the antigen is about 2 to 10.

A compound of Formula 1202 is contacted with an excess (corresponding to the value of m) of a compound of Formula 1107 to give the corresponding product of Formula 1n, particularly where n is about 1, p is about 30, q is about 4, and m being a function of the antigen is about 2 to 10.

A compound of Formula 1507 is contacted with a compound of Formula 1109 to give the corresponding product of Formula 1m', particularly where n is about 4, p is about 90, q is about 4, t is about 1 or 2, $R^3$ is NHAc, $R^4$ is OH, $R^8$ is CMP, $R^{10}$ is 2-hydroxypropyl and m being a function of the antigen is about 1 to 10.

A compound of Formula 101" is contacted with a compound of Formula 1602 to give the corresponding product of Formula 1c', particularly where n is about 4, p is about 90, t is about 1 or 2, $R^3$ is NHAc, $R^4$ is OH, $R^8$ is CMP, $R^{10}$ is 2-hydroxypropyl and m being a function of the antigen is about 1 to 10.

A compound of Formula 101' is contacted with a compound of Formula 601' to give the corresponding product of Formula 1f', particularly where n is about 4, p is about 90, t is about 1 or 2, $R^3$ is NHAc, $R^4$ is OH, $R^8$ is CMP, $R^{10}$ is 2-hydroxypropyl and m being a function of the antigen is about 1 to 10.

A compound of Formula 101' is contacted with a compound of Formula 701' to give the corresponding product of Formula 1g', particularly where n is about 4, p is about 90, t is about 1 or 2, $R^3$ is NHAc, $R^4$ is OH, $R^8$ is CMP, $R^{10}$ is 2-hydroxypropyl and m being a function of the antigen is about 1 to 10.

Particular Compositions

By way of non-limiting example, a particular group preferred for the compositions, pharmaceutical formulations, methods of manufacture and use of the present disclosure are the following combinations and permutations of substituent groups of Formula 1 (sub-grouped, respectively, in increasing order of preference):

X is a foreign transplant antigen against which transplant recipients develop an unwanted immune response, a foreign antigen to which patients develop an unwanted immune response, a therapeutic protein to which patients develop an unwanted immune response, a self-antigen to which patients develop an unwanted immune response, or a tolerogenic portion thereof.

X is a therapeutic protein to which patients develop an unwanted immune response selected from: Abatacept, Abciximab, Adalimumab, Adenosine deaminase, Ado-trastuzumab emtansine, Agalsidase alfa, Agalsidase beta, Aldeslukin, Alglucerase, Alglucosidase alfa, α-1-proteinase inhibitor, Anakinra, Anistreplase (anisoylated plasminogen streptokinase activator complex), Antithrombin III, Antithymocyte globulin, Ateplase, Bevacizumab, Bivalirudin, Botulinum toxin type A, Botulinum toxin type B, C1-esterase inhibitor, Canakinumab, Carboxypeptidase G2 (Glucarpidase and Voraxaze), Certolizumab pegol, Cetuximab, Collagenase, Crotalidae immune Fab, Darbepoetin-α, Denosumab, Digoxin immune Fab, Dornase alfa, Eculizumab, Etanercept, Factor VIIa, Factor VIII, Factor IX, Factor XI, Factor XIII, Fibrinogen, Filgrastim, Galsulfase, Golimumab, Histrelin acetate, Hyaluronidase, Idursulphase, Imiglucerase, Infliximab, Insulin (including rHu insulin and bovine insulin), Interferon-α2a, Interferon-α2b, Interferon-β1a, Interferon-β1b, Interferon-γ1b, Ipilimumab, L-arginase, L-asparaginase, L-methionase, Lactase, Laronidase, Lepirudin/hirudin, Mecasermin, Mecasermin rinfabate, Methoxy Ofatumumab, Natalizumab, Octreotide, Oprelvekin, Pancreatic amylase, Pancreatic lipase, Papain, Peg-asparaginase, Peg-doxorubicin HCl, PEG-epoetin-β, Pegfilgrastim, Peg-Interferon-α2a, Peg-Interferon-α2b, Pegloticase, Pegvisomant, Phenylalanine ammonia-lyase (PAL), Protein C, Rasburicase (uricase), Sacrosidase, Salmon calcitonin, Sargramostim, Streptokinase, Tenecteplase, Teriparatide, Tocilizumab (atlizumab), Trastuzumab, Type 1 alpha-interferon, Ustekinumab, and vW factor.
  Especially where X is Abciximab, Adalimumab, Agalsidase alfa, Agalsidase beta, Aldeslukin, Alglucosidase alfa, Factor VIII, Factor IX, Infliximab, L-asparaginase, Laronidase, Natalizumab, Octreotide, Phenylalanine ammonia-lyase (PAL), or Rasburicase (uricase).
    Particularly where X is Factor VIII, Factor IX, uricase, PAL or asparaginase.

X is a self-antigen polypeptide selected for treating type 1 diabetes mellitus, pediatric multiple sclerosis, juvenile rheumatoid arthritis, celiac disease, or alopecia universalis.
  Especially where X is a self-antigen polypeptide selected for treating new onset type 1 diabetes mellitus, pediatric multiple sclerosis or celiac disease.

X is a foreign antigen to which patients develop an unwanted immune response
  From peanut, including conarachin (Ara h 1)
  From wheat, including Alpha-gliadin "33-mer" native (SEQ ID NO:20), Alpha-gliadin "33-mer" deamidated (SEQ ID NO:21), Alpha-gliadin (SEQ ID NO:22) and Omega-gliadin (SEQ ID NO:23).
  From cat, including Fel d 1A (UNIPROT P30438) and Cat albumin (UNIPROT P49064).
  From dog, including Can f 1 (UNIPROT O18873) and Dog albumin (UNIPROT P49822).

X is a foreign transplant antigen against which transplant recipients develop an unwanted immune response, e.g. a human leukocyte antigen protein.

X is an antibody, antibody fragment or ligand that specifically binds a circulating protein or peptide or antibody, which circulating protein or peptide or antibody gives rise to transplant rejection, immune response against a therapeutic agent, autoimmune disease, and/or allergy.
  Especially where X binds an endogenous circulating protein or peptide or antibody.

Y is a linker selected from: Formula Ya, Formula Yb, Formula Yh, Formula Yi, Formula Yk, Formula Ym, Formula Yn, Formula Yo and Formula Yp.
  Especially where n is 8 to 90±10%, p is 20 to 100±10%, and q is 3 to 20±3.
    Particularly where n is 40 to 80±10%, p is 30 to 40±10%, and q is 4 to 12±3.
  Especially where Y is Formula Ya, Formula Yb, Formula Ym or Formula Yn.
    Particularly where n is 8 to 90±10%, p is 20 to 100±10% and q is 3 to 20±3.
      More particularly where n is 40 to 80±10%, p is 30 to 40±10%, and q is 4 to 12±3.
    Particularly where Z is conjugated to Y via an ethylacetamido group.
      More particularly where Z is conjugated to Y at its C1.
        More particularly where $R^8$ is CMP.
      More particularly where $R^8$ is CMP.
    Particularly where $R^8$ is CMP.

Y is a linker selected from: Formula Yc, Formula Yf, Formula Yg and Formula Ym.
  Especially where $W_p$ is a random copolymer in which $R^9$ is Et-PEG$_t$-AcN and $R^{10}$ is 2-hydroxypropyl.
    Particularly where t is 1 or 2
      More particularly where t is 1.
    Particularly where p is about 90 and includes about 30 $W^1$ and 60 $W^2$ comonomers.

Z is galactose, galactosamine, N-acetylgalactosamine, glucose, glucosamine or N-acetylglucosamine.
  Especially where Z is galactose or N-acetylgalactosamine conjugated at C1, C2 or C6.
    Particularly where Z is galactose or N-acetylgalactosamine conjugated at C1 or C2.
      More particularly where Z is N-acetylgalactosamine conjugated at C1.
  Especially where Z is glucose or N-acetylglucosamine conjugated at C1, C2 or C6.
    Particularly where Z is glucose or N-acetylglucosamine conjugated at C1 or C2.
      More particularly where Z is N-acetylglucosamine conjugated at C1.

Each of the above-described groups and sub-groups are individually preferred and can be combined to describe further preferred aspects of the disclosure, for example but not by way of limitation, as follows:

X is a self-antigen polypeptide selected for treating type 1 diabetes mellitus, pediatric multiple sclerosis, juvenile rheumatoid arthritis, celiac disease, or alopecia universalis.
  Especially where X is a self-antigen polypeptide selected for treating new onset type 1 diabetes mellitus, pediatric multiple sclerosis or celiac disease.
    Particularly where Y is a linker selected from: Formula Ya, Formula Yb, Formula Yc, Formula Yf, Formula Yg, Formula Yh, Formula Yi, Formula Yk, Formula Ym, Formula Yn, Formula Yo and Formula Yp.

Especially where $W_p$ is a $W^1$ polymer in which $R^9$ is Et-PEG$_t$-AcN or a random copolymer in which $R^9$ is Et-PEG$_t$-AcN and $R^{10}$ is 2-hydroxypropyl.
    Particularly where t is 1 or 2
    More particularly where t is 2.
    More particularly where t is 1.
    Particularly where p is about 90
    More particularly where $W_p$ is a random copolymer and includes about 30 $W^1$ and 60 $W^2$ comonomers.
Especially where n is 8 to 90±10%, p is 20 to 100±10%, and q is 3 to 20±3.
    Particularly where n is 40 to 80±10%, p is 30 to 40±10%, and q is 4 to 12±3.
Especially where Y is Formula Ya, Formula Yb, Formula Ym or Formula Yn.
    Particularly where n is 8 to 90±10%, p is 20 to 100±10% and q is 3 to 20±3.
    More particularly where n is 40 to 80±10%, p is 30 to 40±10%, and q is 4 to 12±3.
    Even more particularly where Z is conjugated to Y via an ethylacetamido group.
    More particularly where Z is conjugated to Y via an ethylacetamido group.
    Particularly where Z is conjugated to Y via an ethylacetamido group.
Especially where Z is galactose, galactosamine or N-acetylgalactosamine.
    Particularly where Z is galactose or N-acetylgalactosamine conjugated at C1, C2 or C6.
    More particularly where Z is galactose or N-acetylgalactosamine conjugated at C1 or C2.
    Even more particularly where Z is N-acetylgalactosamine conjugated at C1.
Especially where Z is glucose, glucosamine or N-acetylglucosamine.
    Particularly where Z is glucose or N-acetylglucosamine conjugated at C1, C2 or C6.
    More particularly where Z is glucose or N-acetylglucosamine conjugated at C1 or C2.
    Even more particularly where Z is N-acetylglucosamine conjugated at C1.
Particularly where Y is a linker selected from: Formula Yc, Formula Yf, Formula Yg and Formula Ym.
    Especially where $W_p$ is a random copolymer in which $R^9$ is Et-PEG$_t$-AcN and $R^{10}$ is 2-hydroxypropyl.
    Particularly where t is 1 or 2
    More particularly where t is 1.
    Particularly where p is about 90 and includes about 30 $W^1$ and 60 $W^2$ comonomers.
Particularly where Y is a linker selected from: Formula Yc and Formula Ym.
    Especially where $W_p$ is a random copolymer in which $R^9$ is Et-PEG$_t$-AcN and $R^{10}$ is 2-hydroxypropyl.
    Particularly where t is 1 or 2
    More particularly where t is 1.
    Particularly where p is about 90 and includes about 30 $W^1$ and 60 $W^2$ comonomers.
Particularly where Z is galactose, galactosamine or N-acetylgalactosamine.
    Especially where Z is galactose or N-acetylgalactosamine conjugated at C1, C2 or C6.
    Particularly where Z is galactose or N-acetylgalactosamine conjugated at C1 or C2.
    More particularly where Z is N-acetylgalactosamine conjugated at C1.
Particularly where Z is glucose, glucosamine or N-acetylglucosamine.
    Especially where Z is glucose or N-acetylglucosamine conjugated at C1, C2 or C6.
    More particularly where Z is glucose or N-acetylglucosamine conjugated at C1 or C2.
    Even more particularly where Z is N-acetylglucosamine conjugated at C1.
Especially where Y is a linker selected from: Formula Ya, Formula Yb, Formula Yh, Formula Yi, Formula Yk, Formula Ym, Formula Yn, Formula Yo and Formula Yp.
    Particularly where Y is a linker selected from: Formula Yc, Formula Yf, Formula Yg and Formula Ym.
    Especially where $W_p$ is a random copolymer in which $R^9$ is Et-PEG$_t$-AcN and $R^{10}$ is 2-hydroxypropyl.
    Particularly where t is 1 or 2
    More particularly where t is 1.
    Particularly where p is about 90 and includes about 30 $W^1$ and 60 $W^2$ comonomers.
    Particularly where Y is a linker selected from: Formula Yc and Formula Ym.
    Especially where $W_p$ is a random copolymer in which $R^9$ is Et-PEG$_t$-AcN and $R^{10}$ is 2-hydroxypropyl.
    Particularly where t is 1 or 2
    More particularly where t is 1.
    Particularly where p is about 90 and includes about 30 $W^1$ and 60 $W^2$ comonomers.
    Particularly where n is 8 to 90±10%, p is 20 to 100±10%, and q is 3 to 20±3.
    More particularly where n is 40 to 80±10%, p is 30 to 40±10%, and q is 4 to 12±3.
    Particularly where Y is Formula Ya, Formula Yb, Formula Ym or Formula Yn.
    More particularly where n is 8 to 90±10%, p is 20 to 100±10% and q is 3 to 20±3.
    More preferably where n is 40 to 80±10%, p is 30 to 40±10%, and q is 4 to 12±3.
    More particularly where Z is conjugated to Y via an ethylacetamido group.
Especially where Z is galactose, galactosamine or N-acetylgalactosamine.
    Particularly where Z is galactose or N-acetylgalactosamine conjugated at C1, C2 or C6.
    More particularly where Z is galactose or N-acetylgalactosamine conjugated at C1 or C2.
    More preferably where Z is N-acetylgalactosamine conjugated at C1.
    More particularly where Y is a linker selected from: Formula Yc, Formula Yf, Formula Yg and Formula Ym.
    Especially where $W_p$ is a random copolymer in which $R^9$ is Et-PEG$_t$-AcN and $R^{10}$ is 2-hydroxypropyl.
    Particularly where t is 1 or 2
    More particularly where t is 1.
    Particularly where p is about 90 and includes about 30 $W^1$ and 60 $W^2$ comonomers.
Especially where Z is glucose, glucosamine or N-acetylglucosamine.

Particularly where Z is glucose or N-acetylglucosamine conjugated at C1, C2 or C6.
More particularly where Z is glucose or N-acetylglucosamine conjugated at C1 or C2.
More preferably where Z is N-acetylglucosamine conjugated at C1.
More particularly where Y is a linker selected from: Formula Yc, Formula Yf, Formula Yg and Formula Ym.
Especially where $W_p$ is a random copolymer in which $R^9$ is Et-PEG$_t$-AcN and $R^{10}$ is 2-hydroxypropyl.
Particularly where t is 1 or 2
More particularly where t is 1.
Particularly where p is about 90 and includes about 30 $W^1$ and 60 $W^2$ comonomers.
More particularly where Y is a linker selected from: Formula Yc and Formula Ym.
Especially where $W_p$ is a random copolymer in which $R^9$ is Et-PEG$_t$-AcN and $R^{10}$ is 2-hydroxypropyl.
Particularly where t is 1 or 2
More particularly where t is 1.
Particularly where p is about 90 and includes about 30 $W^1$ and 60 $W^2$ comonomers.
m is an integer from about 1 to 100.
m is 1, 2, 3, 4, 5, 6, 7, 8, 9, 10, 11, 12, 13, 14, 15, 16, 17, 18, 19, 20, 25, 30, 35, 40, 45, 50, 55, 60, 65 70, 75, 80, 85, 90, 95, 100 or 110.
Particularly m is from about 1 to 20.
m is 1, 2, 3, 4, 5, 6, 7, 8, 9, 10, 11, 12, 13, 14, 15, 16, 17, 18, 19, 20, 21 or 22.
More particularly m is about 10.
m is 9, 10 or 11.
n is an integer representing a mixture including from about 1 to 100
n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.
Particularly n is about 8 to 90.
Particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.
More particularly n is about 40 to 80.
More particularly n is 37, 40, 41, 45, 50, 54, 55, 59, 60, 65, 70, 75, 80, 82, 83 or 88.
n represents a mixture encompassing the ranges 1-4, 2-4, 2-6, 3-8, 7-13, 6-14, 15-25, 26-30, 42-50, 46-57, 60-82, 85-90, 90-110 and 107-113.
Particularly n represents a mixture encompassing the ranges 7-13, 6-14, 15-25, 26-30, 42-50, 46-57, 60-82, 85-90 and 82-99.
More particularly n represents a mixture encompassing the ranges 36-44, 42-50, 46-57, 60-82 and 75-85.
p is an integer representing a mixture including from about 2 to 150.
p is 2, 3, 4, 5, 6, 7, 8, 9, 10, 11, 12, 13, 14, 15, 16, 17, 18, 19, 20, 25, 30, 35, 40, 45, 50, 55, 60, 65 70, 75, 80, 85, 90, 95, 100, 110, 120, 130, 140, 150, 160 or 165.
Particularly where n is an integer representing a mixture including from about 1 to 100.
Particularly n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.
More particularly where n is about 8 to 90.
More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.
Even more particularly where n is about 40 to 80.
Even more particularly n is 37, 40, 41, 45, 50, 54, 55, 59, 60, 65, 70, 75, 80, 82, 83 or 88.
More particularly p is 18, 19, 20, 25, 30, 35, 40, 45, 50, 55, 60, 65 70, 75, 80, 85, 90, 95, 100 or 110.
Particularly where n is an integer representing a mixture including from about 1 to 100.
Particularly n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.
More particularly where n is about 8 to 90.
More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.
Even more particularly where n is about 40 to 80.
Even more particularly n is 37, 40, 41, 45, 50, 54, 55, 59, 60, 65, 70, 75, 80, 82, 83 or 88.
More particularly p is 27, 28, 29, 30, 31, 32, 33, 34, 35, 36, 37, 38, 39, 40, 41, 42, 43, or 44.
Particularly where n is 1, 2, 3, 4, 5, 6, 7, 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95, 99, 100, 105 or 110.
More particularly where n is about 8 to 90.
More particularly n is 8, 9, 10, 11, 12, 13, 14, 15, 16, 17, 18, 19, 20, 22, 25, 30, 34, 35, 37, 40, 41, 45, 50, 54, 55, 59, 60, 65, 70, 75, 80, 82, 83, 85, 88, 90, 95 or 99.
Even more particularly where n is about 40 to 80.
Even more particularly n is 37, 40, 41, 45, 50, 54, 55, 59, 60, 65, 70, 75, 80, 82, 83 or 88.
q is an integer representing a mixture including from about 1 to 44.
q is 1, 2, 3, 4, 5, 6, 7, 8, 9, 10, 11, 12, 13, 14, 15, 16, 17, 18, 19, 20, 25, 30, 35, 40, 44 or 48.

Utility, Testing and Administration

General Utility

The compositions of the disclosure find use in a variety of applications including, as will be appreciated by those in the art, treatment of transplant rejection, immune response against a therapeutic agent, autoimmune disease, and food allergy, among other uses.

In a preferred embodiment, the compositions of the disclosure are used to modulate, particularly down-regulate, antigen-specific undesirable immune response.

The compositions of the disclosure are useful, in additional embodiments, to bind and clear from the circulation specific undesired proteins, including antibodies endogenously generated in a patient (i.e., not exogenous antibodies administered to a patient), peptides and the like, which cause autoimmunity and associated pathologies, allergy, inflammatory immune responses, and anaphylaxis.

In several embodiments according to the present disclosure, antigens are targeted to the liver for presentation via antigen-presenting cells to specifically down-regulate the immune system or for clearance of unwanted circulating proteins. This is distinct from previous uses of liver targeting, for example as described in US 2013/0078216, where the purpose of liver-targeting molecules such as DOM26h-196-61 was the delivery of therapeutic agents to treat liver diseases such as fibrosis, hepatitis, Cirrhosis and liver cancer.

According to several embodiments, the present disclosure provides compositions and methods to treat unwanted immune response to self-antigens and foreign antigens, including but not limited to: a foreign transplant antigen against which transplant recipients develop an unwanted immune response (e.g., transplant rejection), a foreign antigen to which patients develop an unwanted immune (e.g., allergic or hypersensitivity) response, a therapeutic agent to which patients develop an unwanted immune response (e.g., hypersensitivity and/or reduced therapeutic activity), a self-antigen to which patients develop an unwanted immune response (e.g., autoimmune disease)

Autoimmune disease states that can be treated using the methods and compositions provided herein include, but are not limited to: Acute Disseminated Encephalomyelitis (ADEM); Acute interstitial allergic nephritis (drug allergies); Acute necrotizing hemorrhagic leukoencephalitis; Addison's Disease; Alopecia areata; Alopecia universalis; Ankylosing Spondylitis; Arthritis, juvenile; Arthritis, psoriatic; Arthritis, rheumatoid; Atopic Dermatitis; Autoimmune aplastic anemia; Autoimmune gastritis; Autoimmune hepatitis; Autoimmune hypophysitis; Autoimmune oophoritis; Autoimmune orchitis; Autoimmune polyendocrine syndrome type 1; Autoimmune polyendocrine syndrome type 2; Autoimmune thyroiditis; Behcet's disease; Bronchiolitis obliterans; Bullous pemphigoid; Celiac disease; Churg-Strauss syndrome; Chronic inflammatory demyelinating polyneuropathy; Cicatricial pemphigoid; Crohn's disease; Coxsackie myocarditis; Dermatitis herpetiformis Duhring; Diabetes mellitus (Type 1); Erythema nodosum; Epidermolysis bullosa acquisita, Giant cell arteritis (temporal arteritis); Giant cell myocarditis; Goodpasture's syndrome; Graves' disease; Guillain-Barre syndrome; Hashimoto's encephalitis; Hashimoto's thyroiditis; IgG4-related sclerosing disease; Lambert-Eaton syndrome; Mixed connective tissue disease; Mucha-Habermann disease; Multiple sclerosis; Myasthenia gravis; Optic neuritis; Neuromyelitis optica; Pemphigus vulgaris and variants; Pernicious angemis; Pituitary autoimmune disease; Polymyositis; Postpericardiotomy syndrome; Premature ovarian failure; Primary Biliary Cirrhosis; Primary sclerosing cholangitis; Psoriasis; Rheumatic heart disease; Sjogren's syndrome; Systemic lupus erythematosus; Systemic sclerosis; Ulcerative colitis; Undifferentiated connective tissue disease (UCTD); Uveitis; Vitiligo; and Wegener's granulomatosis.

A particular group of autoimmune disease states that can be treated using the methods and compositions provided herein include, but are not limited to: Acute necrotizing hemorrhagic leukoencephalitis; Addison's Disease; Arthritis, psoriatic; Arthritis, rheumatoid; Autoimmune aplastic anemia; Autoimmune hypophysitis; Autoimmune gastritis; Autoimmune polyendocrine syndrome type 1; Bullous pemphigoid; Celiac disease; Coxsackie myocarditis; Dermatitis herpetiformis Duhring; Diabetes mellitus (Type 1); Epidermolysis bullosa acquisita; Giant cell myocarditis; Goodpasture's syndrome; Graves' disease; Hashimoto's thyroiditis; Mixed connective tissue disease; Multiple sclerosis; Myasthenia gravis; Neuromyelitis optica; Pernicious angemis; Pemphigus vulgaris and variants; Pituitary autoimmune disease; Premature ovarian failure; Rheumatic heart disease; Systemic sclerosis; Sjogren's syndrome; Systemic lupus erythematosus; and Vitiligo.

In the embodiments employing an antigen against which an unwanted immune response is developed, such as food antigens, treatment can be provided for reactions against, for example: peanut, apple, milk, egg whites, egg yolks, mustard, celery, shrimp, wheat (and other cereals), strawberry and banana.

As will be appreciated by those skilled in the art, a patient can be tested to identify a foreign antigen against which an unwanted immune response has developed, and a composition of the disclosure can be developed based on that antigen.

Testing

In establishing the utility of the compositions and methods of the disclosure, specificity in binding to antigen-presenting cells in the liver (particularly binding to hepatocytes and specifically ASGPR) should initially be determined. This can be accomplished, for example, by employing a marker (such as the fluorescent marker phycoerythrin ("PE")) in a composition of the disclosure. The composition is administered to suitable experimental subjects. Controls, e.g., unconjugated PE or vehicle (saline) are administered to other group(s) of subjects. The composition and controls are allowed to circulate for a period of 1 to 5 hours, after which the spleens and livers of the subjects are harvested and measured for fluorescence. The specific cells in which fluorescence is found can be subsequently identified. Compositions of the disclosure, when tested in this manner, show higher levels of concentration in the antigen-presenting cells of the liver as compared with unconjugated PE or vehicle.

Effectiveness in immune modulation can be tested by measuring the proliferation of OT-I CD8$^+$ cells (transplanted into host mice) in response to the administration of a composition of the disclosure incorporating a known antigen, such as ovalbumin ("OVA"), as compared with administration of the antigen alone or just vehicle. Compositions of the disclosure, when tested in this manner, show an increase of OT-I cell proliferation as compared with antigen alone or vehicle, demonstrating increased CD8+ T-cell cross-priming. To distinguish T cells being expanded into a functional effector phenotype from those being expanded and deleted, the proliferating OT-I CD8$^+$ T cells can be phenotypically analyzed for molecular signatures of exhaustion [such as programmed death-1 (PD-1), FasL, and others], as well as Annexin-V binding as a hallmark of apoptosis and thus deletion. The OT-I CD8$^+$ T cells can also be assessed for their responsiveness to an antigen challenge with adjuvant in order to demonstrate functional non-responsiveness, and thus immune tolerance, towards the antigen. To do so, the cells are analyzed for inflammatory signatures after administration of compositions of the disclosure into host mice followed by an antigen challenge. Compositions of the disclosure when tested in this manner demonstrate very low (e.g., background) levels of inflammatory OT-I CD8$^+$ T cell responses towards OVA in comparison to control groups, thus demonstrating immune tolerance.

Humoral immune response can be tested by administering a composition of the disclosure incorporating a known antigen, such as OVA, as compared with the administration of the antigen alone or just vehicle, and measuring the levels of resulting antibodies. Compositions of the disclosure when tested in this manner show very low (e.g., background) levels of antibody formation responsive to their administration and the administration of vehicle, with significantly higher levels of antibody formation responsive to administration of the antigen.

Effectiveness in tolerization against an antigen can be tested as above with reference to humoral immune response, where several weeks following treatment(s) with a composition of the disclosure a group of subjects is challenged by administration of the antigen alone, followed by measuring the levels of antibodies to the antigen. Compositions of the disclosure when tested in this manner show low levels of antibody formation responsive to challenge with the antigen in groups pretreated with such compositions as compared to groups that are not pretreated.

Disease-focused experimental models are well known to those skilled in the art and include the NOD (or non-obese diabetic) mouse model of autoimmunity and tolerance and the EAE (experimental autoimmune encephalomyelitis) model for the human inflammatory demyelinating disease, multiple sclerosis. In particular, the NOD mouse develops spontaneous autoimmune diabetes (similar to type 1a diabetes in humans). Groups of NOD mice are treated with test compound or a negative control, followed by measurement of blood glucose. Successful treatment corresponds to likelihood of treating diabetes in humans or proof of mechanism for approaches to the treatment of other autoimmune diseases. (See, e.g., Anderson and Bluestone, *Annu. Rev. Immunol.* 2005; 23:447-85.)

Administration

The compositions of the disclosure are administered at a therapeutically effective dosage, e.g., a dosage sufficient to provide treatment for the disease states previously described. Administration of the compounds of the disclosure or the pharmaceutically acceptable salts thereof can be via any of the accepted modes of administration for agents that serve similar utilities.

While human dosage levels have yet to be optimized for the compounds of the disclosure, these can initially be extrapolated from the about 10 μg to 100 μg doses administered for mice. Generally, an individual human dose is from about 0.01 to 2.0 mg/kg of body weight, preferably about 0.1 to 1.5 mg/kg of body weight, and most preferably about 0.3 to 1.0 mg/kg of body weight. Treatment can be administered for a single day or a period of days, and can be repeated at intervals of several days, one or several weeks, or one or several months. Administration can be as a single dose (e.g., as a bolus) or as an initial bolus followed by continuous infusion of the remaining portion of a complete dose over time, e.g., 1 to 7 days. The amount of active compound administered will, of course, be dependent on any or all of the following: the subject and disease state being treated, the severity of the affliction, the manner and schedule of administration and the judgment of the prescribing physician. It will also be appreciated that amounts administered will depend upon the molecular weight of the antigen, antibody, antibody fragment or ligand as well as the size of the linker.

The compositions of the disclosure can be administered either alone or in combination with other pharmaceutically acceptable excipients. While all typical routes of administration are contemplated (e.g. oral, topical, transdermal, injection (intramuscular, intravenous, or intra-arterial)), it is presently preferred to provide liquid dosage forms suitable for injection. The formulations will typically include a conventional pharmaceutical carrier or excipient and a composition of the disclosure or a pharmaceutically acceptable salt thereof. In addition, these compositions can include other medicinal agents, pharmaceutical agents, carriers, and the like, including, but not limited to the therapeutic protein, peptide, antibody or antibody-like molecule corresponding to the antigen (X) employed in the composition of the disclosure, and other active agents that can act as immune-modulating agents and more specifically can have inhibitory effects on B-cells, including anti-folates, immune suppressants, cyostatics, mitotic inhibitors, and anti-metabolites, or combinations thereof.

Generally, depending on the intended mode of administration, the pharmaceutically acceptable composition will contain about 0.1% to 95%, preferably about 0.5% to 50%, by weight of a composition of the disclosure, the remainder being suitable pharmaceutical excipients, carriers, etc. Dosage forms or compositions containing active ingredient in the range of 0.005% to 95% with the balance made up from non-toxic carrier can be prepared.

Liquid pharmaceutically administrable compositions can, for example, be prepared by dissolving, dispersing, etc. an active composition of the disclosure (e.g., a lyophilized powder) and optional pharmaceutical adjuvants in a carrier, such as, for example, water (water for injection), saline, aqueous dextrose, glycerol, glycols, ethanol or the like (excluding galactoses), to thereby form a solution or suspension. If desired, the pharmaceutical composition to be administered can also contain minor amounts of nontoxic auxiliary substances such as wetting agents, emulsifying agents, stabilizing agents, solubilizing agents, pH buffering agents and the like, for example, sodium acetate, sodium citrate, cyclodextrine derivatives, sorbitan monolaurate, triethanolamine acetate and triethanolamine oleate, etc., osmolytes, amino acids, sugars and carbohydrates, proteins and polymers, salts, surfactants, chelators and antioxidants, preservatives, and specific ligands. Actual methods of preparing such dosage forms are known, or will be apparent, to those skilled in this art; for example, see Remington: *The Science and Practice of Pharmacy*, Pharmaceutical Press, 22nd Edition, 2012. The composition or formulation to be administered will, in any event, contain a quantity of the active compound in an amount effective to treat the symptoms of the subject being treated.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes. All references cited herein are incorporated by reference in their entirety.

Example 1

F1aA-OVA-$m_4$-$n_{80}$ (or F1a-OVA-$m_4$-$n_{80}$-2NGAL)

1A. Formula 103' where X' is OVA and m is 4

In an endotoxin-free tube, OVA (5.0 mg, 0.00012 mmol) was added to 100 μl of pH 8.0 PBS containing 5 mM EDTA and stirred. Separately, 1 mg of Traut's Reagent was dissolved in 100 μl of pH 7.0 PBS, and 16 μl (0.00119 mmol) of the Traut's Reagent solution so obtained was added to the stirred solution of OVA with continued stirring. After 1 hour, excess Traut's Reagent was removed using a centrifugal size exclusion column to afford the corresponding product of Formula 103'.

1B. Formula 106A where n is 80

In an endotoxin-free tube, galactosamine (10.0 mg, 0.04638 mmol) was dissolved with stirring in 100 µl of pH 8.0 PBS containing 5 mM EDTA. Pyridyl dithiol-poly (ethylene glycol)-NHS ester (Formula 104 where n is 80) (16.23 mg, 0.00464 mmol) dissolved in 100 µl of pH 7.0 PBS was added to the stirring solution of galactosamine. After 1 hour, the resulting pyridyl dithiol-poly(ethylene glycol)-N-acetylgalactosamine (Formula 106A) was ready to be used without further purification.

1C. Formula 1aA where X' is OVA, m is 4, n is 80 (and Z' is C2 Galactosamine)

Figure 5:
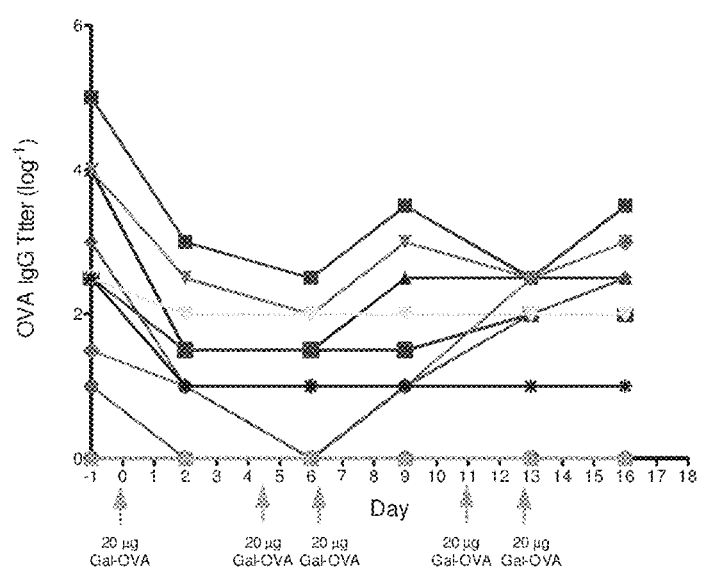
FIG. 5 shows that administration of F1aA-OVA-$m_4$-$n_{80}$ (Gal-OVA) in repeated doses over time is able to deplete OVA-specific antibodies from the serum of mice.
Figures 6A, 6B, 6C:
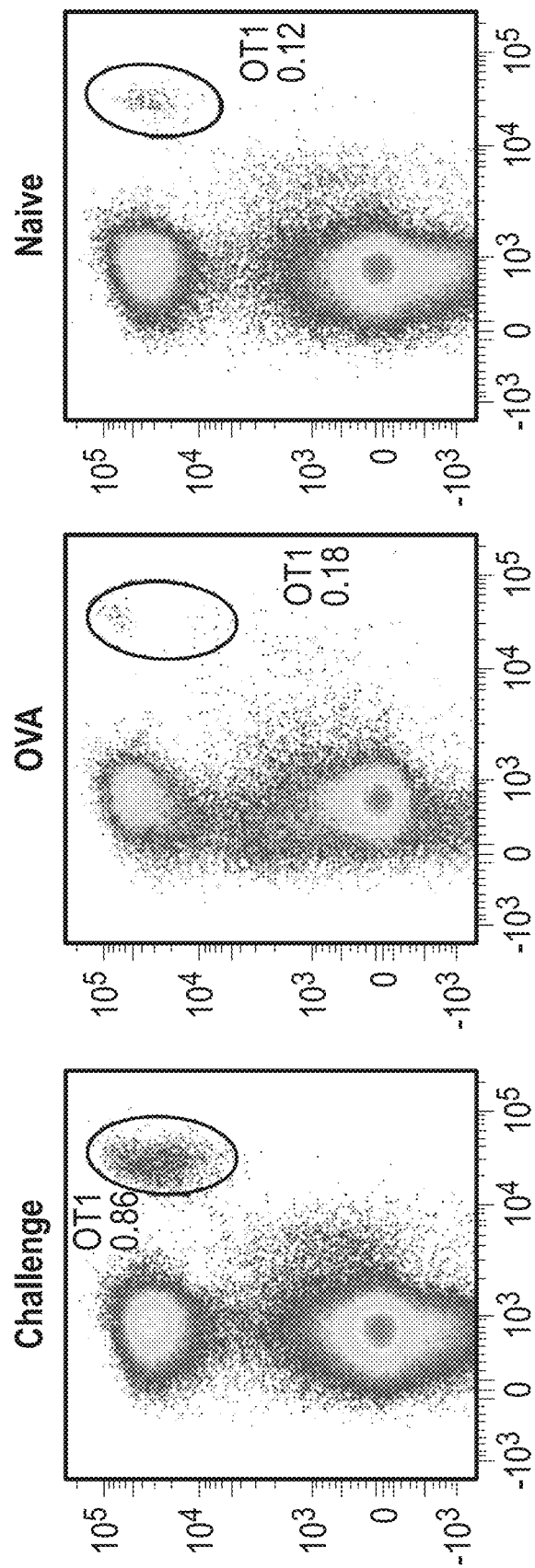
FIGS. 6A-6F depict data related to the mitigation of the OVA-specific immune response.
Figures 6D, 6E, 6F:
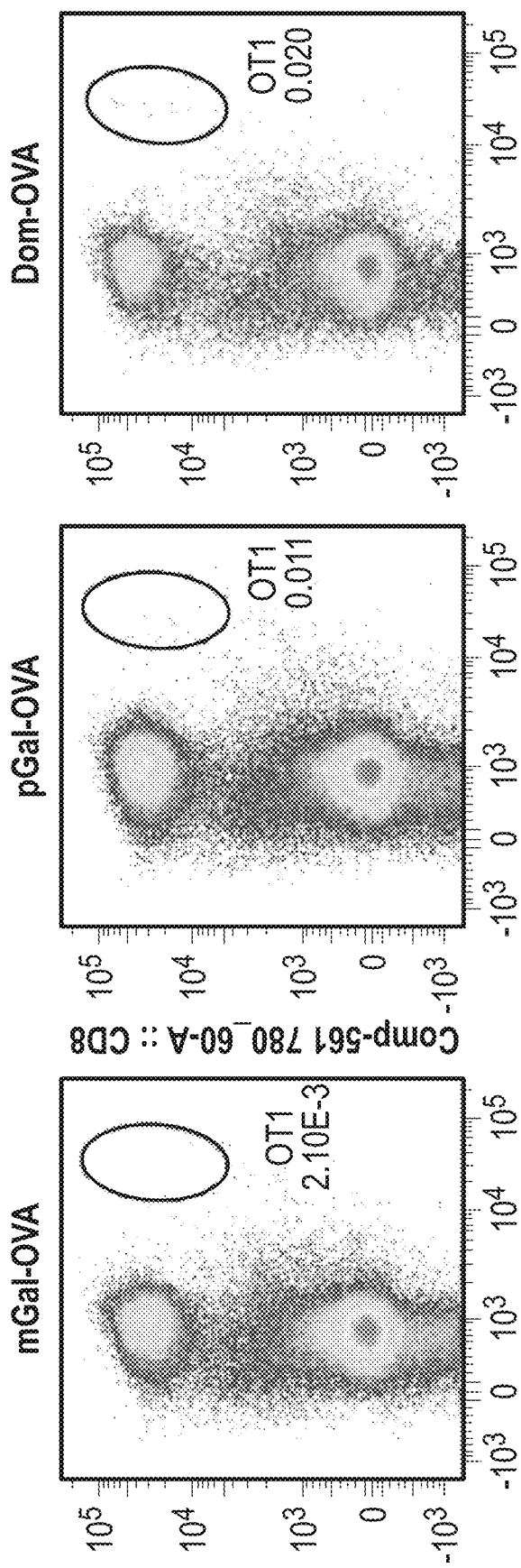
Figure 7A:
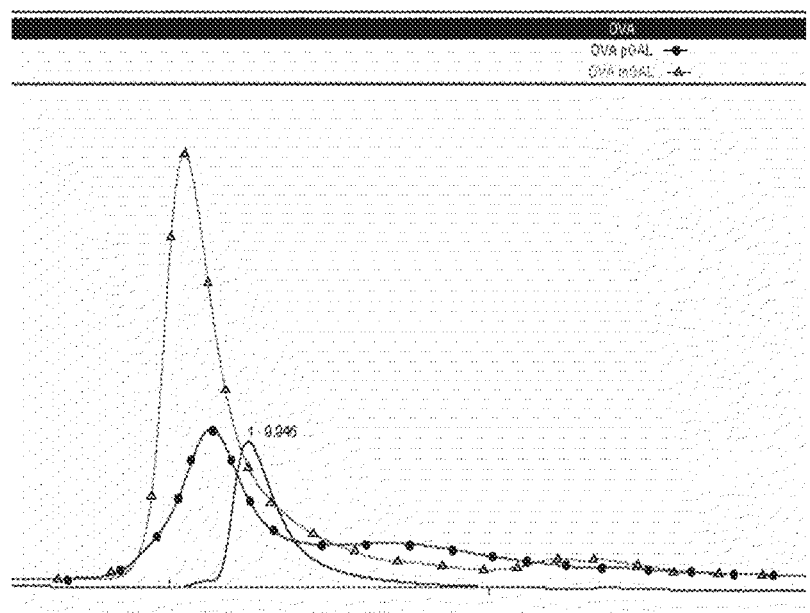
FIGS. 7A-7B shows the characterization of F1aA-OVA-$m_4$-$n_{80}$ and F1b-OVA-$m_1$-$n_{44}$-$p_{34}$.
Figure 7B:
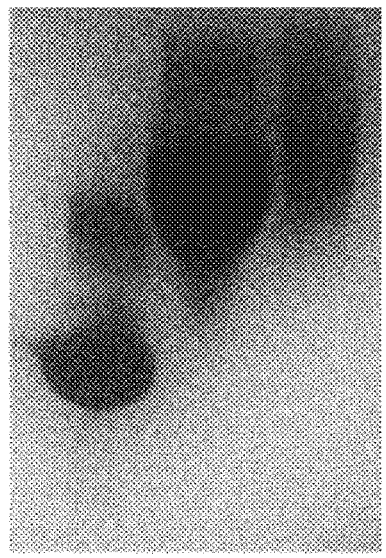

The purified OVA-Traut conjugate of Formula 103' prepared in Example 1A was added directly to the stirring product of Formula 106A prepared in Example 1B. After 1 hour, the resulting product of Formula 1a was purified by passing the reaction mixture through a centrifugal size exclusion column. Characterization (UHPLC SEC, gel electrophoresis) confirmed product identity. (See FIG. 5.)

1D. Other Compounds of Formula 103'

By following the procedure described in Example 1A and substituting OVA with the following:
Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
Insulin (SEQ ID NO:1),
GAD-65 (SEQ ID NO:2),
IGRP (SEQ ID NO:3)
MBP (SEQ ID NO:4),
MOG (SEQ ID NO:5),
PLP (SEQ ID NO:6),
MBP13-32 (SEQ ID NO:7),
MBP83-99 (SEQ ID NO:8),
MBP111-129 (SEQ ID NO:9),
MBP146-170 (SEQ ID NO:10),
MOG1-20 (SEQ ID NO:11),
MOG35-55 (SEQ ID NO:12),
PLP139-154 (SEQ ID NO:13),
MART1 (SEQ ID NO:14),
Tyrosinase (SEQ ID NO:15),
PMEL (SEQ ID NO:16),
Aquaporin-4 (SEQ ID NO:17),
S-arrestin (SEQ ID NO:18),
IRBP (SEQ ID NO:19),
Conarachin (UNIPROT Q6PSU6),
Alpha-gliadin "33-mer" native (SEQ ID NO:20),
Alpha-gliadin "33-mer" deamidated (SEQ ID NO:21),
Alpha-gliadin (SEQ ID NO:22),
Omega-gliadin (SEQ ID NO:23),
Fel d 1A (UNIPROT P30438),
Cat albumin (UNIPROT P49064),
Can f (UNIPROT O18873),
Dog albumin (UNIPROT P49822), and
RhCE (UNIPROT P18577), there are obtained the following corresponding compounds of Formula 103' where:
X is Abciximab and m is 10,
X is Adalimumab and m is 11,
X is Agalsidase alfa and m is 14,
X is Agalsidase beta and m is 14,
X is Aldeslukin and m is 6,
X is Alglucosidase alfa and m is 13,
X is Factor VIII and m is 100,
X is Factor IX and m is 18,
X is L-asparaginase and m is 5,
X is Laronidase and m is 7,
X is Octreotide and m is 1,
X is Phenylalanine ammonia-lyase and m is 12,
X is Rasburicase and m is 12,
X is Insulin (SEQ ID NO:1) and m is 2,
X is GAD-65 (SEQ ID NO:2) and m is 8,
X is IGRP (SEQ ID NO:3) and m is 7,
X is MBP (SEQ ID NO:4) and m is 6,
X is MOG (SEQ ID NO:5) and m is 5,
X is PLP (SEQ ID NO:6) and m is 8,
X is MBP13-32 (SEQ ID NO:7) and m is 1,
X is MBP83-99 (SEQ ID NO:8) and m is 1,
X is MBP111-129 (SEQ ID NO:9) and m is 1,
X is MBP146-170 (SEQ ID NO:10) and m is 2,
X is MOG1-20 (SEQ ID NO:11) and m is 1,
X is MOG35-55 (SEQ ID NO:12) and m is 2,
X is PLP139-154 (SEQ ID NO:13) and m is 3,
X is MART1 (SEQ ID NO:14) and m is 4,
X is Tyrosinase (SEQ ID NO:15) and m is 8,
X is PMEL (SEQ ID NO:16) and m is 5,
X is Aquaporin-4 (SEQ ID NO:17) and m is 4,
X is S-arrestin (SEQ ID NO:18) and m is 12,
X is IRBP (SEQ ID NO:19) and m is 21,
X is Conarachin and m is 21,
X is Alpha-gliadin "33-mer" native (SEQ ID NO:20) and m is 1,
X is Alpha-gliadin "33-mer" deamidated (SEQ ID NO:21) and m is 1,
X is Alpha-gliadin (SEQ ID NO:22) and m is 1,
X is Omega-gliadin (SEQ ID NO:23) and m is 1,
X is Fel d 1 and m is 4,
X is Cat albumin and m is 16,
X is Can f 1 and m is 6,
X is Dog albumin and m is 23, and
X is RhCE and m is 10.

1E. Other Compounds of Formula 1aA

By following the procedure described in Example 1C and substituting the compounds of Formula 103', for example as obtained in Example 1D, there are obtained the following corresponding compounds of Formula 1aA:
F1aA-Abciximab-$m_{10}$-$n_{80}$,
F1aA-Adalimumab-$m_{11}$-$n_{80}$,
F1aA-Agalsidase alfa-$m_{14}$-$n_{80}$,
F1aA-Agalsidase beta-$m_{14}$-$n_{80}$,
F1aA-Aldeslukin-$m_{6}$-$n_{80}$,
F1aA-Alglucosidase alfa-$m_{13}$-$n_{80}$,
F1aA-Factor VIII-$m_{100}$-$n_{80}$,
F1aA-Factor IX-$m_{18}$-$n_{80}$,
F1aA-L-asparaginase-$m_{5}$-$n_{80}$,
F1aA-Laronidase-$m_{7}$-$n_{80}$,
F1aA-Octreotide-$m_{1}$-$n_{80}$,
F1aA-Phenylalanine ammonia-lyase-$m_{12}$-$n_{80}$,
F1aA-Rasburicase-$m_{12}$-$n_{80}$,
F1aA-Insulin-$m_{2}$-$n_{80}$,
F1aA-GAD-65-$m_{8}$-$n_{80}$,
F1aA-IGRP-$m_{7}$-$n_{80}$, F1aA-MBP-$m_6$-$n_{80}$,
F1aA-MOG-$m_5$-$n_{80}$,
F1aA-PLP-$m_8$-$n_{80}$,
F1aA-MBP13-32-$m_1$-$n_{80}$,
F1aA-MBP83-99-$m_1$-$n_{80}$,
F1aA-MBP111-129-$m_1$-$n_{80}$,
F1aA-MBP146-170-$m_2$-$n_{80}$,
F1aA-MOG1-20-$m_1$-$n_{80}$,
F1aA-MOG35-55-$m_2$-$n_{80}$,
F1aA-PLP139-154-$m_3$-$n_{80}$,
F1aA-MART1-$m_4$-$n_{80}$,
F1aA-Tyrosinase-$m_8$-$n_{80}$,
F1aA-PMEL-$m_5$-$n_{80}$,
F1aA-Aquaporin-4-$m_4$-$n_{80}$,
F1aA-S-arrestin-$m_{12}$-$n_{80}$,
F1aA-IRBP-$m_{21}$-$n_{80}$,
F1aA-Conarachin-$m_{21}$-$n_{80}$,
F1aA-Alpha-gliadin "33-mer" native-$m_1$-$n_{80}$,
F1aA-Alpha-gliadin "33-mer" deamidated-$m_1$-$n_{80}$,
F1aA-Alpha-gliadin-$m_1$-$n_{80}$,
F1aA-Omega-gliadin-$m_1$-$n_{80}$,
F1aA-Fel d 1-$m_4$-$n_{80}$,
F1aA-Cat albumin-$m_{16}$-$n_{80}$,
F1aA-Can f 1-$m_6$-$n_{80}$,
F1aA-Dog albumin-$m_{23}$-$n_{80}$, and
F1aA-RhCE-$m_{10}$-$n_{80}$.

1F. Other Compounds of Formula 106A

By following the procedure described in Example 1B and substituting the pyridyl dithiol-poly(ethylene glycol)-NHS ester (Formula 104 where n is 80) with the following:
Formula 104 where n is 12,
Formula 104 where n is 33,
Formula 104 where n is 40,
Formula 104 where n is 43,
Formula 104 where n is 50,
Formula 104 where n is 60,
Formula 104 where n is 75, and
Formula 104 where n is 80,
there are obtained the following corresponding compounds of Formula 106A where:
n is 12,
n is 33,
n is 40,
n is 43,
n is 50,
n is 60,
n is 75, and
n is 84.

1G. Other Compounds of Formula 1aA

By following the procedure described in Example 1E and substituting the compound of Formula 106A with the compounds obtained in Example 1F, there are obtained the corresponding compounds of Formula 1aA where n is 12, 33, 40, 43, 50, 60, 75 and 84, such as:
F1aA-Insulin-$m_2$-$n_{12}$,
F1aA-Insulin-$m_2$-$n_{33}$,
F1aA-Insulin-$m_2$-$n_{40}$,
F1aA-Insulin-$m_2$-$n_{43}$,
F1aA-Insulin-$m_2$-$n_{50}$,
F1aA-Insulin-$m_2$-$n_{60}$,
F1aA-Insulin-$m_2$-$n_{75}$, and
F1aA-Insulin-$m_2$-$n_{84}$.

1H. Other Compounds of Formula 1aA

Similarly, by following the procedures described in Example 1A-G and substituting the compound glucosamine for galactosamine, there are obtained the corresponding compounds of Formula 1aA where Z' is C2 glucosamine.

Example 2

F1b-OVA-$m_1$-$n_4$-$p_{34}$-2NAcGAL

2A. Formula 103' where X' is Ovalbumin and m is 1

In an endotoxin-free tube, OVA (6.5 mg, 0.000155 mmol) was added to 200 µl of pH 8.0 PBS containing 5 mM EDTA and stirred. Separately, 1 mg of Traut's Reagent was dissolved in 100 µl of pH 7.0 PBS, and 43 µl (0.00310 mmol) of the Traut's Reagent solution so obtained was added to the stirred solution of OVA with continued stirring. After 1 hour, non-reacted Traut's Reagent was removed using a centrifugal size exclusion column to afford the product of Formula 103'.

2B. Formula 1b where X' is Ovalbumin, m is 1, n is 4, p is 34, $R^9$ is a Direct Bond and Z" is 2NAcGAL In a micro centrifuge tube, poly(Galactosamine Methacrylate)-(pyridyl disulfide) (Formula 201) (20.0 mg, 0.0020 mmol) was solubilized in 50 µl of pH 8.0 PBS containing 5 mM EDTA. To this was added the purified OVA-Traut product from Example 2A followed by stirring for 1 hour. The resulting product of Formula 1b was purified by passing the reaction mixture through a centrifugal size exclusion column. Characterization (UHPLC SEC, gel electrophoresis) confirmed the identity of the product. (See FIG. 5.)

2C. Other Compounds of Formula 1b

By following the procedure described in Example 2B and substituting the compounds of Formula 103', for example as obtained in Example 1D, there are obtained the following corresponding compounds of Formula 1b:
F1b-Abciximab-$m_{10}$-$n_4$-$p_{34}$-2NAcGAL,
F1b-Adalimumab-$m_{11}$-$n_4$-$p_{34}$-2NAcGAL,
F1b-Agalsidase alfa-$m_{14}$-$n_4$-$p_{34}$-2NAcGAL,
F1b-Agalsidase beta-$m_{14}$-$n_4$-$p_{34}$-2NAcGAL,
F1b-Aldeslukin-$m_6$-$n_4$-$p_{34}$-2NAcGAL,
F1b-Alglucosidase alfa-$m_{13}$-$n_4$-$p_{34}$-2NAcGAL,
F1b-Factor VIII-$m_{100}$-$n_4$-$p_{34}$-2NAcGAL,
F1b-Factor IX-$m_{18}$-$n_4$-$p_{34}$-2NAcGAL,
F1b-L-asparaginase-$m_5$-$n_4$-$p_{34}$-2NAcGAL,
F1b-Laronidase-$m_7$-$n_4$-$p_{34}$-2NAcGAL,
F1b-Octreotide-$m_1$-$n_4$-$p_{34}$-2NAcGAL,
F1b-Phenylalanine ammonia-lyase-$m_{12}$-$n_4$-$p_{34}$-2NAcGAL,
F1b-Rasburicase-$m_{12}$-$n_4$-$p_{34}$-2NAcGAL,
F1b-Insulin-$m_2$-$n_4$-$p_{34}$-2NAcGAL,
F1b-GAD-65-$m_8$-$n_4$-$p_{34}$-2NAcGAL,
F1b-IGRP-$m_7$-$n_4$-$p_{34}$-2NAcGAL,
F1b-MBP-$m_6$-$n_4$-$p_{34}$-2NAcGAL,
F1b-MOG-$m_5$-$n_4$-$p_{34}$-2NAcGAL,
F1b-PLP-$m_8$-$n_4$-$p_{34}$-2NAcGAL,
F1b-MBP13-32-$m_1$-$n_4$-$p_{34}$-2NAcGAL,
F1b-MBP83-99-$m_1$-$n_4$-$p_{34}$-2NAcGAL,
F1b-MBP111-129-$m_1$-$n_4$-$p_{34}$-2NAcGAL,
F1b-MBP146-170-$m_2$-$n_4$-$p_{34}$-2NAcGAL,
F1b-MOG1-20-$m_1$-$n_4$-$p_{34}$-2NAcGAL,
F1b-MOG35-55-$m_2$-$n_4$-$p_{34}$-2NAcGAL,
F1b-PLP139-154-$m_3$-$n_4$-$p_{34}$-2NAcGAL,
F1b-MART1-$m_4$-$n_4$-$p_{34}$-2NAcGAL,
F1b-Tyrosinase-$m_8$-$n_4$-$p_{34}$-2NAcGAL,
F1b-PMEL-$m_5$-$n_4$-$p_{34}$-2NAcGAL,
F1b-Aquaporin-4-$m_4$-$n_4$-$p_{34}$-2NAcGAL,
F1b-S-arrestin-$m_{12}$-$n_4$-$p_{34}$-2NAcGAL,
F1b-IRBP-$m_{21}$-$n_4$-$p_{34}$-2NAcGAL,
F1b-Conarachin-$m_{21}$-$n_4$-$p_{34}$-2NAcGAL,
F1b-Alpha-gliadin "33-mer" native-$m_1$-$n_4$-$p_{34}$-2NAcGAL, F1b-Alpha-gliadin "33-mer" deamidated-$m_1$-$n_4$-$p_{34}$-2NAcGAL,
F1b-Alpha-gliadin-$m_1$-$n_4$-$p_{34}$-2NAcGAL,
F1b-Omega-gliadin-$m_1$-$n_4$-$p_{34}$-2NAcGAL,
F1b-Fel d 1-$m_4$-$n_4$-$p_{34}$-2NAcGAL,
F1b-Cat albumin-$m_{16}$-$n_4$-$p_{34}$-2NAcGAL,
F1b-Can f 1-$m_6$-$n_4$-$p_{34}$-2NAcGAL,
F1b-Dog albumin-$m_{23}$-$n_4$-$p_{34}$-2NAcGAL, and
F1b-RhCE-$m_{10}$-$n_4$-$p_{34}$-2NAcGAL.

1D. Other Compounds of Formula 1b

Similarly, by following the procedures described in Example 2B-C and substituting the compound poly(Glucosamine Methacrylate)-(pyridyl disulfide) or poly(Galactosamine Methacrylate)-(pyridyl disulfide), there are obtained the corresponding compounds of Formula 1b where Z" is 2-NAcGLU.

Example 3

F1f-OVA-$m_1$-$n_4$-$p_{33}$-2NAcGAL

3A. Formula 1f where X' is Ovalbumin and m is 1, n is 4, p is 33, $R^9$ is a Direct Bond and Z" is 2NAcGAL In an endotoxin-free tube, OVA (4.0 mg, 0.0000952381 mmol) was added to 0.1 ml of pH 7.4 PBS and stirred. Separately, poly-(n-Acetylgalactosamine)-p-nitrophenyol carbonate of Formula 601 where n is 4 and p is 33 (33.0 mg, 0.002380952 mmol) was added to 100 µl of pH 7.5 PBS and vortexed until dissolved. The two solutions were combined and the mixture was stirred vigorously for 1 hour. The mixture was then collected and dialyzed for 3 days against pH 7.4 PBS (30 kDa molecular weight cut off) to afford the product of Formula 1f.

3B. Formula 1f where X' is Ovalbumin and m is 1, n is 4, p is 33, $R^9$ is a Direct Bond and Z" is 2NAcGLU Similarly, by following the procedure of Example 3A and substituting poly-(n-Acetylglucosamine)-p-nitrophenyol carbonate for poly-(n-Acetylgalactosamine)-p-nitrophenyol carbonate, there is obtained the corresponding compound of Formula 1f where Z" is 2NAcGLU.

Example 4

F1g-PVA-$m_1$-$p_{90}$-2NAcGAL

4A. Formula 1g where X' is Ovalbumin and m is 1, p is 90, $R^9$ is a Direct Bond and Z" is 2NAcGAL In an endotoxin-free tube, OVA (5.0 mg, 0.000119048 mmol) was added to 0.2 ml of pH 7.4 PBS and stirred. To the stirring solution was added 75 mg (0.00297619 mmol) of Poly(Galactosamine Methacrylate)-NHS (Formula 701) dissolved in 0.4 ml of pH 7.4 PBS. The mixture was allowed to stir for 2 hours. The mixture was then collected and dialyzed for 3 days against pH 7.4 PBS (30 kDa molecular weight cut off) to afford the product of Formula 1g.

4B. Formula 1g where X' is Ovalbumin and m is 1, p is 90, $R^9$ is a Direct Bond and Z" is 2NAcGLU Similarly, by following the procedure of Example 4A and substituting Poly(Glucosamine Methacrylate)-NHS for Poly(Galactosamine Methacrylate)-NHS, there is obtained the corresponding compound of Formula 1 g where Z" is 2NAcGLU.

Example 5

F1h-OVA-$m_2$-$n_{45}$-$p_{55}$-$q_4$-2NAcGAL

5A. Formula 802' where X' is Ovalbumin, m is 2 and n is 45

In an endotoxin-free tube, OVA (3.0 mg, 0.0000714286 mmol) was added to 150 µl of pH 8.0 PBS containing 5 mM EDTA and stirred. Dibenzocyclooctyne-PEG-(p-nitrophenyl carbonate) (Formula 801) (5.265 mg, 0.002142857 mmol) dissolved in DMF was added to the OVA solution and stirred for 1 hour. The excess dibenzocyclooctyne-PEG-(p-nitrophenyl carbonate) was removed using a centrifugal size exclusion column to afford the product of Formula 802'.

5B. Formula 1h where X' is Ovalbumin, m is 2, n is 45, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-acetylgalactosamine) (33 mg, 0.002142857 mmol) was dissolved in 100 µl of pH 7.4 PBS and added to the product of Example 5A with stirring. After 1 hour, the resulting product of Formula 1h was purified by centrifugal size exclusion chromatography.

5C. Formula 1 h where X' is Ovalbumin, m is 2, n is 45, p is 55, q is 4, $R^8$ is $CH_2$, $R^9$ is a Direct Bond and Z" is 2NAcGLU Similarly, by following the procedure of Example 5B and substituting Poly(Glucosamine Methacrylate)-NHS for Poly(Galactosamine Methacrylate)-NHS, there is obtained the corresponding compound of Formula 1 h where Z" is 2NAcGLU.

Example 6

F1j-OVA-$m_{10}$-$n_{45}$-$p_{55}$-$q_4$-2NAcGAL

6A. Formula 103' where X' is Ovalbumin and m is 10

In an endotoxin-free tube, OVA (5.0 mg, 0.00019 mmol) was added to 150 µl of pH 8.0 PBS containing 5 mM EDTA and stirred. Separately, 1 mg of Taut's Reagent was dissolved in 100 µl of pH 7.0 PBS, and 16 µl (0.0019 mmol) of the Traut's Reagent solution so obtained was added to the stirred solution of OVA with continued stirring. After 1 hour, non-reacted Traut's Reagent was removed using a centrifugal size exclusion column to afford the product of Formula 103'.

6B. Formula 902" where X' is Ovalbumin, m is 10 and n is 45

Dibenzocyclooctyne-PEG-(pyridyl disulfide) (Formula 901 where n is 45) (6.0 mg, 0.00238 mmol) was dissolved in DMF and the resulting solution was added to the OVA solution obtained in Example 6A and stirred for 1 hour. The excess dibenzocyclooctyne-PEG-(pyridyl disulfide) was removed using centrifugal size exclusion chromatography to afford the product of Formula 902".

6C. Formula 1j where X' is Ovalbumin, m is 10, n is 45, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-acetylgalactosamine) (36 mg, 0.00238 mmol) was dissolved in 150 µl of pH 7.4 PBS and added to the product of Example 6B with stirring. After 1 hour, the resulting product of Formula 1j was purified (excess p(GMA)-N3 removed) by centrifugal size exclusion chromatography. Characterization (UHPLC SEC, gel electrophoresis) confirmed the identity of the product.

6D. Formula 1j where X' is Ovalbumin, m is 10, n is 45, p is 55, q is 4, $R^8$ is $CH_2$, $R^9$ is a Direct Bond and Z" is 2NAcGLU Similarly, by following the procedure of Example 6C and substituting Poly(Glucosamine Methacrylate)-NHS for Poly (Galactosamine Methacrylate)-NHS, there is obtained the corresponding compound of Formula 1j where Z" is 2NAc-GLU.

Example 7

F1L-OVA-$m_2$-$n_{80}$-$p_{55}$-$q_4$-2NAcGAL

7A. Formula 1002 where X' is Ovalbumin, m is 2 and n is 80

Dibenzocyclooctyne-PEG-(pyridyl disulfide) (Formula 1001 where n is 80) (9.0 mg, 0.00238 mmol) was dissolved in DMF and the resulting solution was added to a purified OVA solution of Formula 103' (where X' is Ovalbumin and m is 2), for example prepared as described in Example 6A and stirred for 1 hour. The excess dibenzocyclooctyne-PEG-(pyridyl disulfide) was removed using centrifugal size exclusion chromatography to afford the product of Formula 1002.

7B. Formula 1L where X' is Ovalbumin, m is 2, n is 80, p is 55, q is 4, $R^8$ is $CH_2$, $R^9$ is a Direct Bond and Z" is 2NAcGAL Poly(Galactosamine Methacrylate)-N3 (Formula 803 where p is 55, q is 4 and Z" is N-Acetylgalactosamine) (36 mg, 0.00238 mmol) was dissolved in 150 µl of pH 7.4 PBS and added to the product of Example 7A with stirring. After 1 hour, the resulting product of Formula 1L was purified (excess poly(Galactosamine Methacrylate)-N3 removed) by centrifugal size exclusion chromatography. Characterization (UHPLC SEC, gel electrophoresis) confirmed the identity of the product.

7C. Formula 1L where X' is Ovalbumin, m is 2, n is 80, p is 55, q is 4, $R^8$ is $CH_2$, $R^9$ is a Direct Bond and Z" is 2NAcGLU Similarly, by following the procedure of Example 7B and substituting Poly(Glucosamine Methacrylate)-NHS for Poly (Galactosamine Methacrylate)-NHS, there is obtained the corresponding compound of Formula 1jLwhere Z" is 2NAc-GLU.

Example 8

Preparation of Poly(Galactosamine Methacrylate) Polymers

8A. Galactosamine Methacrylate

To stirred galactosamine hydrochloride (2.15 g, 10.0 mmol) was added 0.5 M sodium methoxide (22 ml, 11.0 mmol). After 30 minutes, methacrylate anhydride (14.694 g, 11.0 mmol) was added and stirring continued for 4 hours. The resulting galactosamine methacrylate was loaded onto silica gel via rotovap and purified via column chromatography using DCM:MeOH (85:15).

8B. Formula 201 where n is 4 and p is 30

Galactose methacrylate (600 mg, 2.43 mmol), 2-(2-(2-(2-(pyridin-2-yldisulfanyl)ethoxy)ethoxy)ethoxy)ethyl 2-((phenylcarbonothioyl)thio)acetate (44.8 mg, 0.081 mmol) and AIBN (3.174089069 mg, 0.016 mmol) were added to 1.5 ml of DMF in a Schlenk Flask. The reaction mixture was subjected to 4 freeze-thaw cycles and then stirred at 70° C. for 6 hours. The desired polymer product of Formula 201 was precipitated in 12 ml of methanol, and excess solvent was removed under reduced pressure.

8C. Formula 201 where n is 4 and p is 30

Similarly, by following the procedure of Example 8B and substituting Glucose methacrylate for galactose methacrylate there are obtained the corresponding poly(Glucosamine methacrylate) polymers.

Example 9

Preparation of F1aA-PE-$m_3$-$n_{80}$

9A. Formula 103' where X' is Phycoerythrin

In an endotoxin-free tube, phycoerythrin ("PE") (purchased from Pierce) (200 µl, 0.000004 mmol) was added to 50 µl of pH 8.0 PBS containing 5 mM EDTA and stirred. Separately, 1 mg of Taut's Reagent was dissolved in 100 µl of pH 7.0 PBS, and 2 µl (0.00013 mmol) of the Traut's Reagent solution so obtained was added to the stirred solution of PE with continued stirring. After 1 hour, excess Traut's Reagent was removed using a centrifugal size exclusion column to afford the product of Formula 103'.

9B. Formula 106A where n is 80

In an endotoxin-free tube, galactosamine (7.0 mg, 0.03246 mmol) was dissolved with stirring in 100 µl of pH 8.0 PBS containing 5 mM EDTA. Pyridyl dithiol-poly (ethylene glycol)-NHS ester (Formula 104 where n is 80) (16.23 mg, 0.00464 mmol) dissolved in 50 µl of pH 7.0 PBS was added to the stirring solution of galactosamine. After 1 hour, the resulting product of Formula 106A was ready to be used without further purification.

9C. Formula 1a where X' is Phycoerythrin, m is 3, n is 80 and Z' is Galactosamine The purified PE-Traut conjugates prepared in Example 9A were added directly to the stirring product of Formula 106A prepared in Example 9B. After 1 hour, the resulting product of Formula 1a was purified by passing the reaction mixture through a centrifugal size exclusion column. Characterization (UHPLC SEC, gel electrophoresis) confirmed the identity of the product.

9D. Formula 1a where X' is Phycoerythrin, m is 3, n is 80 and Z' is Glucosamine

Similarly, by following the procedure of Example 9B and C and substituting glucosamine for galactosamine there is obtained the corresponding compound of Formula 1a where Z" is glucosamine.

Example 10

Hepatic Distribution

10A.

F1aA-PE-$m_3$-$n_{80}$ was prepared, for example, as described in Example 9. A 30 µg/100 µl solution in sterile saline was prepared for injection.

The F1aA-PE-$m_3$-$n_{80}$ solution (30 μg) was administered to one of three groups of C57 black 6 mice 3 per group) via tail vein injection. The two other groups of mice received an equivalent volume of phycoerythrin in 100 μl of saline or saline vehicle. Three hours after administration, the livers and spleens of these animals were harvested and the level of cellular fluorescents in these organs was determined by flow cytometry as an indication of cellular PE content.

As shown in FIGS. 1A-1D, sinusoidal endothelial cells (LSECs) (1A), hepatocytes (1C), Kupffer cells (KC) (1B), and other antigen-presenting cells (APCs) (1D) from the livers of mice treated with F1aA-PE-$m_3$-$n_{80}$ exhibited at least a three-fold increase in fluorescence as compared with animals that received PE solution. No detectible difference in fluorescence was found in spleen cells harvested from the three groups. These results confirm that F1aA-PE-$m_3$-$n_{80}$ has sufficient specificity for binding to antigen-presenting cells in the liver.

10B.

By following the procedure described in Example 10A and substituting F1aA-PE-$m_3$-$n_{80}$ with the compounds F1b-PE-$m_3$-$n_4$-$p_{34}$-2NAcGAL, F1f-PE-$m_3$-$n_4$-$p_{33}$-2NAcGAL, F1g-PE-$m_3$-$p_{90}$-2NAcGAL, F1h-PE-$m_3$-$n_{45}$-$p_{55}$-$q_4$-2NAcGAL, F1j-PE-$m_3$-$n_{45}$-$p_{55}$-$q_4$-2NAcGAL, F1L-PE-$m_3$-$n_{80}$-$p_{55}$-$q_4$-2NAcGAL, F1m-PE-$m_3$-$n_{80}$-$p_{30}$-$q_4$-CMP-2NHAc, F1m-PE-$m_3$-$n_{62}$-$p_{30}$-$q_8$-CMP-2OH, F1n-PE-$m_3$-$n_1$-$p_{30}$-$q_4$-CMP-2NHAc and F1n-PE-$m_3$-$n_{33}$-$p_{30}$-$q_8$-CMP-2OH, prepared, for example, as described with reference to Example 9 by substitution for X in Examples 2B, 3, 4, 5B, 6B, 7B, 15G, 15L, 16B and 16F, respectively it is confirmed that the compounds F1aA-PE-$m_3$-$n_{80}$ with the compounds F1b-PE-$m_3$-$n_4$-$p_{34}$-2NAcGAL, F1f-PE-$m_3$-$n_4$-$p_{33}$-2NAcGAL, F1g-PE-$m_3$-$p_{90}$-2NAcGAL, F1h-PE-$m_3$-$n_{45}$-$p_{55}$-$q_4$-2NAcGAL, F1j-PE-$m_3$-$n_{45}$-$p_{55}$-$q_4$-2NAcGAL, F1L-PE-$m_3$-$n_{80}$-$p_{55}$-$q_4$-2NAcGAL, F1m-PE-$m_3$-$n_{80}$-$p_{30}$-$q_4$-CMP-2NHAc, F1m-PE-$m_3$-$n_{62}$-$p_{30}$-$q_8$-CMP-2OH, F1n-PE-$m_3$-$n_1$-$p_{30}$-$q_4$-CMP-2NHAc and F1n-PE-$m_3$-$n_{33}$-$p_{30}$-$q_8$-CMP-2OH have sufficient specificity for binding to antigen-presenting cells in the liver.

10C.

By following the procedure described in Example 10A and 10B and substituting the corresponding glucosylated compounds for the galactosylated compounds, it is confirmed that the glucolsylated compounds have sufficient specificity for binding to antigen-presenting cells in the liver.

Example 11

Proliferation of Antigen-Specific OT1 CD8+ T Cells

11A.

F1aA-OVA-$m_4$-$n_{80}$ synthesized, for example, as described in Example 1, was prepared as a 10 µg/100 µl saline solution for injection. On day 0, 106 OT-I T cells were fluorescently labeled and adoptively transferred into 3 groups of CD 45.2 mice (5 per group) via tail vein injection. The next day (i.e. Day 1), to each of the 3 groups of mice were administered, respectively, 10 µg of F1aA-OVA-m4-n80, OVA or saline via tail vein injection. On day 6, the animals were sacrificed and the % of splenic proliferating OT-I cells was determined via florescence activated cell sorting.

Figures 1A, 1B, 1C, 1D:
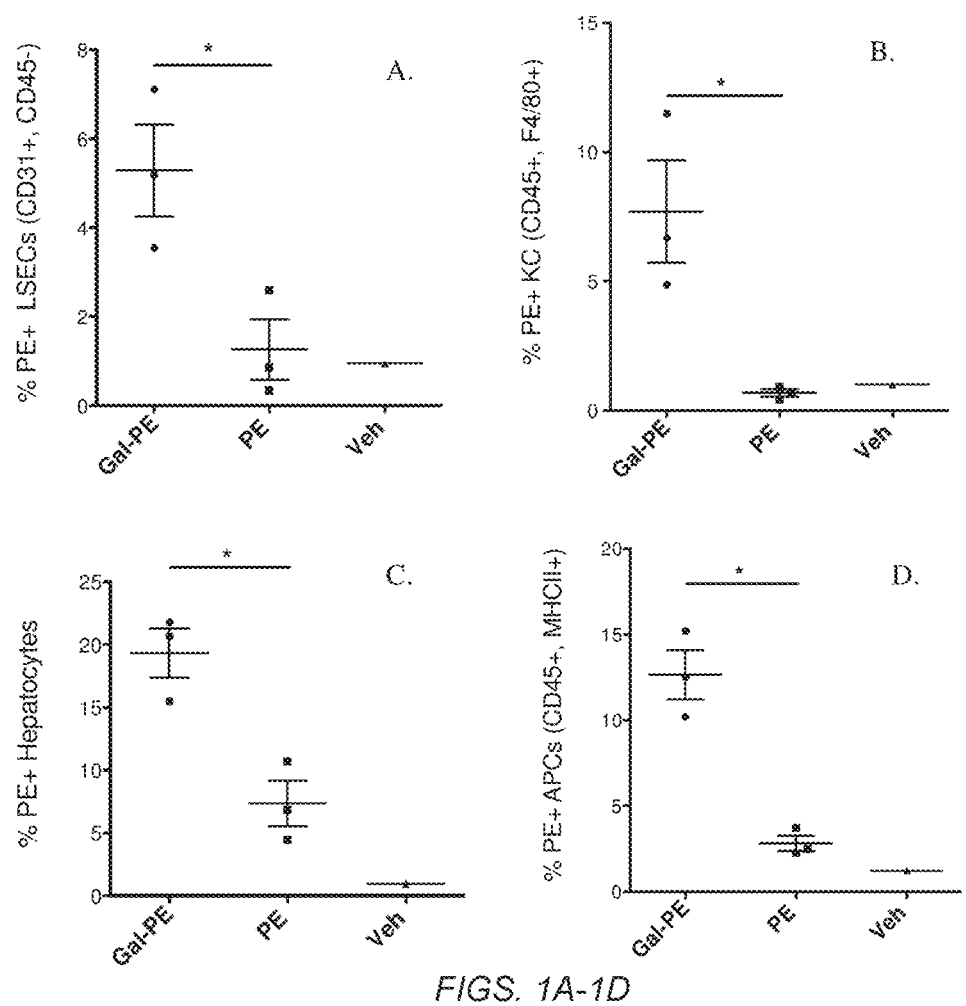
FIGS. 1A-1D are a series of graphs showing differential cellular uptake of galactose conjugates.
Figure 2:
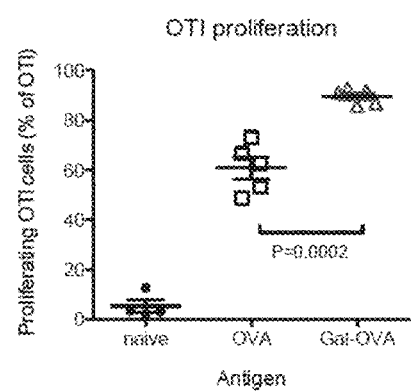
FIG. 2 is a graph showing proliferation of OT-I CD8+ T cells in mice treated with F1aA-OVA-$m_4$-$n_{80}$ (Gal-OVA), OVA or saline (i.e. naïve), with greatest proliferation seen in the Gal-OVA treated group.

The results from this study (see FIG. 2) show that the percentage of proliferating OTI T cells in mice treated with F1aA-OVA-$m_4$-$n_{80}$ ("Gal-OVA" in FIG. 2) was significantly greater than the percentage of proliferating OTI cells in the spleens of mice treated with OVA or saline ("naïve" in FIG. 2). The increase in OTI cell-proliferation demonstrates the increased CD8+ T-cell cross-priming in animals treated with F1aA-OVA-$m_4$-$n_{80}$ versus the other therapies. In concert with the results from Example 12, these results indicate that the ability of F1aA-OVA-$m_4$-$n_{80}$ to target antigens to the liver increases OVA presentation by antigen presenting cells in the liver to OVA-specific OTI T cells.

11B.

Figures 3A, 3B:
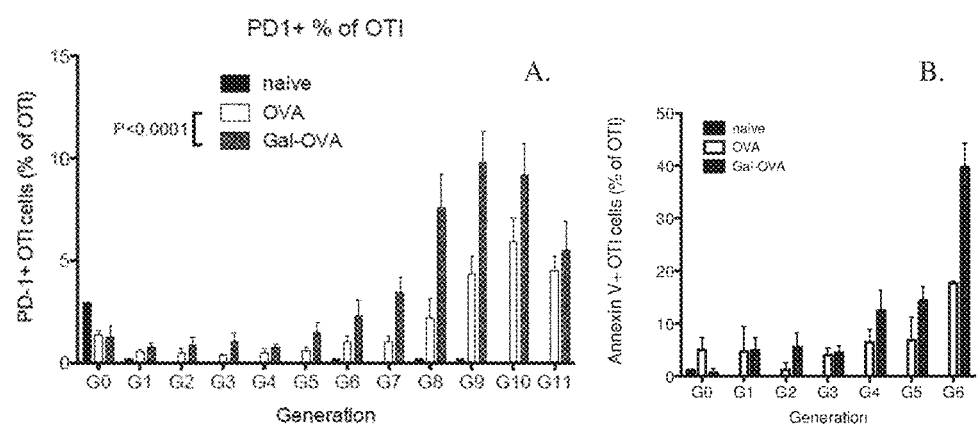
FIGS. 3A-3B are a series of graphs depicting data related to marker expression on T cells.

To distinguish T cells being expanded into a functional effector phenotype from those being expanded and deleted, the proliferating OTI CD8$^+$ T cells were analyzed for phosphatidylserine exposure by way of Annexin-V binding, as a hallmark of apoptosis and thus deletion, as well as the exhaustion marker programmed death-1 (PD-1). As shown in FIGS. 3A-3B, F1aA-OVA-$m_4$-$n_{80}$ ("Gal-OVA" in FIGS. 3A-3B) induced much higher numbers of Annexin-V$^+$ and PD-1$^+$ proliferating OTI CD8$^+$ T cells than soluble OVA. These data demonstrate that, in accordance with several embodiments disclosed herein, coupling an antigen to which tolerance is to be induced with linkers and liver targeting moieties as disclosed herein result in unexpectedly enhanced generation of T cells having the capacity to be immunologically functional.

11C.

By following the procedure described in Examples 11A and 11B, and substituting F1aA-OVA-$m_4$-$n_8$ with the compounds of Formula 1 obtained, for example, as described in Examples 3A, 4A, 5B, 6C, 7B and 19G, it is shown the compounds from Examples 3A, 4A, 5B, 6C, 7B and 19G induce much higher numbers of Annexin-V$^+$ and PD-1$^+$ proliferating OTI CD8$^+$ T cells than soluble OVA.

11D.

By following the procedure described in Examples 11A and 11B and substituting F1aA-OVA-$m_4$-$n_8$ with the compounds of Formulae 1 and 2 obtained, for example, as described in Examples 1E, 1G, 2C, 15I, 15L, 16B, 16D and 16F, and substituting OVA with the antigens corresponding to X (or X' or X"), respectively, it is shown that the compounds from Examples 1E, 1G, 2C, 15I, 15L, 16B, 16D and 16F induce much higher numbers of Annexin-V$^+$ and PD-1$^+$ proliferating OTI CD8$^+$ T cells than soluble antigen X.

11E.

By following the procedure described in Example 11A-D and substituting the corresponding glucosylated compounds for the galactosylated compounds, it is confirmed that the glucolsylated compounds induce much higher numbers of Annexin-V$^+$ and PD-1$^+$ proliferating OTI CD8$^+$ T cells than soluble antigen X.

Example 12

F1aA-OVA-$m_4$-$n_8$ does not Induce an OVA-Specific Antibody Response

12A.

Figure 4:
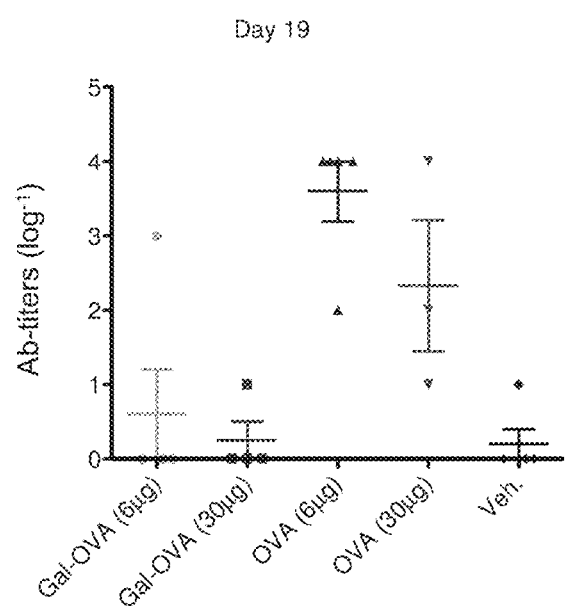
FIG. 4 is a graph showing that galactose conjugation [F1aA-OVA-$m_4$-$n_{80}$ (Gal-OVA)] decreases the immunogenicity of OVA as determined by OVA-specific antibody titers (shown in Ab titers log$^{-1}$).

In order to assess the humoral immune response to F1aA-OVA-$m_4$-$n_8$ we treated mice with a weekly i.v. injection of either F1aA-OVA-$m_4$-$n_8$ or OVA, then measured the levels of OVA-specific antibodies in the blood. On day 0, 7, and 14 of the experiment, mice were administered an i.v. injection of 100 µl of saline containing one of the following: 1.) 6 µg of OVA; 2.) 6 µg of F1aA-OVA-$m_4$-$n_8$; 3.) 30 µg of OVA; 4.) 30 µg of F1aA-OVA-$m_4$-$n_8$, or 5.) saline alone. Each group contained 5 mice. On day 19, the mice were bled via cheek puncture, and the titer of OVA-specific antibodies in each mouse's blood was determined via ELISA. The results for this study show that although mice treated with 6 and 30 µg of OVA had increased OVA-specific antibody titers, mice treated with both 6 and 30 µg of F1aA-OVA-$m_4$-$n_8$ ("Gal-OVA" in FIG. 4) had blood titers similar to mice treated with saline (i.e. vehicle treated animals) (FIG. 4). For example mice treated with 6 and 30 µg of OVA had an average antibody titer of 3.5 and 2.5, respectively; whereas, mice treated with 6 and 30 µg of OVA had an average antibody titer of 0.75 and 0.25, respectively. Thus, these data demonstrate that coupling an antigen to which immune tolerance is desired to a linker and liver targeting moiety according to several embodiments disclosed herein results in significantly less antigen specific antibody generation. As such, these data demonstrate that the immune response to the antigen delivered to the liver by the compositions disclosed herein is reduced.

12B.

By following the procedure described in Example 12A and substituting F1aA-OVA-$m_4$-$n_8$ with the compounds of Formula 1 obtained, for example, as described in Examples 3A, 4A, 5B, 6C, 7B and 15G, it is shown that mice treated with the compounds from Examples 3A, 4A, 5B, 6C, 7B and 15G have OVA-specific antibody titers similar to mice treated with saline.

12C.

By following the procedure described in Example 12B and substituting F1aA-OVA-$m_4$-$n_8$ with the compounds of Formula 1 obtained, for example, as described in Examples 1E, 1G, 2C, 15I, 15L, 16B, 16D and 16F, and substituting OVA with the antigens corresponding to X (or X' or X"), respectively, it is shown that mice treated with the compounds from Examples 1E, 1G, 2C, 15I, 15L, 16B, 16D and 16F have antigen X-specific antibody titers similar to mice treated with saline.

12D.

By following the procedure described in Example 12A-C and substituting the corresponding glucosylated compounds for the galactosylated compounds, it is confirmed that the glucolsylated compounds have antigen X-specific antibody titers similar to mice treated with saline.

Example 13

F1aA-OVA-$m_4$-$n_8$ Depletes OVA-Specific Antibodies

13A.

Mice that had different OVA-antibody blood titers (each mouse had a titer from 0 to 4.5) were treated with an i.v. injection of 20 µg of F1aA-OVA-$m_4$-$n_8$ solubilized in 100 μl saline. Mice were given i.v. injections of F1aA-OVA-$m_4$-$n_8$ on days 0, 5, 7, 12, and 14 (Injections of F1aA-OVA-$m_4$-$n_8$ are labeled as "Gal-OVA" and shown as green arrows on the x-axis of FIG. 5). In order to determine the ability of F1aA-OVA-$m_4$-$n_8$ to deplete serum OVA-specific antibodies, the mice were bled on day −1 to establish an initial antibody titer and then subsequent bleeds were carried out after each injection of F1aA-OVA-$m_4$-$n_8$ on days 2, 6, 9. 13, and 16. The antibody titer for each mouse was determined via ELISA. The results from this study show that F1aA-OVA-$m_4$-$n_8$ is able to deplete serum antibody levels in mice. For example, one day after the first F1aA-OVA-$m_4$-$n_8$ injection (i.e. day 2), mice with positive OVA-antibody titers experience a 5 to 100-fold decrease in serum antibody levels (FIG. 5). These results show that although over the course of the 19 day experiment, antibody titers did increase for certain mice, the titer levels never reached the initial antibody titer measured on Day −1 and subsequent doses of F1aA-OVA-$m_4$-$n_8$ were effective in reducing these transient increases in antibody titers. These results demonstrate that F1aA-OVA-$m_4$-$n_8$ has the specificity to bind serum OVA-specific antibodies and the kinetics required to deplete OVA-specific serum antibodies.

13B.

By following the procedure described in Example 13A and substituting F1aA-OVA-$m_4$-$n_8$ with the compounds of Formula 1 obtained, for example, as described in Examples 3A, 4A, 5B, 6C, 7B and 15G, it is shown that the compounds from Examples 3A, 4A, 5B, 6C, 7B and 15G have the specificity to bind serum OVA-specific antibodies and the kinetics required to deplete OVA-specific serum antibodies.

13C.

By following the procedure described in Example 13A and substituting F1aA-OVA-$m_4$-$n_8$ with the compounds of Formula 1 obtained, for example, as described in Examples 1E, 1G, 2C, 10D, 15I, 15L, 16B, 16D and 16F, and substituting OVA with the antigens corresponding to X (or X' or X"), respectively, it is shown that the compounds from Examples 1E, 1G, 2C, 15I, 15L, 16B, 16D and 16F have the specificity to bind serum antigen X-specific antibodies and the kinetics required to deplete antigen X-specific serum antibodies.

13D.

By following the procedure described in Example 13A-C and substituting the corresponding glucosylated compounds for the galactosylated compounds, it is confirmed that the glucolsylated compounds have the specificity to bind serum antigen X-specific antibodies and the kinetics required to deplete antigen X-specific serum antibodies.

Example 14

OT-1 Challenge-to-Tolerance Model

14A.

Using an established OTI challenge-to-tolerance model (Liu, Iyoda, et al., 2002), the ability of F1aA-OVA-$m_4$-$n_8$ (mGal-OVA) and F1b-OVA-$m_1$-$n_4$-$p_{34}$ (pGal-OVA) to prevent subsequent immune responses to vaccine-mediated antigen challenge were demonstrated—even with a challenge involving a very strong bacterially-derived adjuvant (i.e. lipopolysaccharide). To tolerize, 233 nmol of either F1aA-OVA-$m_4$-$n_8$, F1b-OVA-$m_1$-$n_4$-$p_{34}$, or soluble OVA were intravenously administered in 100 μl saline at 1 and 6 days following adoptive transfer of OTI $CD8^+$ ($CD45.2^+$) T cells to $CD45.1^+$ mice (n=5 mice per group). After 9 additional days to allow potential deletion of the transferred T cells, the recipient mice were then challenged with OVA (10 μg) adjuvanted with lipopolysaccharide (LPS) (50 ng) by intradermal injection. Characterization of the draining lymph nodes 4 d after challenge allowed a determination as to whether or not deletion actually took place.

14B.

Intravenous administration of F1aA-OVA-$m_4$-$n_8$ and F1b-OVA-$m_1$-$n_4$-$p_{34}$ resulted in profound reductions in OTI $CD8^+$ T cell populations in the draining lymph nodes as compared to mice treated with unmodified OVA prior to antigen challenge with LPS, demonstrating deletional tolerance. For example, FIGS. 6A-6F show that the draining lymph nodes from mice treated with either F1aA-OVA-$m_4$-$n_8$ (mGal-OVA) and F1b-OVA-$m_1$-$n_4$-$p_{34}$ (pGal-OVA) contained over 9-fold fewer OTI $CD8^+$ T cells as compared to OVA-treated mice, and more than 43-fold fewer than the challenge control mice that did not receive intravenous injections of antigen; responses in spleen cells were similar. These results demonstrate that F1aA-OVA-$m_4$-$n_8$ and F1b-OVA-$m_1$-$n_4$-$p_{34}$ mitigated an OVA-specific immune response after adjuvented OVA challenge, thus establishing that the compositions disclosed herein are suitable for induction of immune tolerance. As to characterization, FIG. 7 shows characterization of F1aA-OVA-$m_4$-$n_{80}$ and F1b-OVA-$m_1$-$n_{44}$-$p_{34}$.

14C.

By following the procedure described in Examples 14A and B, and substituting F1aA-OVA-$m_4$-$n_8$ and F1b-OVA-$m_1$-$n_4$-$p_{34}$ with the compounds of Formula 1 obtained, for example, as described in Examples 3A, 4A, 5B, 6C, 7B and 15G, it is shown that the compounds from Examples 3A, 4A, 5B, 6C, 7B and 15G mitigate an OVA-specific immune response after adjuvented OVA challenge.

14D.

By following the procedure described in Examples 14A and B, and substituting F1aA-OVA-$m_4$-$n_8$ and F1b-OVA-$m_1$-$n_4$-$p_{34}$ with the compounds of Formula 1 obtained, for example, as described in Examples 1E, 1G, 2C, 15I, 15L, 16B, 16D and 16F, and substituting OVA with the antigens corresponding to X (or X' or X"), respectively, it is shown that the compounds from Examples 1E, 1G, 2C, 15I, 15L, 16B, 16D and 16F mitigate an antigen X-specific immune response after adjuvented antigen X challenge.

14E.

By following the procedure described in Example 14A-D and substituting the corresponding glucosylated compounds for the galactosylated compounds, it is confirmed that the glucolsylated compounds mitigate an antigen X-specific immune response after adjuvanted antigen X challenge.

Example 15

F1m-OVA-$m_2$-$n_{80}$-$p_{30}$-$q_4$-CMP-2NHAc

15A. Formula 1102 where $R^3$ is NHAc and $R^4$ is OH

N-Acetyl-D-galactosamine (Formula 1101 where $R^3$ is NHAc and $R^4$ is OH) (5g, 22.6 mmol) was added to a stirred solution of chloroethanol (200 ml) at room temperature. The solution was cooled to 4° C. and acetylchloride was added drop-wise to the solution. The solution was brought to room temperature and then heated to 70° C. After 4 hours, the unreacted choroethanol was removed under reduced pressure. 100 ml of ethanol was added to the crude product and the resulting solution was stirred in the presence of carbon for 2 hours. The solution was filtered, and the solvent was removed under reduced pressure. The corresponding product of Formula 1102, N-(2-(2-chloroethoxy)-4,5-dihydroxy-6-(hydroxymethyl)tetrahydro-2H-pyran-3-yl)acetamide, was used without further purification.

15B. Formula 1103 where $R^3$ is NHAc and $R^4$ is OH

The N-(2-(2-chloroethoxy)-4,5-dihydroxy-6-(hydroxymethyl)tetrahydro-2H-pyran-3-yl)acetamide prepared in Example 15A (2g, 7.4 mmol) was added to a stirred solution of DMF (100 ml) and sodium azide (4g, 61.5 mmol). The solution was headed at 90° C. for 12 hours and then filtered. The residual solvent was removed under reduced pressure and the crude product was purified via flash chromatography (10% MeOH in dichloromethane) to give the corresponding product of Formula 1103, N-(2-(2-azidoethoxy)-4,5-dihydroxy-6-(hydroxymethyl)tetrahydro-2H-pyran-3-yl)acetamide.

15C. Formula 1104 where $R^3$ is NHAc and $R^4$ is OH

The N-(2-(2-azidoethoxy)-4,5-dihydroxy-6-(hydroxymethyl)tetrahydro-2H-pyran-3-yl)acetamide prepared in Example 15B (2 g, 6.9 mmol) was added to a solution of palladium on carbon and ethanol (50 ml). The solution was stirred under hydrogen gas (3 atm) for 4 hours. The resulting solution was filtered and the residual solvent was removed under reduced pressure to afford the corresponding product of Formula 1104, N-(2-(2-aminoethoxy)-4,5-dihydroxy-6-(hydroxymethyl)tetrahydro-2H-pyran-3-yl)acetamide, which was used without further purification.

15D. Formula 1105 where $R^3$ is NHAc and $R^4$ is OH

The N-(2-(2-aminoethoxy)-4,5-dihydroxy-6-(hydroxymethyl)tetrahydro-2H-pyran-3-yl)acetamide prepared in Example 15C (1.0 g, 3.78 mmol) was added to a solution of methacrylate anhydride (0.583 g, 3.78 mmol) in DMF (50 ml). Triethylamine was then added to the solution and the reaction was stirred for 2 hours at room temperature. After 2 hours, the excess solvent was removed under reduced pressure, and the corresponding product of Formula 1105, N-(2-((3-acetamido-4,5-dihydroxy-6-(hydroxymethyl)tetrahydro-2H-pyran-2-yl)oxy)ethyl)methacrylamide, was isolated via flash chromatography.

15E. Formula 1107 where p is 30, q is 4, $R^3$ is NHAc, $R^4$ is OH and $R^8$ is CMP An azide-modified uRAFT agent of Formula 1106 where q is 4 (28 mg) was added to a solution of N-(2-((3-acetamido-4,5-dihydroxy-6-(hydroxymethyl)tetrahydro-2H-pyran-2-yl)oxy)ethyl)methacrylamide prepared in Example 15D (579 mg, 1.74 mmol) and azobisisobutyronitrile (2.2 mg, 0.0116 mmol) in DMF. The reaction mixture was subjected to 4 free-pump-thaw cycles, and then stirred at 70° C. After 12 hours, the polymer product of Formula 1107, where p is 30 and q is 4 was precipitated from the reaction mixture via the addition of methanol. The solvent was decanted from the solid and the solid was collected and residual solvent was removed via reduced pressure.

15F. Formula 1109 where X' is OVA, m is 2 and n is 80

Ovalbumin (5 mg, 0.00012 mmol) was added to 100 μl of sodium phosphate buffer (pH 8.0) and stirred. To this solution was added 5 mg of the compound of Formula 1108 where n is 80. After 1 hour, the unreacted compound of Formula 1108 was removed from the solution via centrifugal size-exclusion chromatography. The resulting buffered solution containing the corresponding product of Formula 1109 was used in the next reaction without further purification.

15G. Formula 1m where X' is OVA, m is 2, n is 80, p is 30, q is 4, $R^3$ is NHAc and $R^8$ is CMP The solution prepared in Example 15F was added to 100 μl of sodium phosphate buffer (pH 8.0) which contained 10 mg of the product of Formula 1107 prepared in Example 15E. The reaction was allowed to stir for 2 hours and then the excess Formula 1107 was removed via centrifugal size exclusion chromatography to afford the corresponding isomeric product of Formula 1m in solution, which was used in biological studies without further purification. The $R^3$ substituent is shown in the name of the title compound as 2NHAc.

15H. Other Compounds of Formula 1109

By following the procedure described in Example 15F and substituting OVA with the following:

Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
Insulin (SEQ ID NO:1),
GAD-65 (SEQ ID NO:2),
IGRP (SEQ ID NO:3)
MBP (SEQ ID NO:4),
MOG (SEQ ID NO:5),
PLP (SEQ ID NO:6),
MBP13-32 (SEQ ID NO:7),
MBP83-99 (SEQ ID NO:8),
MBP111-129 (SEQ ID NO:9),
MBP146-170 (SEQ ID NO:10), MOG1-20 (SEQ ID NO:11),
MOG35-55 (SEQ ID NO:12),
PLP139-154 (SEQ ID NO:13),
MART1 (SEQ ID NO:14),
Tyrosinase (SEQ ID NO:15),
PMEL (SEQ ID NO:16),
Aquaporin-4 (SEQ ID NO:17),
S-arrestin (SEQ ID NO:18),
IRBP (SEQ ID NO:19),
Conarachin (UNIPROT Q6PSU6),
Alpha-gliadin "33-mer" native (SEQ ID NO:20),
Alpha-gliadin "33-mer" deamidated (SEQ ID NO:21),
Alpha-gliadin (SEQ ID NO:22),
Omega-gliadin (SEQ ID NO:23),
Fel d 1A (UNIPROT P30438),
Cat albumin (UNIPROT P49064),
Can f 1 (UNIPROT O18873),
Dog albumin (UNIPROT P49822), and
RhCE (UNIPROT P18577),
there are obtained the following corresponding compounds of Formula 1109 where n is 80:
  X is Abciximab and m is 10,
  X is Adalimumab and m is 11,
  X is Agalsidase alfa and m is 14,
  X is Agalsidase beta and m is 14,
  X is Aldeslukin and m is 6,
  X is Alglucosidase alfa and m is 13,
  X is Factor VIII and m is 100,
  X is Factor IX and m is 18,
  X is L-asparaginase and m is 5,
  X is Laronidase and m is 7,
  X is Octreotide and m is 1,
  X is Phenylalanine ammonia-lyase and m is 12,
  X is Rasburicase and m is 12,
  X is Insulin (SEQ ID NO:1) and m is 2,
  X is GAD-65 (SEQ ID NO:2) and m is 8,
  X is IGRP (SEQ ID NO:3) and m is 7,
  X is MBP (SEQ ID NO:4) and m is 6,
  X is MOG (SEQ ID NO:5) and m is 5,
  X is PLP (SEQ ID NO:6) and m is 8,
  X is MBP13-32 (SEQ ID NO:7) and m is 1,
  X is MBP83-99 (SEQ ID NO:8) and m is 1,
  X is MBP111-129 (SEQ ID NO:9) and m is 1,
  X is MBP146-170 (SEQ ID NO:10) and m is 2,
  X is MOG1-20 (SEQ ID NO:11) and m is 1,
  X is MOG35-55 (SEQ ID NO:12) and m is 2,
  X is PLP139-154 (SEQ ID NO:13) and m is 3,
  X is MART1 (SEQ ID NO:14) and m is 4,
  X is Tyrosinase (SEQ ID NO:15) and m is 8,
  X is PMEL (SEQ ID NO:16) and m is 5,
  X is Aquaporin-4 (SEQ ID NO:17) and m is 4,
  X is S-arrestin (SEQ ID NO:18) and m is 12,
  X is IRBP (SEQ ID NO:19) and m is 21,
  X is Conarachin and m is 21,
  X is Alpha-gliadin "33-mer" native (SEQ ID NO:20) and m is 1,
  X is Alpha-gliadin "33-mer" deamidated (SEQ ID NO:21) and m is 1,
  X is Alpha-gliadin (SEQ ID NO:22) and m is 1,
  X is Omega-gliadin (SEQ ID NO:23) and m is 1,
  X is Fel d 1 and m is 4,
  X is Cat albumin and m is 16,
  X is Can f 1 and m is 6,
  X is Dog albumin and m is 23, and
  X is RhCE and m is 10.

15I. Other Compounds of Formula 1m

By following the procedure described in Example 15G and substituting the compounds of Formula 1109, for example as obtained in Example 15H, there are obtained the following corresponding compounds of Formula 1m:
  F1m-Abciximab-$m_{10}$-$n_{80}$-$p_{30}$-$q_4$-CMP-2NHAc,
  F1m-Adalimumab-$m_{11}$-$n_{80}$-$p_{30}$-$q_4$-CMP-2NHAc,
  F1m-Agalsidase alfa-$m_{14}$-$n_{80}$-$p_{30}$-$q_4$-CMP-2NHAc,
  F1m-Agalsidase beta-$m_{14}$-$n_{80}$-$p_{30}$-$q_4$-CMP-2NHAc,
  F1m-Aldeslukin-$m_6$-$n_{80}$-$p_{30}$-$q_4$-CMP-2NHAc,
  F1m-Alglucosidase alfa-$m_{13}$-$n_{80}$-$p_{30}$-$q_4$-CMP-2NHAc,
  F1m-Factor VIII-$m_{100}$-$n_{80}$-$p_{30}$-$q_4$-CMP-2NHAc,
  F1m-Factor IX-$m_{18}$-$n_{80}$-$p_{30}$-$q_4$-CMP-2NHAc,
  F1m-L-asparaginase-$m_5$-$n_{80}$-$p_{30}$-$q_4$-CMP-2NHAc,
  F1m-Laronidase-$m_7$-$n_{80}$-$p_{30}$-$q_4$-CMP-2NHAc,
  F1m-Octreotide-$m_1$-$n_{80}$-$p_{30}$-$q_4$-CMP-2NHAc,
  F1m-Phenylalanine ammonia-lyase-$m_{12}$-$n_{80}$-$p_{30}$-$q_4$-CMP-2NHAc,
  F1m-Rasburicase-$m_{12}$-$n_{80}$-$p_{30}$-$q_4$-CMP-2NHAc,
  F1m-Insulin-$m_2$-$n_{80}$-$p_{30}$-$q_4$-CMP-2NHAc,
  F1m-GAD-65-$m_8$-$n_{80}$-$p_{30}$-$q_4$-CMP-2NHAc,
  F1m-IGRP-$m_7$-$n_{80}$-$p_{30}$-$q_4$-CMP-2NHAc,
  F1m-MBP-$m_6$-$n_{80}$-$p_{30}$-$q_4$-CMP-2NHAc,
  F1m-MOG-$m_5$-$n_{80}$-$p_{30}$-$q_4$-CMP-2NHAc,
  F1m-PLP-$m_8$-$n_{80}$-$p_{30}$-$q_4$-CMP-2NHAc,
  F1m-MBP13-32-$m_1$-$n_{80}$-$p_{30}$-$q_4$-CMP-2NHAc,
  F1m-MBP83-99-$m_1$-$n_{80}$-$p_{30}$-$q_4$-CMP-2NHAc,
  F1m-MBP111-129-$m_1$-$n_{80}$-$p_{30}$-$q_4$-CMP-2NHAc,
  F1m-MBP146-170-$m_2$-$n_{80}$-$p_{30}$-$q_4$-CMP-2NHAc,
  F1m-MOG1-20-$m_1$-$n_{80}$-$p_{30}$-$q_4$-CMP-2NHAc,
  F1m-MOG35-55-$m_2$-$n_{80}$-$p_{30}$-$q_4$-CMP-2NHAc,
  F1m-PLP139-154-$m_3$-$n_{80}$-$p_{30}$-$q_4$-CMP-2NHAc,
  F1m-MART1-$m_4$-$n_{80}$-$p_{30}$-$q_4$-CMP-2NHAc,
  F1m-Tyrosinase-$m_8$-$n_{80}$-$p_{30}$-$q_4$-CMP-2NHAc,
  F1m-PMEL-$m_5$-$n_{80}$-$p_{30}$-$q_4$-CMP-2NHAc,
  F1m-Aquaporin-4-$m_4$-$n_{80}$-$p_{30}$-$q_4$-CMP-2NHAc,
  F1m-S-arrestin-$m_{12}$-$n_{80}$-$p_{30}$-$q_4$-CMP-2NHAc,
  F1m-IRBP-$m_{21}$-$n_{80}$-$p_{30}$-$q_4$-CMP-2NHAc,
  F1m-Conarachin-$m_{21}$-$n_{80}$-$p_{30}$-$q_4$-CMP-2NHAc,
  F1m-Alpha-gliadin "33-mer" native-$m_1$-$n_{80}$-$p_{30}$-$q_4$-CMP-2NHAc,
  F1m-Alpha-gliadin "33-mer" deamidated-$m_1$-$n_{80}$-$p_{30}$-$q_4$-CMP-2NHAc,
  F1m-Alpha-gliadin-$m_1$-$n_{80}$-$p_{30}$-$q_4$-CMP-2NHAc,
  F1m-Omega-gliadin-$m_1$-$n_{80}$-$p_{30}$-$q_4$-CMP-2NHAc,
  F1m-Fel d 1-$m_4$-$n_{80}$-$p_{30}$-$q_4$-CMP-2NHAc,
  F1m-Cat albumin-$m_{18}$-$n_{80}$-$p_{30}$-$q_4$-CMP-2NHAc,
  F1m-Can f 1-$m_6$-$n_{80}$-$p_{30}$-$q_4$-CMP-2NHAc,
  F1m-Dog albumin-$m_{23}$-$n_{80}$-$p_{30}$-$q_4$-CMP-2NHAc, and
  F1m-RhCE-$m_{10}$-$n_{80}$-$p_{30}$-$q_4$-CMP-2NHAc.

15J. Formula 1107 where p is 30, q is 8, $R^3$ is OH, $R^4$ is OH and $R^8$ is CMP By following the procedure described in Example 15A and substituting the N-acetyl-D-galactosamine with galactose, and following through to the procedure described in Example 15E except using an azide-modified uRAFT agent of Formula 1106 where q is 8, there is obtained the compound of Formula 1107 where p is 30, q is 8, $R^3$ is OH, $R^4$ is OH and $R^8$ is CMP.

15K. Formula 1109 where n is 62 and where X' and m are as in Example 19H

By following the procedure described in Example 15F, substituting the OVA with the compounds as described in Example 15H and employing the compound of Formula 1108 where n is 62, there are obtained the corresponding compounds of Formula 1109 where n is 62.

15L. Other Compounds of Formula 1m

By following the procedure described in Example 15G and substituting the compound of Formula 1107 with the compounds obtained in Example 15J, and substituting the compound of Formula 1109 with the compounds obtained in Example 15K, there are obtained the following corresponding compounds of Formula 1m:

F1m-Abciximab-$m_{10}$-$n_{62}$-$p_{30}$-$q_8$-CMP-2OH,
F1m-Adalimumab-$m_{11}$-$n_{62}$-$p_{30}$-$q_8$-CMP-2OH,
F1m-Agalsidase alfa-$m_{14}$-$n_{62}$-$p_{30}$-$q_8$-CMP-2OH,
F1m-Agalsidase beta-$m_{14}$-$n_{62}$-$p_{30}$-$q_8$-CMP-2OH,
F1m-Aldeslukin-$m_6$-$n_{62}$-$p_{30}$-$q_8$-CMP-2OH,
F1m-Alglucosidase alfa-$m_{13}$-$n_{62}$-$p_{30}$-$q_8$-CMP-2OH,
F1m-Factor VIII-$m_{100}$-$n_{62}$-$p_{30}$-$q_8$-CMP-2OH,
F1m-Factor IX-$m_{18}$-$n_{62}$-$p_{30}$-$q_8$-CMP-2OH,
F1m-L-asparaginase-$m_5$-$n_{62}$-$p_{30}$-$q_8$-CMP-2OH,
F1m-Laronidase-$m_7$-$n_{62}$-$p_{30}$-$q_8$-CMP-2OH,
F1m-Octreotide-$m_1$-$n_{62}$-$p_{30}$-$q_8$-CMP-2OH,
F1m-Phenylalanine ammonia-lyase-$m_{12}$-$n_{62}$-$p_{30}$-$q_8$-CMP-2OH,
F1m-Rasburicase-$m_{12}$-$n_{62}$-$p_{30}$-$q_8$-CMP-2OH,
F1m-Insulin-$m_2$-$n_{62}$-$p_{30}$-$q_8$-CMP-2OH,
F1m-GAD-65-$m_8$-$n_{62}$-$p_{30}$-$q_8$-CMP-2OH,
F1m-IGRP-$m_7$-$n_{62}$-$p_{30}$-$q_8$-CMP-2OH,
F1m-MBP-$m_6$-$n_{62}$-$p_{30}$-$q_8$-CMP-2OH,
F1m-MOG-$m_5$-$n_{62}$-$p_{30}$-$q_8$-CMP-2OH,
F1m-PLP-$m_8$-$n_{62}$-$p_{30}$-$q_8$-CMP-2OH,
F1m-MBP13-32-$m_1$-$n_{62}$-$p_{30}$-$q_8$-CMP-2OH,
F1m-MBP83-99-$m_1$-$n_{62}$-$p_{30}$-$q_8$-CMP-2OH,
F1m-MBP111-129-$m_1$-$n_{62}$-$p_{30}$-$q_8$-CMP-2OH,
F1m-MBP146-170-$m_2$-$n_{62}$-$p_{30}$-$q_8$-CMP-2OH,
F1m-MOG1-20-$m_1$-$n_{62}$-$p_{30}$-$q_8$-CMP-2OH,
F1m-MOG35-55-$m_2$-$n_{62}$-$p_{30}$-$q_8$-CMP-2OH,
F1m-PLP139-154-$m_3$-$n_{62}$-$p_{30}$-$q_8$-CMP-2OH,
F1m-MART1-$m_4$-$n_{62}$-$p_{30}$-$q_8$-CMP-2OH,
F1m-Tyrosinase-$m_8$-$n_{62}$-$p_{30}$-$q_8$-CMP-2OH,
F1m-PMEL-$m_5$-$n_{62}$-$p_{30}$-$q_8$-CMP-2OH,
F1m-Aquaporin-4-$m_4$-$n_{62}$-$p_{30}$-$q_8$-CMP-2OH,
F1m-S-arrestin-$m_{12}$-$n_{62}$-$p_{30}$-$q_8$-CMP-2OH,
F1m-IRBP-$m_{21}$-$n_{62}$-$p_{30}$-$q_8$-CMP-2OH,
F1m-Conarachin-$m_{21}$-$n_{62}$-$p_{30}$-$q_8$-CMP-2OH,
F1m-Alpha-gliadin "33-mer" native-$m_1$-$n_{62}$-$p_{30}$-$q_8$-CMP-2OH,
F1m-Alpha-gliadin "33-mer" deamidated-$m_1$-$n_{62}$-$p_{30}$-$q_8$-CMP-2OH,
F1m-Alpha-gliadin-$m_1$-$n_{62}$-$p_{30}$-$q_8$-CMP-2OH,
F1m-Omega-gliadin-$m_1$-$n_{62}$-$p_{30}$-$q_8$-CMP-2OH,
F1m-Fel d 1-$m_4$-$n_{62}$-$p_{30}$-$q_8$-CMP-2OH,
F1m-Cat albumin-$m_{16}$-$n_{62}$-$p_{30}$-$q_8$-CMP-2OH,
F1m-Can f 1-$m_6$-$n_{62}$-$p_{30}$-$q_8$-CMP-2OH,
F1m-Dog albumin-$m_{23}$-$n_{62}$-$p_{30}$-$q_8$-CMP-2OH, and
F1m-RhCE-$m_{10}$-$n_{62}$-$p_{30}$-$q_8$-CMP-2OH.

15M. Other Compounds of Formula 1m

By following the procedure described in Examples 15A-L and substituting the galactosamine or galactose with glucosamine or glucose, respectively, there are obtained the corresponding glucosylated compounds of Formula 1m.

Example 16

F1n-insulin-$m_2$-$n_1$-$p_{30}$-$q_4$-CMP-2NHAc

16A. Formula 1202 where X' is Insulin, m is 2 and n is 1

Recombinant human insulin (5 mg) was added to 100 µl of DMF containing 10 µl of triethylamine and stirred until the insulin became soluble. To this solution was added 10 mg (0.0161 mmol) of a linker precursor of Formula 1201 where n is 1 and the reaction was allowed to stir. After 1 hour, 1.3 ml of tert-butyl methyl ether was added to isolate the corresponding product of Formula 1202, which was recovered as the precipitate. Residual DMF and tert-butyl methyl ether were removed under reduced pressure. Characterization via liquid chromatography, mass spectroscopy and polyacrylamide gel electrophoresis confirmed the identity of the product. The modified insulin product of Formula 1202 was used without further purification.

16B. Formula 1n where X' is Insulin, m is 2, n is 1, p is 30, q is 4 and $R^8$ is CMP The product of Formula 1202 obtained in Example 16A was resuspended in 100 µl of DMF. The polymer product of Formula 1107 obtained in Example 15E (10 mg) was added and the reaction was allowed to stir for 1 hour. After 1 hour, the reaction products were precipitated via the addition of dichloromethane (1.3 ml). The product was filtered and the residual solvent was removed under reduced pressure. The crude product was then resuspended in 500 µl of PBS, and the low molecular weight components were removed via centrifugal size exclusion chromatography to afford the corresponding isomeric product of Formula 1n. Characterization via liquid chromatography, mass spectroscopy and polyacrylamide gel electrophoresis confirmed the identity of the product. The modified insulin product of Formula 1202 was used without further purification.

16C. Other Compounds of Formula 1202

By following the procedure described in Example 16A and substituting insulin with the following:

Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
GAD-65 (SEQ ID NO:2),
IGRP (SEQ ID NO:3)
MBP (SEQ ID NO:4),
MOG (SEQ ID NO:5),
PLP (SEQ ID NO:6),
MBP13-32 (SEQ ID NO:7),
MBP83-99 (SEQ ID NO:8),
MBP111-129 (SEQ ID NO:9),
MBP146-170 (SEQ ID NO:10),
MOG1-20 (SEQ ID NO:11),
MOG35-55 (SEQ ID NO:12),
PLP139-154 (SEQ ID NO:13),
MART1 (SEQ ID NO:14),
Tyrosinase (SEQ ID NO:15),
PMEL (SEQ ID NO:16),
Aquaporin-4 (SEQ ID NO:17),
S-arrestin (SEQ ID NO:18),
IRBP (SEQ ID NO:19),
Conarachin (UNIPROT Q6PSU6),
Alpha-gliadin "33-mer" native (SEQ ID NO:20),
Alpha-gliadin "33-mer" deamidated (SEQ ID NO:21),
Alpha-gliadin (SEQ ID NO:22),
Omega-gliadin (SEQ ID NO:23),
Fel d 1A (UNIPROT P30438),
Cat albumin (UNIPROT P49064), Can f 1 (UNIPROT O18873),
Dog albumin (UNIPROT P49822), and
RhCE (UNIPROT P18577),
there are obtained the following corresponding compounds of Formula 1202 where n is 1:
  X is Abciximab and m is 10,
  X is Adalimumab and m is 11,
  X is Agalsidase alfa and m is 14,
  X is Agalsidase beta and m is 14,
  X is Aldeslukin and m is 6,
  X is Alglucosidase alfa and m is 13,
  X is Factor VIII and m is 100,
  X is Factor IX and m is 18,
  X is L-asparaginase and m is 5,
  X is Laronidase and m is 7,
  X is Octreotide and m is 1,
  X is Phenylalanine ammonia-lyase and m is 12,
  X is Rasburicase and m is 12,
  X is GAD-65 (SEQ ID NO:2) and m is 8,
  X is IGRP (SEQ ID NO:3) and m is 7,
  X is MBP (SEQ ID NO:4) and m is 6,
  X is MOG (SEQ ID NO:5) and m is 5,
  X is PLP (SEQ ID NO:6) and m is 8,
  X is MBP13-32 (SEQ ID NO:7) and m is 1,
  X is MBP83-99 (SEQ ID NO:8) and m is 1,
  X is MBP111-129 (SEQ ID NO:9) and m is 1,
  X is MBP146-170 (SEQ ID NO:10) and m is 2,
  X is MOG1-20 (SEQ ID NO:11) and m is 1,
  X is MOG35-55 (SEQ ID NO:12) and m is 2,
  X is PLP139-154 (SEQ ID NO:13) and m is 3,
  X is MART1 (SEQ ID NO:14) and m is 4,
  X is Tyrosinase (SEQ ID NO:15) and m is 8,
  X is PMEL (SEQ ID NO:20) and m is 5,
  X is Aquaporin-4 (SEQ ID NO:21) and m is 4,
  X is S-arrestin (SEQ ID NO:22) and m is 12,
  X is IRBP (SEQ ID NO:19) and m is 21,
  X is Conarachin and m is 21,
  X is Alpha-gliadin "33-mer" native (SEQ ID NO:20) and m is 1,
  X is Alpha-gliadin "33-mer" deamidated (SEQ ID NO:21) and m is 1,
  X is Alpha-gliadin (SEQ ID NO:22) and m is 1,
  X is Omega-gliadin (SEQ ID NO:27) and m is 1,
  X is Fel d 1 and m is 4,
  X is Cat albumin and m is 16,
  X is Can f 1 and m is 6,
  X is Dog albumin and m is 23, and
  X is RhCE and m is 10.

16D. Other Compounds of Formula 1n

By following the procedure described in Example 16B and substituting the compounds of Formula 1202, for example as obtained in Example 16C, there are obtained the following corresponding compounds of Formula 1m:
  F1n-Abciximab-$m_{10}$-$n_1$-$p_{30}$-$q_4$-CMP-2NHAc,
  F1n-Adalimumab-$m_{11}$-$n_1$-$p_{30}$-$q_4$-CMP-2NHAc,
  F1n-Agalsidase alfa-$m_{14}$-$n_1$-$p_{30}$-$q_4$-CMP-2NHAc,
  F1n-Agalsidase beta-$m_{14}$-$n_1$-$p_{30}$-$q_4$-CMP-2NHAc,
  F1n-Aldeslukin-$m_6$-$n_1$-$p_{30}$-$q_4$-CMP-2NHAc,
  F1n-Alglucosidase alfa-$m_{13}$-$n_1$-$p_{30}$-$q_4$-CMP-2NHAc,
  F1n-Factor VIII-$m_{100}$-$n_1$-$p_{30}$-$q_4$-CMP-2NHAc,
  F1n-Factor IX-$m_{18}$-$n_1$-$p_{30}$-$q_4$-CMP-2NHAc,
  F1n-L-asparaginase-$m_5$-$n_1$-$p_{30}$-$q_4$-CMP-2NHAc,
  F1n-Laronidase-$m_7$-$n_1$-$p_{30}$-$q_4$-CMP-2NHAc,
  F1n-Octreotide-$m_1$-$n_1$-$p_{30}$-$q_4$-CMP-2NHAc,
  F1n-Phenylalanine ammonia-lyase-$m_{12}$-$n_1$-$p_{30}$-$q_4$-CMP-2NHAc,
  F1n-Rasburicase-$m_{12}$-$n_1$-$p_{30}$-$q_4$-CMP-2NHAc,
  F1n-GAD-65-$m_8$-$n_1$-$p_{30}$-$q_4$-CMP-2NHAc,
  F1n-IGRP-$m_7$-$n_1$-$p_{30}$-$q_4$-CMP-2NHAc,
  F1n-MBP-$m_6$-$n_1$-$p_{30}$-$q_4$-CMP-2NHAc,
  F1n-MOG-$m_5$-$n_1$-$p_{30}$-$q_4$-CMP-2NHAc,
  F1n-PLP-$m_8$-$n_1$-$p_{30}$-$q_4$-CMP-2NHAc,
  F1n-MBP13-32-$m_1$-$n_1$-$p_{30}$-$q_4$-CMP-2NHAc,
  F1n-MBP83-99-$m_1$-$n_1$-$p_{30}$-$q_4$-CMP-2NHAc,
  F1n-MBP111-129-$m_1$-$n_1$-$p_{30}$-$q_4$-CMP-2NHAc,
  F1n-MBP146-170-$m_2$-$n_1$-$p_{30}$-$q_4$-CMP-2NHAc,
  F1n-MOG1-20-$m_1$-$n_1$-$p_{30}$-$q_4$-CMP-2NHAc,
  F1n-MOG35-55-$m_2$-$n_1$-$p_{30}$-$q_4$-CMP-2NHAc,
  F1n-PLP139-154-$m_3$-$n_1$-$p_{30}$-$q_4$-CMP-2NHAc,
  F1n-MART1-$m_4$-$n_1$-$p_{30}$-$q_4$-CMP-2NHAc,
  F1n-Tyrosinase-$m_8$-$n_1$-$p_{30}$-$q_4$-CMP-2NHAc,
  F1n-PMEL-$m_5$-$n_1$-$p_{30}$-$q_4$-CMP-2NHAc,
  F1n-Aquaporin-4-$m_4$-$n_1$-$p_{30}$-$q_4$-CMP-2NHAc,
  F1n-S-arrestin-$m_{12}$-$n_1$-$p_{30}$-$q_4$-CMP-2NHAc,
  F1n-IRBP-$m_{21}$-$n_1$-$p_{30}$-$q_4$-CMP-2NHAc,
  F1n-Conarachin-$m_{21}$-$n_1$-$p_{30}$-$q_4$-CMP-2NHAc,
  F1n-Alpha-gliadin "33-mer" native-$m_1$-$n_1$-$p_{30}$-$q_4$-CMP-2NHAc,
  F1n-Alpha-gliadin "33-mer" deamidated-$m_1$-$n_1$-$p_{30}$-$q_4$-CMP-2NHAc,
  F1n-Alpha-gliadin-$m_1$-$n_1$-$p_{30}$-$q_4$-CMP-2NHAc,
  F1n-Omega-gliadin-$m_1$-$n_1$-$p_{30}$-$q_4$-CMP-2NHAc,
  F1n-Fel d 1-$m_4$-$n_1$-$p_{30}$-$q_4$-CMP-2NHAc,
  F1n-Cat albumin-$m_{16}$-$n_1$-$p_{30}$-$q_4$-CMP-2NHAc,
  F1n-Can f 1-$m_6$-$n_1$-$p_{30}$-$q_4$-CMP-2NHAc,
  F1n-Dog albumin-$m_{23}$-$n_1$-$p_{30}$-$q_4$-CMP-2NHAc, and
  F1n-RhCE-$m_{10}$-$n_1$-$p_{30}$-$q_4$-CMP-2NHAc.

16E. Formula 1202 where n is 33 and where X' and m are as in Example 20C

By following the procedure described in Example 16F, substituting the insulin with the compounds as described in Example 16C and employing the compound of Formula 1201 where n is 33, there are obtained the corresponding compounds of Formula 1202 where n is 33.

16F. Other Compounds of Formula 1n

By following the procedure described in Example 16B and substituting the compound of Formula 1107 with the compounds obtained in Example 15J, and substituting the compound of Formula 1202 with the compounds obtained in Example 16E, there are obtained the following corresponding compounds of Formula 1n:
  F1n-Abciximab-$m_{10}$-$n_{33}$-$p_{30}$-$q_8$-CMP-2OH,
  F1n-Adalimumab-$m_{11}$-$n_{33}$-$p_{30}$-$q_8$-CMP-2OH,
  F1n-Agalsidase alfa-$m_{14}$-$n_{33}$-$p_{30}$-$q_8$-CMP-2OH,
  F1n-Agalsidase beta-$m_{14}$-$n_{33}$-$p_{30}$-$q_8$-CMP-2OH,
  F1n-Aldeslukin-$m_6$-$n_{33}$-$p_{30}$-$q_8$-CMP-2OH,
  F1n-Alglucosidase alfa-$m_{13}$-$n_{33}$-$p_{30}$-$q_8$-CMP-2OH,
  F1n-Factor VIII-$m_{100}$-$n_{33}$-$p_{30}$-$q_8$-CMP-2OH,
  F1n-Factor IX-$m_{18}$-$n_{33}$-$p_{30}$-$q_8$-CMP-2OH,
  F1n-L-asparaginase-$m_5$-$n_{33}$-$p_{30}$-$q_8$-CMP-2OH,
  F1n-Laronidase-$m_7$-$n_{33}$-$p_{30}$-$q_8$-CMP-2OH,
  F1n-Octreotide-$m_1$-$n_{33}$-$p_{30}$-$q_8$-CMP-2OH,
  F1n-Phenylalanine ammonia-lyase-$m_{12}$-$n_{33}$-$p_{30}$-$q_8$-CMP-2OH,
  F1n-Rasburicase-$m_{12}$-$n_{33}$-$p_{30}$-$q_8$-CMP-2OH,
  F1n-GAD-65-$m_8$-$n_{33}$-$p_{30}$-$q_8$-CMP-2OH,
  F1n-IGRP-$m_7$-$n_{33}$-$p_{30}$-$q_8$-CMP-2OH,
  F1n-MBP-$m_6$-$n_{33}$-$p_{30}$-$q_8$-CMP-2OH,
  F1n-MOG-$m_5$-$n_{33}$-$p_{30}$-$q_8$-CMP-2OH,
  F1n-PLP-$m_8$-$n_{33}$-$p_{30}$-$q_8$-CMP-2OH,
  F1n-MBP13-32-$m_1$-$n_{33}$-$p_{30}$-$q_8$-CMP-2OH,
  F1n-MBP83-99-$m_1$-$n_{33}$-$p_{30}$-$q_8$-CMP-2OH,
  F1n-MBP111-129-$m_1$-$n_{33}$-$p_{30}$-$q_8$-CMP-2OH,
  F1n-MBP146-170-$m_2$-$n_{33}$-$p_{30}$-$q_8$-CMP-2OH, F1n-MOG1-20-$m_1$-$n_{33}$-$p_{30}$-$q_8$-CMP-2OH,
F1n-MOG35-55-$m_2$-$n_{33}$-$p_{30}$-$q_8$-CMP-2OH,
F1n-PLP139-154-$m_3$-$n_{33}$-$p_{30}$-$q_8$-CMP-2OH,
F1n-MART1-$m_4$-$n_{33}$-$p_{30}$-$q_8$-CMP-2OH,
F1n-Tyrosinase-$m_8$-$n_{33}$-$p_{30}$-$q_8$-CMP-2OH,
F1n-PMEL-$m_5$-$n_{33}$-$p_{30}$-$q_8$-CMP-2OH,
F1n-Aquaporin-4-$m_4$-$n_{33}$-$p_{30}$-$q_8$-CMP-2OH,
F1n-S-arrestin-$m_{12}$-$n_{33}$-$p_{30}$-$q_8$-CMP-2OH,
F1n-IRBP-$m_{21}$-$n_{33}$-$p_{30}$-$q_8$-CMP-2OH,
F1n-Conarachin-$m_{21}$-$n_{33}$-$p_{30}$-$q_8$-CMP-2OH,
F1n-Alpha-gliadin "33-mer" native-$m_1$-$n_{33}$-$p_{30}$-$q_8$-CMP-2OH,
F1n-Alpha-gliadin "33-mer" deamidated-$m_1$-$n_{33}$-$p_{30}$-$q_8$-CMP-2OH,
F1n-Alpha-gliadin-$m_1$-$n_{33}$-$p_{30}$-$q_8$-CMP-2OH,
F1n-Omega-gliadin-$m_1$-$n_{33}$-$p_{30}$-$q_8$-CMP-2OH,
F1n-Fel d 1-$m_4$-$n_{33}$-$p_{30}$-$q_8$-CMP-2OH,
F1n-Cat albumin-$m_{16}$-$n_{33}$-$p_{30}$-$q_8$-CMP-2OH,
F1n-Can f 1-$m_6$-$n_{33}$-$p_{30}$-$q_8$-CMP-2OH,
F1n-Dog albumin-$m_{23}$-$n_{33}$-$p_{30}$-$q_8$-CMP-2OH, and
F1n-RhCE-$m_{10}$-$n_{33}$-$p_{30}$-$q_8$-CMP-2OH.

16G. Other Compounds of Formula 1n

By following the procedure described in Examples 16A-F and substituting the galactosylating moieties with glucosylating moieties, there are obtained the corresponding glucosylated compounds of Formula 1n.

Example 17

Formula 1507 where p is 90, t is 1, $R^3$ is NHAc and $R^4$ is OH

17A. Formula 1502 where t is 1, $R^3$ is NHAc and $R^4$ is OH

N-Acetyl-D-glucosamine (Formula 1101 where $R^3$ is NHAc and $R^4$ is OH) (5.0 g, 22.6 mmol) was added to a stirred solution of 2-(2-chloroethoxy)ethan-1-ol (50 ml) at room temperature. The solution was cooled to 4° C. and acetylchloride was added drop-wise to the solution. The solution was brought to room temperature and then heated to 70° C. After 4 hours, the reaction mixture was added to 200 ml of ethyl acetate. The precipitate that formed was collected, added to 100 ml of ethanol and stirred in the presence of carbon for 2 hours. The solution was filtered, and the solvent was removed under reduced pressure. The corresponding product of Formula 1502, N-acetyl-D-glucosamine-2-(chloroethoxy)ethanol, was used without further purification.

17B. Formula 1503 where t is 1, $R^3$ is NHAc and $R^4$ is OH

N-Acetyl-D-glucosamine-2-(chloroethoxy)ethanol (2.0 g, 6.11 mmol) was added to a stirred solution of DMF (100 ml) and sodium azide (4.0 g, 61.5 mmol). The solution was headed at 90° C. for 12 hours and then filtered. The residual solvent was removed under reduced pressure and the crude product was purified via flash chromatography (10% MeOH in dichloromethane) to give the corresponding product of Formula 1503, N-acetyl-D-glucosamine-2-(azideoethoxy) ethanol.

17C. Formula 1504 where t is 1, $R^3$ is NHAc and $R^4$ is OH

N-Acetyl-D-glucosamine-2-(azideoethoxy)ethanol (2.0 g, 5.9 mmol) was added to a solution of palladium on carbon and ethanol (50 ml). The solution was stirred under hydrogen gas (3 atm) for 4 hours. The resulting solution was filtered and the residual solvent was removed under reduced pressure to afford the corresponding product of Formula 1504, N-acetyl-D-glucosamine-2-(amineoethoxy)ethanol.

17D. Formula 1505 where t is 1, $R^3$ is NHAc and $R^4$ is OH

N-Acetyl-D-glucosamine-2-(amineoethoxy)ethanol (1.0 g, 3.25 mmol) was added to a solution of methacrylate anhydride (0.583 g, 3.78 mmol) in DMF (50 ml). Triethylamine was then added to the solution and the reaction was stirred for 2 hours at room temperature. After 2 hours, the excess solvent was removed under reduced pressure, and the corresponding product of Formula 1505, ((2S,3S,4S,5R,6S)-4,5-dihydroxy-6-(hydroxymethyl)-2-(2-(2-methacrylamido-ethoxy)ethoxy)tetrahydro-2H-pyran-3-yl)carbamic acid, was isolated via flash chromatography.

17E. Formula 1507 where p is 90, q is 4, t is 1, $R^3$ is NHAc, $R^4$ is OH, $R^8$ is CMP, and $R^{10}$ is 2-hydroxypropyl A 25 ml Schlenk flask was charged with a compound of Formula 1505, the product of Example 17D (272 mg, 0.72 mmol), N-(2-hydroxypropyl)methacrylamide ("HPMA", used as received from the manufacturer) (211 mg, 1.47 mmol), an azide-modified uRAFT agent of Formula 1106 where q is 4 and $R^8$ is CMP (10.41 mg, 0.0217 mmol), azobis(isobutyronitril) (0.98 mg, 0.005 mmol), and 1.2 ml dimethylformamide. The reaction mixture was subjected to four freeze-pump-thaw degassing cycles and then stirred at 70° C. for 20 hours. The corresponding random polymeric product of Formula 1507 was recovered by precipitating the reaction mixture in acetone. Excess acetone was removed at reduced pressure to provide the random polymeric product, which was used without further purification.

17F. Formula 1507 where p is 90, q is 4, t is 1, $R^3$ is NHAc, $R^4$ is OH, $R^8$ is CMP, and $R^{10}$ is 2-hydroxypropyl, Using N-acetyl-D-galactosamine By following the procedures of Examples 17A through 17E and substituting N-acetyl-D-galactosamine for N-acetyl-D-glucosamine in the procedure of Example 17A, there was obtained the corresponding galactosyl compound of Formula 1507.

17G. Compounds of Formula 1507 where t is Other than 1

By following the procedures of Examples 17A through 17E and substituting 2-(2-chloroethoxy)ethan-1-ol with:
2-(2-(2-chloroethoxy)ethoxy)ethan-1-ol will afford the corresponding compound of Formula 1507 where t is 2,
2-(2-(2-(2-chloroethoxy)ethoxy)ethoxy)ethan-1-ol will afford the corresponding compound of Formula 1507 where t is 3,
2-(2-(2-(2-chloroethoxy)ethoxy)ethoxy)ethoxy)ethan-1-ol will afford the corresponding compound of Formula 1507 where t is 4,
2-(2-(2-(2-(2-chloroethoxy)ethoxy)ethoxy)ethoxy)ethan-1-ol will afford the corresponding compound of Formula 1507 where t is 5, and
2-(2-(2-(2-(2-(2-chloroethoxy)ethoxy)ethoxy)ethoxy)ethoxy)ethan-1-ol will afford the corresponding compound of Formula 1507 where t is 6.

17H. Compounds of Formula 1507 Having a Plurality of $W^1$ Groups where t Varies By following the procedure of Example 17E and substituting the compound of Formula 1505 where t is 1 with 0.36 mmol each of Formula 1505 where t is 2 and 4, (prepared, for example, as described in Example 17F by following the procedures of Examples 17A through 17D) there is obtained the corresponding random copolymer of Formula 1507 having about 15 $W^1$ groups where t is 2, 15 $W^1$ groups where t is 4 and 60 $W^2$ groups.

17I. Compounds of Formula 1507 Having a Mixture of Glucosyl and Galactosyl Moieties By following the procedure of Example 17E and substituting the compound of Formula 1505 with 0.36 mmol each of glucosyl and galactosyl Formula 1505 (prepared, for example, as described in Example 17D and in Example 17F by following the procedures of Examples 17A through 17D) there is obtained the corresponding random copolymer of Formula 1507 having about 15 glucosyl $W^1$ groups, 15 galactosyl $W^1$ groups and 60 $W^2$ groups.

Example 17.1

Formula 1507 where t is 1, $R^3$ is NHAc and $R^4$ is OH

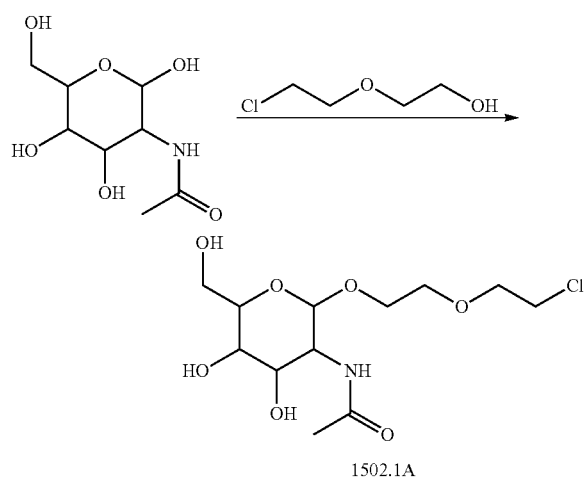

17.1A. Formula 1502 where t is 1, $R^3$ is NHAc and $R^4$ is OH: 2-(2-(2-chloroethoxy)ethoxy)-α-NAc-Galactosamine (1502.1A).

Acetyl chloride (4.35 mL, 61.05 mmol) was added dropwise to the ice-cold solution of NHAc protected D-Galactosamine (10.0 g) in 2-(2'-Chloroethoxy)ethanol (40 mL). The mixture was stirred for 15 minutes at 4° C. and then was transferred to the oil bath at 70° C. The reaction was left mixing under cooling condenser for 4 hours. After that time, a dark brown solution was cooled down and poured into 400 mL solution of ethyl acetate and dichloromethane (3:1, v/v) in order to get rid of an excess of unreacted chloroethanol. The mixture was placed in a freezer for 30 minutes and then decanted from dark brown, sticky precipitate. The precipitate was dissolved in anhydrous ethanol and activated charcoal was added. The suspension was mixed for 1.5 hours and then filtered off through Celite and washed with ethanol. In the last step, ethanol was evaporated in vacuum to provide 12.8 g of product (1502.1A) (95.24% yield).

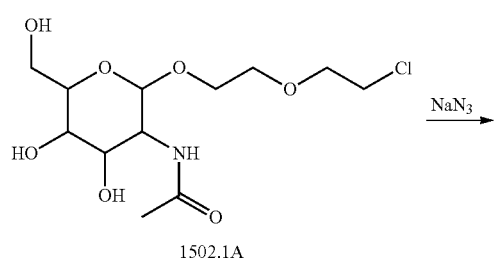

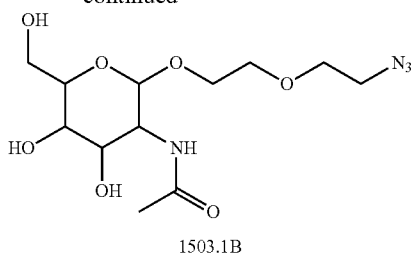

17.1B. Formula 1503 where t is 1, $R^3$ is NHAc and $R^4$ is OH; 2-(2-(2-Azidoethoxy)ethoxy)-α-NAc-Galactosamine (1503.1B).

A compound (1502.1A) (5.0 g) was dissolved in 20 mL of N,N-dimethylformamide. To that solution, sodium azide (26628-22-8) was added (5.0 g). The suspension was placed in an oil bath and stirred over night at 80° C. After the night, the reaction mixture was filtered off through Celite. The solvent was then evaporated under high pressure to provide an oily, brown substance. Final product was purified via flash chromatography (82.2% yield).

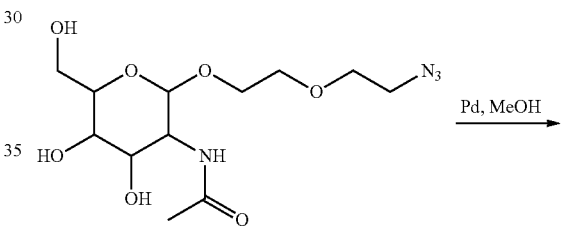

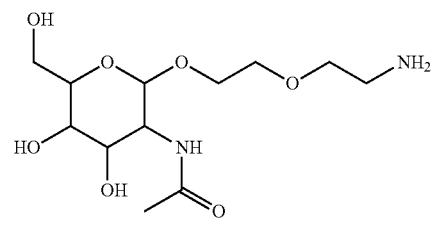

17.1C. Formula 1504 where t is 1, $R^3$ is NHAc and $R^4$ is OH; 2-(2-(2-aminoethoxy)ethoxy)-α-NAc-Galactosamine (1504.1C).

A suspension of (1503.1B) (5.5 g) and 10% palladium on carbon (ca. 500 mg) in 20 mL of ethanol was hydrogenated in a Shlenk flask with an initial pressure of 2 bars of hydrogen gas. The reduction process was controlled by TLC. After 3 hours reaction was completed and the suspension was filtered through Celite (78% yield).

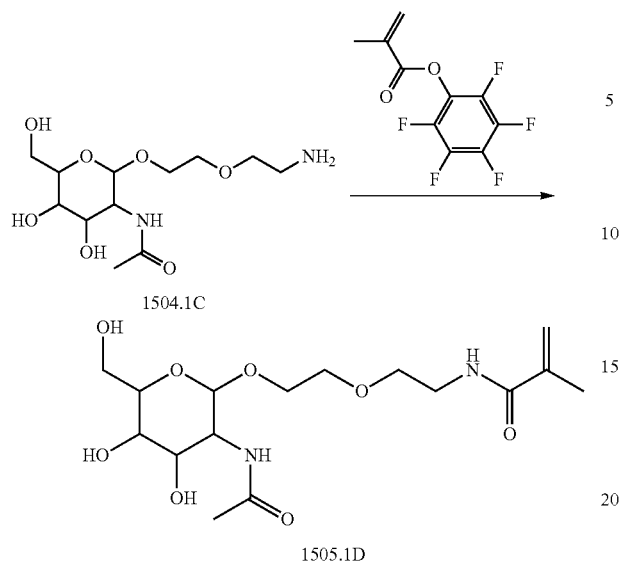

17.1D. Formula 1505 where t is 1, $R^3$ is NHAc and $R^4$ is OH; α-NAc-Glactosamine-amine-methacrylate (1505.1D)

A compound (1504.1C) (4.5 g) was dissolved in 10 mL of N,N-dimethylformamide. To that solution, triethylamine (3 mL) was added and the mixture was cooled down to 4° C. Subsequently, pentafluorophenyl methacrylate (13642-97-2) (4.38 mL) was added drop-wise with constant stirring. After 30 minutes, ice-bath was removed and the reaction was allowed to stir at room temperature for the next 4 hours. Next, the solvent was evaporated and the residual was adsorbed on silica gel. The purification of crude material using flash chromatography (dichloromethane:methanol 95:5, v/v) provided 3.8g of NAc-Galactosamine monomer (α-NAc-Glactosamine-amine-methacrylate (1505.1D)) (64.73% yield).

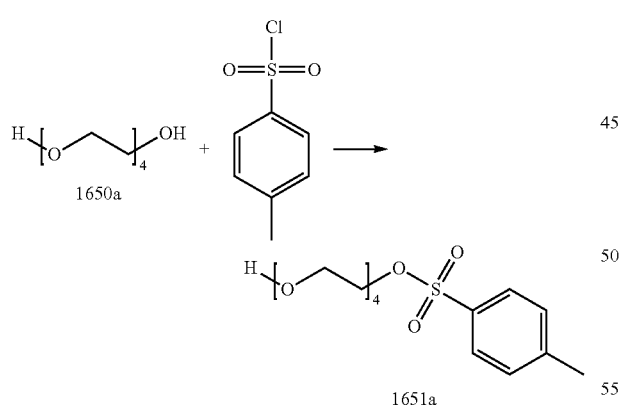

Tetraethylene glycol mono p-toluenesulfonate (1651a).

Tetraethylene glycol (1650a) (112-60-7) (2.5 g) and pyridine (1.0 g) were added to 50 mL of dichloromethane and stirred for 20 minutes at 0° C. To that solution, p-toluenesulfonyl chloride (98-59-9)(2.37) in 15 mL of dichloromethane was added slowly. The reaction mixture was then stirred for 2h at 0° C. followed by 4h at room temperature. After that time, the solvent was evaporated and crude product was purified via flash chromatography (ethyl acetate:hexane 6:4, v/v) to afford 1651a (44% yield).

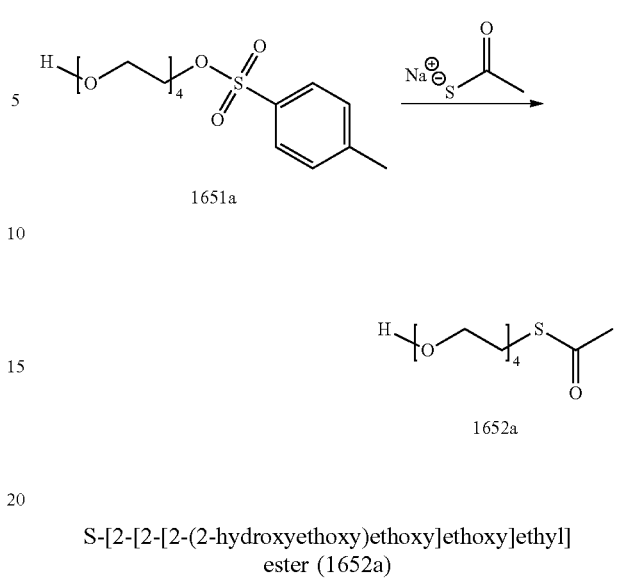

S-[2-[2-[2-(2-hydroxyethoxy)ethoxy]ethoxy]ethyl] ester (1652a)

To a suspension of potassium thioacetate (10387-40-3) (10.1 g, 88 mmol) in 650 mL of DMF was added a solution of (1651a) (15.4 g) in 100 mL of DMF. The mixture was stirred at room temperature for 1 h and then at 90 C for 4 h. After filtration, the solvent was evaporated under reduced pressure. The residue was dissolved in ethyl acetate (150 mL) and washed with water (2×50 mL) and brine (2×50 mL). The aqueous wash solutions were reextracted with ethyl acetate (2×50 mL), and the combined organic layers were dried over magnesium sulfate and evaporated under reduced pressure to give a yellow oil product 1652a (45% yield)

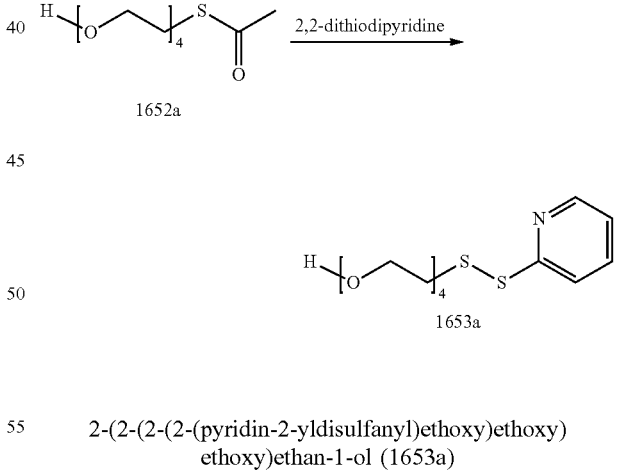

2-(2-(2-(2-(pyridin-2-yldisulfanyl)ethoxy)ethoxy) ethoxy)ethan-1-ol (1653a)

Sodium methoxide (1.40 ml of 0.5M in methanol) was added dropwise to a stirred solution of (1652a) (70.9 mg) and 2,2-dithiodipyridine (2127-03-9) (77.4 mg, 0.351 mmol) in anhydrous methanol (3 mL) under an argon atmosphere. After 2 h the reaction was concentrated with silica to a powder, and the crude product was purified by flash chromatography over silica (1:1 hexanes:EtOAc) to afford 1653a as a clear, pale yellow liquid (26.3 mg, 44% yield).

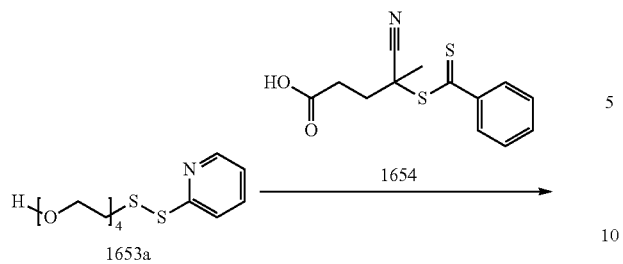

1653a → 1654

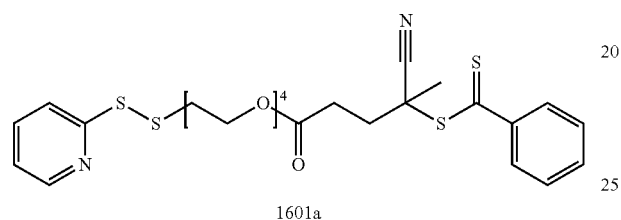

1601a uRAFT Agent (1601a)

Compound 1653a (1g) was added dropwise to a stirred solution of 4-Cyano-4-(thiobenzoylthio)pentanoic acid (1.1g) (201611-92-9), N,N'-Dicyclohexylcarbodiimide (538-75-0) (0.5 g) and 4-Dimethylaminopyridine (DMAP) (1122-58-3) (0.1 g) in DCM (15 ml). The reaction was stirred at 0 C for 2 h then allowed to warm to room temperature. After 3 h, the reaction was filtered through celite and the solvent was removed via reduced pressure. The final product (1601a) was recovered from flash chromatography (67% yield).

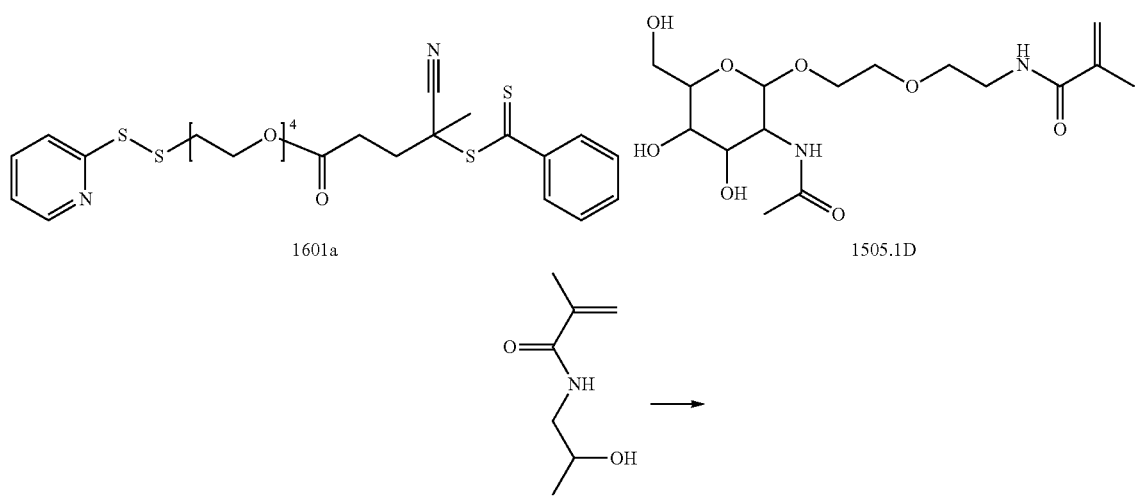

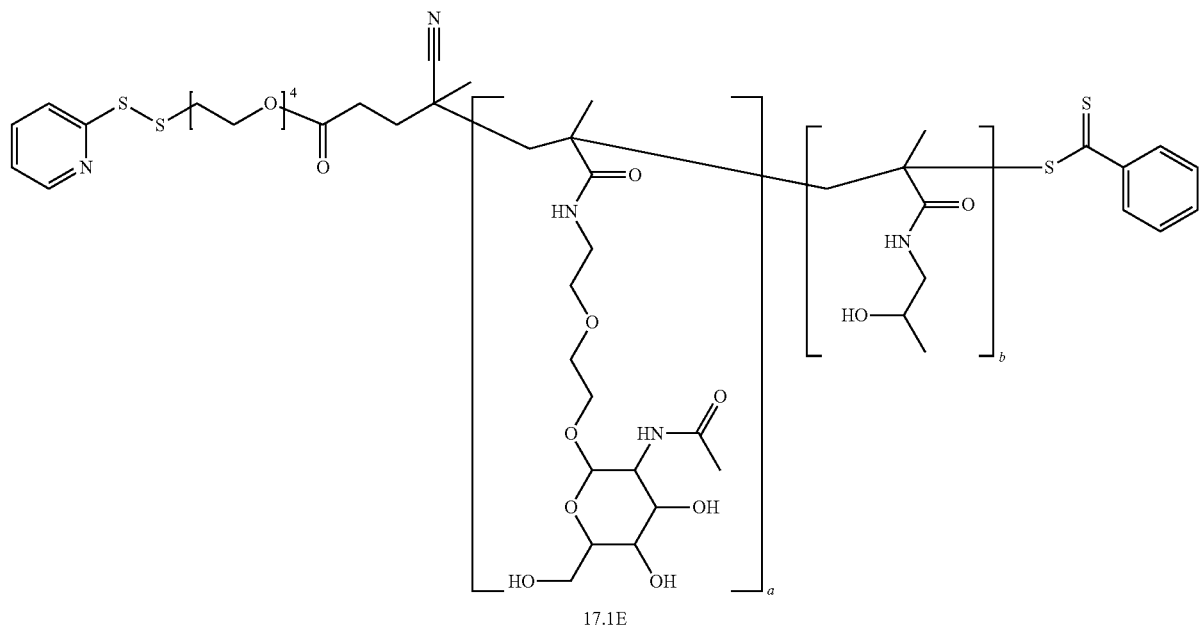

17.1E pGal (17.1E)

The following conditions were performed using the α-NAc-Glactosamine-amine-methacrylate (e.g., 1505.1D) monomer to afford 17.1E. In some embodiments, the α-NAc-Glucosamine-amine-methacrylate monomer (e.g., 1505.2D) can be used instead to afford a glucosamine-based polymer. In some embodiments, a is an integer between about 0 to about 150, about 1 to about 100, about 1 to about 50, about 1 to about 10, or about 1 to about 5. In some embodiments, b is an integer between about 0 to about 150, about 1 to about 100, about 1 to about 50, about 1 to about 10, or about 1 to about 5.

Compound 1601a, 1505.1D, Azobisisobutyronitrile (78-67-1), and N-(2-hydroxypropyl)methacrylamide (21442-01-3) were added to DMF (1 ml). The reaction mixture was subjected to 4 freeze-pump-thaw degassing cycles before being stirred for 20 h at 70 C. The polymeric product was recovered via precipitation from acetone. The excess solvent was removed under reduced pressure (55% yield).

Example 17.2

Formula 1507 where t is 1, $R^3$ is NHAc and $R^4$ is OH

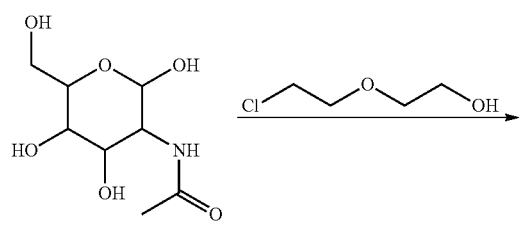

17.2A. Formula 1502 where t is 1, $R^3$ is NHAc and $R^4$ is OH; 2-(2-(2-chloroethoxy)ethoxy)-α-NAc-Glucosamine (1502.2A).

Acetyl chloride (75-36-5) (4.35 mL, 61.05 mmol) was added dropwise to the ice-cold solution of D-Glucosamine (7512-17-6) (10.0 g) in 2-(2'-Chloroethoxy)ethanol (628-89-7) (40 mL). The mixture was stirred for 15 minutes at 4° C. and then was transferred to the oil bath at 70° C. The reaction was left mixing under cooling condenser for 4 hours. After that time, a dark brown solution was cooled down and poured into 400 mL solution of ethyl acetate and dichloromethane (3:1, v/v) in order to get rid of an excess of unreacted chloroethanol. The mixture was placed in a freezer for 30 minutes and then decanted from dark brown, sticky precipitate. The precipitate was dissolved in anhydrous ethanol and activated charcoal was added. The suspension was mixed for 1.5 hours and then filtered off through Celite and washed with ethanol. In the last step, ethanol was evaporated in vacuum to afford 1502.2A (76% yield).

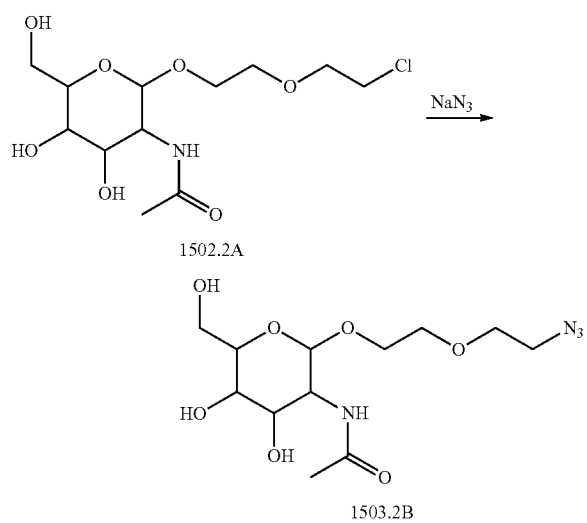

1502.2A 1503.2B 17.2B. Formula 1503 where t is 1, $R^3$ is NHAc and $R^4$ is OH; 2-(2-(2-Azidoethoxy)ethoxy)-α-NAc-Glucosamine (1503.2B).

A compound (1502.2A) (5.0 g) was dissolved in 20 mL of N,N-dimethylformamide. To that solution, sodium azide (26628-22-8) was added (5.0 g). The suspension was placed in an oil bath and stirred over night at 80° C. After the night, the reaction mixture was filtered off through Celite. The solvent was then evaporated under high pressure to provide an oily, brown substance. The final product 1503.2B was purified via flash chromatography (75.4% yield).

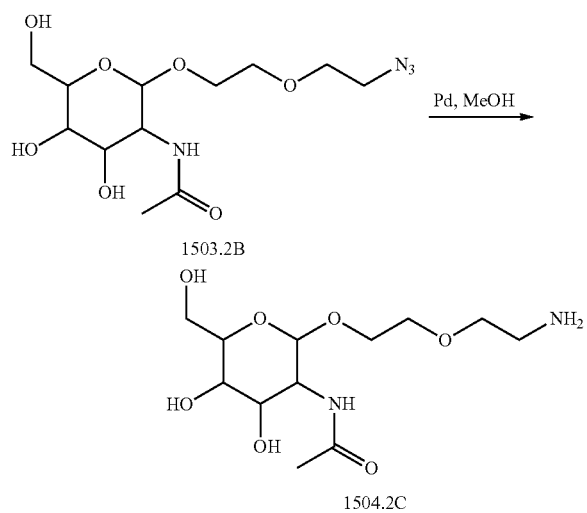 [SMILES: CC(=O)NC1C(OCCOCCN=[N+]=[N-])OC(CO)C(O)C1O ; CC(=O)NC1C(OCCOCCN)OC(CO)C(O)C1O]

1503.2B 1504.2C 17.2C. Formula 1504 where t is 1, $R^3$ is NHAc and $R^4$ is OH; 2-(2-(2-aminoethoxy)ethoxy)-α-NAc-Glucosamine (1504.2C).

A suspension of (1503.2B) (5.5 g) and 10% palladium on carbon (ca. 500 mg) in 20 mL of ethanol was hydrogenated in a Shlenk flask with an initial pressure of 2 bars of hydrogen gas. The reduction process was controlled by TLC. After 3 hours reaction was completed and the suspension was filtered through Celite to afford 1504.2C (65% yield).

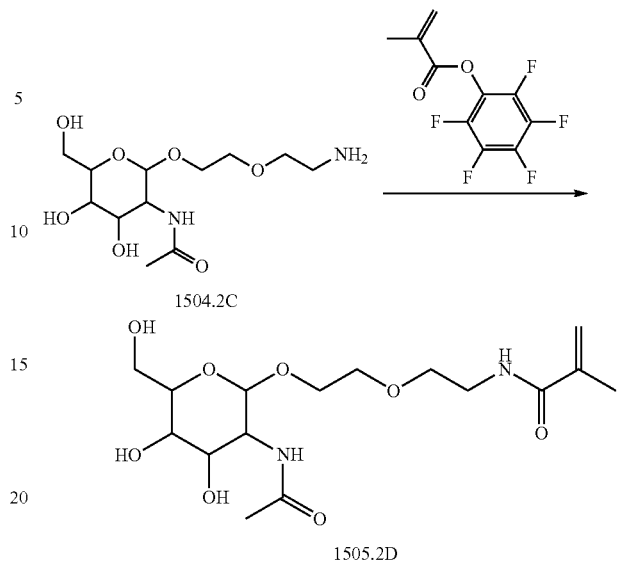

1504.2C 1505.2D 17.2D. Formula 1505 where t is 1, $R^3$ is NHAc and $R^4$ is OH; α-NAc-Glucosamine-amine-methacrylate (1505.2D).

Compound 1504.2C (4.5 g) was dissolved in 10 mL of N,N-dimethylformamide. To that solution, triethylamine (3 mL) was added and the mixture was cooled down to 4° C. Subsequently, pentafluorophenyl methacrylate (13642-97-2) (4.38 mL) was added drop-wise with constant stirring. After 30 minutes, ice-bath was removed and the reaction was allowed to stir at room temperature for the next 4 hours. Next, the solvent was evaporated and the residual was adsorbed on silica gel. The purification of crude material using flash chromatography (dichloromethane:methanol 95:5, v/v) provided 3.8g of NAc-Glucosamine monomer 1505.2D (74% yield).

Example 18

Formula 1m' where X' is OVA, m is 1-3, n is 79, p is 90 (30 $W^1$+60 $W^2$), q is 4, t is 1, $R^3$ is NHAc, $R^4$ is OH, $R^8$ is CMP, and $R^{10}$ is 2-Hydroxypropyl 18A. Formula 1109 where X' is OVA, m is 1-3 and n is 79

A solution of Formula 101' where X' is OVA (10 mg of endotoxin-free ovalbumin) in pH 7.6 PBS was added to Formula 1108 where n Is 79 (10 mg) in an endotoxin-free tube. The reaction mixture was allowed to stir at room temperature. After 1 hour, any unconjugated Formula 1108 was removed via centrifugal size exclusion chromatography to afford the corresponding product of Formula 1109, which was used without further purification.

18B. Formula 1m' where X' is OVA, m is 1-3, n is 79, p is 90, q is 4, t is 1, $R^3$ is NHAc, $R^4$ is OH, $R^8$ is CMP, and $R^{10}$ is 2-hydroxypropyl The Formula 1109 solution obtained in Example 18A was then added to Formula 1507 as obtained in Example 17E (20 mg) in an endotoxin-free tube and stirred at room temperature to afford the corresponding product of Formula 1m' ("F1m'-OVA-$m_{1-3}$-$n_{79}$-$p_{90}$-$q_4$-CMP-poly-(EtPEG$_1$AcN-1NAcGLU$_{30}$-ran-HPMA$_{60}$"), which was purified from the reaction mixture via fast protein liquid chromatography (FPLC) using a Superdex 200 prep grade column and used without further purification.

18C. Formula 1m' where X' is OVA, m is 1-3, n is 79, p is 90, q is 4, t is 1, $R^3$ is NHAc, $R^4$ is OH, $R^8$ is CMP, and $R^{10}$ is 2-hydroxypropyl, Using N-acetyl-D-galactosamine By following the procedure of Example 18B and substituting the galactosyl compound of Formula 1507 as obtained in Example 17F there was obtained the corresponding galactosyl compound of Formula 1m' ("F1m'-OVA-$m_{1-3}$-$n_{79}$-$p_{90}$-$q_4$-CMP-poly-(EtPEG$_1$AcN-1NAcGAL$_{30}$-ran-HPMA$_{60}$").

18D. Other Compounds of Formula 1m' where X' is OVA, m is 1-3, n is 79, p is 90, q is 4, t is 1, $R^3$ is NHAc, $R^4$ is OH, $R^8$ is CMP, and $R^{10}$ is 2-hydroxypropyl By following the procedures described in Example 18A, 18B and 18C and substituting OVA with the following:
Abciximab,
Adalimumab,
Agalsidase alfa,
Agalsidase beta,
Aldeslukin,
Alglucosidase alfa,
Factor VIII,
Factor IX,
L-asparaginase,
Laronidase,
Octreotide,
Phenylalanine ammonia-lyase,
Rasburicase,
GAD-65 (SEQ ID NO:2),
IGRP (SEQ ID NO:3)
MBP (SEQ ID NO:4),
MOG (SEQ ID NO:5),
PLP (SEQ ID NO:6),
MBP13-32 (SEQ ID NO:7),
MBP83-99 (SEQ ID NO:8),
MBP111-129 (SEQ ID NO:9),
MBP146-170 (SEQ ID NO:10),
MOG1-20 (SEQ ID NO:11),
MOG35-55 (SEQ ID NO:12),
PLP139-154 (SEQ ID NO:13),
MART1 (SEQ ID NO:14),
Tyrosinase (SEQ ID NO:15),
PMEL (SEQ ID NO:16),
Aquaporin-4 (SEQ ID NO:17),
S-arrestin (SEQ ID NO:18),
IRBP (SEQ ID NO:19),
Conarachin (UNIPROT Q6PSU6),
Alpha-gliadin "33-mer" native (SEQ ID NO:20),
Alpha-gliadin "33-mer" deamidated (SEQ ID NO:21),
Alpha-gliadin (SEQ ID NO:22),
Omega-gliadin (SEQ ID NO:23),
Fel d 1A (UNIPROT P30438),
Cat albumin (UNIPROT P49064),
Can f 1 (UNIPROT O18873),
Dog albumin (UNIPROT P49822), and
RhCE (UNIPROT P18577),
there are obtained the following corresponding glucosyl and galactosyl compounds of Formula 1m':
X' is Abciximab and m is 10,
X' is Adalimumab and m is 11,
X' is Agalsidase alfa and m is 14,
X' is Agalsidase beta and m is 14,
X' is Aldeslukin and m is 6,
X' is Alglucosidase alfa and m is 13,
X' is Factor VIII and m is 100,
X' is Factor IX and m is 18,
X' is L-asparaginase and m is 5,
X' is Laronidase and m is 7,
X' is Octreotide and m is 1,
X' is Phenylalanine ammonia-lyase and m is 12,
X' is Rasburicase and m is 12,
X' is GAD-65 (SEQ ID NO:2) and m is 8,
X' is IGRP (SEQ ID NO:3) and m is 7,
X' is MBP (SEQ ID NO:4) and m is 6,
X' is MOG (SEQ ID NO:5) and m is 5,
X' is PLP (SEQ ID NO:6) and m is 8,
X' is MBP13-32 (SEQ ID NO:7) and m is 1,
X' is MBP83-99 (SEQ ID NO:8) and m is 1,
X' is MBP111-129 (SEQ ID NO:9) and m is 1,
X' is MBP146-170 (SEQ ID NO:10) and m is 2,
X' is MOG1-20 (SEQ ID NO:11) and m is 1,
X' is MOG35-55 (SEQ ID NO:12) and m is 2,
X' is PLP139-154 (SEQ ID NO:13) and m is 3,
X' is MART1 (SEQ ID NO:14) and m is 4,
X' is Tyrosinase (SEQ ID NO:15) and m is 8,
X' is PMEL (SEQ ID NO:16) and m is 5,
X' is Aquaporin-4 (SEQ ID NO:17) and m is 4,
X' is S-arrestin (SEQ ID NO:18) and m is 12,
X' is IRBP (SEQ ID NO:19) and m is 21,
X' is Conarachin and m is 21,
X' is Alpha-gliadin "33-mer" native (SEQ ID NO:20) and m is 1,
X' is Alpha-gliadin "33-mer" deamidated (SEQ ID NO:21) and m is 1,
X' is Alpha-gliadin (SEQ ID NO:22) and m is 1,
X' is Omega-gliadin (SEQ ID NO:23) and m is 1,
X' is Fel d 1 and m is 4,
X' is Cat albumin and m is 16,
X' is Can f 1 and m is 6,
X' is Dog albumin and m is 23, and
X' is RhCE and m is 10.

18E. Compounds of Formulae 1h', 1i', 1j', 1k', 1L', and 1n'

By following the procedures described in Example 18B, 18C and 18D and substituting Formula 1109 with the following:
Formula 802 will afford the corresponding random copolymers of Formula 1 h',
Formula 902 will afford the corresponding random copolymers of Formula 1i',
Formula 902 made with a compound of Formula 103' will afford the corresponding random copolymers of Formula 1j',
Formula 1002 will afford the corresponding random copolymers of Formula 1 k',
Formula 1002 made with a compound of Formula 103' will afford the corresponding random copolymers of Formula 1L', and
Formula 1202 will afford the corresponding random copolymers of Formula 1n'.

18F. Other Compounds of Formulae 1h', 1i', 1j', 1k', 1L', 1m' and 1n'

By following the procedures described in Example 18B, 18C, 18D and 18E, and substituting Formula 1507 with the compounds prepared as described in Examples 17G, 17H and 17I, there are obtained the corresponding compounds of Formulae 1h', 1i', 1j', 1k', 1L', 1m' and 1n' where t is other than 1, having a plurality of t groups, and having a mixture of glucosyl and galactosyl moieties.

Example 19

Formula 1c' where X" is Insulin-B, m is 1, n is 4, p is 90 (30 $W^1$+60 $W^2$), t is 1, $R^3$ is NHAc, $R^4$ is OH, $R^8$ is CMP, and $R^{10}$ is 2-hydroxypropyl 19A. Formula 1602 where n is 4, p is 90, t is 1, $R^3$ is NHAc, $R^4$ is OH, $R^8$ is CMP, and $R^{10}$ is 2-hydroxypropyl A 25 ml Schlenk flask was charged with ((2S,3S,4S,5R,6S)-4,5-dihydroxy-6-(hydroxymethyl)-2-(2-(2-methacrylamidoethoxy)ethoxy)tetrahydro-2H-pyran-3-yl)carbamic acid (272 mg, 0.72 mmol) (Formula 1505, prepared, for example, as described in Example 17D), HPMA (211 mg, 1.47 mmol) (Formula 1506), a dithio-pyridyl functionalized uRAFT agent of Formula 1601 where n is 4 and $R^8$ is CMP (12.5 mg, 0.0217 mmol), azobis(isobutyronitril) (0.98 mg, 0.005 mmol), and 1.2 ml dimethylformamide. The reaction mixture was subjected to four freeze-pump-thaw degassing cycles then stirred at 70° C. for 20 hours. The corresponding random polymeric product of Formula 1602 (having about 30 $W^1$ groups and about 60 $W^2$ groups) was recovered by precipitating the reaction mixture in acetone. Excess acetone was removed at reduced pressure to provide the random polymeric product, which was used without further purification.

19B. Formula 1c' where X" is Insulin-B, m is 1, n is 4, p is 90 (30 $W^1$+60 $W^2$), t is 1, $R^3$ is NHAc, $R^4$ is OH, $R^8$ is CMP, and $R^{10}$ is 2-hydroxypropyl The Formula 1602 solution obtained in Example 19A (20 mg) was suspended in 200 µl of dimethylformamide and added to an endotoxin-free tube containing Insulin-B (1 mg) and stirred at room temperature for 3 hours to afford the corresponding product of Formula 1c' ("F1c'-Insulin-B-$m_1$-$n_4$-$p_{90}$-CMP-poly-(EtPEG$_1$AcN-1NAcGLU$_{30}$-ran-HPMA$_{60}$"). The reaction mixture was then precipitated in acetone and purified from the reaction mixture via fast protein liquid chromatography (FPLC) using a Superdex 200 prep grade column and used without further purification.

19C. Formula 1c' where X" is Insulin-B, m is 1, n is 4, p is 90 (30 $W^1$+60 $W^2$), t is 1, $R^3$ is NHAc, $R^4$ is OH, $R^8$ is CMP, and $R^{10}$ is 2-hydroxypropyl, Using N-acetyl-D-galactosamine By following the procedure of Examples 19A and 19B and substituting ((2S,3S,4S,5S,6S)-4,5-dihydroxy-6-(hydroxymethyl)-2-(2-(2-methacrylamidoethoxy)ethoxy)tetrahydro-2H-pyran-3-yl)carbamic acid for Formula 1505, there was obtained the corresponding galactosyl compound of Formula 1c' ("F1c'-Insulin-B-$m_1$-$n_4$-$p_{90}$-CMP-poly-(EtPEG$_1$AcN-1NAcGAL$_{30}$-ran-HPMA$_{60}$").

19D. Formula 1c' where X" is P31, m is 1, n is 4, p is 90 (30$W^1$+ 60 $W^2$), t is 1, $R^3$ is NHAc, $R^4$ is OH, $R^8$ is CMP, and $R^{10}$ is 2-hydroxypropyl By following the procedure of Examples 19B and 19C and substituting 20 mg of P31 for Insulin-B, there were obtained the corresponding glucosyl and galactosyl compounds of Formula 1c' where X" is P31.

19E. Compounds of Formulae 1f' and 1g'

By following the procedures of Examples 19A and 19B and substituting the uRAFT agent of Formula 1601 with a uRAFT agent of Formulae 600' or 700' there are obtained the corresponding compounds of Formulae 601' or 701', which are in turn contacted with a compound of Formula 101' to afford the corresponding compound of Formula 1f' or Formula 1g', respectively.

Example 20

OT-1 Challenge-to-Tolerance Model

20A.

As discussed above in Example 14, F1aA-OVA-$m_4$-$n_8$ and F1b-OVA-$m_1$-$n_4$-$p_{34}$ mitigated an OVA-specific immune response after adjuvented OVA challenge.

20B.

A total of 3×10$^5$ CFSE-labeled OTI CD8+ T cells and 3×10$^5$ CFSE-labeled OTII CD4+ T cells were injected into CD45.1+ recipient mice. At 1 and 6 days following adoptive transfer, mice were i.v. administered saline solutions containing OVA, F1m'-OVA-$m_{1-3}$-$n_{79}$-$p_{90}$-$q_4$-CMP-poly-(EtPEG$_1$AcN-1NAcGAL$_{30}$-ran-HPMA$_{60}$ ["OVA-p(Gal-HPMA)"], F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ ["OVA-p(Glu-HPMA)"], or saline alone. Each mouse treated with formulations containing OVA in its free or conjugated form, received the molar equivalent of 20 µg OVA. At 15 d following adoptive transfer, mice were challenged with 5 µg of OVA and 25 ng of ultrapure E. coli LPS (InvivoGen) in 25 µL of saline injected intradermally into each rear leg pad (Hock method: total dose of 10 µg of OVA and 50 ng of LPS). Mice were sacrificed 4 days following challenge, and spleen and draining lymph node cells were isolated for restimulation. For flow cytometry analysis of intracellular cytokines, cells were restimulated in the presence of 1 mg/mL OVA or 1 µg/mL SIINFEKL peptide (Genscript) for 3 h. Brefeldin-A (5 µg/mL; Sigma) was added, and restimulation was resumed for an additional 3 h before staining and flow cytometry analysis.

As shown in FIGS. 8A-8B, the administration of OVA-p(Gal-HPMA) and OVA-p(Glu-HPMA) resulted in significant reduction in the percentages of OT-I cells (out of the total CD8+ T-cell population) and OT-II cells (out of the total CD4+ T-cell population). FIG. 8A shows that OVA-p(Gal-HPMA) and OVA-p(Glu-HPMA) administration significantly reduced OT-I cells as compared to mice receiving repeat administrations of OVA alone (e.g., unconjugated). Reduction was even greater when compared to mice receiving only OVA and LPS challenge (e.g., that received saline injections). Notably, the reduction resulting from treatment with OVA-p(Gal-HPMA) and OVA-p(Glu-HPMA) reduced OT-I cell levels to levels not significantly different from naïve mice. Similarly, as shown in FIG. 8B, OVA-p(Gal-HPMA) and OVA-p(Glu-HPMA) administration resulted in significant reduction in OT-II cells as compared to mice receiving unconjugated OVA or challenge alone. These data indicate that the production of cells that are specifically designed to react when encountering OVA as an antigen decreases, indicative of a reduction in immune response to OVA.

Additionally, the administration of OVA-p(Gal-HPMA) and OVA-p(Glu-HPMA) resulted in significant increases in antigen-specific regulatory T-cells in the lymph node and spleen of mice. As shown in FIG. 9A, treatment with either of these conjugates induced significant increases in CD25+/FoxP3+ cells in the lymph node. Likewise, FIG. 9B shows significant increases (vs. naïve, challenge (saline alone), and OVA treated animals) in CD25+/FoxP3+OT-II cells. These data indicate that regulatory T cell production is upregulated, which in turn, indicates that the immune system is negatively modulated with respect to its response to OVA (e.g., less responsive, or more tolerant).

Further building on the above data showing the increased tolerance to an antigen after delivery of that antigen complex with a liver targeting moiety is the data shown in FIG. 10. In this experiment, the percentage of cells expressing interferon gamma (IFNγ) was measured. IFNγ is produced by CD4 and CD8 T cells after antigen-specific immunity develops. As shown in FIG. 10, mice receiving only saline pre-challenge have approximately 60% of the total OTI cells expressing IFNγ. In contrast, OVA-treated mice have about 40% IFNγ-expressing cells. Nearly the same as naïve mice, the OTI cells of OVA-p(Gal-HPMA) and OVA-p(Glu- HPMA)-treated mice have less than 20% IFNγ positive cells. This significant reduction in IFNγ indicates a reduction in the mechanisms that drive antigen-specific immunity. Collectively, and in view of the additional disclosure herein, these data demonstrate that targeting an antigen to the liver can reduce the antigen-specific immune response to that antigen. In particular, targeting with glucose or galactose results in significant shifts in the cell populations responsible for antigen-specific immunity, that shift demonstrating a tolerance to the specific antigen.

20C.

By following the procedures described in Example 20A or 20B and substituting the tested OVA compositions with other compositions of Formula 1 followed by challenge with the unconjugated antigen X, the treated animals demonstrate a tolerance to the specific antigen X.

Example 21

OTI/OTII Challenge to Tolerance Model

Using the model of Example 20, additionally with OTII cells (which are CD4$^+$ T cells from CD45.2$^+$ mice, analogous to the CD8$^+$ T cell OTI cells), the ability of F1m'-OVA-$m_{1-3}$-$n_{79}$-$p_{90}$-$q_4$-CMP-poly-(EtPEG$_1$AcN-1NAc-GAL$_{30}$-ran-HPMA$_{60}$ ["OVA-p(Gal-HPMA)"] and F1m'-OVA-$m_{1-3}$-$n_{79}$-$p_{90}$-$q_4$-CMP-poly-(EtPEG$_1$AcN-1NAcGLU$_{30}$-ran-HPMA$_{60}$ ["OVA-p(Glu-HPMA)"] to induce T regulatory responses and prevent subsequent responses to vaccine-mediated antigen challenge were demonstrated, moreover using different dosing regimens. $3\times10^5$ CFSE-labeled OTI and $3\times10^5$ CFSE-labeled OTII cells were adoptively transferred to CD45.1$^+$ mice (n=8 mice per group) on day 0. On days 1, 4 and 7, tolerogenic doses or control doses were administered. In one regimen, OVA was provided at a dose of 2.5 µg at day 1, 2.5 µg at day 4, and 16 µg at day 7. In another, OVA was provided at a dose of 7 µg at day 1, 7 µg at day 4, and 7 µg at day 7, for the same total dose. Likewise, pGal-OVA and pGlu-OVA were each administered in other groups at the same dosings of 2.5 µg at day 1, 2.5 µg at day 4, and 16 µg at day 7 or 7 µg at day 1, 7 µg at day 4, and 7 µg at day 7, all doses being on an OVA equivalent dose basis. In a final group, saline was administered on the same days. On day 14, the recipient mice were then challenged with OVA (10 µg) adjuvanted with lipopolysaccharide (50 ng) by intradermal injection. Characterization of the draining lymph nodes was done on day 19, to allow determination as to whether or not deletion actually took place and whether regulatory T cells were induced from the adoptively transferred cells.

Profound tolerance was induced in the CD4+ T cell compartment, as shown in FIGS. 11A-11B. In terms of total cell frequencies, both dosing regimens of both OVA-p(Gal-HPMA) and OVA-p(Glu-HPMA) resulted in equivalent low levels of OTII cells after challenge, statistically lower than by treatment of OVA (* and # indicate p<0.05, ** and ## indicate p<0.01), as shown in FIG. 11A. When the cells that remained were analyzed by flow cytometry for the presence of the transcription factor FoxP3 and the receptor CD25, the numbers of FoxP3+CD25+ cells (markers of T regulatory cells) was statistically significantly elevated compared to treatment with OVA alone, as shown in FIG. 11B. Here, the number of T regulatory cells was statistically higher with the 2.5 µg/2.5 µg/16 µg dosing regimen compared to the 7 µg/7 µg/7 µg dosing regimen, with both OVA-p(Gal-HPMA) and OVA-p(Glu-HPMA) treatment.

Profound tolerance was also induced in the CD8+ T cell compartment, as shown in FIGS. 12A-12B. In terms of total cell frequencies, both dosing regimens of both OVA-p(Gal-HPMA) and OVA-p(Glu-HPMA) resulted in equivalent low levels of OTI cells after challenge, statistically lower than by treatment of OVA (* and # indicate p<0.05, ** and ## indicate p<0.01), as shown in FIG. 12A. When the cells that remained were analyzed by flow cytometry for the expression of IFN-γ after re-exposure to OVA antigen, the frequency of cells expressing this inflammatory cytokine was decreased in the groups receiving the 2.5 µg/2.5 µg/16 µg dosing regimen compared to the 7 µg/7 µg/7 µg dosing regimen, with both OVA-p(Gal-HPMA) and OVA-p(Glu-HPMA) treatment, as shown in FIG. 12B.

Example 22

BDC2.5 Study

22A.

CD4+ T-cells of the transgenic NOD-BDC2.5 mice express the diabetogenic BDC-2.5 specific regulatory T-cell receptor (TCR). BDC2.5 T-cells specifically target the islet beta-cell autoantigen, chromogranin-A. T-cells were isolated from the spleens of transgenic NOD-BDC2.5 mice and cultured for 4 days in DMEM supplemented with 10% (vol/vol) FBS, 0.05 mM β-mercaptoethanol, 1% puromycin/streptomycin, and 0.5 µM P31 peptide, a mimotope of islet beta-cell autoantigen chromogranin-A that stimulates T-cells expressing the BDC2.5 T-cell receptor. Following stimulation with P31, cells were washed with basal DMEM and analyzed for purity by flow cytometry, and $5\times10^6$ T-cells were i.v. injected into normoglycemic NOD/ShiLtJ mice. At 8 h and 3 days after adoptive transfer, mice were i.v. administered saline, 10 µg F1c'-P31-$m_1$-$n_4$-$p_{90}$-CMP-poly-(EtPEG$_1$AcN-1NAcGLU$_{30}$-ran-HPMA$_{60}$, 10 µg F1c'-P31-$m_1$-$n_4$-$p_{90}$-CMP-poly-(EtPEG$_1$AcN-1NAcGAL$_{30}$-ran-HPMA$_{60}$, or an equimolar dose of P31 peptide. Starting on day 4, diabetes onset was monitored by measuring nonfasting blood glucose levels using an AccuCheck Aviva glucometer (Roche). Mice were considered diabetic at blood glucose readings ≥300 mg/dL. After two hyperglycemic readings, mice were euthanized. The data resulting from this experiment is shown in the time course of FIG. 13. As shown, the mice receiving saline developed diabetic blood glucose levels within 4-8 days of adoptive transfer. Similarly, mice receiving P31 (unconjugated) developed diabetic blood glucose levels within about 7-10 days after transfer. In stark contrast, mice receiving F1c'-P31-$m_1$-$n_4$-$p_{90}$-CMP-poly-(EtPEG$_1$AcN-1NAcGLU$_{30}$-ran-HPMA$_{60}$ or F1c'-P31-$m_1$-$n_4$-$p_{90}$-CMP-poly-(EtPEG$_1$AcN-1NAcGAL$_{30}$-ran-HPMA$_{60}$ maintained relatively steady blood glucose values (<200 mg/dl) for over 40 days.

22B.

By following the procedures described in Example 21A and substituting the tested compositions with other compositions of Formula 1 where X is Insulin-B or proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein and SST G-protein coupled receptors 1-5, such as F1aA-Insulin-$m_2$-$n_{80}$, F1aA-Insulin-$m_2$-$n_{12}$, F1aA-Insulin-$m_2$-$n_{33}$, F1aA-Insulin-$m_2$-$n_{40}$, F1aA-Insulin-$m_2$-$n_{43}$, F1aA-Insulin-$m_2$-$n_{50}$, F1aA-Insulin-$m_2$-$n_{60}$, F1aA-Insulin-$m_2$-$n_{75}$, F1aA-Insulin-$m_2$-$n_{84}$, F1b-Insulin-$m_2$-$n_4$-$p_{34}$-2NAcGAL, F1m-Insulin-$m_2$-$n_{80}$-$p_{30}$-$q_4$-CMP-2NHAc, F1m-Insulin-$m_2$-$n_{62}$-$p_{30}$-$q_8$-CMP-2OH, F1n-insulin-$m_2$-$n_1$-$p_{30}$-$q_4$-CMP-2NHAc, F1c'-Insulin-B-$m_1$-$n_4$-$p_{90}$-CMP-poly-(EtPEG$_1$AcN-1NAcGLU$_{30}$-ran-HPMA$_{60}$ or F1c'-Insulin-B-$m_1$-$n_4$-$p_{90}$-CMP-poly-(EtPEG$_1$AcN-1NAcGAL$_{30}$-ran-HPMA$_{60}$ the blood glucose values in the treated NOD mice remain steady as compared to animals that receive saline.

Example 23

NOD Mouse

23A.

Non-obese diabetic (NOD) mice, such as NOD/ShiLt mice are susceptible to the spontaneous onset of autoimmune diabetes mellitus, which is the result of an autoimmune response to various pancreatic auto-antigens. Diabetes develops in NOD mice as a result of insulitis, characterized by the infiltration of various leukocytes into the pancreatic islets. As diabetes develops, there is a leukocytic infiltration of the pancreatic islets followed by significant decreases in insulin production, and corresponding increases in blood glucose levels.

In order to evaluate the efficacy of a treatment for diabetes mellitus, compositions and methods for the treatment being provided in the present disclosure, starting at 5 weeks of age diabetes onset in a cohort of NOD/ShiLt mice was monitored on a weekly basis by measuring nonfasting blood glucose levels using an AccuCheck Aviva glucometer (Roche). Starting at 6 weeks of age, the mice were divided into control and test groups (n=15 for each group) and treated, respectively, with weekly intravenous injections of saline, 10 µg of F1c'-Insulin-B-$m_1$-$n_4$-$p_{90}$-CMP-poly-(EtPEG$_1$AcN-1NAcGLU$_{30}$-ran-HPMA$_{60}$, or 10 µg of F1c'-Insulin-B-$m_1$-$n_4$-$p_{90}$-CMP-poly-(EtPEG$_1$AcN-1NAcGLU$_{30}$-ran-HPMA$_{60}$ (10 µg). The injections continued for 10 consecutive weeks. The percentage of diabetes free animals was measured over time. Mice were considered diabetic at two consecutive blood glucose readings ≥300 mg/dL or one blood glucose readings ≥450 mg/dL. Mice deemed diabetic were euthanized.

FIG. 14 depicts the data obtained as described above as the percentage of diabetes free animals as measured over time. Mice treated with F1c'-Insulin-B-$m_1$-$n_4$-$p_{90}$-CMP-poly-(EtPEG$_1$AcN-1NAcGLU$_{30}$-ran-HPMA$_{60}$ are shown as filled squares. Mice treated with F1c'-Insulin-B-$m_1$-$n_4$-$p_{90}$-CMP-poly-(EtPEG$_1$AcN-1NAcGAL$_{30}$-ran-HPMA$_{60}$ are shown as filled triangles. Mice treated with saline are shown as filled diamonds. As can readily be appreciated from the data collected from the saline treated animals over time as early as 11 weeks of age, spontaneous diabetes was present. Prevalence increased over time (shown by the downward trend in the graph) with 60% of the tested animals developing diabetes by week 20. As shown in FIG. 14, treating NOD mice with either F1c'-Insulin-B-$m_1$-$n_4$-$p_{90}$-CMP-poly-(EtPEG$_1$AcN-1NAcGLU$_{30}$-ran-HPMA$_{60}$ or F1c'-Insulin-B-$m_1$-$n_4$-$p_{90}$-CMP-poly-(EtPEG$_1$AcN-1NAcGAL$_{30}$-ran-HPMA$_{60}$ reduced the incidences of diabetes onset in NOD mice as compared to animals that received saline. The data demonstrate that administration of insulin coupled with linkers and liver targeting moieties as disclosed herein can successfully reduce the development of type I diabetes mellitus by reducing the autoimmune response to the various pancreatic autoantigens produced.

23B.

By following the procedures described in Example 22A and substituting the tested compositions with other compositions of Formula 1 where X is Insulin-B or proinsulin, preproinsulin, glutamic acid decarboxylase-65 (GAD-65 or glutamate decarboxylase 2), GAD-67, glucose-6 phosphatase 2 (IGRP or islet-specific glucose 6 phosphatase catalytic subunit related protein), insulinoma-associated protein 2 (IA-2), and insulinoma-associated protein 2β (IA-2β), ICA69, ICA12 (SOX-13), carboxypeptidase H, Imogen 38, GLIMA 38, chromogranin-A, HSP-60, caboxypeptidase E, peripherin, glucose transporter 2, hepatocarcinoma-intestine-pancreas/pancreatic associated protein, S100β, glial fibrillary acidic protein, regenerating gene II, pancreatic duodenal homeobox 1, dystrophia myotonica kinase, islet-specific glucose-6-phosphatase catalytic subunit-related protein and SST G-protein coupled receptors 1-5, such as F1aA-Insulin-$m_2$-$n_{80}$, F1aA-Insulin-$m_2$-$n_{12}$, F1aA-Insulin-$m_2$-$n_{33}$, F1aA-Insulin-$m_2$-$n_{40}$, F1aA-Insulin-$m_2$-$n_{43}$, F1aA-Insulin-$m_2$-$n_{50}$, F1aA-Insulin-$m_2$-$n_{60}$, F1aA-Insulin-$m_2$-$n_{75}$, F1aA-Insulin-$m_2$-$n_{84}$, F1b-Insulin-$m_2$-$n_4$-$p_{34}$-2NAcGAL, F1m-Insulin-$m_2$-$n_{80}$-$p_{30}$-$q_4$-CMP-2NHAc, F1m-Insulin-$m_2$-$n_{62}$-$p_{30}$-$q_8$-CMP-2OH, F1n-insulin-$m_2$-$n_1$-$p_{30}$-$q_4$-CMP-2NHAc, F1c'-P31-$m_1$-$n_4$-$p_{90}$-CMP-poly- (EtPEG$_1$AcN-1NAcGLU$_{30}$-ran-HPMA$_{60}$ or F1c'-P31-$m_1$-$n_4$-$p_{90}$-CMP-poly-(EtPEG$_1$AcN-1NAcGAL$_{30}$-ran-HPMA$_{60}$ the incidences of diabetes onset in the treated NOD mice are reduced as compared to animals that receive saline.

Example 24

Biodistribution

In order to examine the biodistribution of antigen glycopolymer conjugates we treated BALB/c mice with fluorescently labeled OVA or fluorescently-labeled OVA conjugated to either p(Gal-HPMA), p(Glu-HPMA), p(Galβ-HPMA), or p(Gluβ-HPMA). The sugar moieties attached to the backbone of p(Gal-HPMA) and p(Glu-HPMA) are attached to the polymer in the α-conformation at the C1 position, whereas the sugars attached to the backbone of p(Galβ-HPMA) and p(Gluβ-HPMA) are attached to the polymer in the β-conformation at the C1 position. OVA was labeled with Dy750. All treatments were given via tail vein injection in 140 µl. Each animal was treated with an equal amount of fluorescent conjugate on a fluorescence unit basis. After 3 hours, the animals were euthanized and the livers of each animal were perfused with saline, then both the livers and spleens were harvested and imaged via an IVIS Spectrum system with appropriate filter set.

FIG. 15 depicts representative images of the fluorescent signals of livers (A) and spleens (B) from animals treated with OVA or OVA glycopolymer conjugates. The formulations are as follows: 1. OVA, 2. F1m'-OVA750-$m_{1-3}$-$n_{79}$-$p_{90}$-$q_4$-CMP-poly-(EtPEG$_1$AcN-1NAcGALβ$_{30}$-ran-HPMA$_{60}$) ["OVA-p(Galβ-HPMA)"], 3. F1m'-OVA750-$m_{1-3}$-$n_{79}$-$p_{90}$-$q_4$-CMP-poly-(EtPEG$_1$AcN-1NAcGAL$_{30}$-ran-HPMA$_{60}$) ["OVA-p(Gal-HPMA)"], 4. F1m'-OVA750-$m_{1-3}$-$n_{79}$-$p_{90}$-$q_4$-CMP-poly-(EtPEG$_1$AcN-1NAcGLUβ$_{30}$-ran-HPMA$_{60}$) ["OVA-p(Gluβ-HPMA)"], 5. F1m'-OVA750-$m_{1-3}$-$n_{79}$-$p_{90}$-$q_4$-CMP-poly-(EtPEG$_1$AcN-1NAcGLU$_{30}$-ran-HPMA$_{60}$) ["OVA-p(Glu-HPMA)"]. Images of the livers from animals treated as described above show that glycopolymer conjugates significantly enhance the delivery of their conjugated antigen to the liver (or spleen) as compared to the uptake of unconjugated antigens. Livers from animals treated with unconjugated OVA have less fluorescent signal as compared to livers from animals treated with OVA conjugated to either p(Gal-HPMA), p(Glu-HPMA), p(Galβ-HPMA), or p(Gluβ-HPMA). Additionally, images of the spleens taken from animals treated as described above show that conjugating antigens to glycopolymers reduces the delivery of antigens to the spleen. Spleens from animals treated with unconjugated OVA have significantly more fluorescent signal as compared to spleens from animals treated with OVA conjugated to either p(Gal-HPMA), p(Glu-HPMA), p(Galβ-HPMA), or p(Gluβ-HPMA). These data are significant in that they demonstrate enhanced targeting of an antigen to which tolerance is desired to the liver and/or spleen, which, as demonstrated by the experimental data presented herein results in reduced immune response (i.e., induced tolerance) to the antigen. In accordance with several embodiments disclosed herein, this induced tolerance can treat, reduce, prevent, or otherwise ameliorate an unwanted immune response that would have otherwise been associated with exposure to the antigen.

Example 25

7-Day OTI/OTII Phenotype Analysis

In order to compare the ability of various glycopolymer-antigen conjugates to induce antigen-specific T cell proliferation as well as upregulate the expression and presentation of various markers of T cell anergy and deletion, mice that had received an infusion of 400,000 carboxyfluorescein succinimidyl ester (CSFE)-labeled OTI cells were treated with an intravenous injection of either OVA or OVA conjugated to either p(Gal-HPMA), p(Glu-HPMA), p(Galβ-HPMA), or p(Gluβ-HPMA) (with formulations as follows: F1m'-OVA-$m_{1-3}$-$n_{79}$-$p_{90}$-$q_4$-CMP-poly-(EtPEG$_1$AcN-1NAcGAL$_{30}$-ran-HPMA$_{60}$) ["OVA-p(Gal-HPMA)"]; F1m'-OVA-$m_{1-3}$-$n_{79}$-$p_{90}$-$q_4$-CMP-poly-(EtPEG$_1$AcN-1NAc-GLU$_{30}$-ran-HPMA$_{60}$) ["OVA-p(Glu-HPMA)"]; F1m'-OVA-$m_{1-3}$-$n_{79}$-$p_{90}$-$q_4$-CMP-poly-(EtPEG$_1$AcN-1NAcGALβ$_{30}$-ran-HPMA$_{60}$) ["OVA-p(Galβ-HPMA)"]; F1m'-OVA-$m_{1-3}$-$n_{79}$-$p_{90}$-$q_4$-CMP-poly-(EtPEG$_1$AcN-1NAcGLUβ$_{30}$-ran-HPMA$_{60}$) ["OVA-p(Gluβ-HPMA)"]. Animals treated with OVA in either its free or conjugated form received 10 μg of OVA on day 1 and day 3 of the experiment. A timeline of the experimental details is shown in FIG. 16A. After 7 days, the mice were sacrificed and the splenocytes of the animals were harvested and analyzed via flow cytometry for phenotypical markers characteristic of T cell anergy, deletion, and memory.

FIG. 16B shows that OVA-glycopolymer conjugates induce more OTI T cell proliferation as compared to the amount of OTI proliferation seen in animals treated with unconjugated OVA. As discussed above, these data further support that, according to several embodiments disclosed herein, the glyoctargeting moieties disclosed herein result in increased antigen-specific T-cell proliferation—a key step in inducing tolerance to an antigen. Interestingly, animals treated with OVA-glycopolymer conjugates containing β-linked sugars induced significantly more proliferation compared to animals treated with glycopolymers containing the same sugar moiety linked to the polymer via an α-linkage (e.g., p(Galβ-HPMA) vs. p(Gal-HPMA)). Unexpectedly, this conformational change in one element of the overall composition leads to an enhanced efficacy in terms of T-cell proliferation, which Applicant believes (without being bound by theory) results from synergistic interaction of the components of the composition with their respective physiological targets. Additionally, the population of OTI cells taken from animals treated with all OVA-glycopolymer conjugates, with the exception of OVA-p(Gal-HPMA), showed significantly more surface expression of the apoptosis marker Annexin V+ as compared to the cells taken from animals treated with OVA (see FIG. 16C). Consistent with data discussed above, this indicates a greater percentage of antigen-specific T cells are being targeted for, or are in, the apoptotic cascade. As shown in FIG. 16D, OTI cells taken from animals treated with OVA-glycopolymer conjugates containing β-linked sugars showed an increased expression of the T cell exhaustion marker PD-1 as compared to animals treated with glycopolymers containing the same sugar moiety linked to the polymer via an α-linkage as well as animals treated with free OVA. In order to maintain long-term tolerance, treatments must reduce the number of long-lasting antigen-specific memory T cells. FIGS. 16E and 16F show that both OVA-p(Galβ-HPMA) and OVA-p(Gluβ-HPMA) induce a significant reduction in OTI cells expressing markers for memory T cells. Both OVA-p(Galβ-HPMA) and OVA-p(Gluβ-HPMA) induce a five-fold decrease in the number of memory T cells compared to animals treated with free OVA. These data further indicate that compositions as disclosed herein can induce tolerance to an antigen (OVA chosen here due to its general acceptance in the field as a "gold standard" antigen), and in several embodiments, can unexpectedly enhance the induction of tolerance (as represented at least in part by antigen-specific T cell proliferation, increased Annexin V expression on antigen-specific T cells, increased exhaustion marker expression on antigen-specific T cells, and reduced expression of memory T cells).

Example 26

Glucose-Coupled Antigens—BDC2.5 Study

This experiment was conducted to test the ability of p(Glu)-antigen conjugates to inhibit the development of CD4 T cell driven auto immunity. A mouse model of antigen-specific T cell induced autoimmune diabetes was used. Autoimmune diabetes was induced by transferring activated BDC2.5 T cells, which carry a T cell receptor for the diabetic autoantigen chromogranin A, into immune compromised mice. Recipient mice were then treated with an autoantigen peptide mimotope, termed p31, or with the p31-p(Glu) conjugates.

Protocol: Freshly isolated splenocytes from female BDC2.5 transgenic mice were stimulated for 4d in DMEM supplemented with 10% FBS, 0.05 mM β-mercaptoethanol, 1% puromycin/streptomycin, and 0.5 μM p31 peptide. Following stimulation, cells were washed with DMEM, resuspended in DMEM, and injected intravenously into normoglycemic NOD/Scid mice. At 8 h following adoptive transfer, mice were intravenously administered saline (naïve), 2 μg of p31, or 2 μg of p31 as p31-pGlu conjugates (glucose in the beta conformation was used in this experiment, though in several embodiments the alpha conformation can be used). Three days after the initial treatment, mice were treated again with saline, 2 μg of p31, or 2 μg of p31 as p31-pGlu conjugates. Starting on day 1, the nonfasting blood glucose levels of each mouse were measured using an Accucheck Aviva glucometer. Mice were considered diabetic upon receiving a single blood sugar measurement over 450 mg/dL, or two consecutive blood sugar readings of over 350 mg/dL. All groups had 7 mice.

Results: As shown in FIG. 17, naïve mice began to develop diabetes (as measured by hyperglycemia) within 5 days of the splenocyte transfer. Within about 7 days, all of the naïve mice developed hyperglycemia. Those mice treated with the control composition (p31; filled circles) began to develop hyperglycemia shortly after the naïve mice. By 8 days post-transfer, all of the p31-treated mice had developed hyperglycemia. In stark contrast, administration of p31-p(Glu) conjugates (filled triangles) results in mice that maintain normal blood glucose levels for a significantly longer period of time as compared to naïve animals and those treated with the p31 peptide alone. At 15 days post-transfer, 100% of the p31-pGlu mice still had normal blood glucose levels.

These results demonstrate that p31-p(Glu) conjugates prevent the development of hyperglycemia in mice. Thus, according to several embodiments disclosed herein, such conjugates are efficacious for use in preventing development of diabetes. In still additional embodiments, p(Glu) conjugates are efficacious for use in reducing advancement of pre-existing diabetes, and in still additional embodiments, efficacious for use in reversing pre-existing diabetes. In additional embodiments, other mimotopes of islet beta-cell autoantigen chromogranin-A can be used. Further, chromogranin-A, as a full-length protein, or fragments thereof can be employed as the antigenic portion of the tolerogenic compositions, according to several embodiments disclosed herein. Additionally, other antigens disclosed herein related to diabetes can be used, in some embodiments, including but not limited to insulin, proinsulin, preproinsulin, GAD-65, GAD-67, IGRP, IA-2, IA-2β, fragments thereof, or mimotopes thereof. Other diabetes related antigens are disclosed herein. Further, in several embodiments, antigens related to other autoimmune diseases can be used, as is disclosed herein. In still additional embodiments, foreign antigens, transplant antigens or other types/classifications may be used, as chromogranin A was employed here, and using this model as a non-limiting example of the ability of compositions as disclosed herein to be used in the induction of tolerance.

Example 27

Memory of Tolerance

The following experiment was conducted to demonstrate that tolerogenic compositions as disclosed herein can establish memory of tolerance. In order to determine if regulatory T cells (Tregs) induced by administration of tolerogenic compositions as disclosed herein (p(Glu)-antigen conjugates were used here as a non-limiting example) are able to establish long term tolerance after the initial administration of the therapies, mice were pre-treated with an infusion of OTII T cells followed by administration of p(Glu)-OVA conjugates. These mice were then were challenged three weeks later with an infusion of OVA-specific T cells and antigen challenge. To demonstrate that any tolerance inducing effect was the result of Tregs, mice treated with p(Glu)-OVA were injected with an anti-CD25 antibody, which has been shown to deplete Tregs.

Protocol: On day zero, C57BL/6 mice received an intravenous infusion of 450,000 OTII cells, then were treated on days 1 and 4 with saline or 1.5 µg of OVA as free OVA or p(Glu)-OVA conjugates (OVA is used herein as a non-limiting example of an antigen to which tolerance is desired; glucose in the beta conformation was used in this experiment, though in several embodiments the alpha conformation can be used). On day 7, mice received a final treatment of saline, or 15 µg of OVA as free OVA or p(Glu)-OVA conjugates. On day 15, half of the animals treated with p(Glu)-OVA were treated with an intraperitoneal injection of 300 µg of anti-CD25 antibody, which has been shown to deplete regulatory T cells (Tregs). On day 29, mice received an infusion of 750,000 OTII T cells and 750,000 OTI T cells. The next day, animals were challenged with 5 µg of OVA and 50 ng of ultrapure LPS in each of the 4 footpads. Five days after antigen challenge, the mice were sacrificed and the number of OTI and OTII T cells in the draining lymph nodes was assessed by flow cytometry. (Groups n=5: Challenge (i.e. vehicle treated animals), OVA, p(Glu)-OVA, p(Glu)-OVA+αCD25). This protocol is schematically depicted in FIG. 18.

Results: The results of this experiment are shown in FIGS. 19A-19B. FIG. 19A depicts the remaining OTI T cells after antigen challenge (as a percentage of total $CD8^+$ cells). FIG. 19B depicts the remaining OTII T cells after antigen challenge (as a percentage of total $CD4^+$ cells). Those mice receiving LPS challenge and OVA absent a tolerogenic composition showed significantly elevated OTI and OTII cells in draining lymph nodes. Those mice receiving pGlu-OVA showed a significant reduction in both OTI and OTII cells. The abrogation of the tolerance induced by pGlu-OVA by the administration of anti-CD25 antibodies demonstrates that there is a role for Tregs in the pGlu-OVA-induced tolerance. Taken together, these data indicate that the tolerogenic compositions disclosed herein are able to induce long-lasting tolerance through the induction of regulatory T cells. This is advantageous, in several embodiments, because the long-lasting tolerance reduces (or in some embodiments eliminates) the need for ongoing administration of the compositions disclosed herein. That being said, in some embodiments, repeated administration is optionally performed.

Example 28

Memory of Tolerance (Endogenous)

The following experiment was conducted to demonstrate that tolerogenic compositions as disclosed herein can establish memory of tolerance from endogenous T cells. This experiment was conducted similarly to Example 27, but the mice did not receive the initial infusion of donor OTII T cells.

In order to determine if Tregs from the endogenous T cell population could be induced by p(Glu)-antigen conjugates and exhibit long-term tolerance, mice were treated with p(Glu)-OVA conjugates. They were then challenged three weeks later with an infusion of OVA-specific T cells and an antigen challenge. To investigate whether the demonstrated tolerance inducing effect was the result of endogenous Tregs, mice were treated with p(Glu)-OVA and later treated with anti-CD25 antibody.

Protocol: On day zero and 3, BL6/C57 mice received an intravenous infusion of saline or 1.5 µg of OVA as free OVA or p(Glu)-OVA conjugates (glucose in the beta conformation was used in this experiment, though in several embodiments the alpha conformation can be used). On day 6, mice received a final treatment of saline, or 15 µg of OVA as free OVA or p(Glu)-OVA conjugates. On day 14, half of the animals treated with p(Glu)-OVA were treated with an intraperitoneal injection of 300 µg of anti-CD25 antibody.

On day 28, mice received an infusion of 750,000 OTII and 750,000 OTI T cells. The next day, animals were challenged with 5 µg of OVA and 50 ng of ultrapure LPS in each of the 4 footpads. Five days after antigen challenge, the mice were sacrificed and the number of OTI and OTII T cells in the draining lymph nodes was assessed by flow cytometry. (Groups n=5: Challenge (i.e. vehicle treated animals), OVA, p(Glu)-OVA, p(Glu)-OVA+αCD25). This protocol is schematically depicted in FIG. 20.

Results: The results of this experiment are shown in FIGS. 21A-21B. FIG. 21A depicts the remaining OTI T cells after antigen challenge (as a percentage of total CD8+ cells). FIG. 21B depicts the remaining OTII T cells after antigen challenge (as a percentage of total CD4+ cells). Those mice receiving LPS challenge and OVA absent a tolerogenic composition showed significantly elevated OTI and OTII cells in draining lymph nodes. Those mice receiving pGlu-OVA showed a significant reduction in both OTI and OTII cells in comparison. The abrogation of the tolerance induced by pGlu-OVA by the administration of anti-CD25 antibodies demonstrates that Tregs derived from the endogenous T cell population play a significant role in the tolerance induction by the pGlu-antigen composition. Taken together, these data indicate that the tolerogenic compositions disclosed herein are able to induce long-lasting tolerance through the induction of endogenous regulatory T cells. This is advantageous, in several embodiments, because the long-lasting tolerance reduces (or in some embodiments eliminates) the need for ongoing administration of the compositions disclosed herein. That being said, in some embodiments, repeated administration is optionally performed. Moreover, these data indicate that supplementing the T cells of a recipient with exogenous T cells is not necessary for induction of tolerance. Rather, the endogenous pool of T cells is sufficient to provide regulatory T cells in appropriate numbers to result in long-term tolerance.

Example 29

Prophylactic Administration of Tolerogenic Compositions Reduces Subsequent Antibody Generation As disclosed herein, in several embodiments, the tolerogenic compositions are useful for the reduction, treatment, prevention or otherwise amelioration of immune responses against antigens of interest. In some embodiments, therefore the ultimate use of the tolerogenic composition, e.g., prevention versus treatment, is determined by the current state of a subject prior to receiving administration of the composition. The present experiment was performed in order to demonstrate that tolerogenic compositions disclosed herein can be used to reduce the degree of antibody generation to a specific antigen, through the prophylactic administration of a tolerogenic composition.

Protocol: The experimental design is depicted in FIG. 22. For pretreatment, there were two groups, those receiving 15 µg of a tolerogenic composition comprising p-Glu-Asparaginase (high dose) and those receiving 2.5 µg of p-Glu-Asparaginase (low dose) (glucose in the beta conformation was used in this experiment, though in several embodiments the alpha conformation can be used). These pretreatment steps are depicted in FIG. 22 as step "A". Note that, asparaginase is used in this experiment as a nonlimiting example of an antigen to which tolerance is desired. As discussed above, numerous other antigens, fragments thereof, or mimotopes thereof can also be used, depending on the embodiment. After the pretreatment, or at the initiation of the experimental protocol for the wild type asparaginase (WT-Asn) and mixed groups, animals were administered either 15 µg of asparaginase or a combination of 12.5 µg of asparaginase along with 2.5 µg of pGlu-Asparaginase. These administrations are depicted as step "B" in FIG. 22. For all experimental groups, step "C" represents collection of a 10 µL blood sample.

Results: results of this experiment are shown in FIG. 23. The trace that show increases in anti-asparaginase antibody titers beginning at approximately two days and steadily increasing to relative values of between 3 and 4 are the result of the administration of asparaginase alone. In contrast, the pretreatment with either high dose or low dose asparaginase significantly reduced the generation of anti-asparaginase antibodies, and consistently held the antibody titer at relatively lower values through the 59 day testing protocol. The negative control group (antigen naïve) shows no development of antigen-specific antibodies.

These data demonstrate that, in addition to treating or reducing a pre-existing immune response to an antigen of interest, in several embodiments, the tolerogenic compositions disclosed herein can also be used in preventing the initial immune response. As shown in this experiment, both high and low doses of glycotargeting therapeutics coupled to an antigen of interest administered as a pretreatment ameliorated the generation of antibodies against the antigen of interest. In several embodiments, such an approach is particularly effective when an exogenous therapeutic agent is to be administered to a patient. In some such embodiments depending upon the therapeutic agent, the tolerogenic composition need not include the entire therapeutic agent as the antigen of interest (although in some embodiments the entire therapeutic agent is included), but rather can include a fragment of the therapeutic agent a particular epitope of the therapeutic agent, or a mimotope of an antigenic region of the therapeutic agent. In some embodiments, the therapeutic agent is a protein drug. Additionally, in some embodiments longer and/or more frequent pretreatment administrations of the tolerogenic composition may serve to even further reduce the generation of antibodies against the antigen of interest. However, in some embodiments a single pretreatment step may be sufficient.

Example 30

Tolerogenic Compositions Ameliorate Multiple Sclerosis

As discussed above, a variety of diseases associated with an immune response, including autoimmune responses, can be treated through the generation and use of tolerogenic compositions as disclosed herein. As a nonlimiting example of such a used in the autoimmune context, the present experiment was designed to determine the efficacy of a tolerogenic composition in the treatment of multiple sclerosis (MS).

The MS-related tolerogenic compositions were tested in a mouse model of multiple sclerosis (experimental autoimmune encephalomyelitis, EAE). The auto-antigen used for vaccination in the model was a peptide derived from myelin oligodendrocyte glycoprotein (MOG), amino acid numbers 35-55 (MOG35-55; SEQ ID NO:24). The auto-antigen utilized for treatment in the model was a slightly longer peptide sequence (MOG30-60; SEQ ID NO:25), which contained the vaccination peptide specified above. The longer therapeutic sequence was used to ensure processing by antigen presenting cells and consequently reduce the tendency of the soluble peptide to bind to cell-surface major histocompatibility complex in the absence of uptake by antigen presenting cells.

Protocol: The experimental protocol is shown in FIG. 24A, with the therapeutic tolerogenic composition shown in FIG. 24B. EAE was induced by immunizing donor B6.SJL mice with MOG35-55/CFA. 11 days later, their spleen cells are harvested and restimulated in culture with MOG35-55 peptide, anti-IFNγ antibodies and IL-12 for 3 days. The resultant encephalitogenic cells were injected into recipient groups of mice, which then develop MS symptoms. Group sizes were 10 mice each, of which half were sacrificed at the peak of disease (Day 11) and half were sacrificed at the end of experiment (Day 20). Body weights were measured 3 times per week and disease state was scored daily, blinded. Control peptide (MOG30-60), glycotargeting peptide (pGlu-MOG30-60; (glucose in the alpha conformation was used in this experiment, though in several embodiments the beta conformation can be used), or vehicle (saline) were given on Days 0, 3, and 6 in either 0.8 µg or 4.0 µg doses. A positive efficacy treatment control (FTY720) was given daily for the duration of the study. FTY720 (fingolimod) is a first-in-class sphingosine 1-phosphate (S1P) receptor modulator deemed effective in Phase II clinical trials for MS.

FIG. 25A shows the assessment of the tolerogenic composition's ability to delay disease onset as compared to control animals. As can be seen, at day 11 (the peak of the disease symptoms for the control group), administration of 0.8 µg of pGlu-MOG$_{30-60}$ (filled triangles) resulted in a significant decrease in the EAE disease score (as compared to the MOG peptide alone). FIG. 25B shows data in relation to reduction of weight loss that is associated with MS. Similar to the EAE disease score, pGlu-MOG$_{30-60}$ showed significantly reduced weight loss at day 11 of the experiment (FIG. 25B; as compared to MOG alone). In contrast, the peptide alone group and the control group exhibited loss of approximately 25% of body weight at the same time point in the experiment.

FIG. 26A corresponds to the assessment of disease onset delay with the higher, 4 µg dose of pGlu-MOG$_{30-60}$. Unexpectedly, the delay in disease onset was strikingly improved (significant vs. both MOG alone and FTY720, with none of the mice in the treatment group (filled triangles) exhibiting a nonzero EAE disease score until 14 days into the experiment. In contrast, by day 6, each of the other experimental groups was showing signs of MS, as evidenced by the increased EAE disease score. Again, similar to EAE disease score, the higher, 4 µg dose of pGlu-MOG$_{30-60}$ resulted in significant reductions in weight loss. At day 11, the pGlu-MOG$_{30-60}$ group (closed triangles) had essentially zero weight loss, while all other groups had lost weight (~2.5 grams in the FTY720 group and ~5 grams in the MOG alone and control groups, see FIG. 26B). Thus, the higher, 4 µg dose of pGlu-MOG$_{30-60}$ yielded significantly (vs. both MOG alone and FTY720) improved retention of weight, which lasted throughout substantially all of the experiment.

As discussed above, this particular experiment was a nonlimiting example of how a tolerogenic composition according to several embodiments disclosed herein could be used to reduce the immune response that a subject generates to an antigen of interest, here an antigen associated with the autoimmune disease multiple sclerosis. As mentioned previously, other antigens, autoantigens, therapeutic proteins, fragments or specific epitopes of any of the preceding, or mimotope of any of the preceding can also successfully be used in accordance with the disclosure provided herein in order to induce immune tolerance.

Example 31

Biodistribution of pGal and pGlu Beta Conjugates

This experiment was conducted to determine the hepatic cell types targeted by pGal and pGlu conjugates as disclosed herein.

Protocol: mice were treated via tail vein injection with 100 µg of OVA fluorescently labeled with the fluorescent dye Dy-649 (OVA649), 100 µg of OVA conjugated to pGluβ (OVA649-pGluβ), or 100 µg of OVA conjugated to pGalβ (OVA649-pGluβ). After 3 h, these mice were sacrificed and the livers were harvested, processed into single cell suspensions, and separated via density gradient centrifugation. The various hepatic cell types were then analyzed for protein content (e.g., as a measure of OVA649) via flow cytometry.

Results: Results show that both OVA649-pGalβ and OVA649-pGluβ conjugates are more effective at targeting liver sinusoidal endothelial cells (LSECs) as compared to OVA649 (FIG. 27A). LSECs taken from animals treated with OVA649-pGalβ had a two-fold increase in mean fluorescent intensity (MFI) and LSECs taken from animal treated with OVA649-pGluβ had a 2.5-fold increase in MFI as compared to LSECs taken from animals treated with OVA649.

Kupffer Cells were also efficiently targeted by OVA649-pGluβ conjugates. The percentage of Kupffer cells that took up OVA649-pGluβ in animals treated with OVA649-pGluβ was significantly greater than the percentage of Kupffer Cells that took up OVA649 (FIG. 27B). In several embodiments, pGlu in the beta conformation is therefore used when it may be desirable to target Kupffer cells. That being said, pGal conjugates can also optionally be used in certain embodiments.

In addition to Kupffer cells, CD11c+ cells also efficiently took up OVA649-pGluβ. The percentage of CD11c+ cells that took up OVA649-pGluβ was significantly greater than the percentage of CD11c+ that were targeted by OVA649 (FIG. 27C). In several embodiments, pGlu in the beta conformation is therefore used when it may be desirable to target CD11C+ cells. That being said, pGal conjugates can also optionally be used in certain embodiments.

Interestingly, both OVA649-pGluβ and OVA649-pGalβ conjugates were more effective at targeting hepatocytes as compared to OVA649. See FIG. 27D. However, the percentage of hepatocytes that took up OVA649-pGalβ was greater than the percentage of hepatocytes targeted by OVA649-pGluβ. Thus, in several embodiments, pGal in the beta conformation is therefore used when it may be desirable to target hepatocytes. That being said, pGlu conjugates can also optionally be used in certain embodiments.

Interestingly, an analysis of the ability of free OVA and OVA-glycopolymer conjugates to target stellate cells showed contrasting results. FIG. 27E shows that OVA targets stellate cells more efficiently than either of the OVA-glycopolymer conjugates.

In several embodiments, combinations of pGlu and pGal conjugates may be desirable and the two types of composition interact synergistically to target the liver (and various cell types in the liver). Also, in several embodiments mixtures of conjugates in the alpha and beta configurations can also be used. As with other experiments disclosed herein, the use of OVA is as a non-limiting example of an antigen to which tolerance is desired. Other antigens disclosed herein, fragments thereof, and mimotopes thereof can also be conjugated to glycotargeting moieties, and tolerance thereto can be induced, based on the disclosure provided herein. In accordance with several embodiments disclosed herein, this induced tolerance can treat, reduce, prevent, or otherwise ameliorate an unwanted immune response that would have otherwise been associated with exposure to the antigen.

While the present disclosure has been described with reference to the specific embodiments thereof, it should be understood by those skilled in the art that various changes can be made and equivalents can be substituted without departing from the true spirit and scope of the disclosure. In addition, many modifications can be made to adapt a particular situation, material, composition of matter, process, process step or steps, to the objective, spirit and scope of the present disclosure. All such modifications are intended to be within the scope of the claims appended hereto. All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as “administering a glycotargeting tolerogenic composition” include “instructing the administration of a glycotargeting tolerogenic composition.” In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as “up to,” “at least,” “greater than,” “less than,” “between,” and the like includes the number recited. Numbers preceded by a term such as “about” or “approximately” include the recited numbers. For example, “about 10 nanometers” includes “10 nanometers.”

What is claimed is:

1. A method of inducing tolerance to an antigen to which a subject develops an unwanted immune response, the method comprising administering a compound Formula 1 to the subject:

$$X \text{---}[Y \text{---} Z]_m \quad \text{Formula 1}$$

where:

m is an integer from 1 to 100;

X comprises an antigen comprising one or more of SEQ ID NOS: 4 to 13, or

X is selected from the group consisting of insulin, proinsulin, preproinsulin or a tolerogenic portion of any of insulin, proinsulin, or preproinsulin;

Y comprises

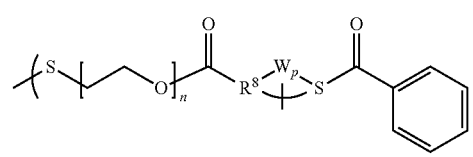

Formula Yc where:

the left bracket "(" indicates the bond between X and Y;

the bottom bracket and ")" indicates the bond between Y and Z;

n is an integer from 1 to 100;

p is an integer from 2 to 150;

$R^8$ is —$CH_2$—$CH_2$—$C(CH_3)(CN)$—; and

W is a copolymer or a random copolymer of the $W^1$ and $W^2$ having p repeat units, where:

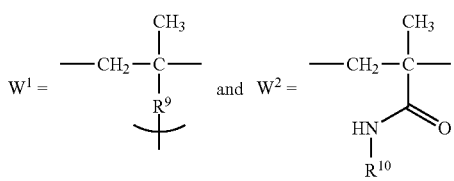

where:

$R^9$ is a direct bond, —C(O)—NH—CH$_2$—CH$_2$—, or —C(O)—NH—(CH$_2$—CH$_2$—O—)$_t$—CH$_2$—CH$_2$—;

t is an integer from 1 to 5; and $R^{10}$ is an aliphatic group, an alcohol or an aliphatic alcohol; and Z comprises one or more liver-targeting moieties.

2. The method of claim 1, wherein Z comprises galactose, galactosamine, N-acetylgalactosamine, glucose, glucosamine or N-acetylglucosamine.

3. The method of claim 2, wherein Z is the beta anomer.

4. The method of claim 2, wherein Z is conjugated at its C1, C2 or C6 to Y.

5. The method of claim 1, wherein:

m is 1 to 3;

$R^9$ is —C(O)—NH—(CH$_2$—CH$_2$—O—)$_t$—CH$_2$—CH$_2$—;

t is 1;

$R^{10}$ is CH$_2$CH$_2$OH; and

Z comprises a liver-targeting moiety comprising one or more of galactose, galactosamine, N-acetylgalactosamine, glucose, glucosamine, and N-acetylglucosamine.

6. The method of claim 1, wherein X comprises an antigen comprising SEQ ID NO: 4.

7. The method of claim 1, wherein X comprises an antigen comprising SEQ ID NO: 5.

8. The method of claim 1, wherein X comprises an antigen comprising SEQ ID NO: 6.

9. The method of claim 1, wherein X comprises an antigen comprising SEQ ID NO: 7.

10. The method of claim 1, wherein X comprises an antigen comprising SEQ ID NO: 8.

11. The method of claim 1, wherein X comprises an antigen comprising SEQ ID NO: 9.

12. The method of claim 1, wherein X comprises an antigen comprising SEQ ID NO: 10.

13. The method of claim 1, wherein X comprises an antigen comprising SEQ ID NO: 11.

14. The method of claim 1, wherein X comprises an antigen comprising SEQ ID NO: 12.

15. The method of claim 1, wherein X comprises an antigen comprising SEQ ID NO: 13.

16. The method of claim 1, wherein X comprises insulin or a tolerogenic portion thereof.

17. The method of claim 1, wherein X comprises proinsulin or a tolerogenic portion thereof.

18. The method of claim 1, wherein X comprises preproinsulin or a tolerogenic portion thereof.

* * * * *